United States Patent
Kim et al.

(10) Patent No.: US 10,790,452 B2
(45) Date of Patent: Sep. 29, 2020

(54) ANTIAROMATIC COMPOUNDS AND ORGANIC LIGHT-EMITTING DEVICES COMPRISING THE SAME

(71) Applicants: SAMSUNG DISPLAY CO., LTD., Yongin, Gyeonggi-do (KR); INDUSTRY-ACADEMIC COOPERATION FOUNDATION GYEONGSANG NATIONAL UNIVERSITY, Jinju-Gyeongnam (KR)

(72) Inventors: Mi-Kyung Kim, Yongin (KR); Yun-Hi Kim, Jinju (KR); Soon-Ki Kwon, Jinju (KR); Chang-Woong Chu, Yongin (KR)

(73) Assignees: Samsung Display Co., Ltd., Yongin-si (KR); Industry-Academic Cooperation Foundation Gyeongsang National University, Jinju (KR)

( * ) Notice: Subject to any disclaimer, the term of this patent is extended or adjusted under 35 U.S.C. 154(b) by 549 days.

(21) Appl. No.: 14/533,028

(22) Filed: Nov. 4, 2014

(65) Prior Publication Data
US 2015/0357578 A1 Dec. 10, 2015

(30) Foreign Application Priority Data
Jun. 10, 2014 (KR) .................. 10-2014-0070265

(51) Int. Cl.
*H01L 51/00* (2006.01)
*C07D 413/14* (2006.01)
(Continued)

(52) U.S. Cl.
CPC ........ *H01L 51/0072* (2013.01); *C07D 245/04* (2013.01); *C07D 401/14* (2013.01);
(Continued)

(58) Field of Classification Search
None
See application file for complete search history.

(56) References Cited

U.S. PATENT DOCUMENTS 3,243,430 A * 3/1966 Metlesics ............... C07C 51/60
540/471
3,409,608 A 11/1968 Topliss et al.
(Continued)

FOREIGN PATENT DOCUMENTS

JP 48-076886 A * 10/1973
KR 10-2006-0116240 A 11/2006
(Continued)

OTHER PUBLICATIONS

Wang et al. (Org. Lett. 2011, 13, p. 709).*
(Continued)

*Primary Examiner* — Jay Yang
(74) *Attorney, Agent, or Firm* — Lewis Roca Rothgerber Christie LLP

(57) ABSTRACT

An antiaromatic compound and an organic light-emitting device including the same. The antiaromatic compound is represented by Formula 1:
(Continued)

Formula 1

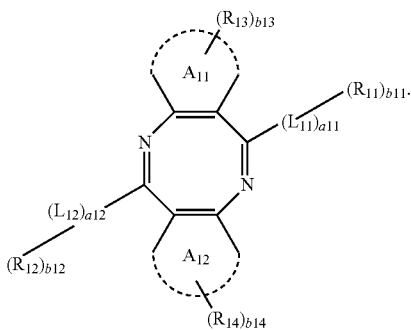

19 Claims, 21 Drawing Sheets

(51) Int. Cl.
| | |
|---|---|
| C07D 401/14 | (2006.01) |
| C07D 471/04 | (2006.01) |
| C07D 245/04 | (2006.01) |
| C07D 471/14 | (2006.01) |
| C07D 403/14 | (2006.01) |
| C09B 57/10 | (2006.01) |
| C09B 3/14 | (2006.01) |
| C09B 57/00 | (2006.01) |
| C09B 1/00 | (2006.01) |
| C09B 23/14 | (2006.01) |
| C09B 3/00 | (2006.01) |
| H01L 51/50 | (2006.01) |

(52) U.S. Cl.
CPC ......... *C07D 403/14* (2013.01); *C07D 413/14* (2013.01); *C07D 471/04* (2013.01); *C07D 471/14* (2013.01); *C09B 1/00* (2013.01); *C09B 3/00* (2013.01); *C09B 3/14* (2013.01); *C09B 23/148* (2013.01); *C09B 57/00* (2013.01); *C09B 57/001* (2013.01); *C09B 57/008* (2013.01); *C09B 57/10* (2013.01); *H01L 51/0067* (2013.01); *H01L 51/006* (2013.01); *H01L 51/0058* (2013.01); *H01L 51/0061* (2013.01); *H01L 51/5072* (2013.01); *H01L 2251/308* (2013.01)

(56) References Cited

U.S. PATENT DOCUMENTS

| | | |
|---|---|---|
| 2005/0197337 A1 | 9/2005 | Malherbe et al. |
| 2006/0058499 A1 | 3/2006 | Lee et al. |
| 2009/0146554 A1 | 6/2009 | Lee et al. |
| 2011/0037063 A1 | 2/2011 | Buesing et al. |
| 2011/0240969 A1 | 10/2011 | Kim et al. |
| 2012/0126180 A1 | 5/2012 | Parham et al. |
| 2012/0235123 A1 | 9/2012 | Lee et al. |
| 2012/0283407 A1 | 11/2012 | Hoppin |
| 2015/0357578 A1 | 12/2015 | Kim et al. |

FOREIGN PATENT DOCUMENTS

| | | |
|---|---|---|
| KR | 10-2009-0059842 A | 6/2009 |
| KR | 10-2009-0081478 A | 7/2009 |
| KR | 10-2010-0133485 A | 12/2010 |
| KR | 10-2011-0015836 A | 2/2011 |
| KR | 10-2011-0049244 A | 5/2011 |
| KR | 10-2011-0088118 A | 8/2011 |
| KR | 10-2011-0111103 A | 10/2011 |
| KR | 10-2012-0038530 A | 4/2012 |
| KR | 10-2012-0056418 A | 6/2012 |
| KR | 10-2012-0107996 A | 10/2012 |
| WO | WO 2011/055912 A1 | 5/2011 |
| WO | WO-2011/076674 A1 * | 6/2011 |
| WO | WO 2011/093609 A1 | 8/2011 |

OTHER PUBLICATIONS

Zhao et al. (Tetrahedron 2012, 68, p. 9665).*
Machine English translation of Yamamoto et al. (JP-48-076886 A). Jul. 30, 2018.*
Eisch et al. (Eur. J. Org. Chem. 2014, 4, p. 818).*
Nadkarni et al. (Indian J. Chem. B 1990, 29B(3), p. 271).*
U.S. Office Action dated Jun. 26, 2017, issued in cross-reference U.S. Appl. No. 14/738,721 (19 pages).

* cited by examiner

ANTIAROMATIC COMPOUNDS AND ORGANIC LIGHT-EMITTING DEVICES COMPRISING THE SAME

CROSS-REFERENCE TO RELATED APPLICATION

This application claims priority to and the benefit of Korean Patent Application No. 10-2014-0070265, filed on Jun. 10, 2014, in the Korean Intellectual Property Office, the disclosure of which is incorporated herein in its entirety by reference.

BACKGROUND

1. Field

One or more embodiments of the present disclosure relate to antiaromatic compounds and organic light-emitting devices including the same.

2. Description of the Related Art

Organic light-emitting devices (OLEDs), which are self-emitting devices, have desired characteristics (such as wide viewing angles, excellent contrast, quick response, high brightness, or excellent driving voltage), and can provide multicolored images.

An organic light-emitting device may have a structure in which a first electrode, a hole transport region, an emission layer, an electron transport region, and a second electrode are sequentially disposed in this order on a substrate. Holes injected from the first electrode move to the emission layer via the hole transport region, while electrons injected from the second electrode move to the emission layer via the electron transport region. Carriers such as the holes and electrons recombine in the emission layer to generate excitons. When the excitons drop from an excited state to a ground state, light is emitted.

SUMMARY

Aspects according to one or more embodiments of the present disclosure are directed toward antiaromatic compounds and organic light-emitting devices including the same.

Additional aspects will be set forth in part in the description which follows and, in part, will be apparent from the description, or may be learned by practice of the presented embodiments.

According to one or more embodiments of the present disclosure, an antiaromatic compound is represented by Formula 1:

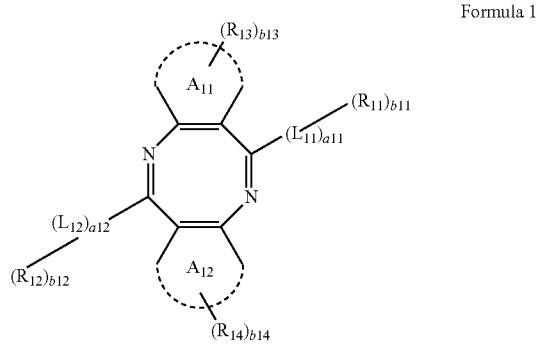

Formula 1 wherein, in Formula 1, $A_{11}$ and $A_{12}$ are each independently selected from a $C_6$-$C_{60}$ arene and a $C_1$-$C_{60}$ heteroarene;

$L_{11}$ and $L_{12}$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted non-aromatic condensed polycyclic group, and a substituted or unsubstituted non-aromatic condensed heteropolycyclic group;

at least one substituent of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted non-aromatic condensed polycyclic group, and the substituted non-aromatic condensed heteropolycyclic group is selected from:

a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and $C_1$-$C_{60}$ alkoxy group;

a $C_1$-$C_{60}$ alkyl group, $C_2$-$C_{60}$ alkenyl group, $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group;

a $C_3$-$C_{10}$ cycloalkyl group, a $C_1$-$C_{10}$ heterocycloalkyl group, a $C_3$-$C_{10}$ group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group; and a $C_3$-$C_{10}$ cycloalkyl group, a $C_1$-$C_{10}$ heterocycloalkyl group, a $C_3$-$C_{10}$ cycloalkenyl group, a $C_1$-$C_{60}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group, each substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group;

a11 and a12 are each independently selected from 0, 1, 2, 3, 4, 5 and 6;

$R_{11}$ and $R_{12}$ are each independently selected from a substituted or unsubstituted $C_6$-$C_{60}$ aryl group, a substituted or unsubstituted $C_1$-$C_{60}$ heteroaryl group, a substituted or unsubstituted non-aromatic condensed polycyclic group, a substituted or unsubstituted non-aromatic condensed heteropolycyclic group, —N($Q_{11}$)($Q_{12}$), —Si($Q_{13}$)($Q_{14}$)($Q_{15}$), and —P($Q_{16}$)($Q_{17}$);

$Q_{11}$ to $Q_{17}$ are each independently selected from a substituted or unsubstituted $C_6$-$C_{60}$ aryl group, and a substituted or unsubstituted $C_1$-$C_{60}$ heteroaryl group;

at least one substituent of the substituted $C_6$-$C_{60}$ aryl group, the substituted $C_1$-$C_{60}$, the substituted non-aromatic condensed polycyclic group, and the substituted non-aromatic condensed heteropolycyclic group is selected from:

a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, $C_2$-$C_{60}$ alkenyl group, $C_2$-$C_{60}$ alkynyl group, and a $C_1$-$C_{60}$ alkoxy group;

a $C_1$-$C_{60}$ alkyl group, $C_2$-$C_{60}$ alkenyl group, $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group;

a $C_3$-$C_{10}$ cycloalkyl group, a $C_1$-$C_{60}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group; and a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group, each substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group;

b11 and b12 are each independently an integer selected from 1 to 3;

$R_{13}$ and $R_{14}$ are each independently selected from:

a hydrogen atom, a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group; and a $C_3$-$C_{10}$ cycloalkyl group, a $C_1$-$C_{60}$ heterocycloalkyl group, a $C_3$-$C_{10}$ cycloalkenyl group, a $C_1$-$C_{60}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group, each substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group; and b13 and b14 are each independently selected from 1, 2, 3, 4, 5, 6, 7, 8, 9 and 10.

According to one or more embodiments of the present disclosure, an organic light-emitting device includes a first electrode, a second electrode facing the first electrode, and an organic layer between the first electrode and the second electrode, and including an emission layer, wherein the organic layer includes at least one of the antiaromatic compound of Formula 1 described above.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
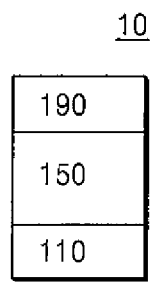
FIG. 1 is a schematic view of a structure of an organic light-emitting device according to an embodiment of the present disclosure.
Figure 2:
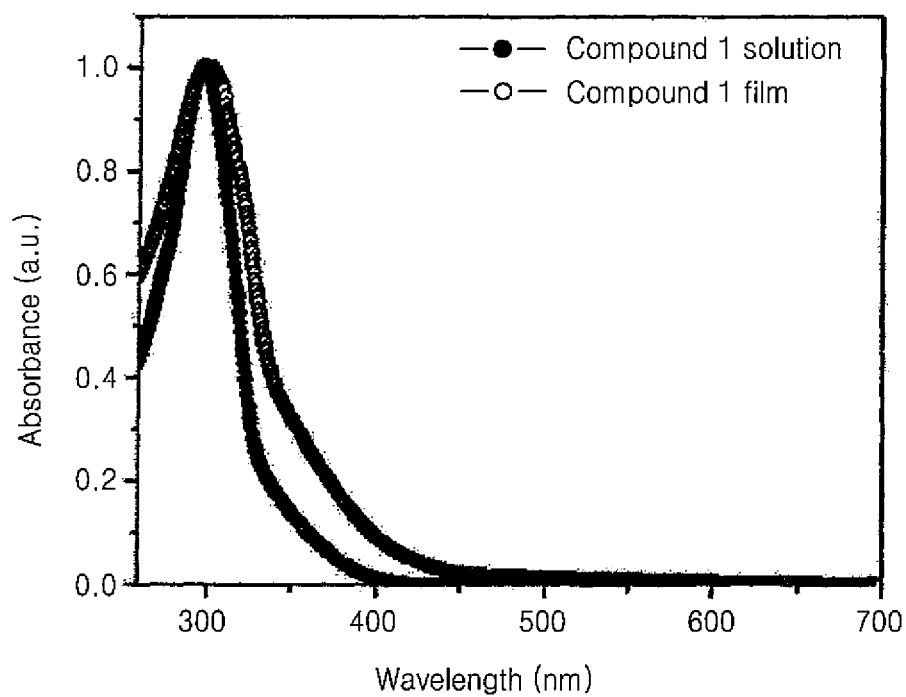
FIG. 2 illustrates the ultraviolet (UV) absorption spectra of Compound 1 in liquid state and in film form.
Figure 3:
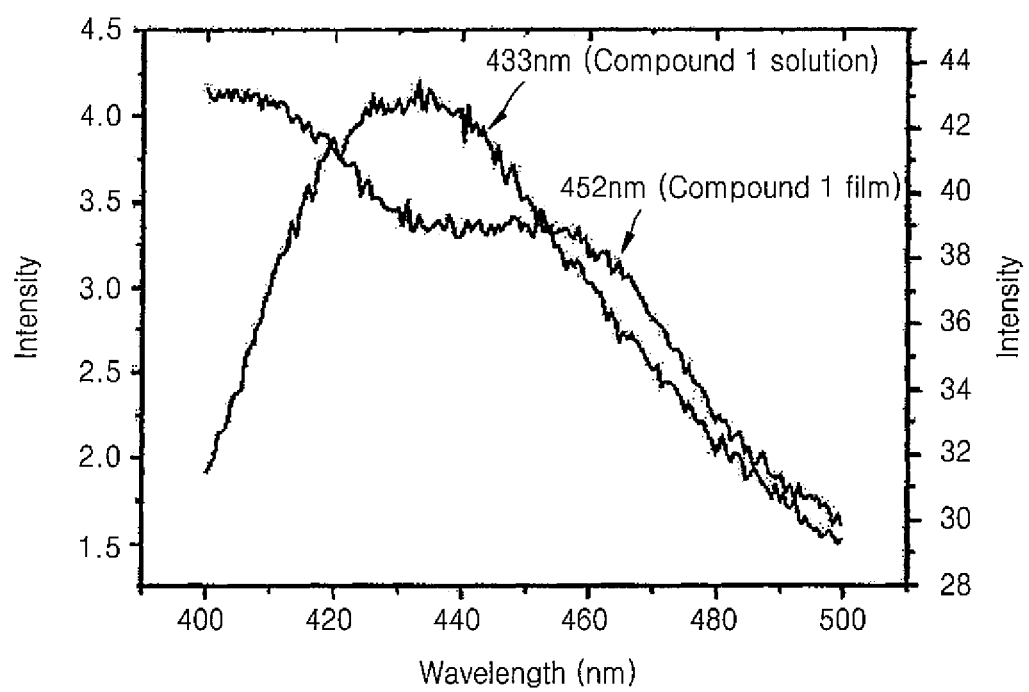
FIG. 3 illustrates the photoluminescence (PL) absorption spectra of Compound 1 in liquid state and in film form.
Figure 4:
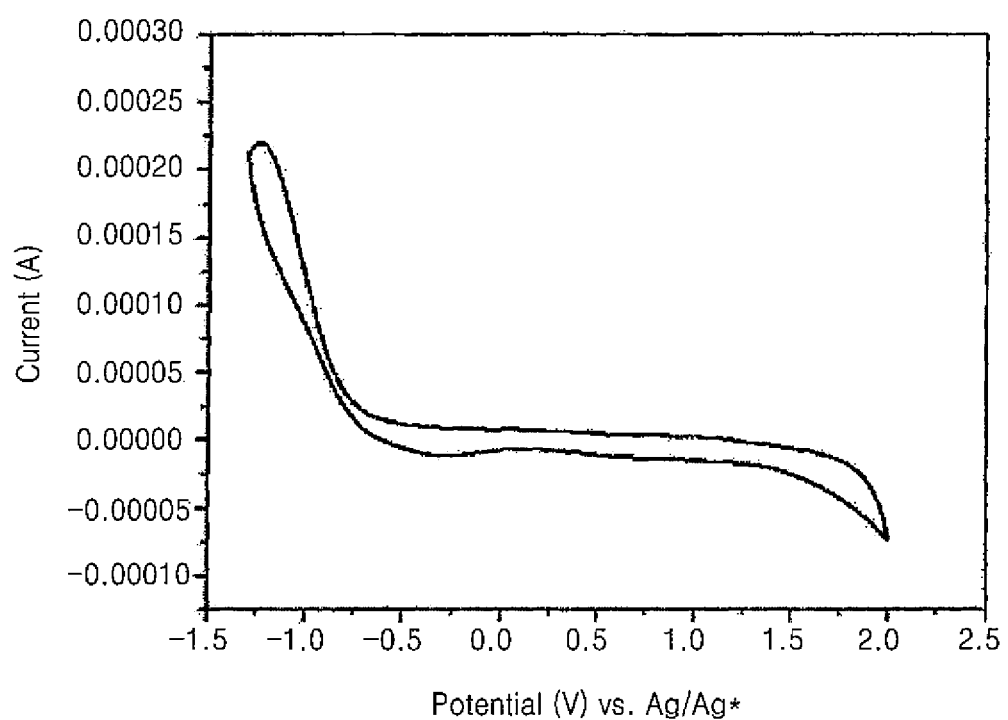
FIG. 4 is a plot of cyclic voltammetry (CV) results for Compound 1.
Figure 5:
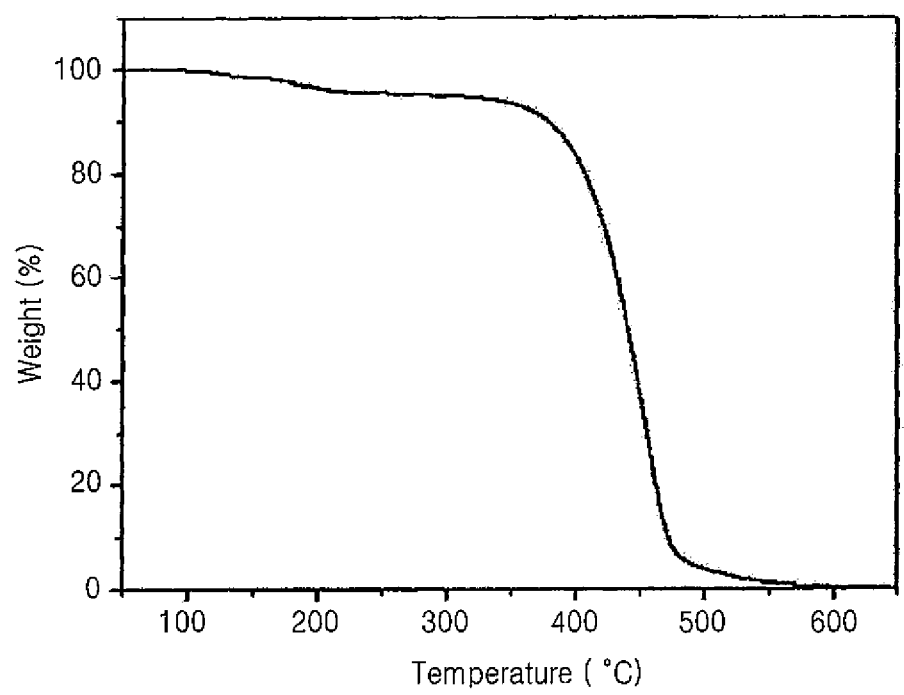
FIG. 5 is a plot of thermogravimetry (TGA) results for Compound 1.
Figure 6:
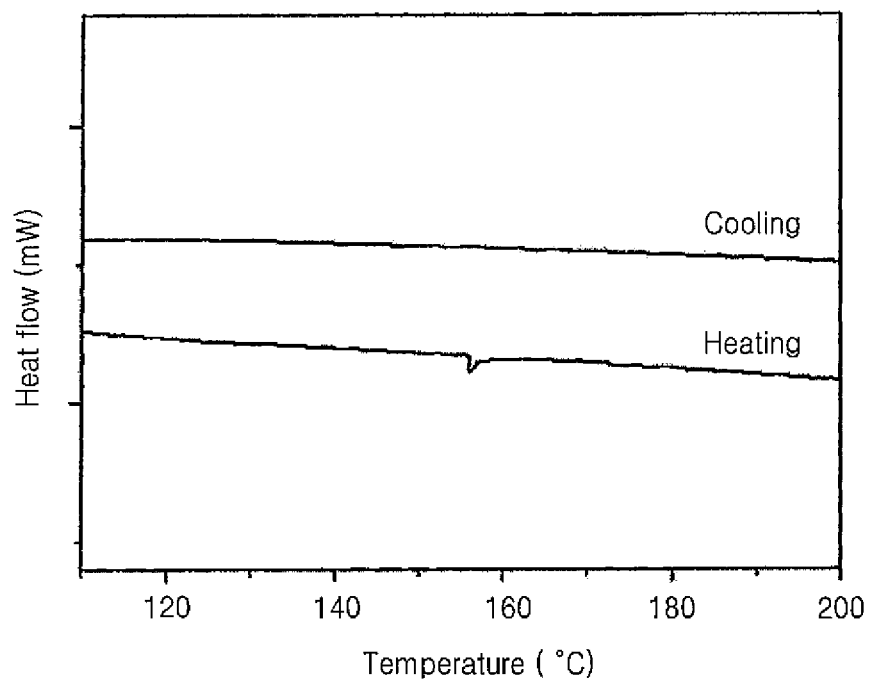
FIG. 6 is a plot of differential scanning calorimetry (DSC) results for Compound 1.
Figure 7:
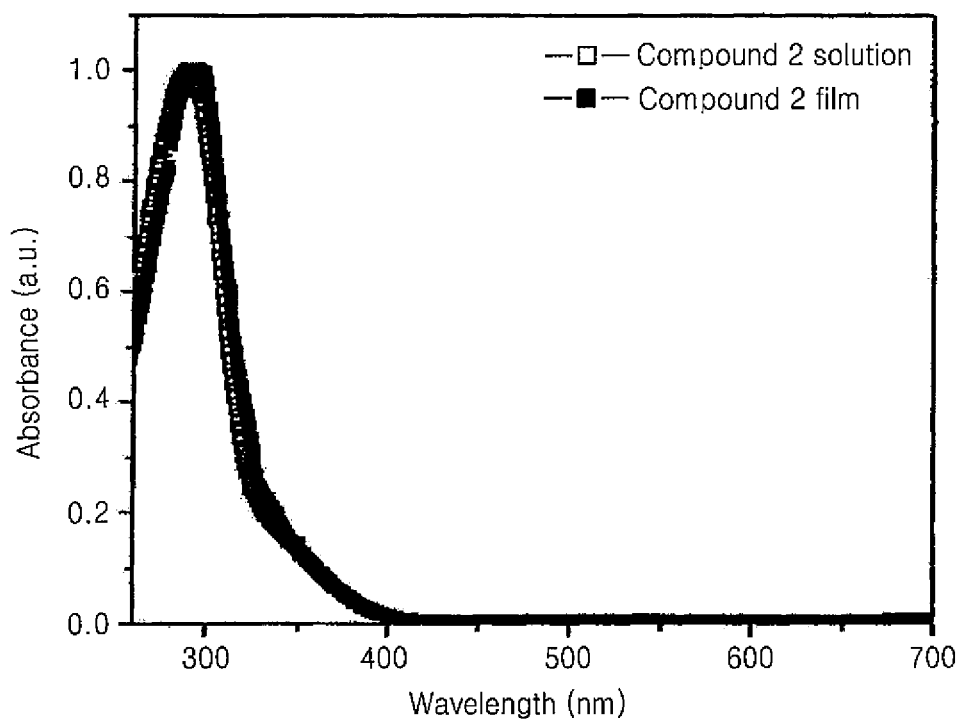
FIG. 7 illustrates the UV absorption spectra of Compound 2 in liquid state and in film form.
Figure 8:
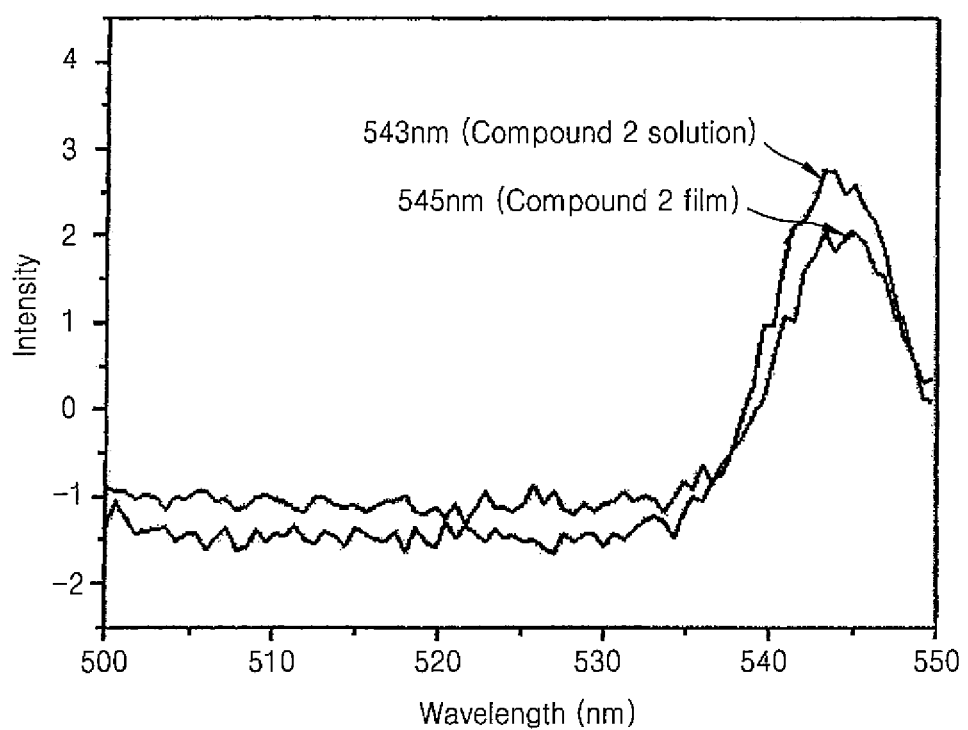
FIG. 8 illustrates the PL absorption spectra of Compound 2 in liquid state and in film form.
Figure 9:
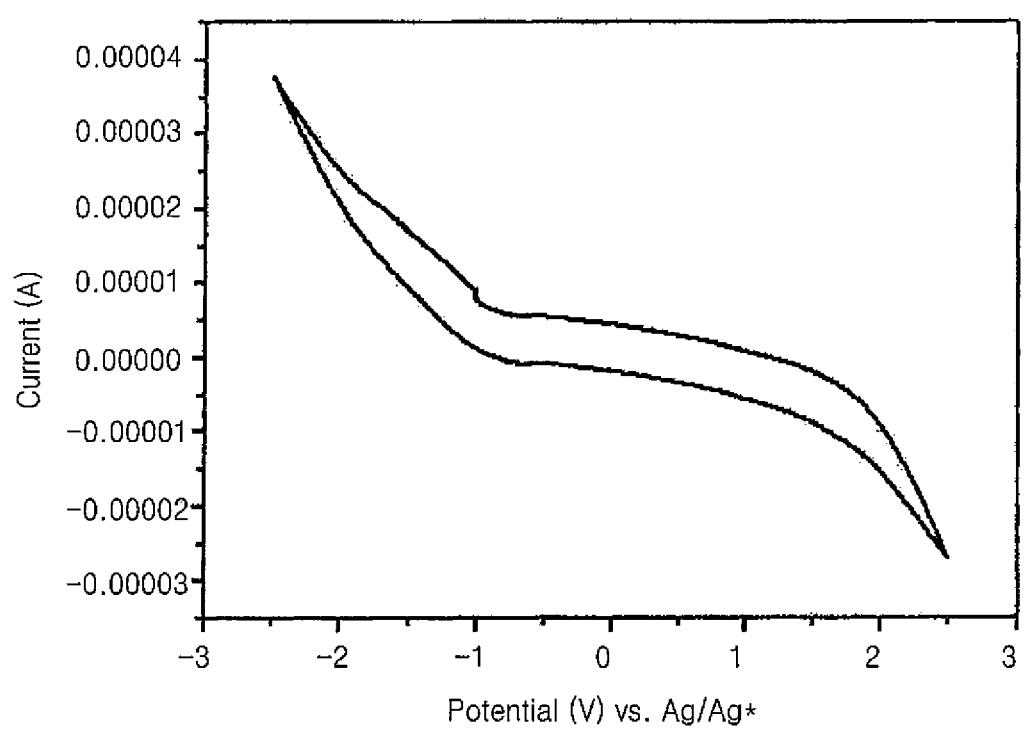
FIG. 9 is a plot of CV results for Compound 2.
Figure 10:
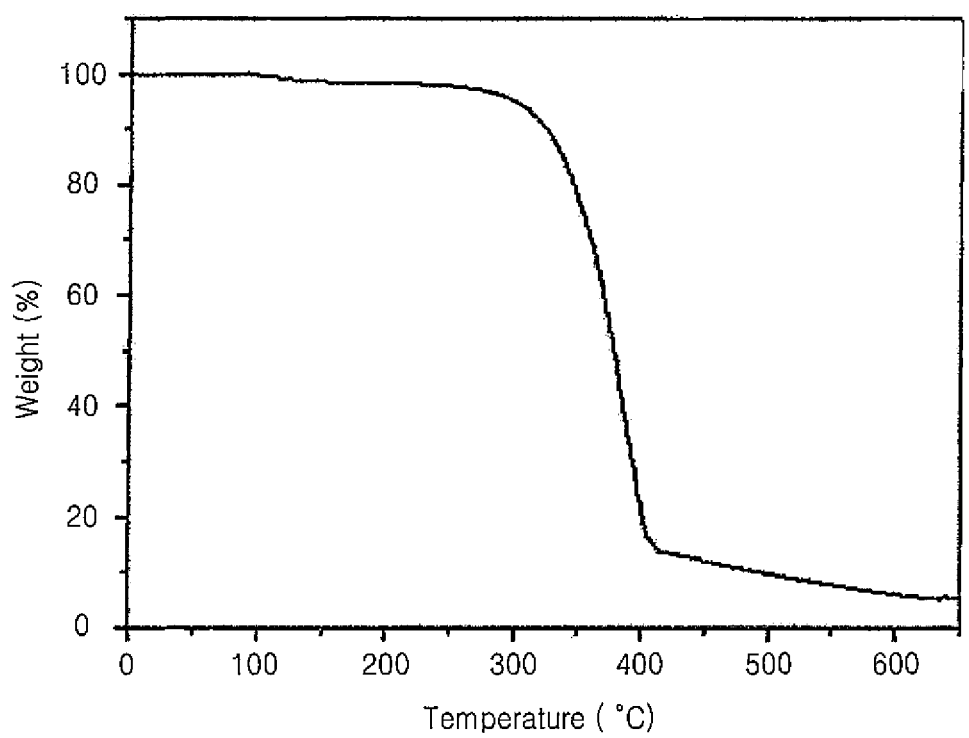
FIG. 10 is a plot of TGA results for Compound 2.
Figure 11:
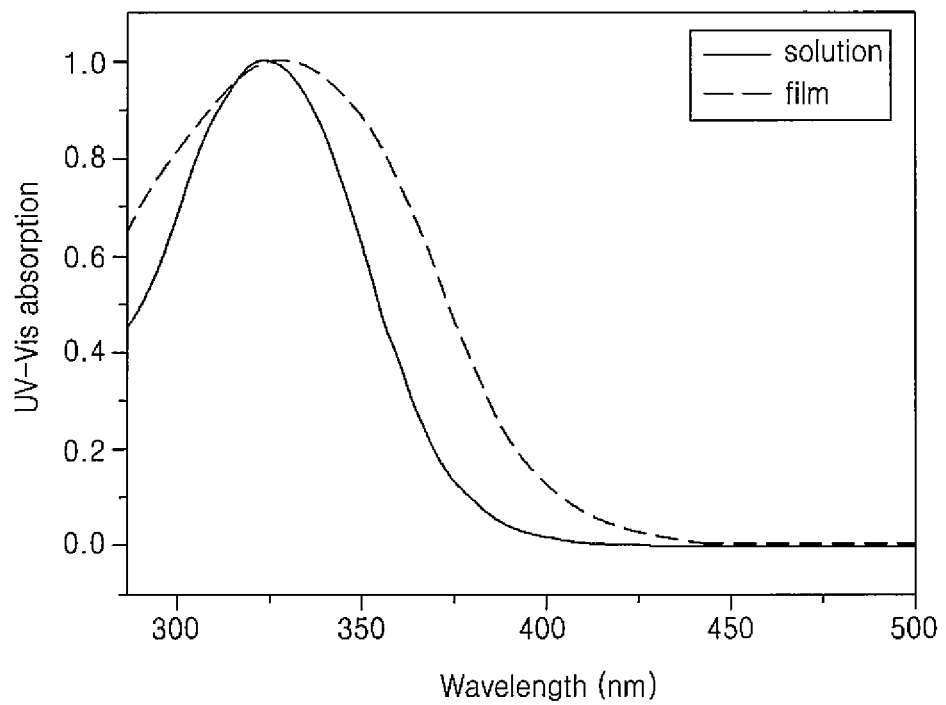
FIG. 11 illustrates the UV absorption spectra of Compound 18 in liquid state and in film form.
Figure 12:
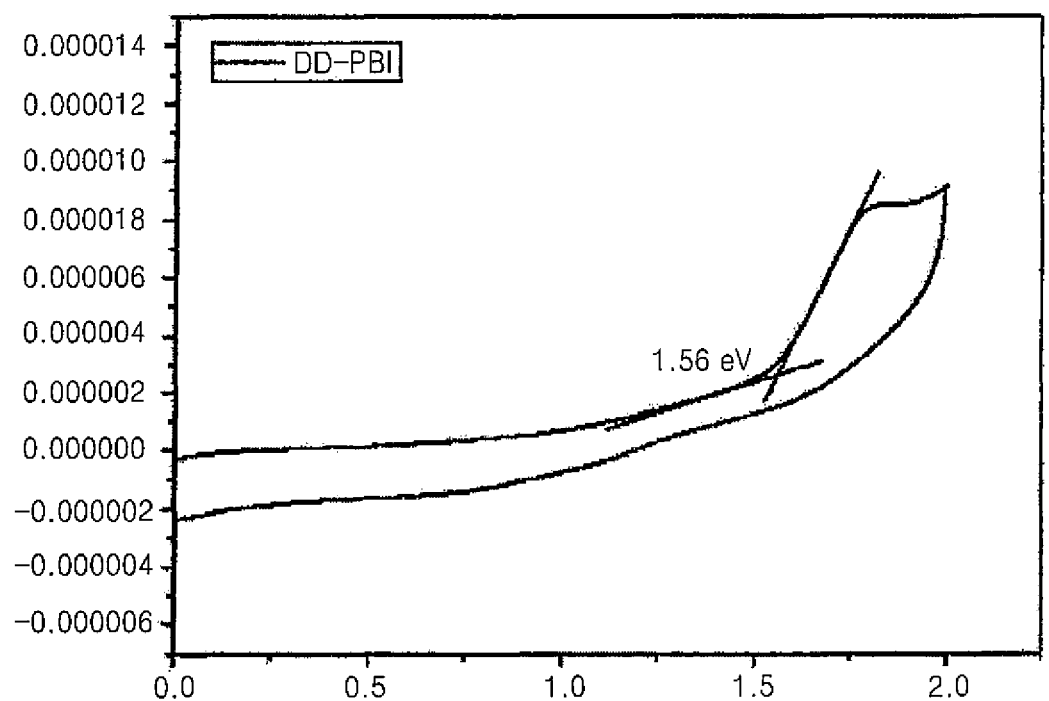
FIG. 12 is a plot of CV results for Compound 18.
Figure 13:
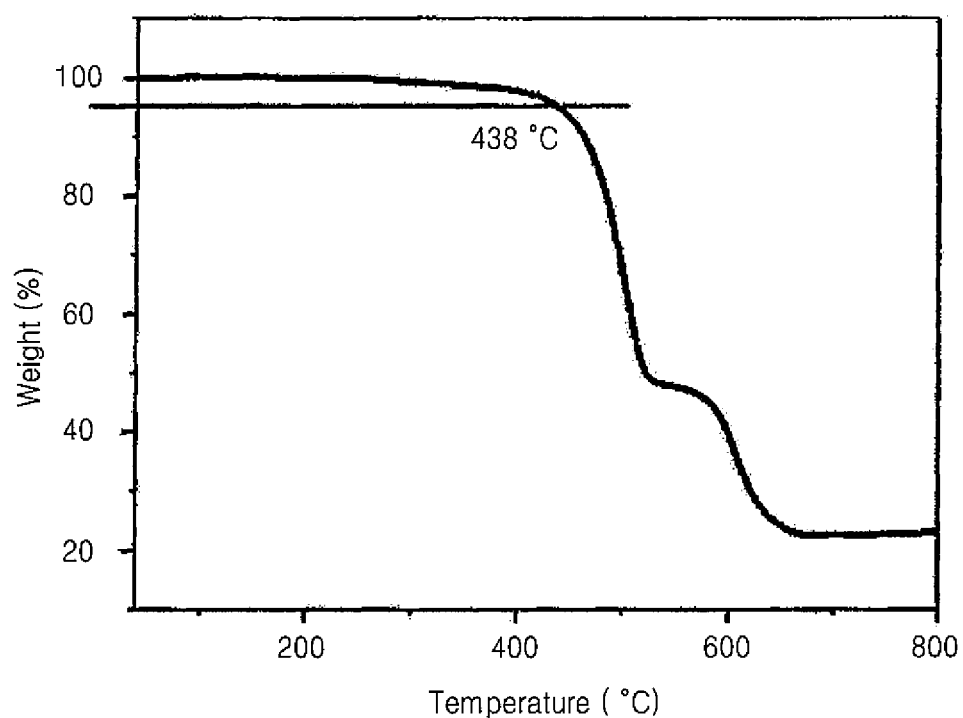
FIG. 13 is a plot of TGA results for Compound 18.
Figure 14:
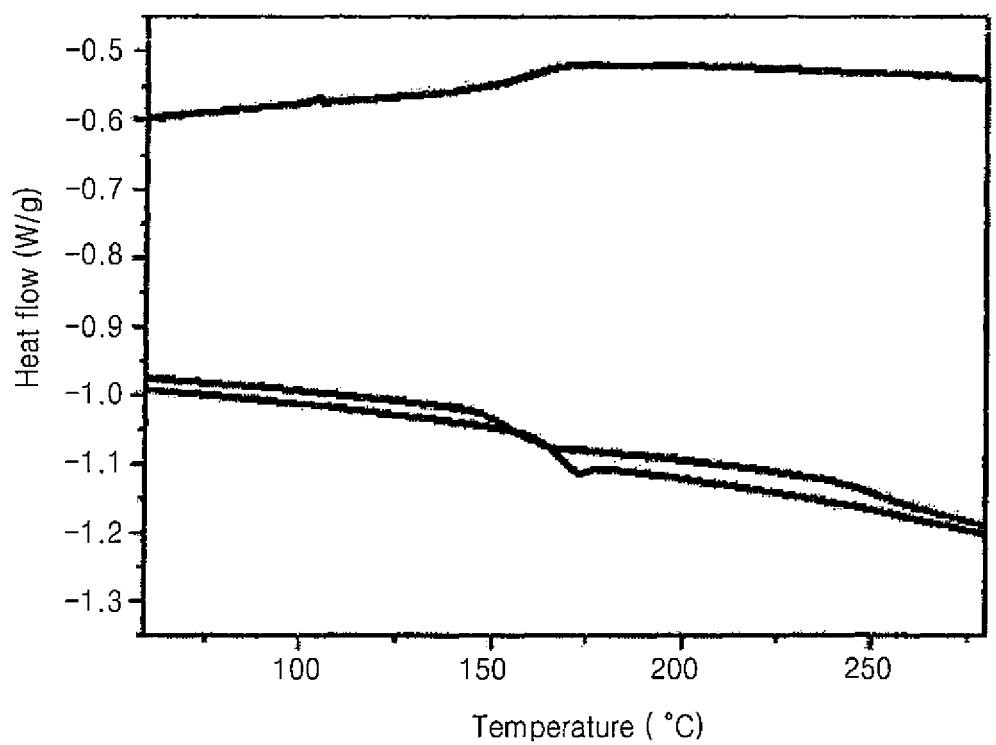
FIG. 14 is a plot of DSC results for Compound 18.
Figure 15:
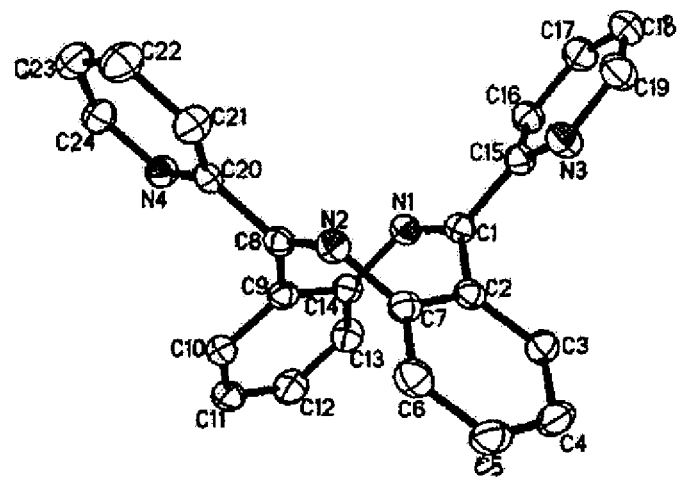
FIG. 15 illustrates a crystalline structure of Compound 140.
Figure 16:
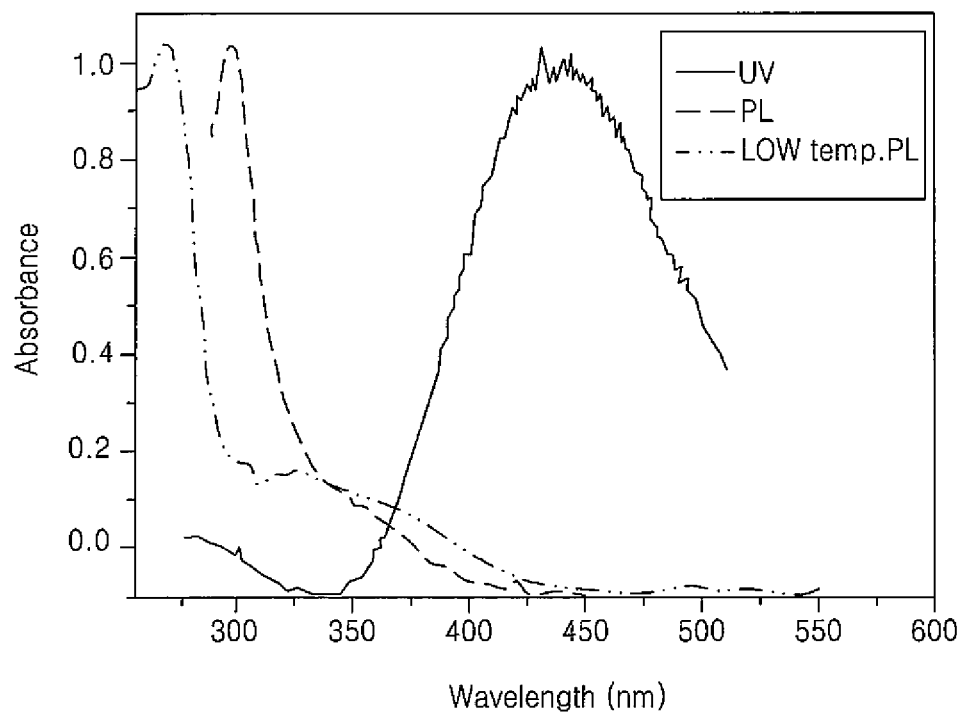
FIG. 16 illustrates the UV absorption spectra of Compound 140 in liquid state and in film form.
Figure 17:
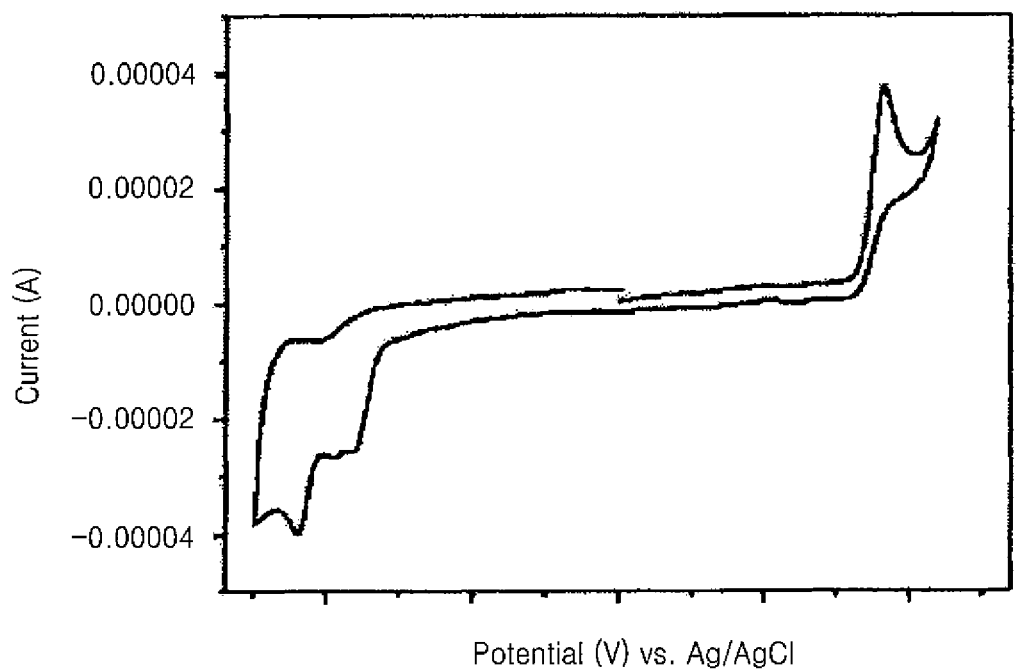
FIG. 17 is a plot of CV results for Compound 140.
Figure 18:
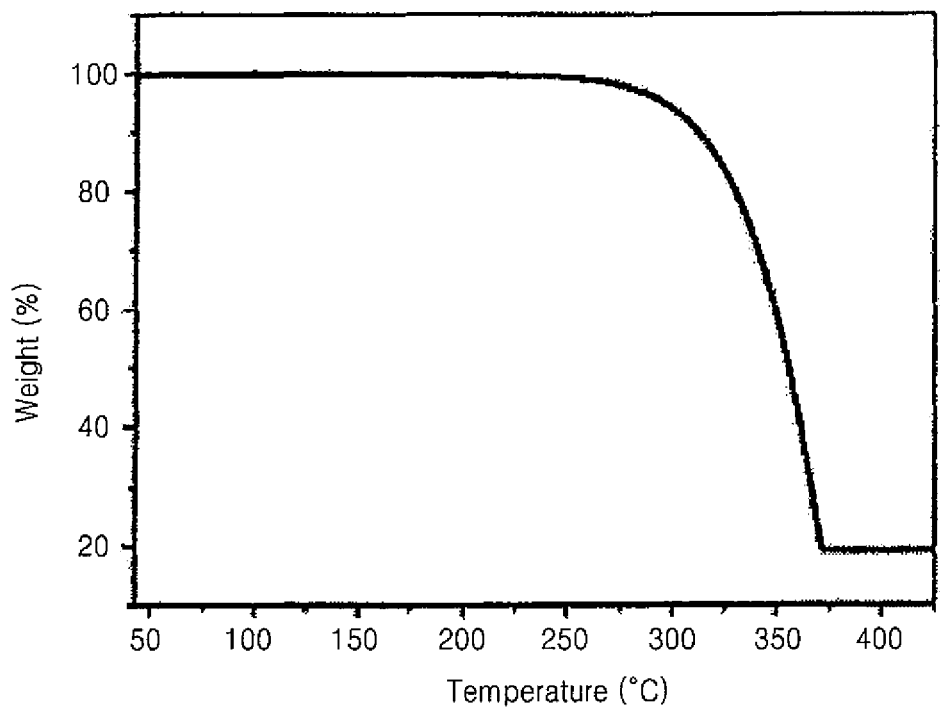
FIG. 18 is a plot of TGA results for Compound 140.
Figure 19:
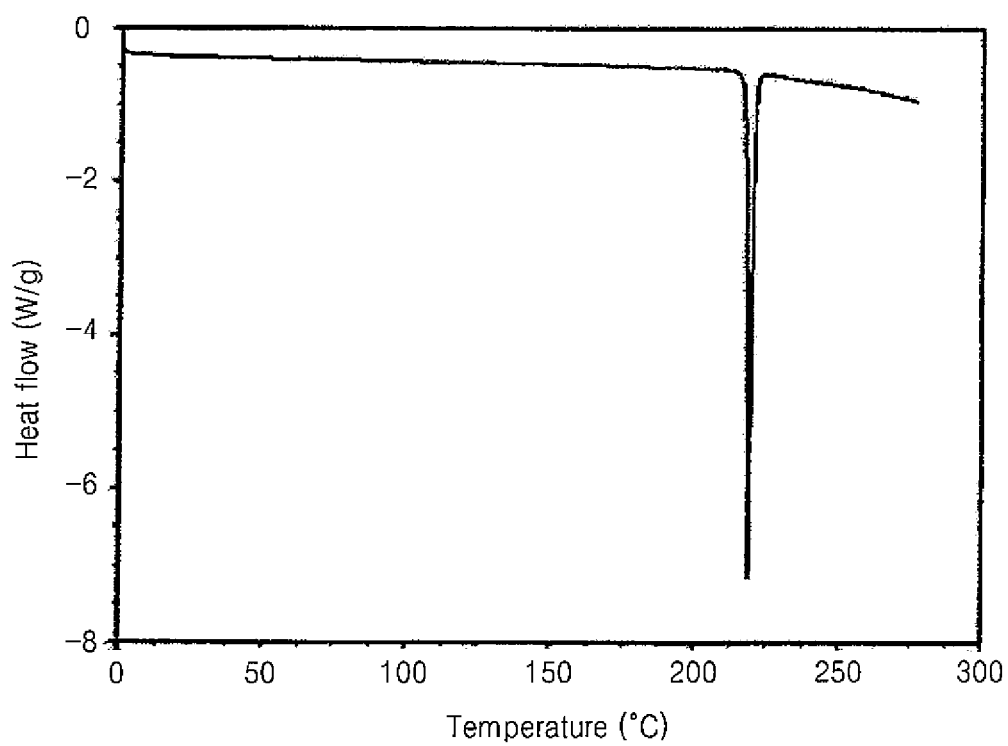
FIG. 19 is a plot of DSC results for Compound 140.
Figure 20:
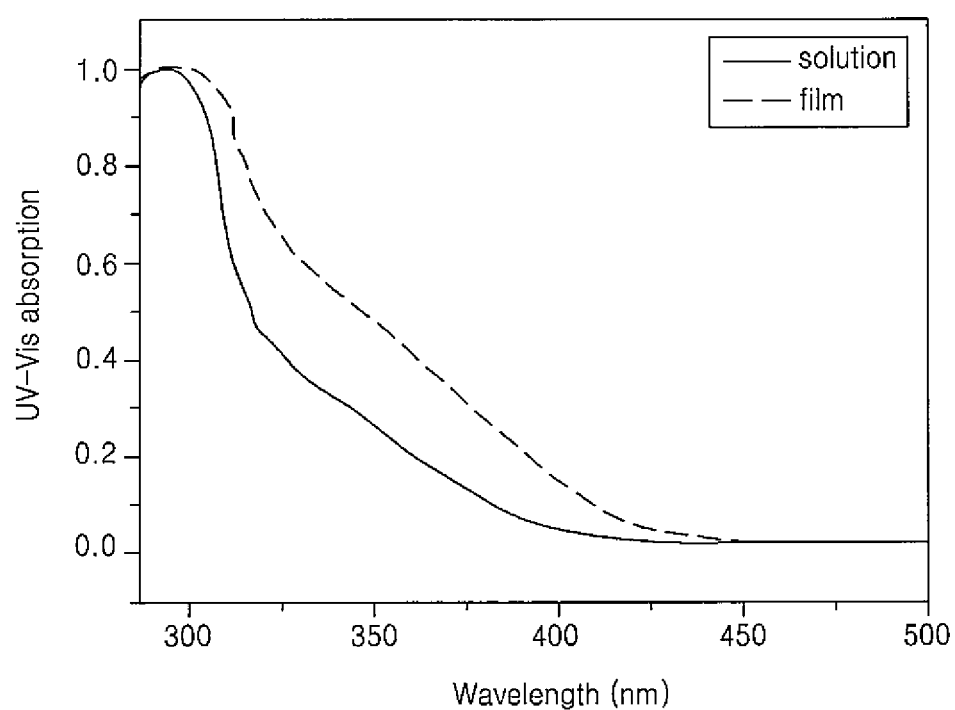
FIG. 20 illustrates the UV absorption spectra of Compound 39 in liquid state and in film form.
Figure 21:
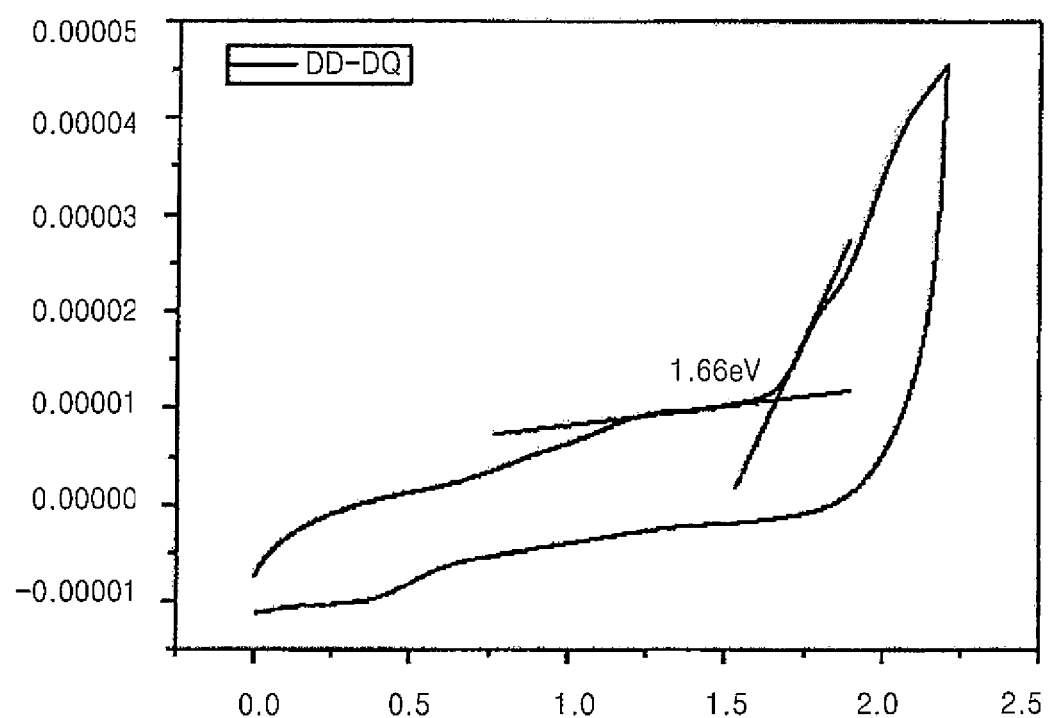
FIG. 21 is a plot of CV results for Compound 39.
Figure 22:
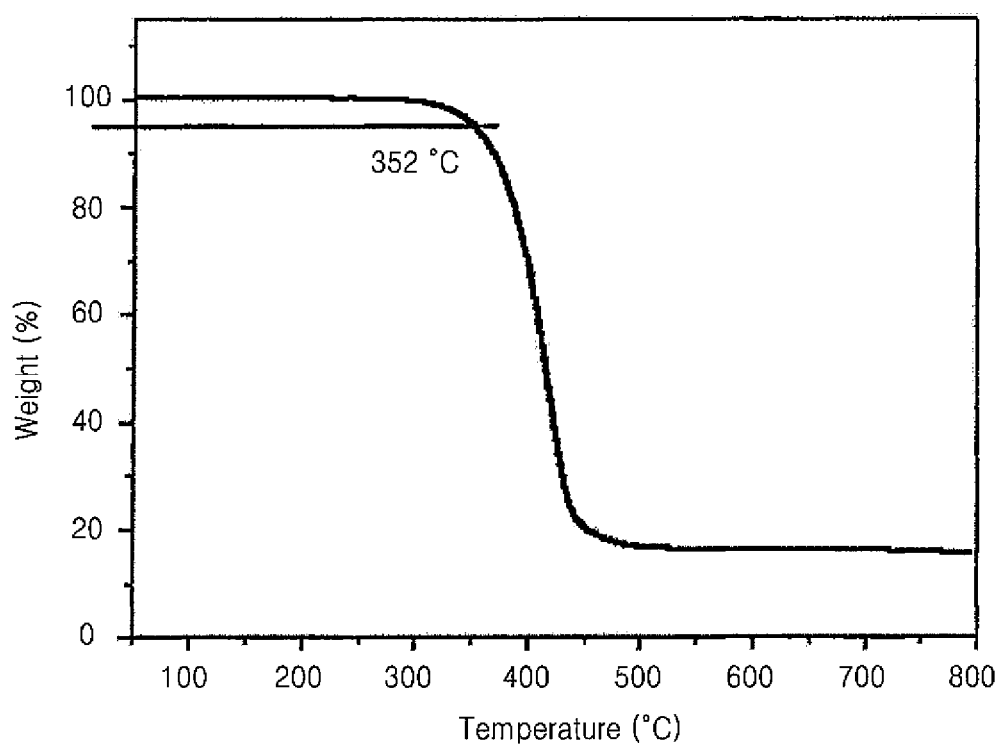
FIG. 22 is a plot of TGA results for Compound 39.
Figure 23:
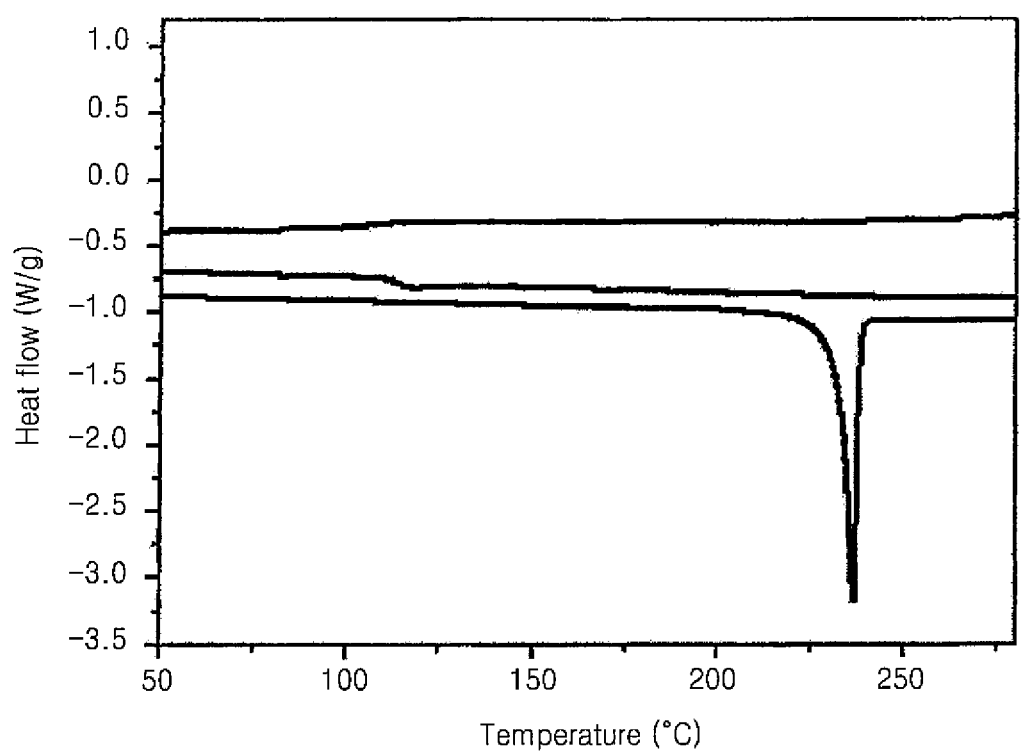
FIG. 23 is a plot of DSC results for Compound 39.

Reference will now be made in more detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list. Further, the use of "may" when describing embodiments of the present invention refers to "one or more embodiments of the present invention."

According to an embodiment of the present disclosure, there is provided an antiaromatic compound represented by Formula 1:

Formula 1

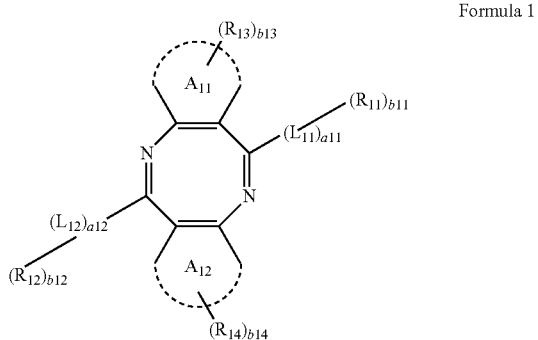

In Formula 1, $A_{11}$ and $A_{12}$ may be each independently selected from a $C_6$-$C_{60}$ arene and a $C_1$-$C_{60}$ heteroarene.

In some embodiments, $A_{11}$ and $A_{12}$ in Formula 1 may be each independently selected from, but not limited to, a benzene, a naphthalene, a phenanthrene, an anthracene, a triphenylene, a pyrene, a chrysene, a pyrrole, a thiophene, a furan, an imidazole, a pyrazole, a thiazole, an oxazole, a pyridine, a pyrazine, a pyrimidine, a pyridazine, an indole, a quinoline, an isoquinoline, a benzoquinoline, a naphthyridine, a quinoxaline, a quinazoline, a phenanthridine, an acridine, a phenanthroline, a phenazine, a benzimidazole, a benzofuran, a benzothiophene, a benzoxazole, a triazole, a triazine, a dibenzofuran, and a dibenzothiophene.

In some other embodiments, in Formula 1, $A_{11}$ and $A_{12}$ may be each independently selected from, but not limited to, a benzene, a naphthalene, a phenanthrene, an anthracene, a triphenylene, a pyridine, a quinoline, an isoquinoline, a naphthyridine, a quinoxaline, and a quinazoline.

In some other embodiments, in Formula 1, $A_{11}$ and $A_{12}$ may be each independently selected from, but not limited to, a benzene, a naphthalene, a pyridine, and a quinoline.

In Formula 1, $L_{11}$ and $L_{12}$ may be each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{60}$ heterocycloalkenylene group, a substituted or unsubstituted $C_6$-$C_{60}$ arylene group, a substituted or unsubstituted $C_1$-$C_{60}$ heteroarylene group, a substituted or unsubstituted non-aromatic condensed polycyclic group, and a substituted or unsubstituted non-aromatic condensed heteropolycyclic group;

at least one substituent of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{60}$ heterocycloalkenylene group, the substituted $C_6$-$C_{60}$ arylene group, the substituted $C_1$-$C_{60}$ heteroarylene group, the substituted non-aromatic condensed polycyclic group, and the substituted non-aromatic condensed heteropolycyclic group may be selected from:

a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and $C_1$-$C_{60}$ alkoxy group;

a $C_1$-$C_{60}$ alkyl group, $C_2$-$C_{60}$ alkenyl group, $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{60}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group; and a $C_3$-$C_{10}$ cycloalkyl group, a $C_1$-$C_{10}$ heterocycloalkyl group, a $C_3$-$C_{10}$ group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group, each substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{60}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group.

In some embodiments, $L_{11}$ and $L_{12}$ in Formula 1 may be each independently selected from, but not limited to, a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thienylene group, a furanylene group, a silolylene group, an imidazolylene group, a pyrazolylene group, a thiazolylene group, an isothiazolylene group, an oxazolylene group, an isooxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothienylene group, a benzosilolylene group, an isobenzothiazolylene group, a benzooxazolylene group, an isobenzooxazolylene group, a triazolylene group, a tetrazolylene group, an oxadiazolylene group, a triazinylene group, a dibenzofuranylene group, a dibenzothiophenylene group, a benzocarbazolyene group, a dibenzocarbazolyene group, and a dibenzosilolylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thienylene group, a furanylene group, a silolylene group, an imidazolylene group, a pyrazolylene group, a thiazolylene group, an isothiazolylene group, an oxazolylene group, an isooxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothienylene group, a benzosilolylene group, an isobenzothiazolylene group, a benzooxazolylene group, an isobenzooxazolylene group, a triazolylene group, a tetrazolylene group, an oxadiazolylene group, a triazinylene group, a dibenzofuranylene group, a dibenzothiophenylene group, a benzocarbazolyene group, a dibenzocarbazolyene group, and a dibenzosilolylene group, each substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coroneryl group, an ovarenyl group, a pyrrolyl group, a thienyl group, a furanyl group, a silolyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuryl group, a benzothienyl group, a benzosilolyl group, an isobenzothiazolyl group, a benzooxazolyl group, an isobenzooxazolyl group, a triazolyl group, a tetrazole group, an oxadiazolyl group, a triazinyl group, a dibenzofuranyl group, a dibenzothienyl group, a benzocarbazolyl group, a dibenzocarbazolyl group, and a dibenzosilolyl group.

In some other embodiments, $L_{11}$ and $L_{12}$ in Formula 1 may be each independently a group represented by one of Formulae 3-1 to 3-32, but are not limited thereto:

3-1

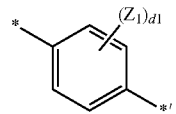

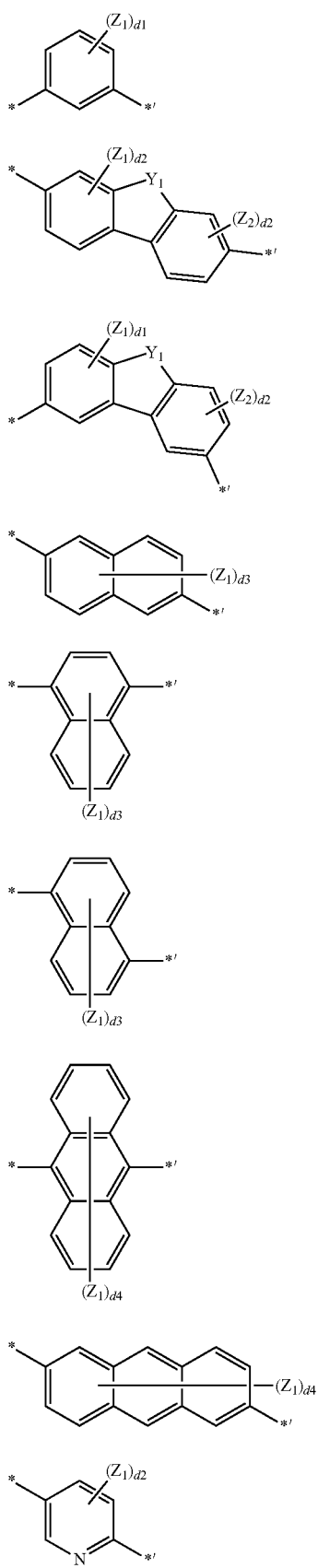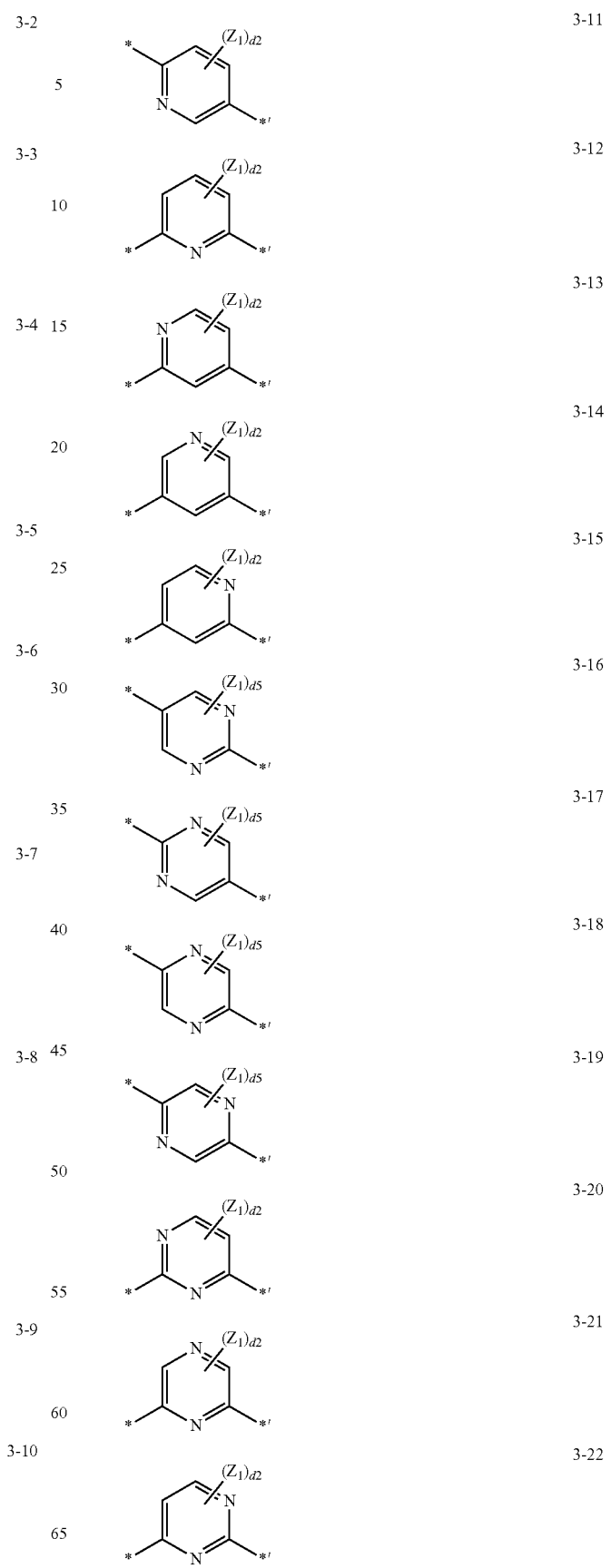

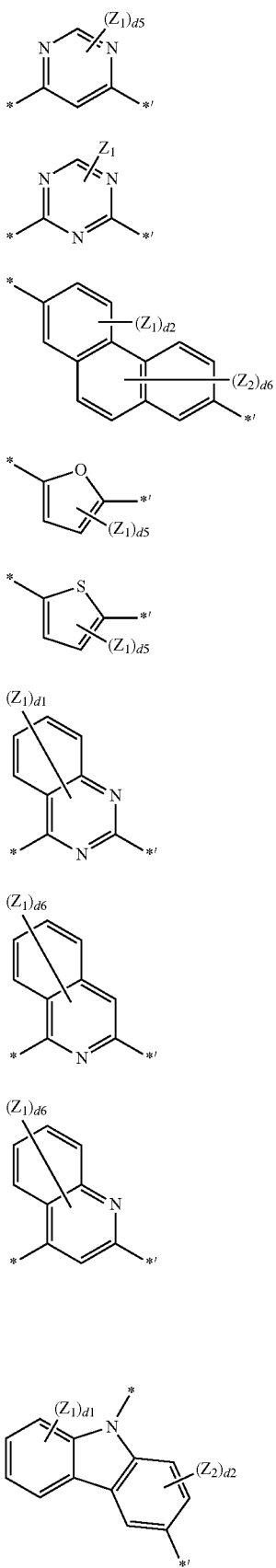
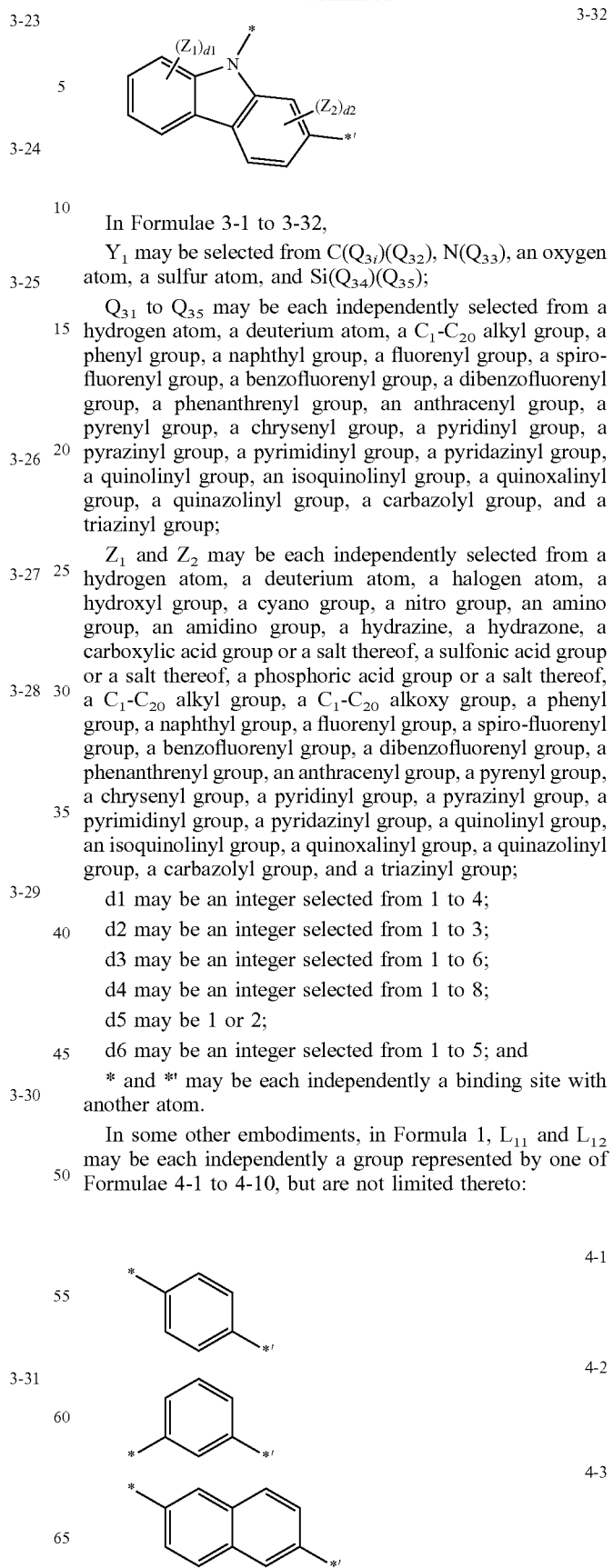

In Formulae 3-1 to 3-32, $Y_1$ may be selected from $C(Q_{31})(Q_{32})$, $N(Q_{33})$, an oxygen atom, a sulfur atom, and $Si(Q_{34})(Q_{35})$;

$Q_{31}$ to $Q_{35}$ may be each independently selected from a hydrogen atom, a deuterium atom, a $C_1$-$C_{20}$ alkyl group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$Z_1$ and $Z_2$ may be each independently selected from a hydrogen atom, a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

d1 may be an integer selected from 1 to 4;

d2 may be an integer selected from 1 to 3;

d3 may be an integer selected from 1 to 6;

d4 may be an integer selected from 1 to 8;

d5 may be 1 or 2;

d6 may be an integer selected from 1 to 5; and

* and *' may be each independently a binding site with another atom.

In some other embodiments, in Formula 1, $L_{11}$ and $L_{12}$ may be each independently a group represented by one of Formulae 4-1 to 4-10, but are not limited thereto:

-continued

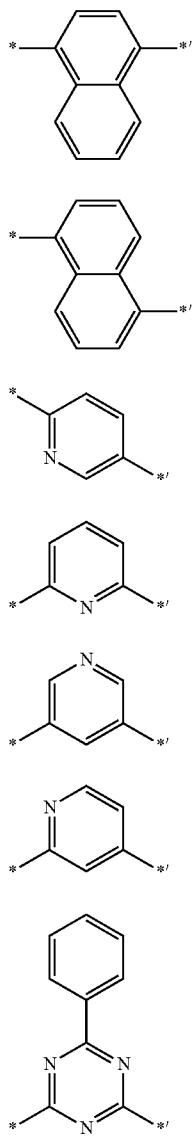

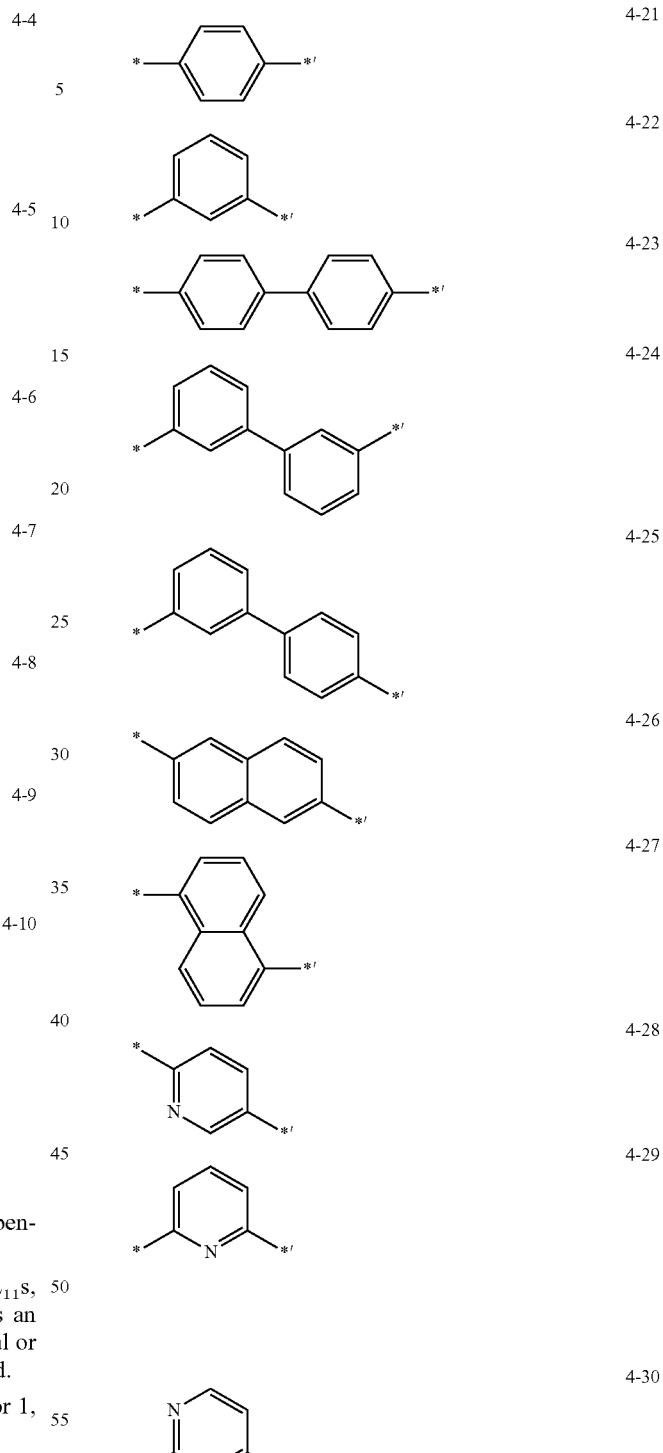

In Formulae 4-1 to 4-10, * and *' may be each independently a binding site with another atom.

In Formula 1, a11, which indicates the number of $L_{11}$s, may be an integer selected from 0 to 6. When a11 is an integer of 2 or more, a plurality of $L_{11}$s may be identical or different. When a11 is 0, $(L_{11})_{a11}$ may be a single bond.

In some embodiments, in Formula 1, a11 may be 0 or 1, but is not limited thereto.

In Formula 1, a12, which indicates the number of $L_{12}$s, may be an integer selected from 0 to 6. When a12 is an integer of 2 or more, a plurality of $L_{12}$s may be identical or different. When a12 is 0, $(L_{12})_{a12}$ may be a single bond.

In some embodiments, in Formula 1, a12 may be 0 or 1, but is not limited thereto.

In some embodiments, in Formula 1, $(L_{11})_{a11}$ and $(L_{12})_{a12}$ may be each independently selected from, but not limited to, a single bond and a group represented by Formulae 4-21 to 4-32:

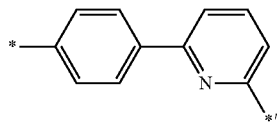

-continued 4-32

In Formulae 4-21 to 4-32,

* and *' may be each independently a binding site with another atom.

In Formula 1, $R_{11}$ and $R_{12}$ may be each independently selected from a substituted or unsubstituted $C_6$-$C_{60}$ aryl group, a substituted or unsubstituted $C_1$-$C_{60}$ heteroaryl group, a substituted or unsubstituted non-aromatic condensed polycyclic group, a substituted or unsubstituted non-aromatic condensed heteropolycyclic group, —N($Q_{11}$)($Q_{12}$), —Si($Q_{13}$)($Q_{14}$)($Q_{15}$), and —P($Q_{16}$)($Q_{17}$);

$Q_{11}$ to $Q_{17}$ may be each independently selected from a substituted or unsubstituted $C_6$-$C_{60}$ aryl group and a substituted or unsubstituted $C_1$-$C_{60}$ heteroaryl group;

at least one substituent of the substituted $C_6$-$C_{60}$ aryl group, the substituted $C_1$-$C_{60}$ heteroaryl group, the substituted non-aromatic condensed polycyclic group, and the substituted non-aromatic condensed heteropolycyclic group may be selected from:

a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, $C_2$-$C_{60}$ alkenyl group, $C_2$-$C_{60}$ alkynyl group, and a $C_1$-$C_{60}$ alkoxy group;

a $C_1$-$C_{60}$ alkyl group, $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group; and a $C_3$-$C_{10}$ cycloalkyl group, a $C_1$-$C_{60}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group, each substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{60}$ group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group.

In some embodiments, in Formula 1, $R_{11}$ and $R_{12}$ may be each independently selected from:

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuryl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, —N($Q_{11}$)($Q_{12}$), —Si($Q_{13}$)($Q_{14}$)($Q_{15}$), and —P($Q_{16}$)($Q_{17}$); and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coroneryl group, an ovarenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuryl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group, each substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coroneryl group, an ovarenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuryl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group; and $Q_{11}$ to $Q_{17}$ may be each independently selected from:

a phenyl group, a naphthyl group, a fluorenyl group, an anthracenyl group, a pyrenyl group, a pyridinyl group, a pyrazinyl group, a pyrimidinyl group, a pyridazinyl group, a quinolinyl group, an isoquinolinyl group, a carbazolyl group, and a triazinyl group; and a phenyl group, a naphthyl group, a fluorenyl group, an anthracenyl group, a pyrenyl group, a pyridinyl group, a pyrazinyl group, a pyrimidinyl group, a pyridazinyl group, a quinolinyl group, an isoquinolinyl group, a carbazolyl group, and a triazinyl group, each substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coroneryl group, an ovarenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuryl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group. However, embodiments of the present disclosure are not limited thereto.

In some other embodiments, in Formula 1, $R_{11}$ and $R_{12}$ may be each independently selected from:

a phenyl group, a naphthyl group, an anthracenyl group, a phenanthrenyl group, a fluorenyl group, a pyridinyl group, a pyrazinyl group, an imidazole group, a benzimidazole group, a triazolyl group, a triazinyl group, an oxadiazolyl group, a quinolinyl group, an isoquinolinyl group, —N($Q_{11}$)($Q_{12}$), —Si($Q_{13}$)($Q_{14}$)($Q_{15}$), and —P($Q_{16}$)($Q_{17}$);

a phenyl group, a naphthyl group, an anthracenyl group, a phenanthrenyl group, a fluorenyl group, a pyridinyl group, a pyrazinyl group, an imidazole group, a benzimidazole group, a triazole group, a triazine group, an oxadiazolyl group, a quinolinyl group, and an isoquinolinyl group, each substituted with at least one selected from a deuterium atom, a halogen atom, a cyano group, a nitro group, a $C_1$-$C_{20}$ alkyl group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and $Q_{11}$ to $Q_{17}$ may be each independently selected from:

a phenyl group, a naphthyl group, a fluorenyl group, a pyridinyl group, a carbazolyl group, and a triazinyl group; and a phenyl group, a naphthyl group, a fluorenyl group, a pyridinyl group, a carbazolyl group, and a triazinyl group, each substituted with at least one selected from a deuterium atom, a halogen atom, a cyano group, a nitro group, a $C_1$-$C_{20}$ alkyl group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

In some other embodiments, $R_{11}$ and $R_{12}$ in Formula 1 may be each independently selected from, but not limited to, a group represented by Formulae 5-1 to 5-39:

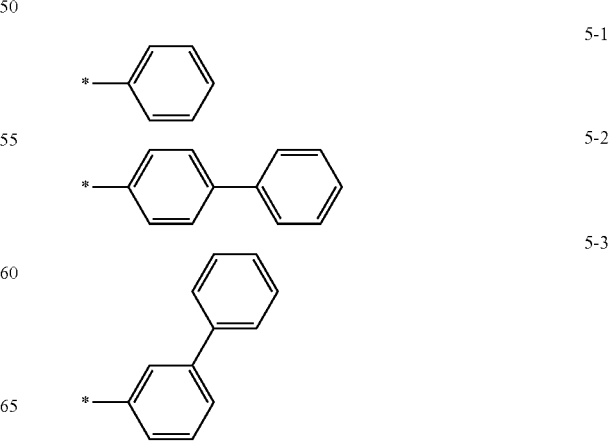

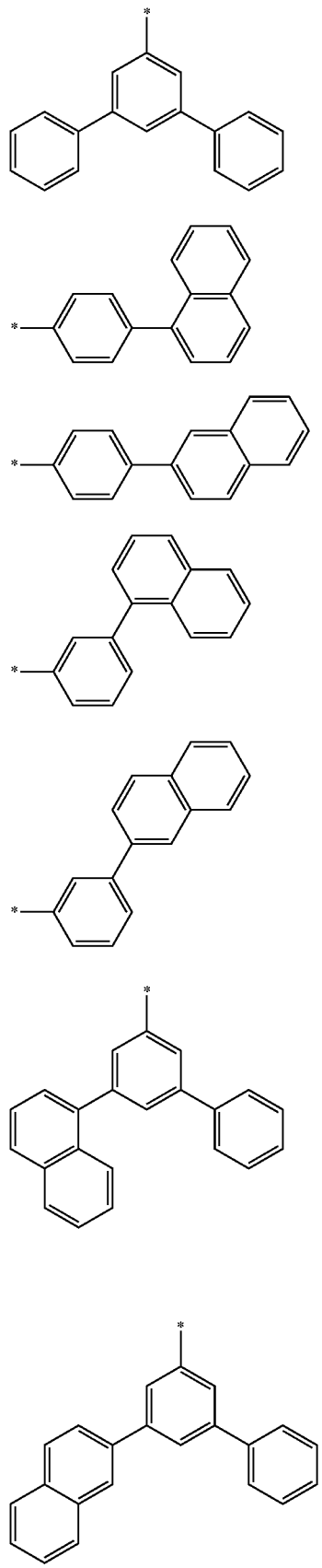
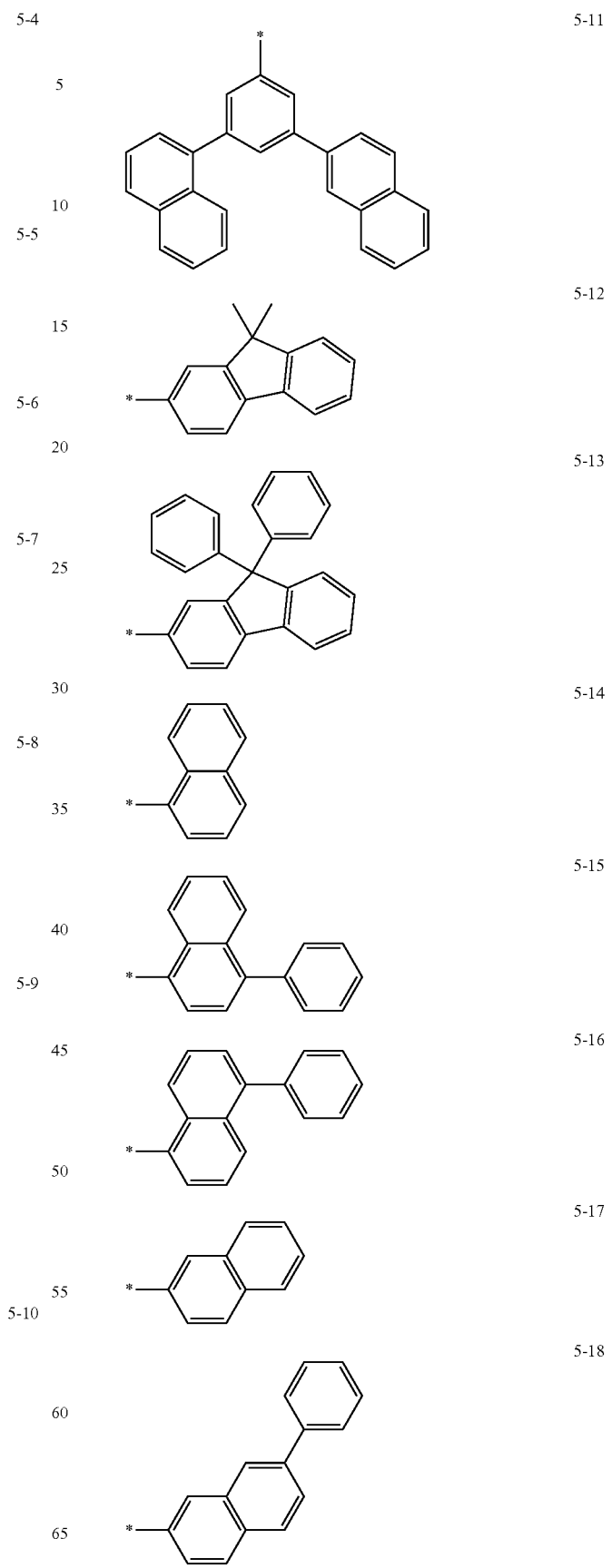

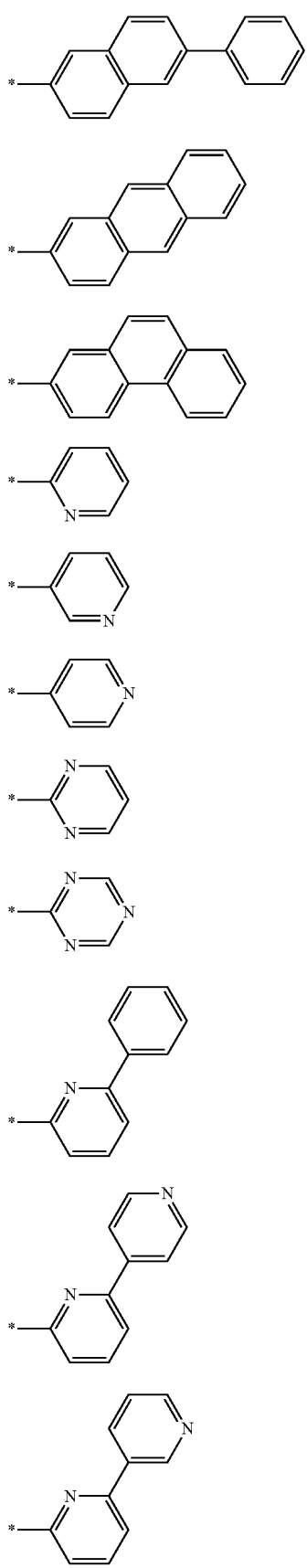
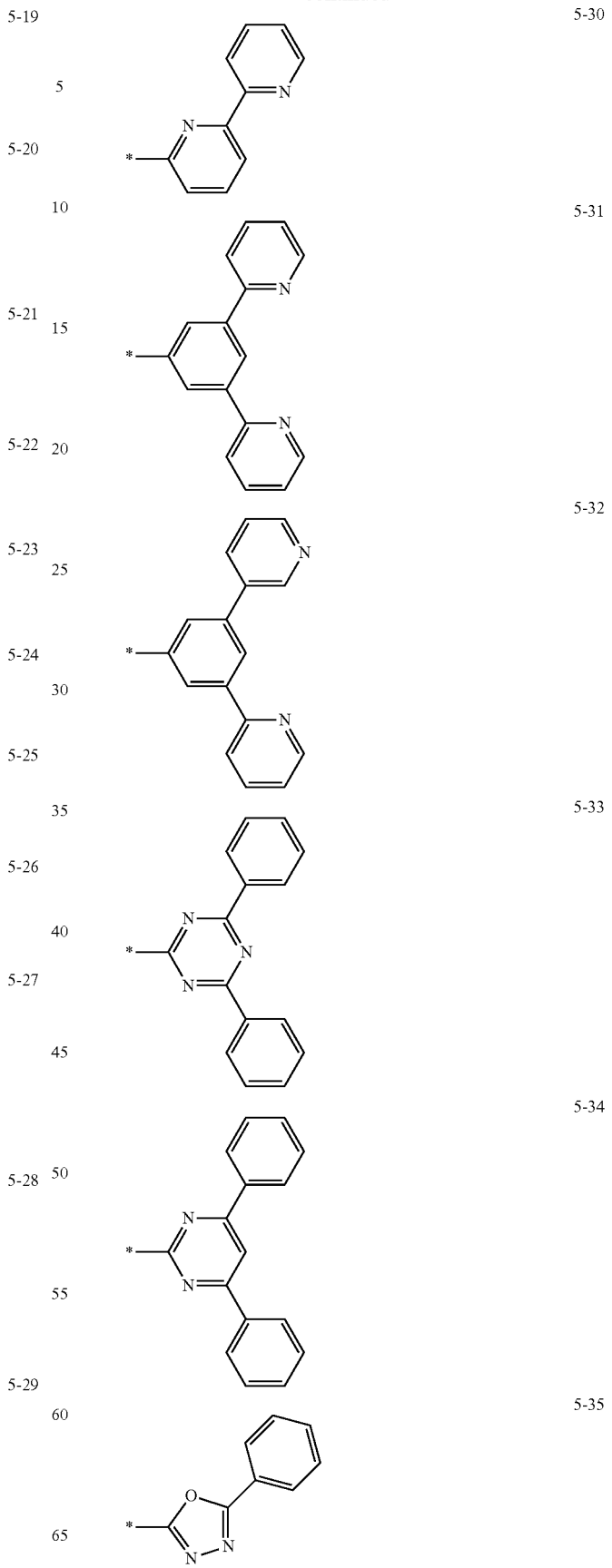

-continued

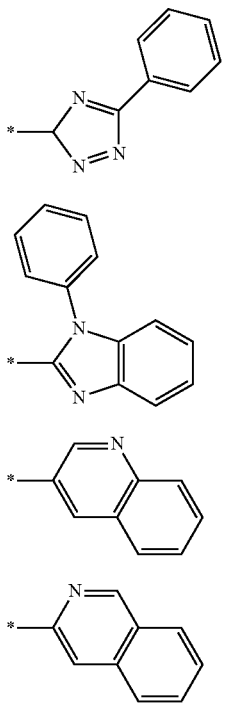

In Formulae 5-1 to 5-39, * may be each independently a binding site with another atom.

In Formula 1, b11, which indicates the number of $R_{11}$s, may be an integer selected from 1 to 3. When b11 is an integer of 2 or more, a plurality of $R_{11}$s may be identical or different.

For example, b11 may be an integer of 1, but is not limited thereto.

In Formula 1, b12, which indicates the number of $R_{12}$s, may be an integer selected from 1 to 3. When b12 is an integer of 2 or more, a plurality of $R_{12}$s may be identical or different.

For example, b12 may be 1, but is not limited thereto.

In Formula 1, $R_{13}$ and $R_{14}$ may be each independently selected from:

a hydrogen atom, a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, $C_2$-$C_{60}$ alkynyl group, and a $C_1$-$C_{60}$ alkoxy group;

a $C_1$-$C_{60}$ alkyl group, $C_2$-$C_{60}$ alkenyl group, $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_3$-$C_{10}$ group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ group, a $C_1$-$C_{60}$ heteroaryl group, a non-aromatic condensed polycyclic group, and a non-aromatic condensed heteropolycyclic group;

a $C_3$-$C_{10}$ cycloalkyl group, a $C_1$-$C_{10}$ heterocycloalkyl group, a $C_3$-$C_{10}$ group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group; and a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group, each substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group.

In some embodiments, $R_{13}$ and $R_{14}$ in Formula 1 may be each independently selected from, but not limited to, a hydrogen atom, a deuterium atom, a halogen atom, a cyano group, a nitro group, and a $C_1$-$C_{60}$ alkyl group;

a $C_1$-$C_{60}$ alkyl group substituted with at least one of a deuterium atom, a halogen atom, a cyano group, a nitro group, a $C_6$-$C_{60}$ aryl group, a $C_1$-$C_{60}$ heteroaryl group, a non-aromatic condensed polycyclic group, and a non-aromatic condensed heteropolycyclic group;

a $C_6$-$C_{60}$ aryl group, a $C_1$-$C_{60}$ heteroaryl group, a non-aromatic condensed polycyclic group, and a non-aromatic condensed heteropolycyclic group; and a $C_6$-$C_{60}$ aryl group, a $C_1$-$C_{60}$ heteroaryl group, a non-aromatic condensed polycyclic group, and a non-aromatic condensed heteropolycyclic group, each substituted with at least one of a deuterium atom, a halogen atom, a cyano group, a nitro group, a $C_1$-$C_{60}$ alkyl group, a $C_6$-$C_{60}$ aryl group, a $C_1$-$C_{60}$ heteroaryl group, a non-aromatic condensed polycyclic group, and a non-aromatic condensed heteropolycyclic group.

In some other embodiments, $R_{13}$ and $R_{14}$ in Formula 1 may be each independently selected from, but not limited to, a hydrogen atom, a methyl group, an ethyl group, a phenyl group, and a pyridinyl group.

For example, each of $R_{13}$ and $R_{14}$ in Formula 1 may be a hydrogen atom, but $R_{13}$ and $R_{14}$ are not limited thereto.

In Formula 1, b13, which indicates the number of $R_{13}$s, may be an integer selected from 1 to 10. When b13 is an integer of 2 or more, a plurality of $R_{13}$s may be identical or different.

In Formula 1, b14, which indicates the number of $R_{14}$s, may be an integer selected from 1 to 10. When b14 is an integer of 2 or more, a plurality of $R_{14}$s may be identical or different.

In some embodiments, the antiaromatic compound of Formula 1 may be represented by one of Formulae 1A to 1E:

Formula 1A
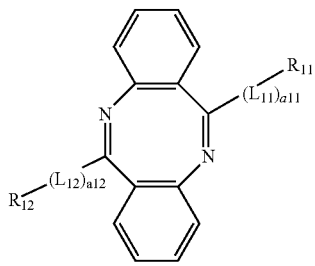
Formula 1B
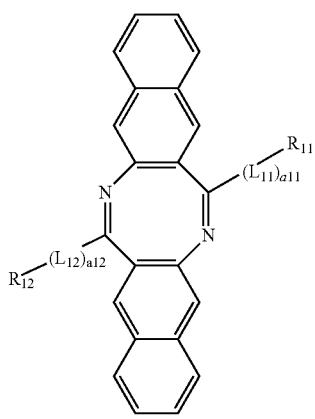
Formula 1C
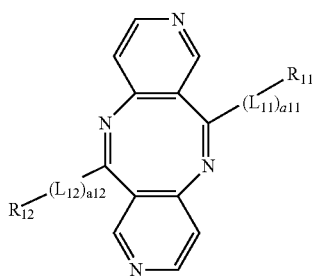
Formula 1D
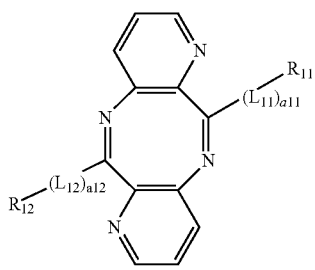
Formula 1E
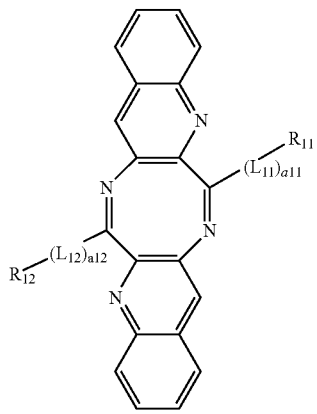
In Formulae 1A to 1E, $L_{11}$, $L_{12}$, a11, a12, $R_{11}$, and $R_{12}$ may be the same as those defined above.
For example, the antiaromatic compound of Formula 1 may be represented by one of Formulae 1F to 1J:
Formula 1F
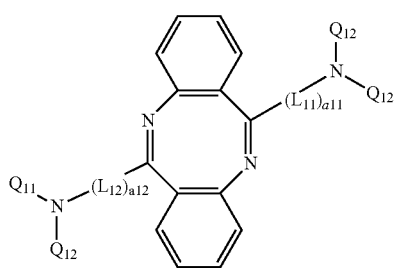
Formula 1G
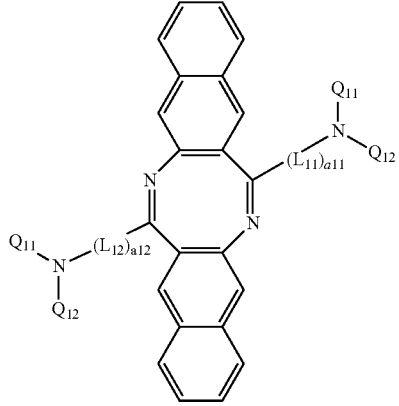
Formula 1H
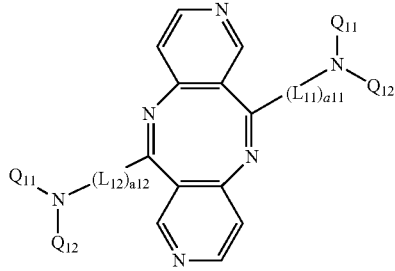

Formula 1I

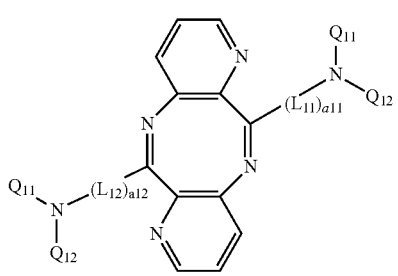

Formula 1J

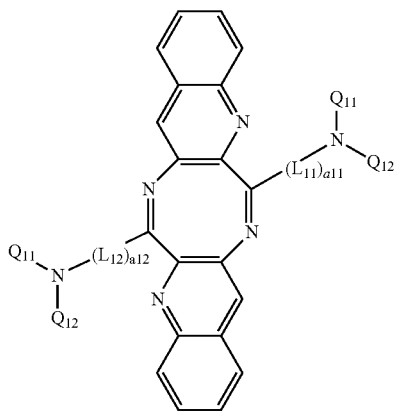

In Formulae 1F to 1J, $L_{11}$, $L_{12}$, a11, a12, $Q_{11}$, and $Q_{12}$ may be the same as those defined above.

In some embodiments, the antiaromatic compound may be represented by one of Formulae 1A to 1E, wherein, in Formulae 1A to 1E, $L_{11}$ and $L_{12}$ may be each independently represented by one of Formulae 4-1 to 4-10; a11 and a12 may be each independently 0 or 1; and $R_{11}$ and $R_{12}$ may be each independently a group represented by one of Formulae 5-1 to 5-39. However, embodiments of the present disclosure are not limited thereto.

In some embodiments, the antiaromatic compound may be represented by one of Formulae 1A and 1B, wherein, in Formulae 1A and 1B, $L_{11}$ and $L_{12}$ may be each independently represented by one of Formulae 4-1 to 4-10; a11 and a12 may be each independently 0 or 1; and $R_{11}$ and $R_{12}$ may be each independently a group represented by one of Formulae 5-22 to 5-39. However, embodiments of the present disclosure are not limited thereto.

In some embodiments, the antiaromatic compound may be represented by one of Formulae 1C to 1E, wherein, in Formulae 1C to 1E, $L_{11}$ and $L_{12}$ may be each independently represented by one of Formulae 4-1 to 4-5; a11 and a12 may be each independently 0 or 1; and $R_{11}$ and $R_{12}$ may be each independently a group represented by one of Formulae 5-1 to 5-21. However, embodiments of the present disclosure are not limited thereto.

In some embodiments, the antiaromatic compound of Formula 1 may be one selected from the following compounds 1 to 247. However, embodiments of the present disclosure are not limited thereto:

1

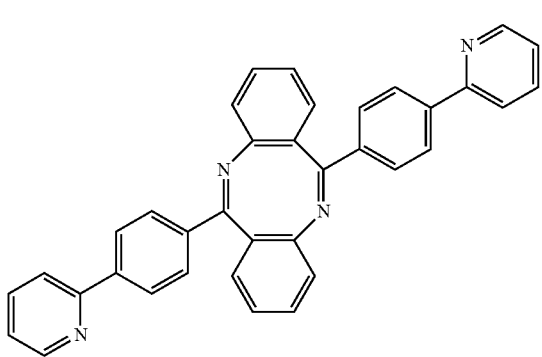

2

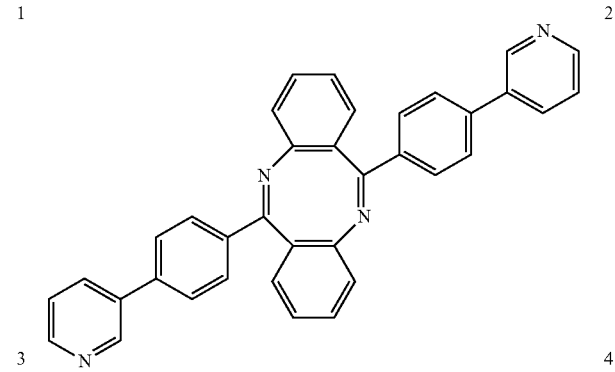

3

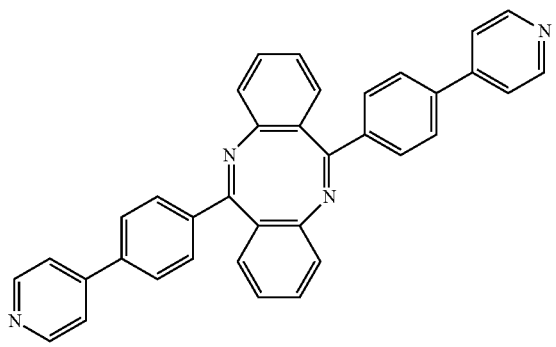

4

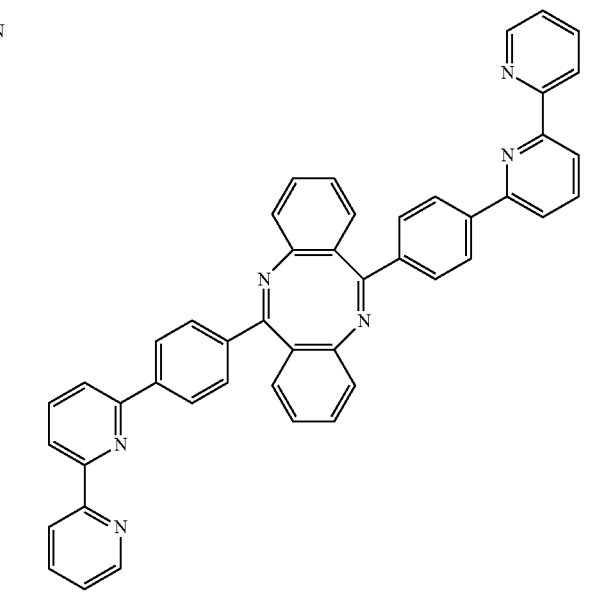

-continued
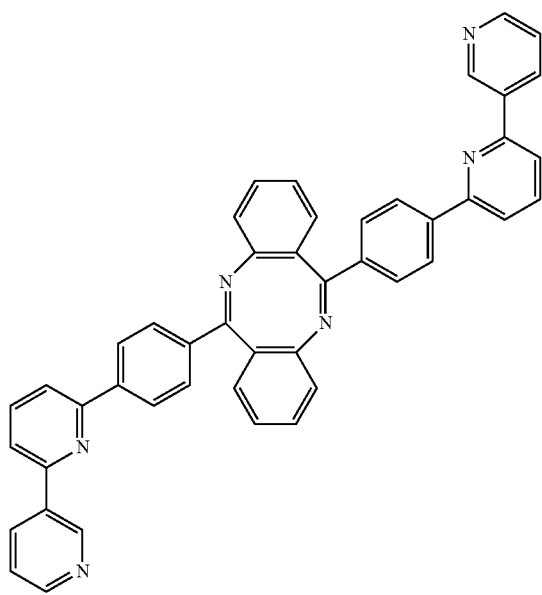
5
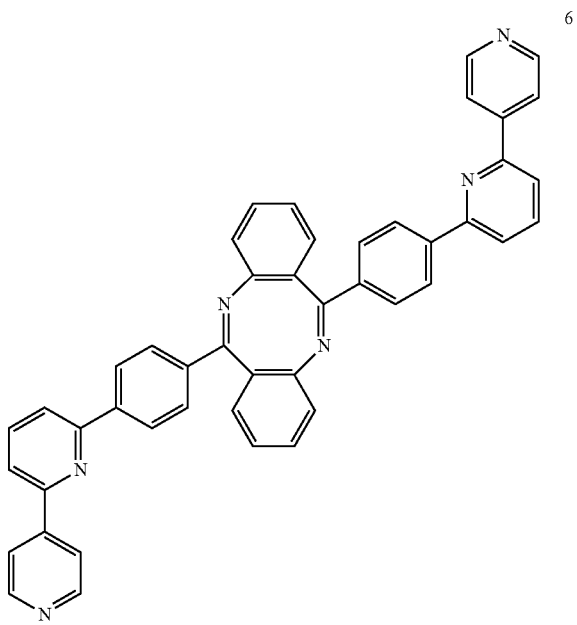
6
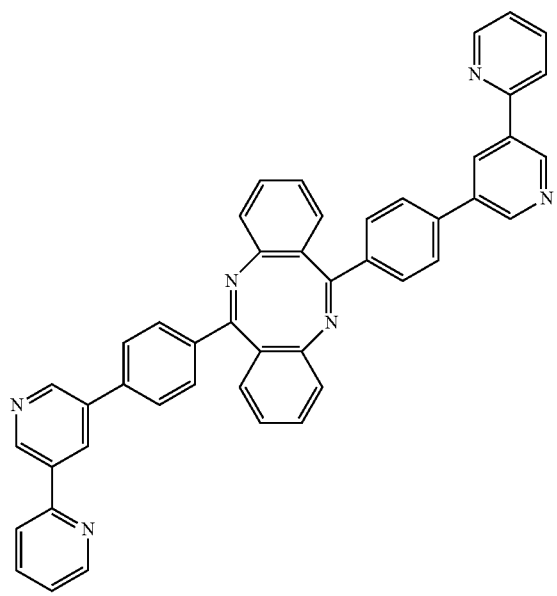
7
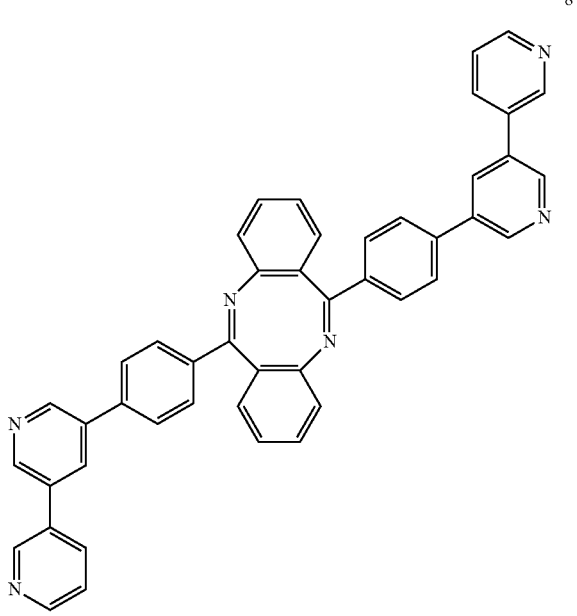
8

-continued
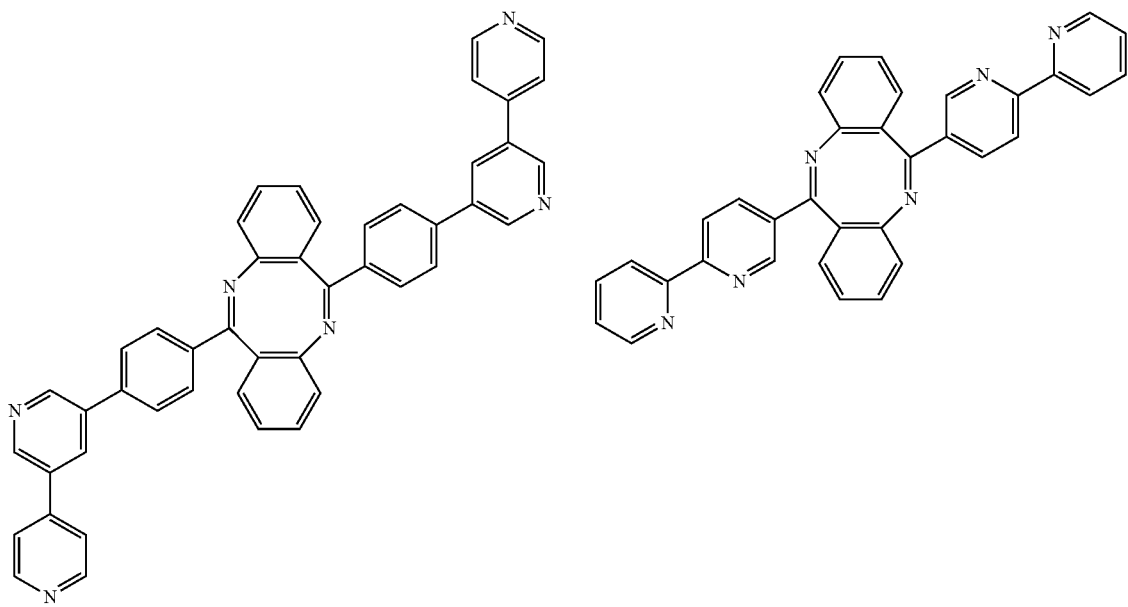
9
10
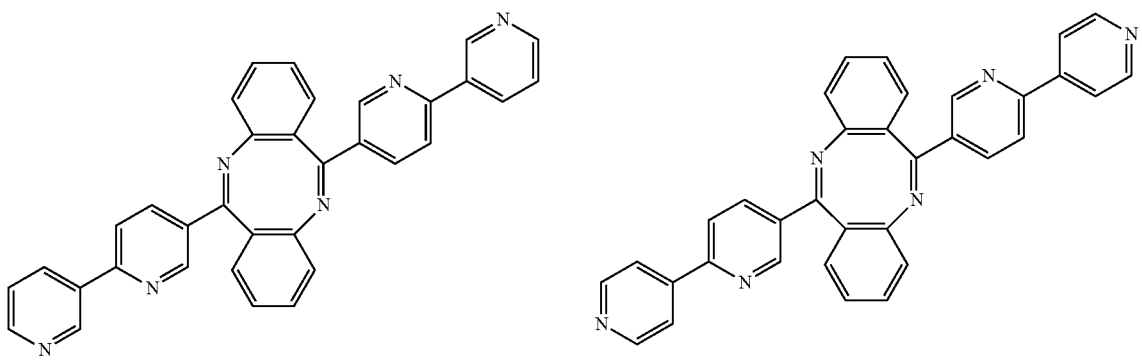
11
12
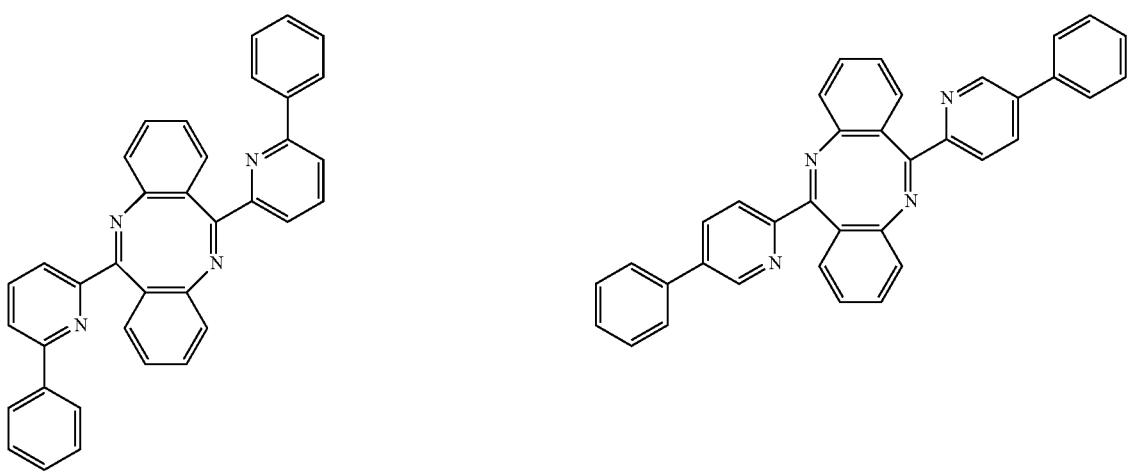
13
14

15
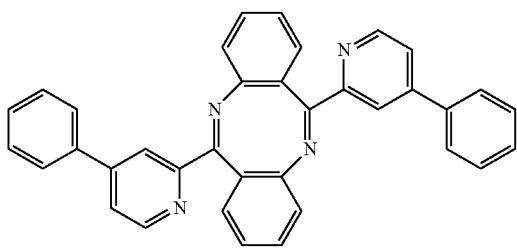
16
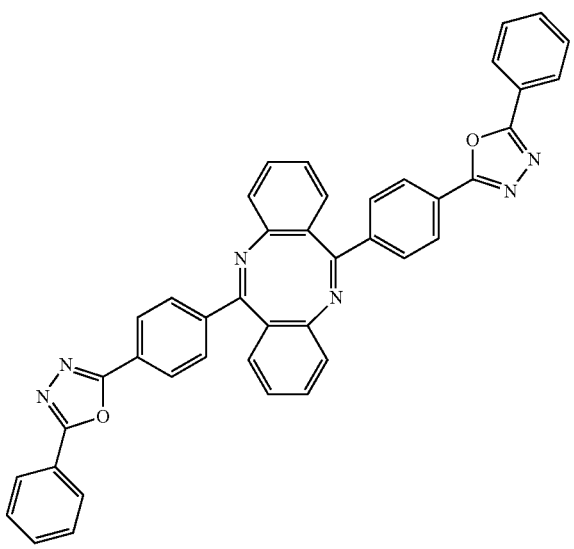
17
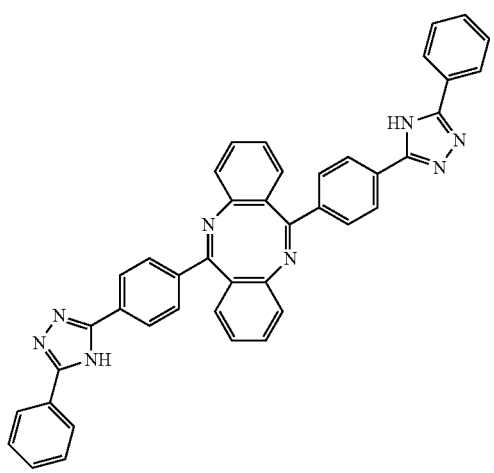
18
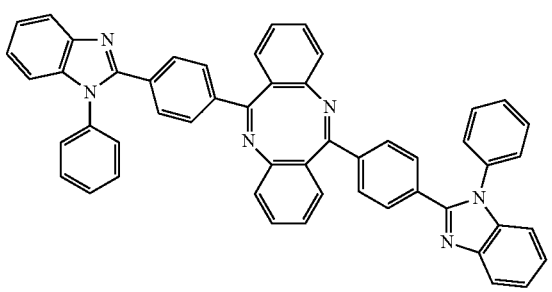
19
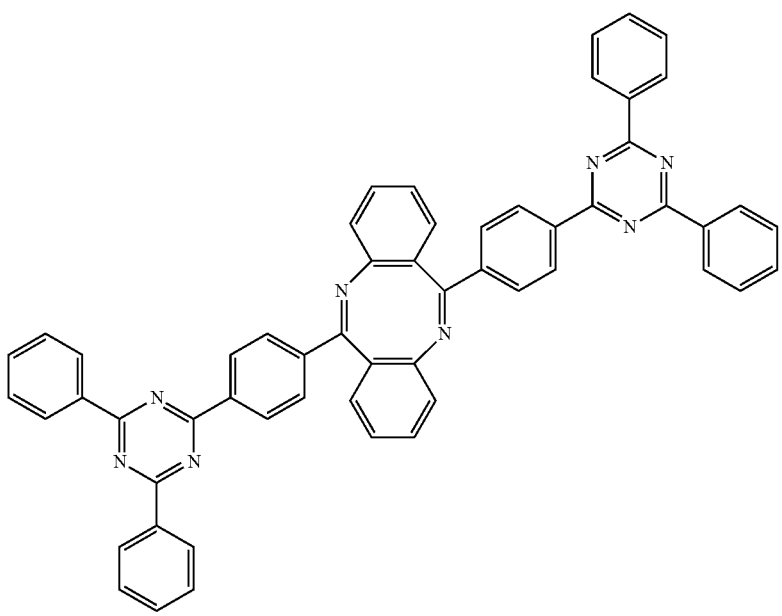

-continued
20
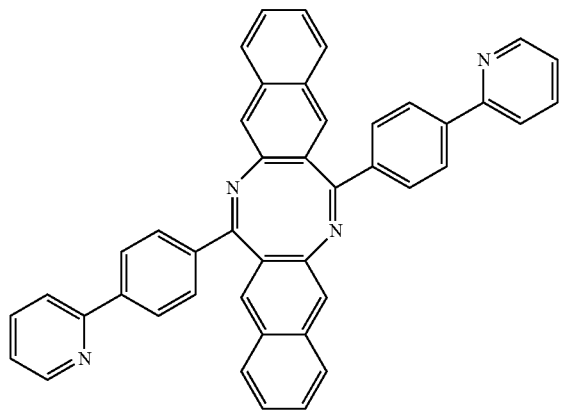
21
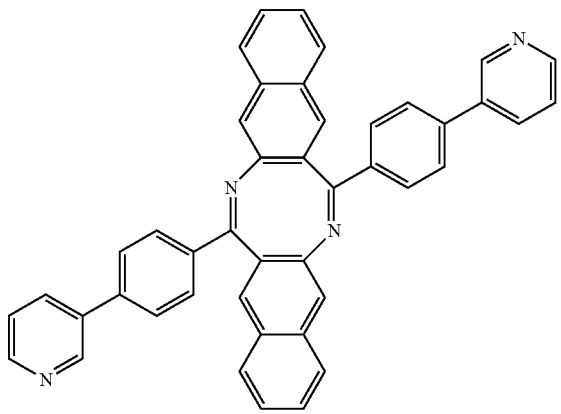
22
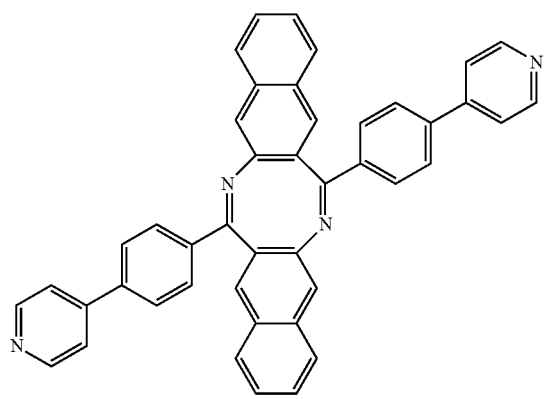
23
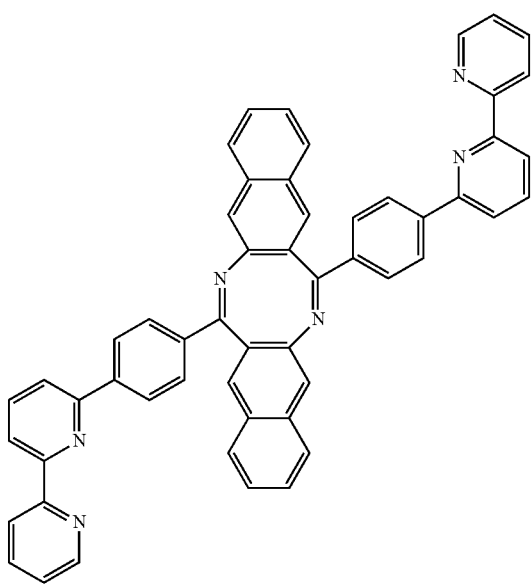
24
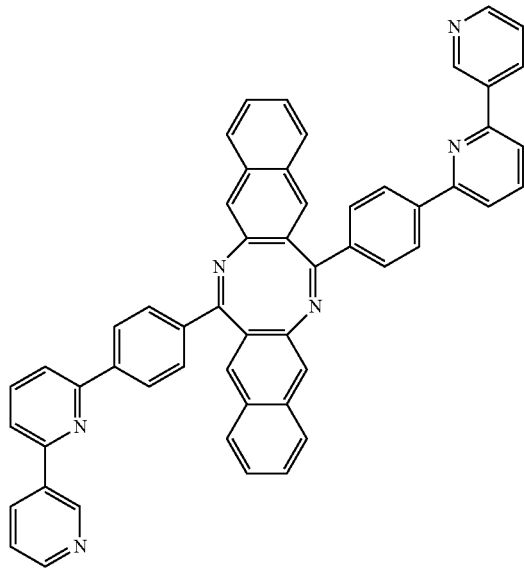
25
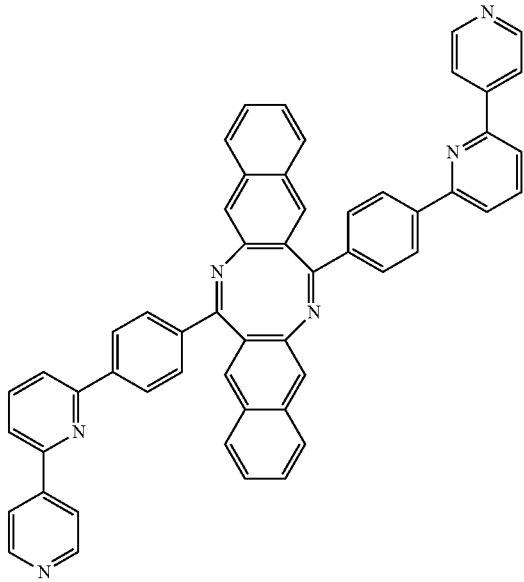

-continued
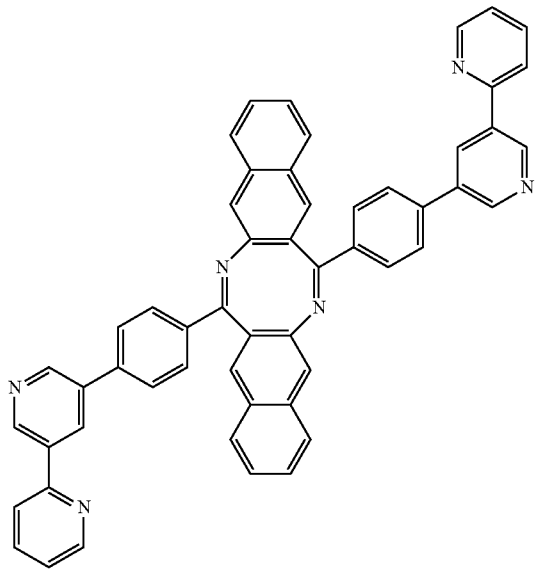
26
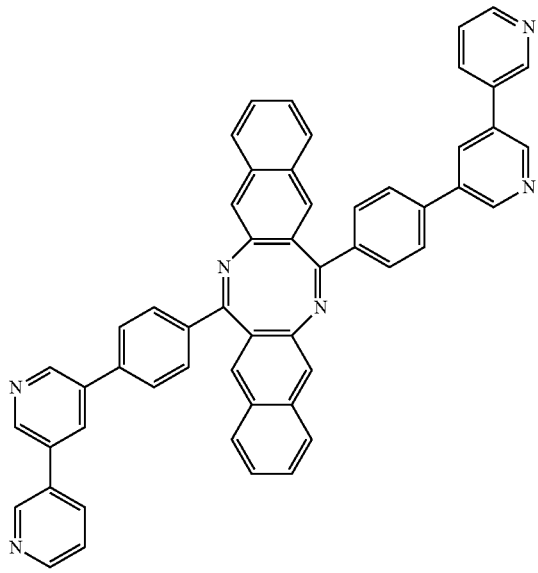
27
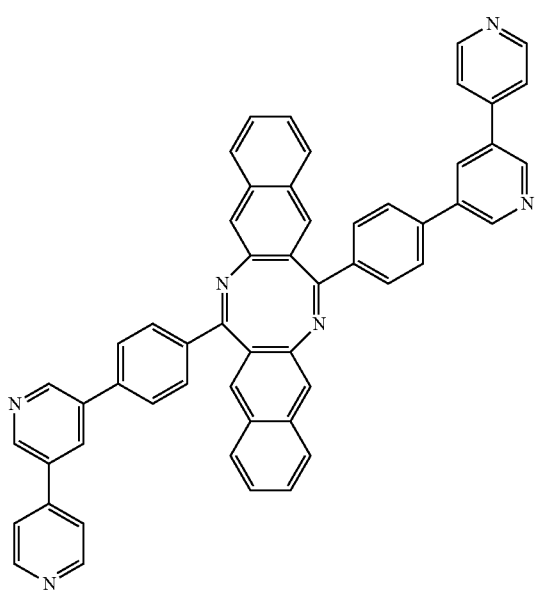
28
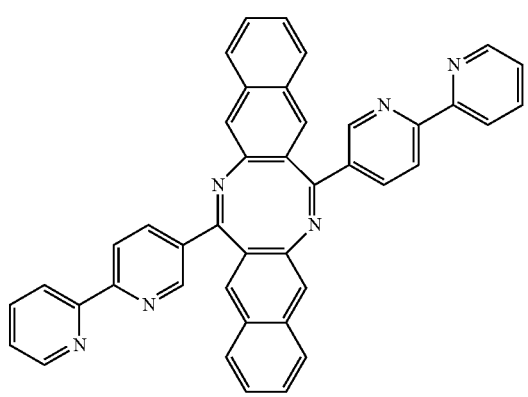
29
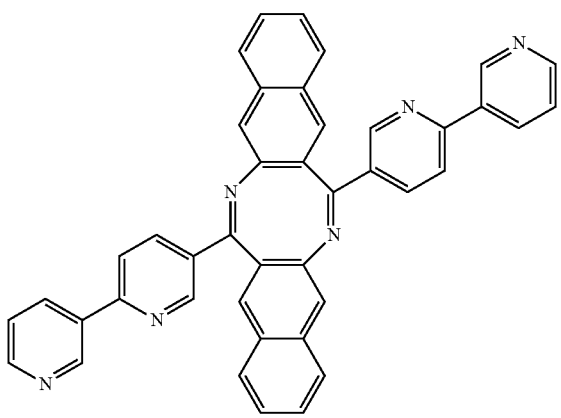
30
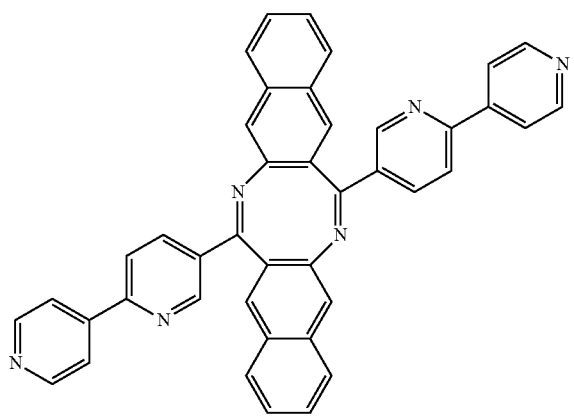
31

-continued
32
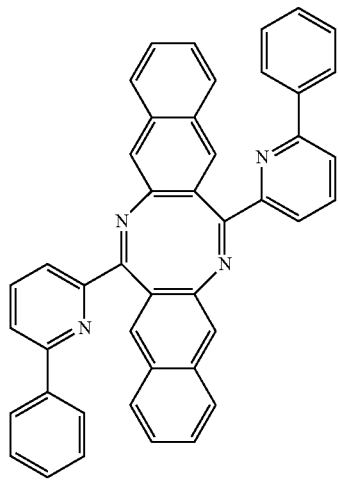
33
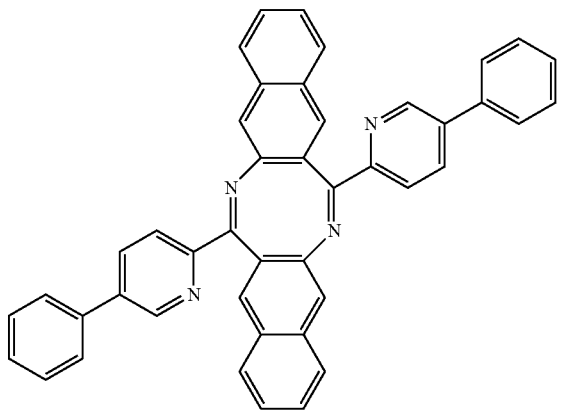
34
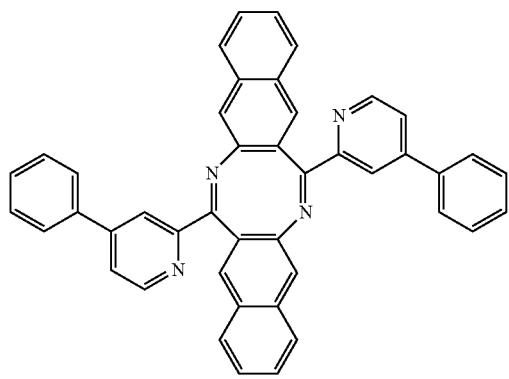
35
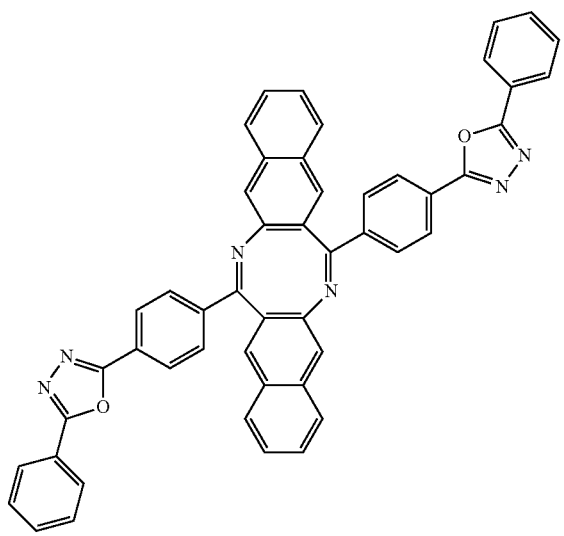
36
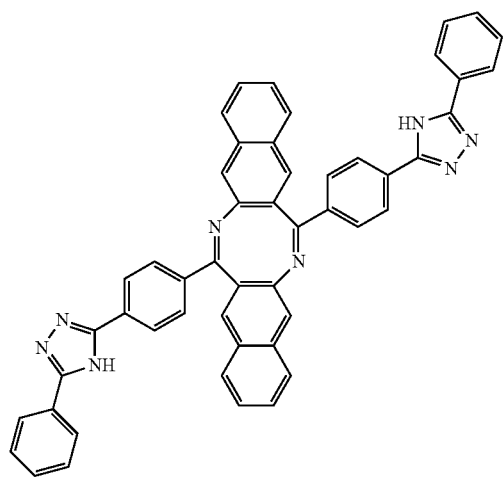
37
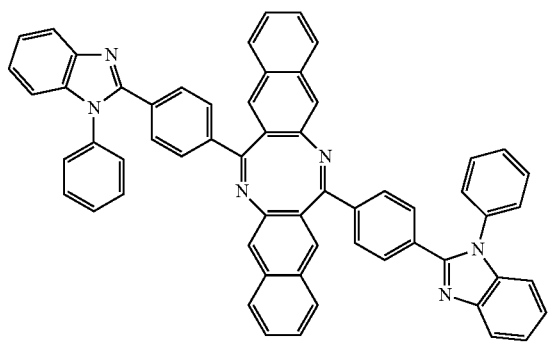

38
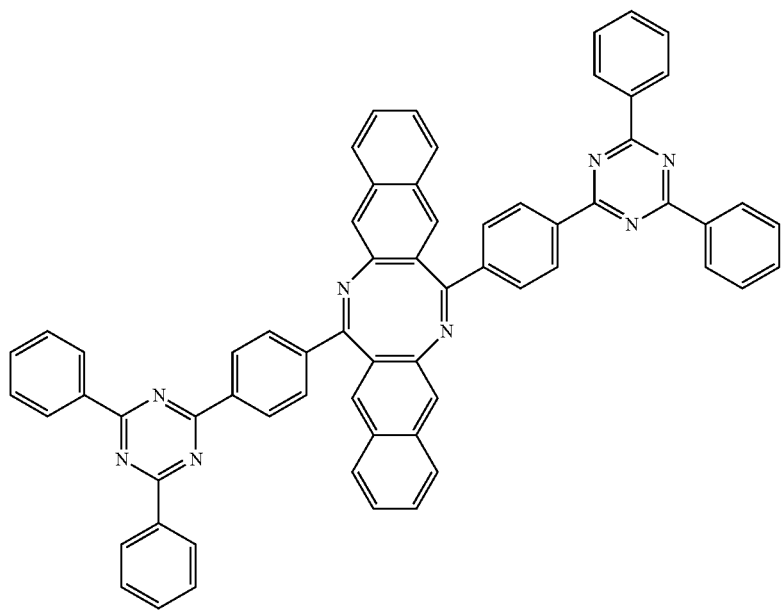
39
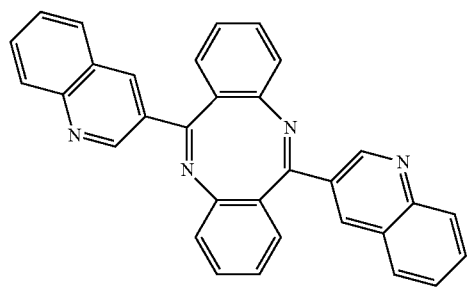
40
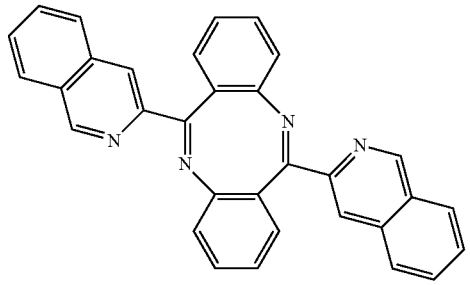
41
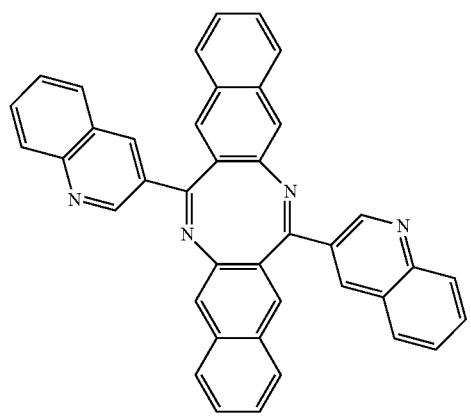
42
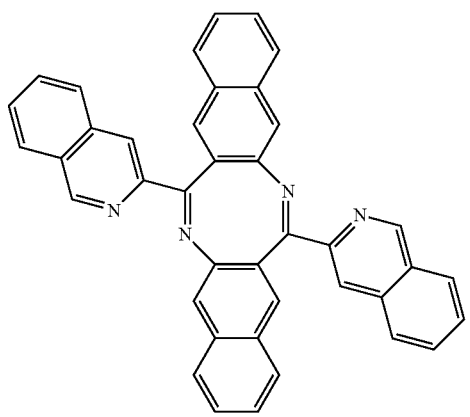

-continued
43
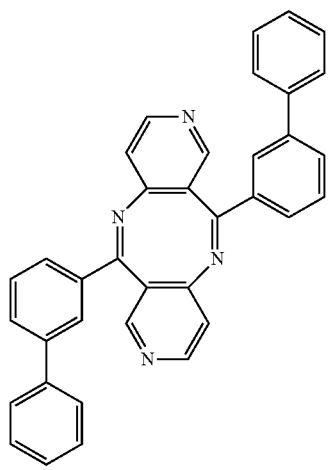
44
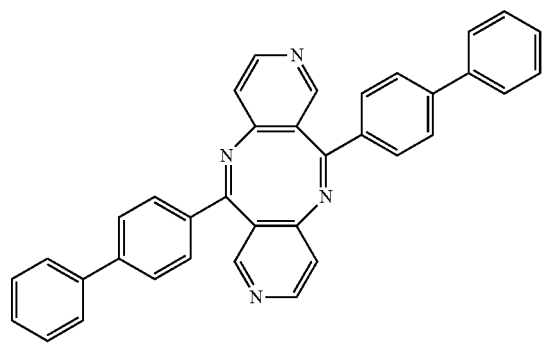
45
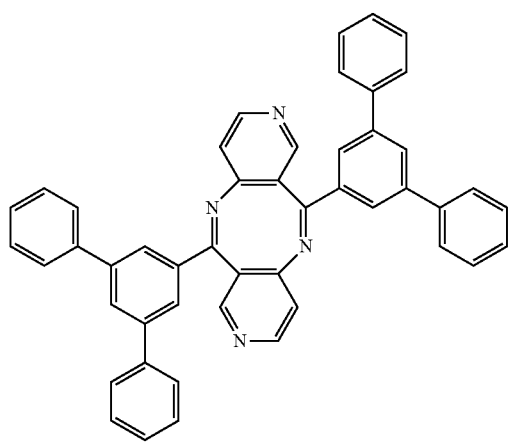
46
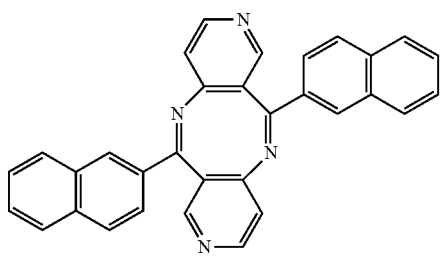
47
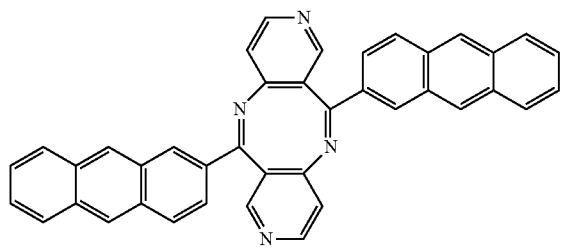
48
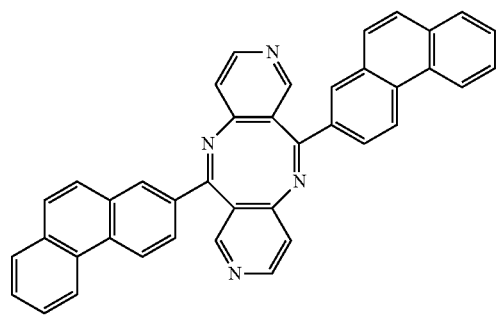

-continued
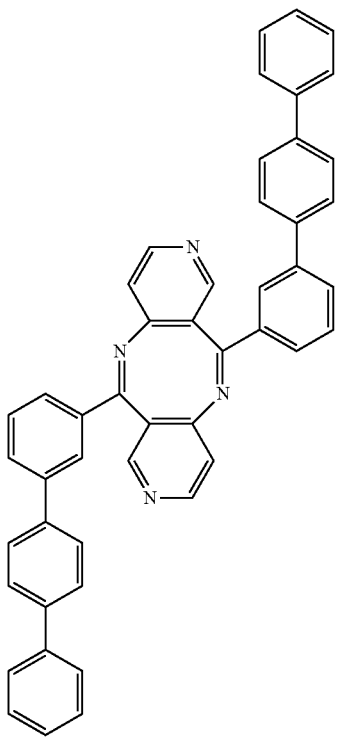
49
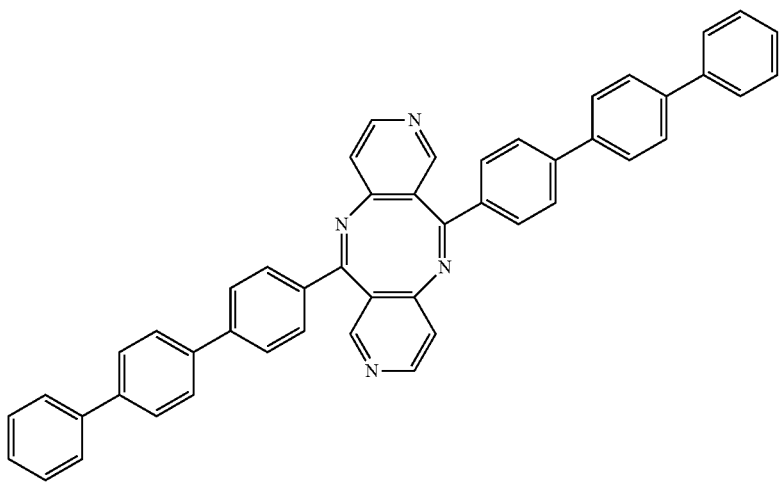
50

-continued
51
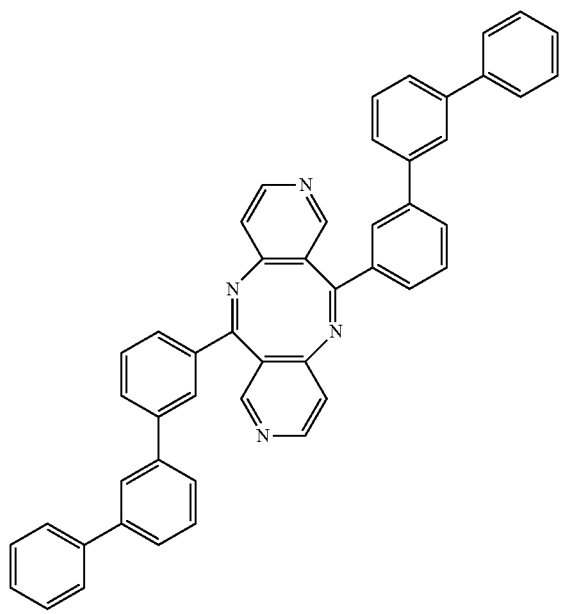
52
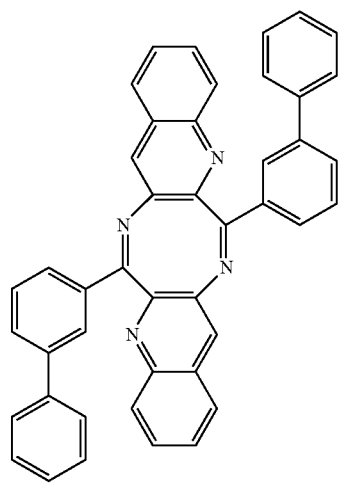
53
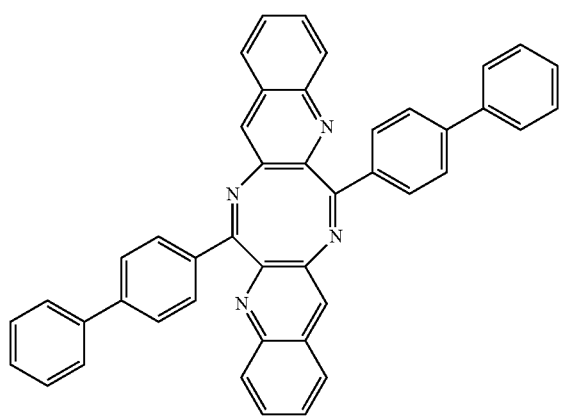
54
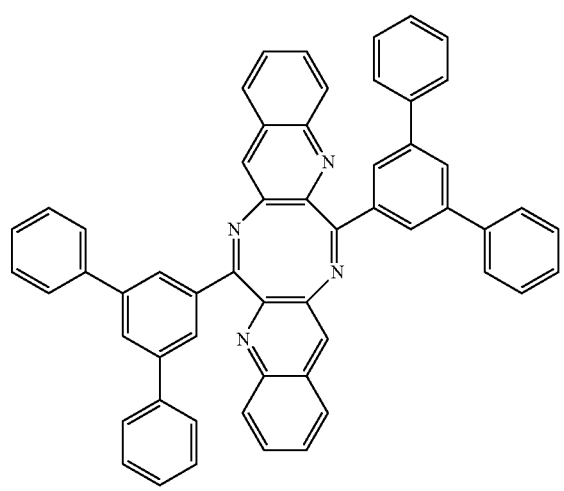
55
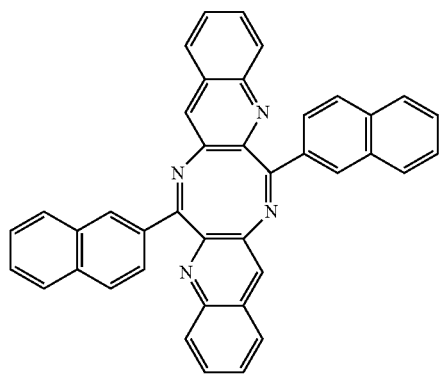
56
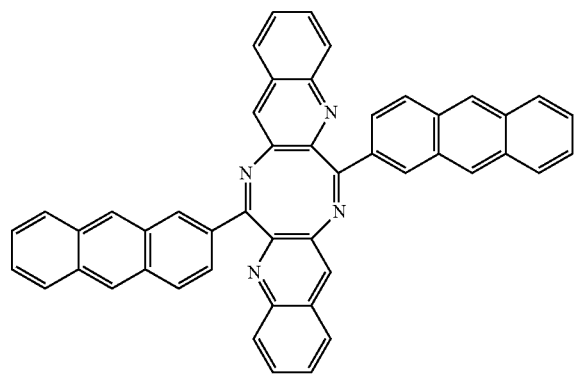

-continued
57
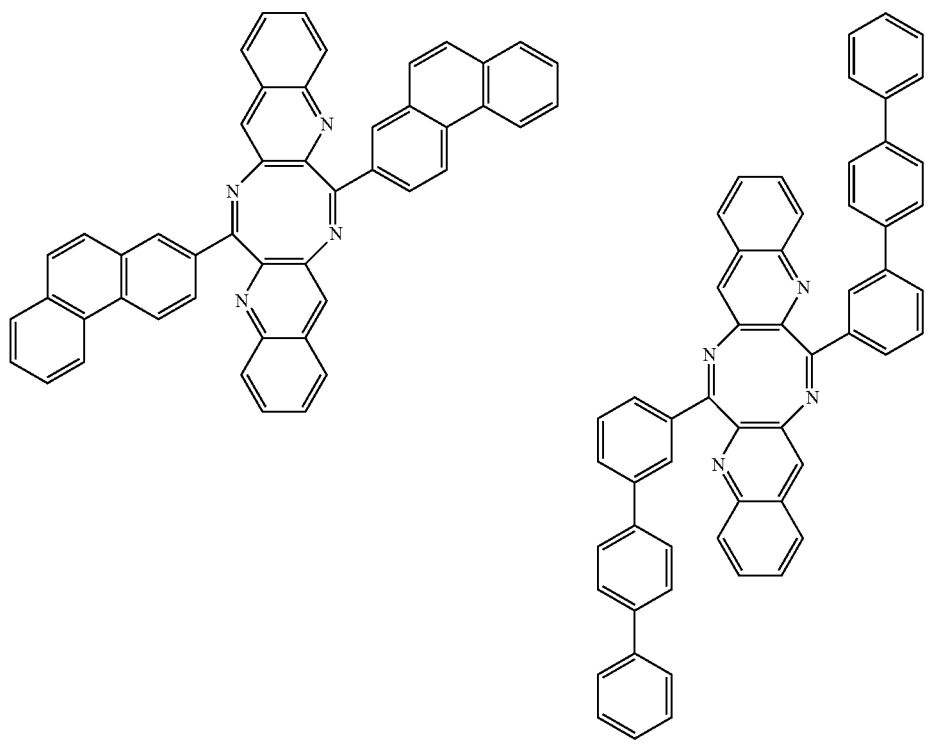
58
59
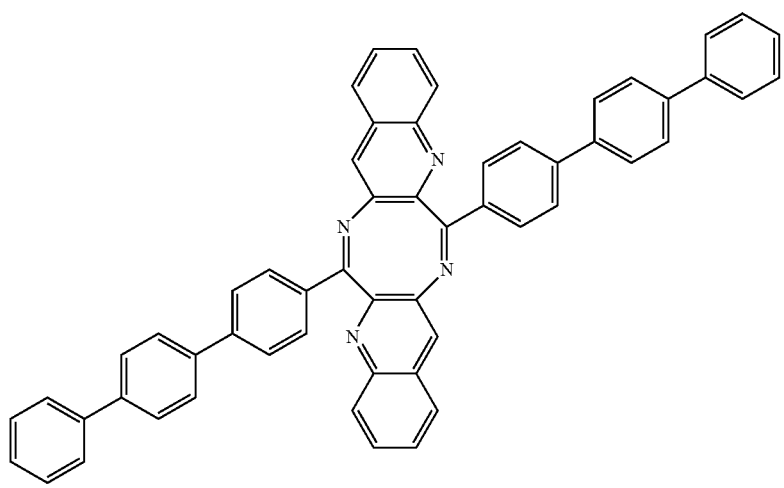

-continued
60
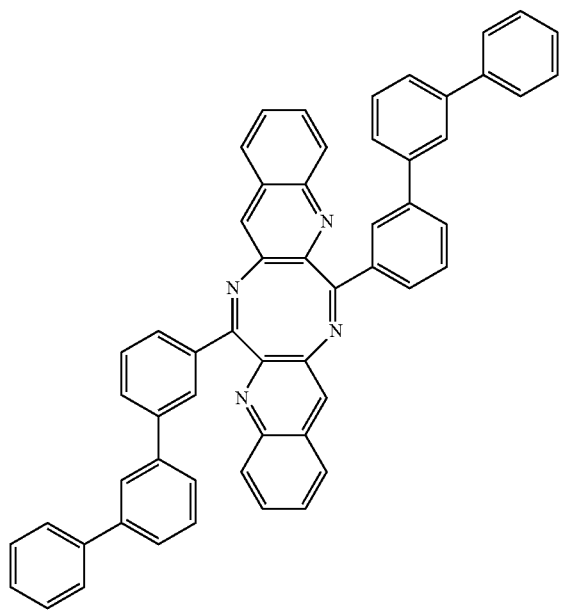
61
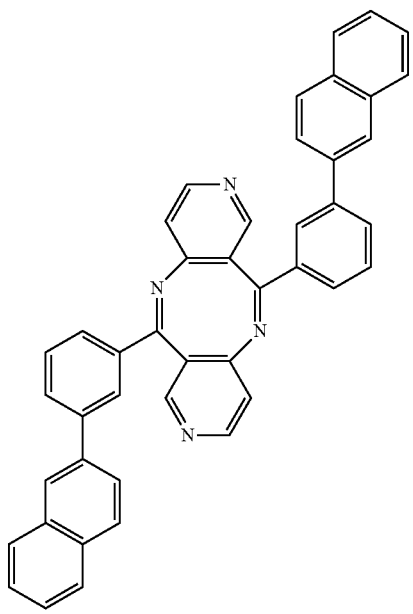
62
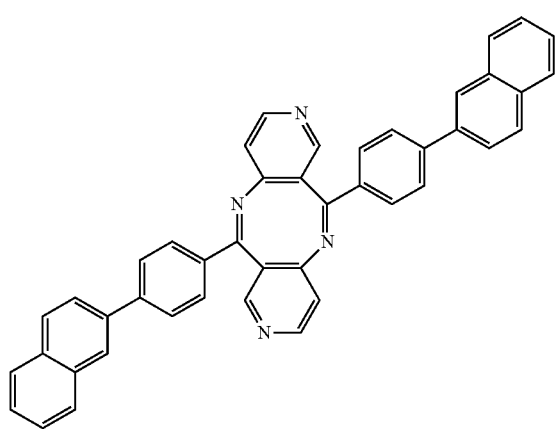
63
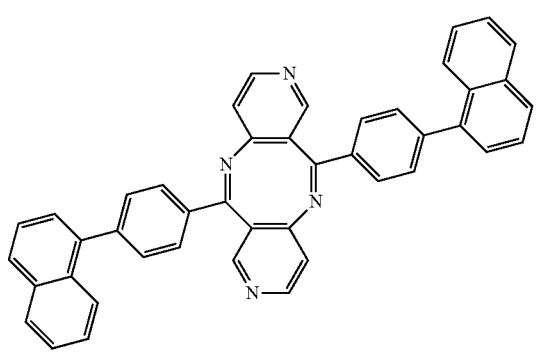
64
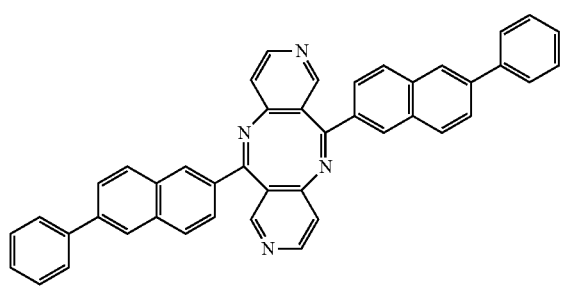
65
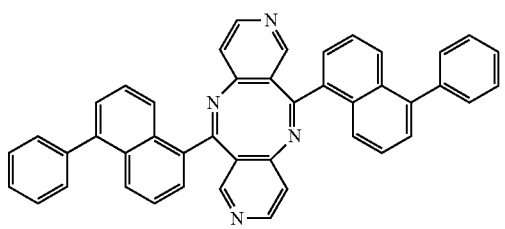

-continued
66
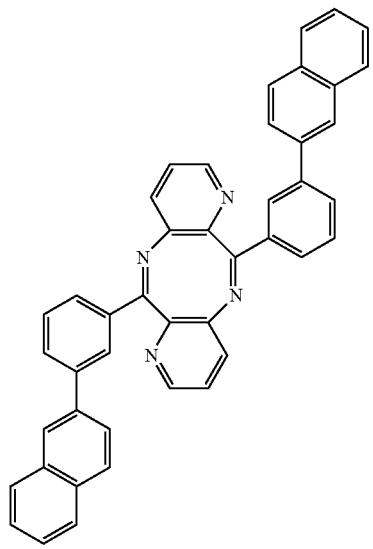
67
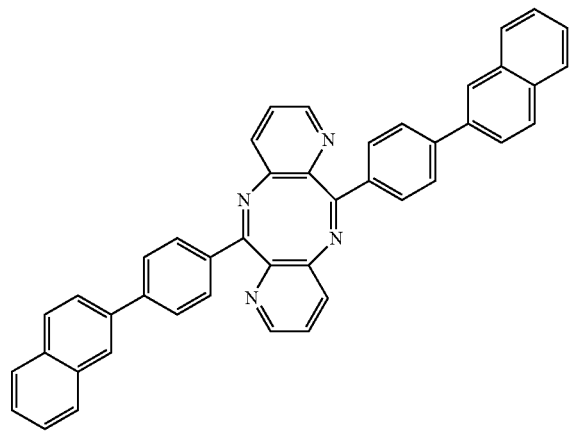
68
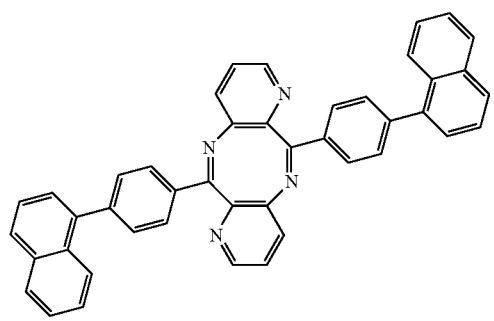
69
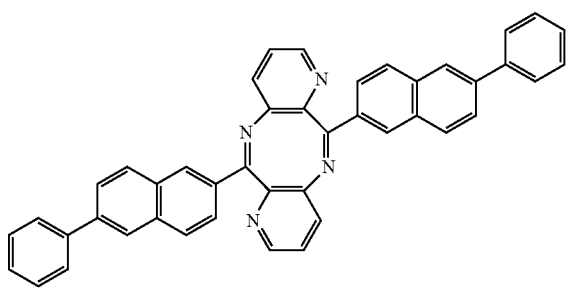
70
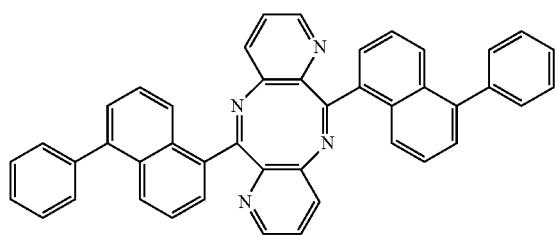
71
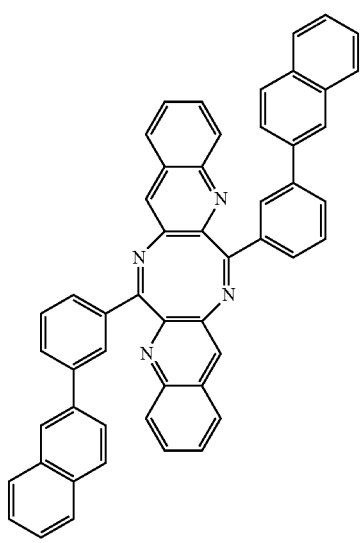

72
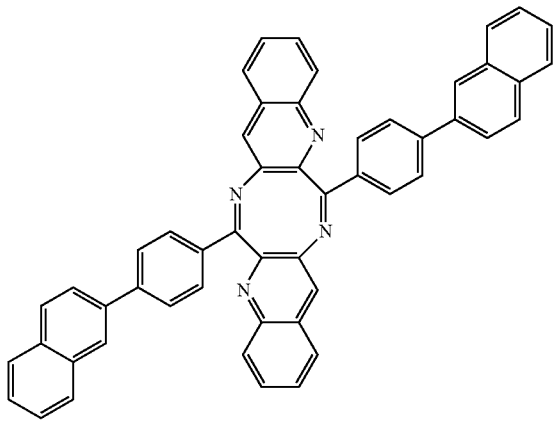
73
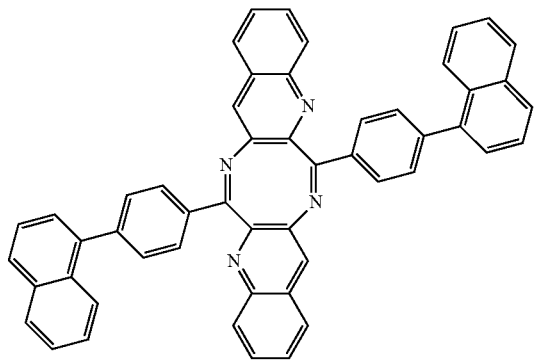
74
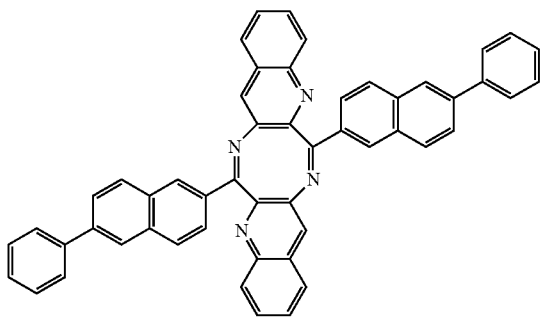
75
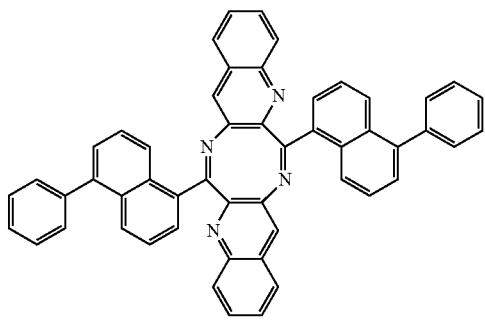
76
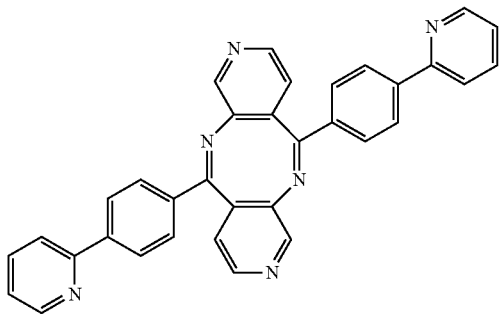
77
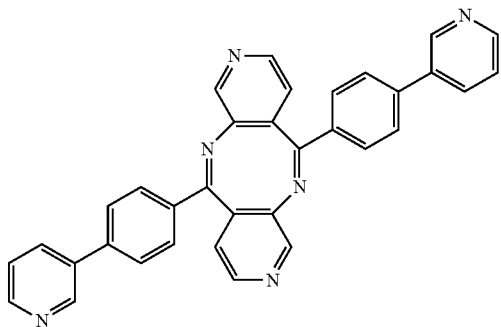

78
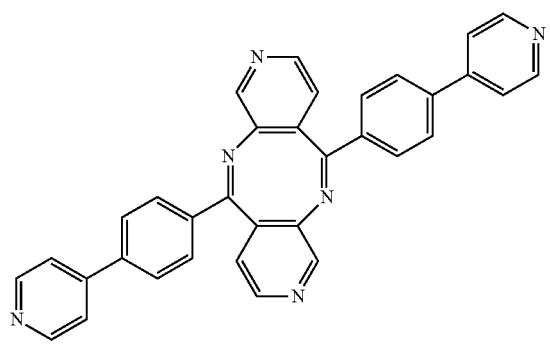
79
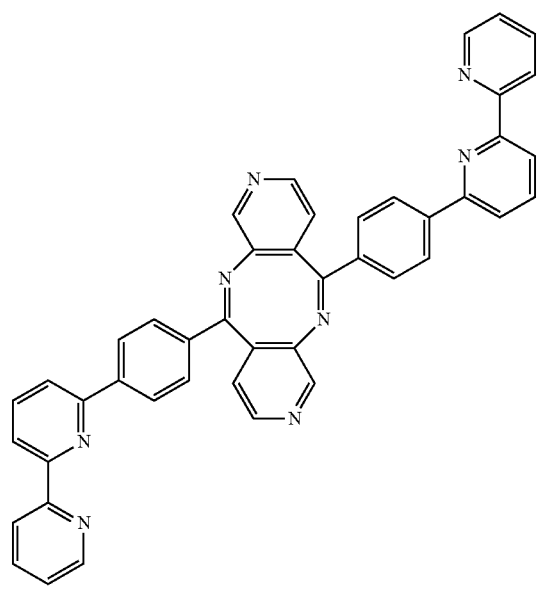
80
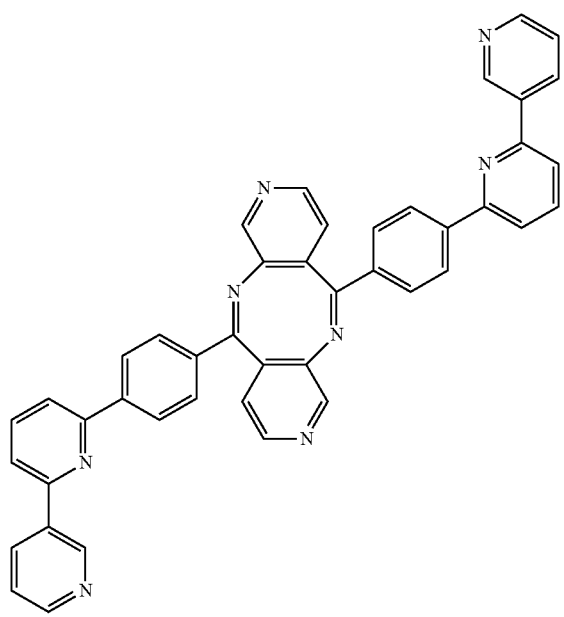
81
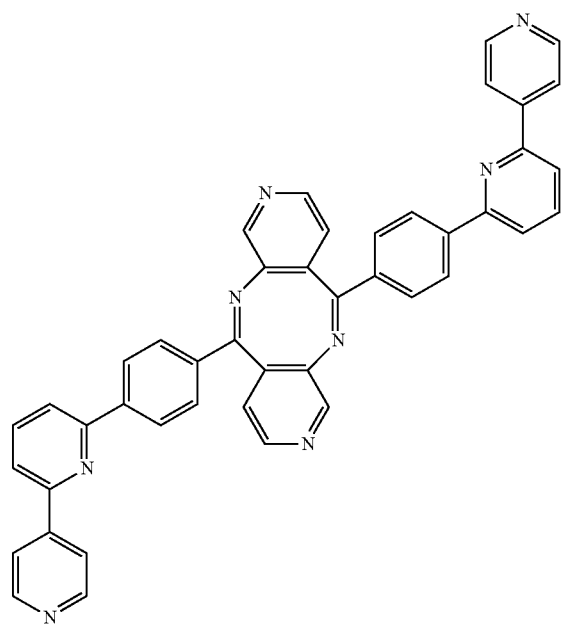

-continued
82
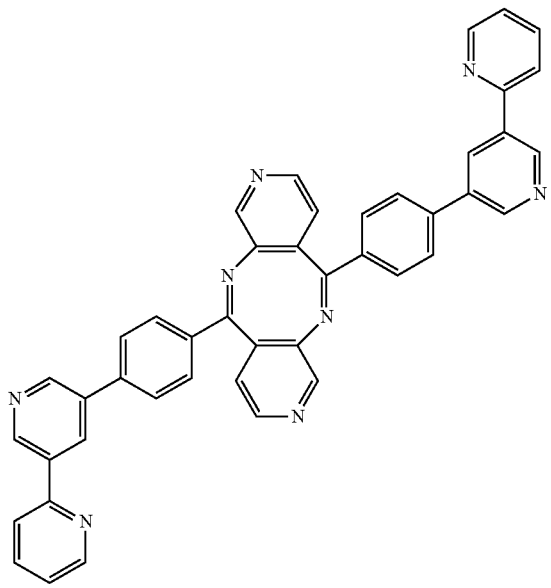
83
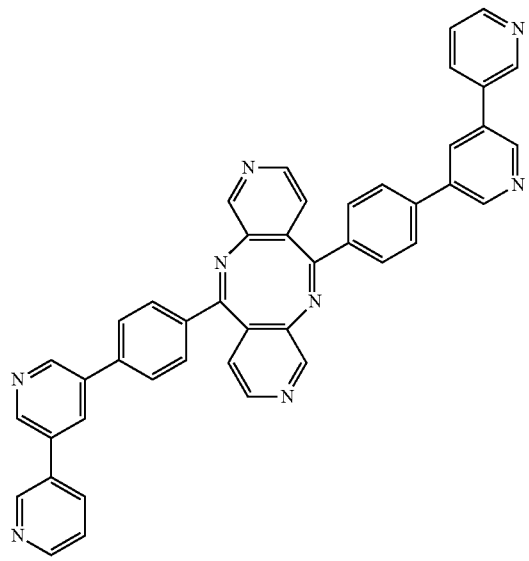
84
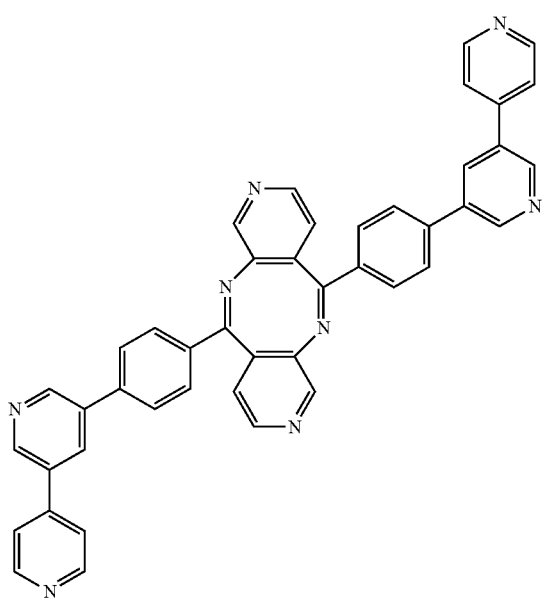
85
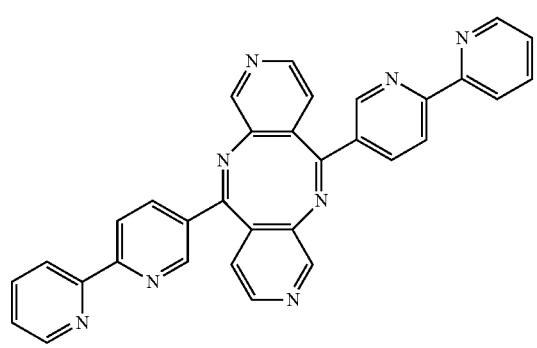
86
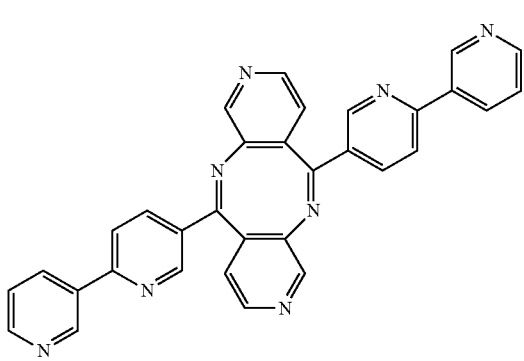
87
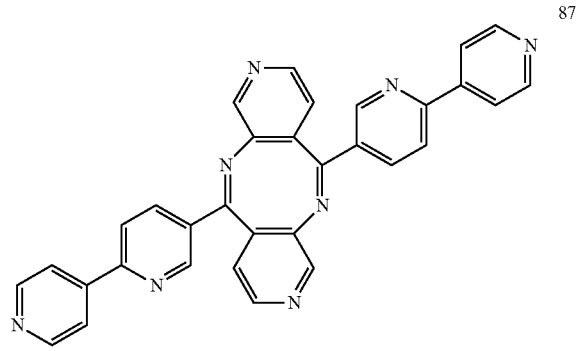

-continued
88
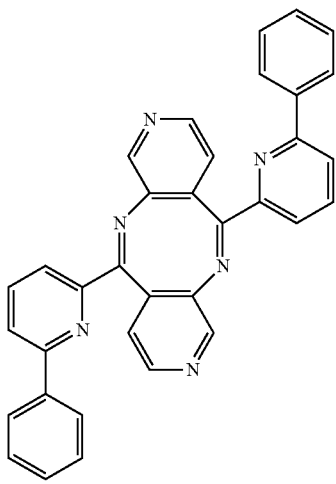
89
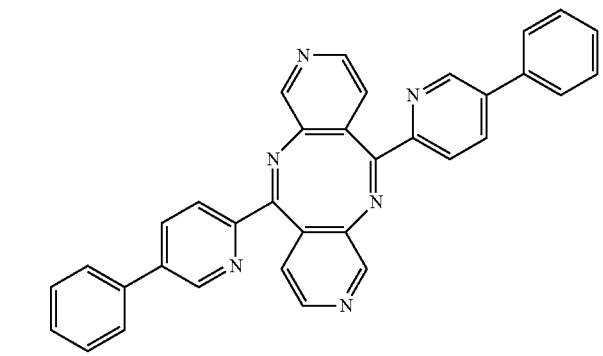
90
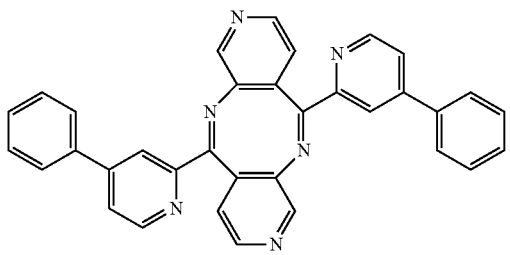
91
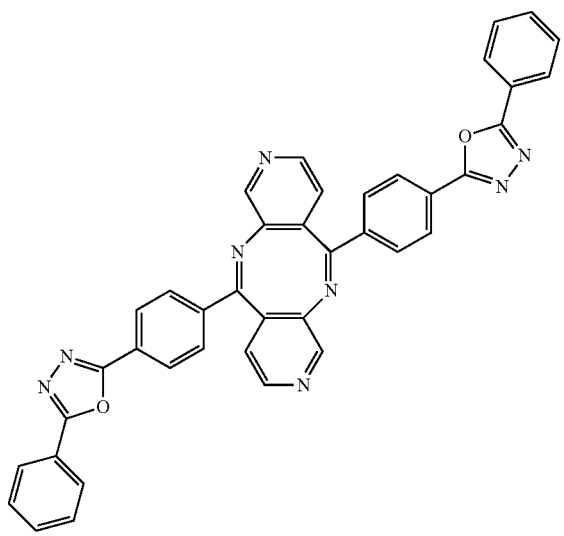
92
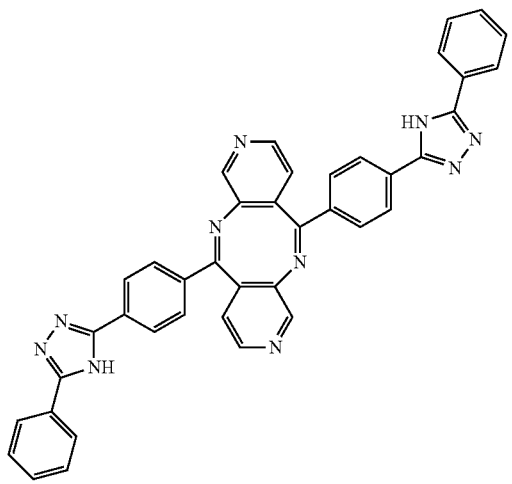
93
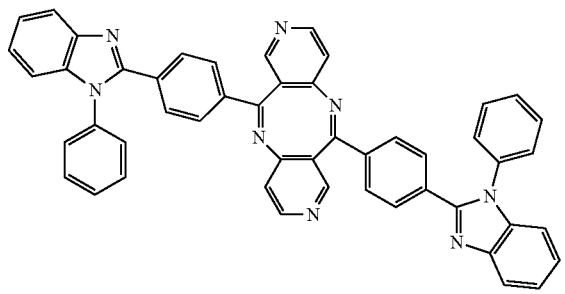

-continued
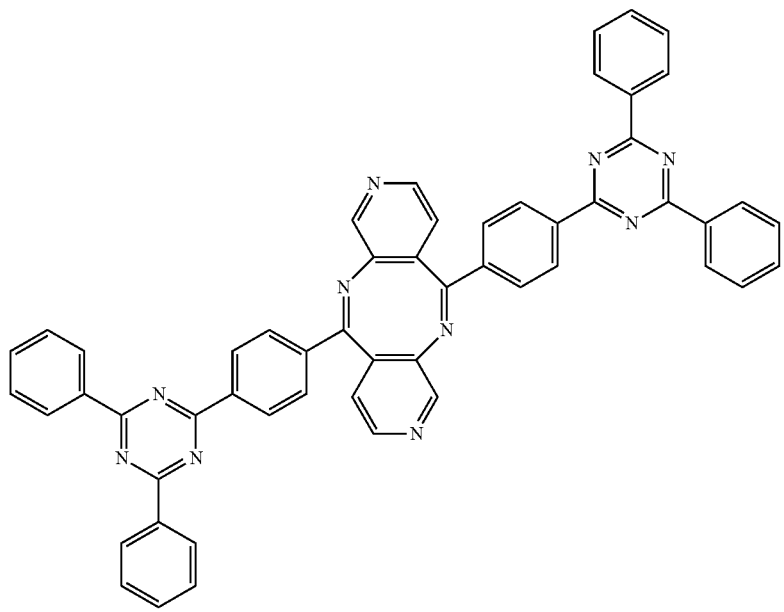
94
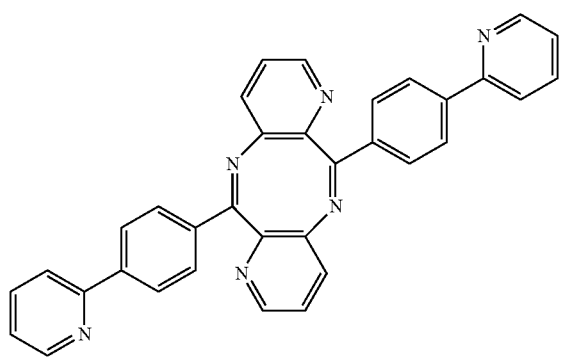
95  96
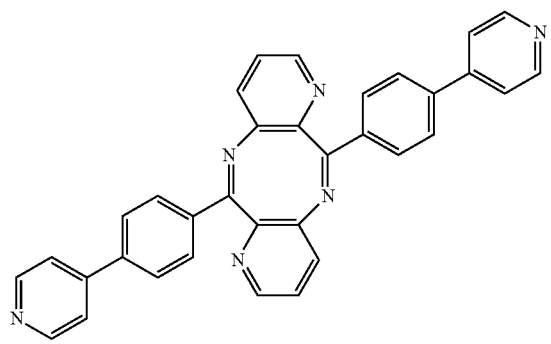
97
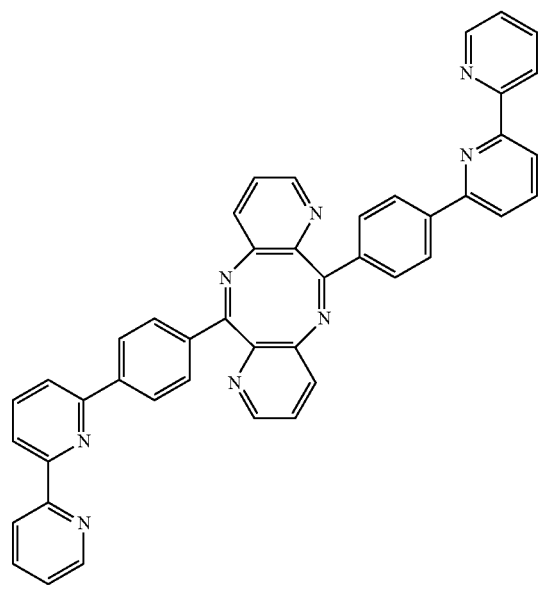
98

-continued
99
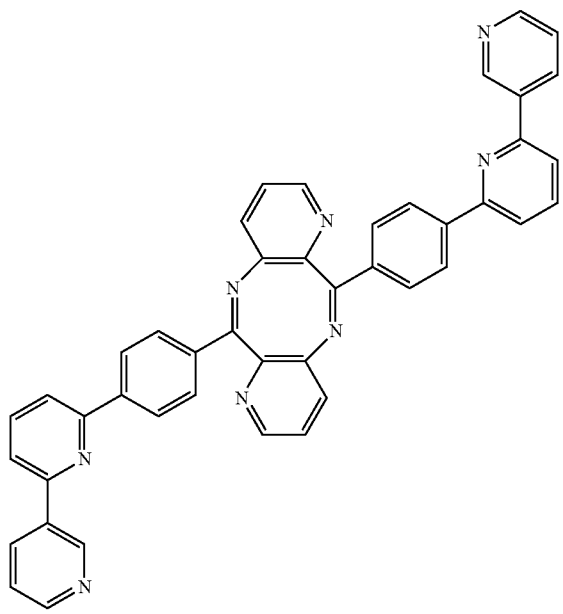
100
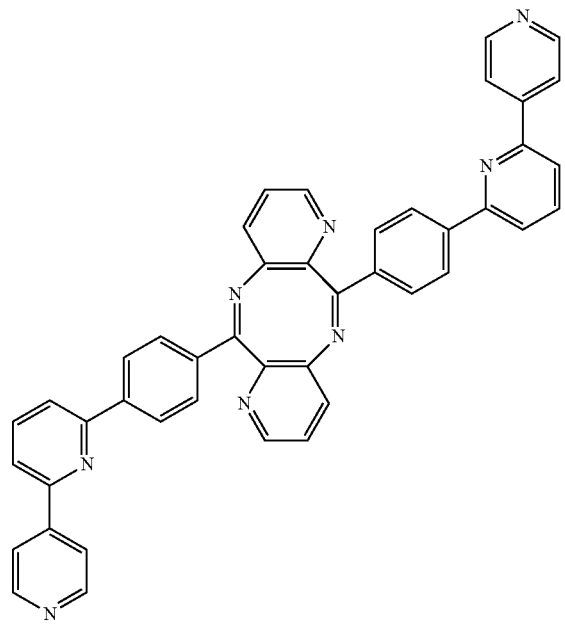
101
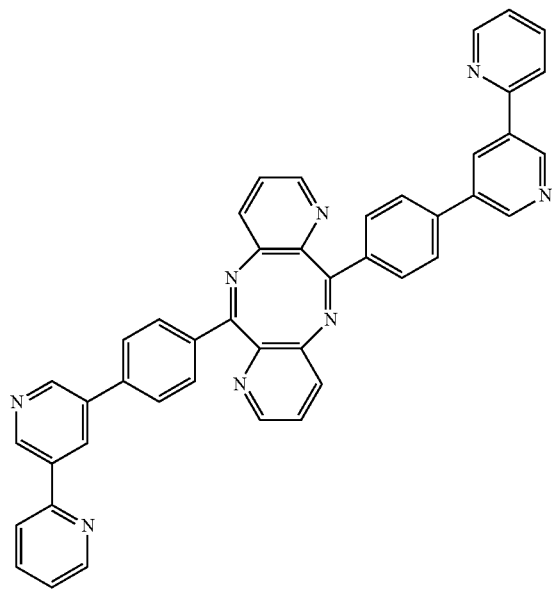
102
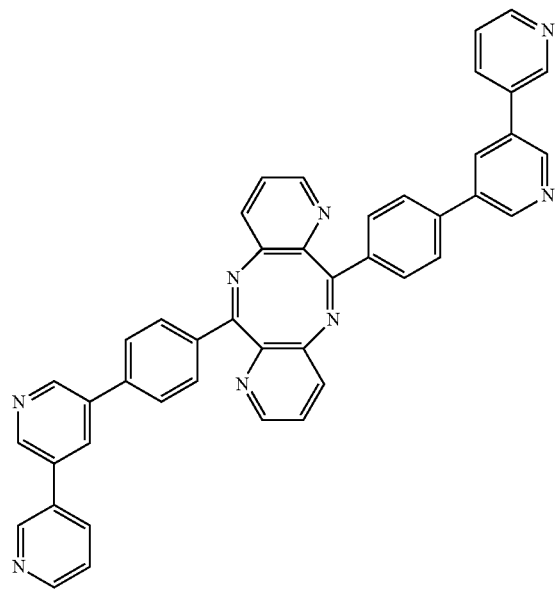

-continued
103
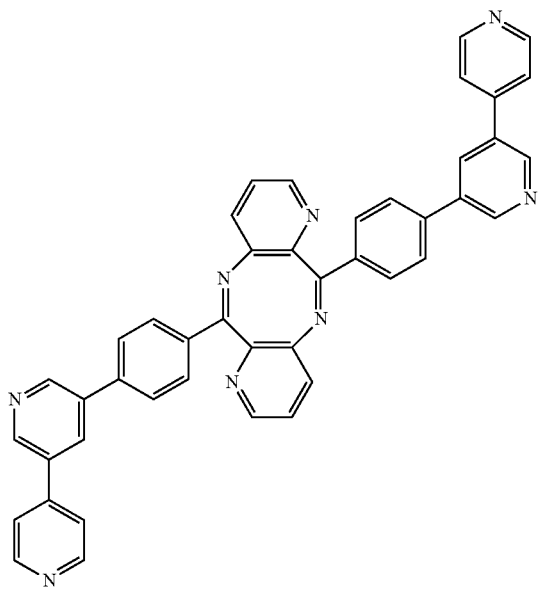
104
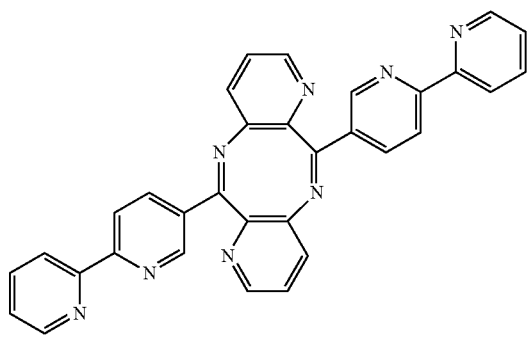
105
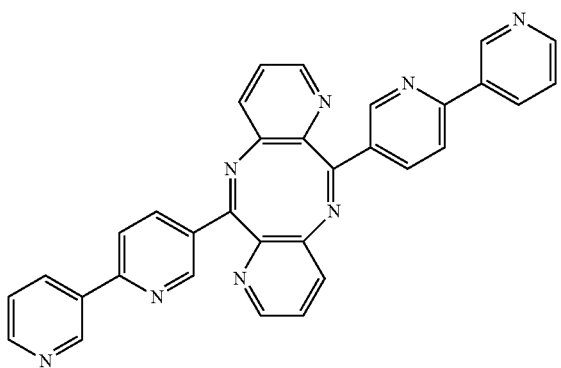
106
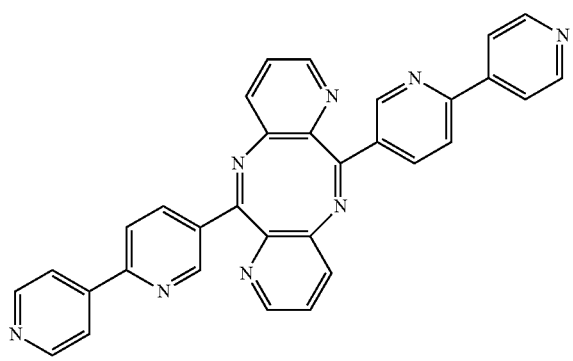
107
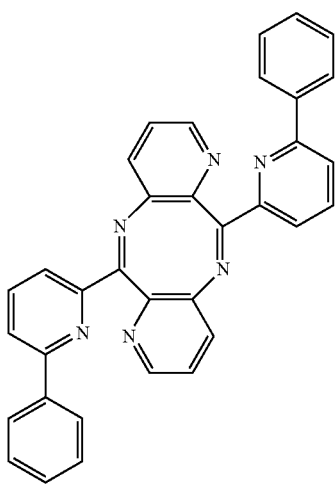
108
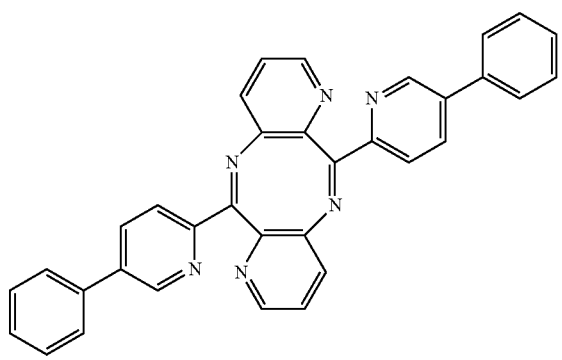

-continued
109
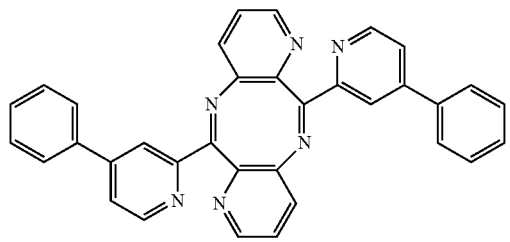
110
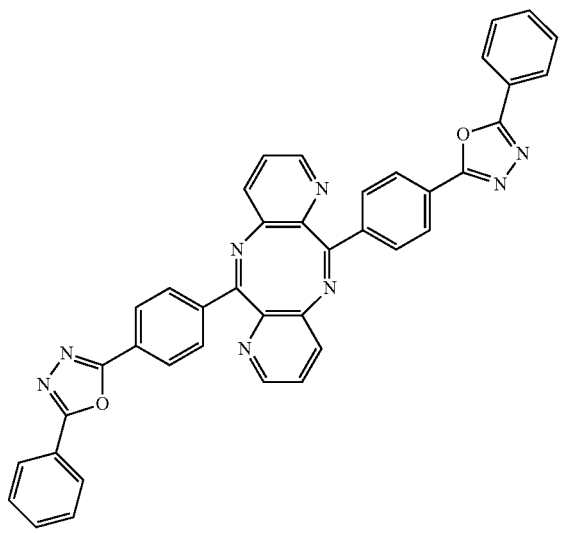
111
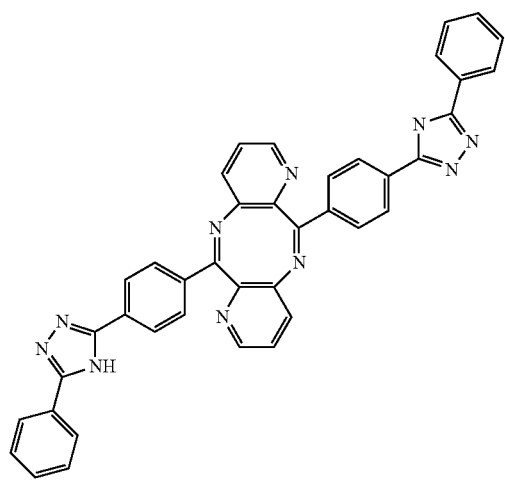
112
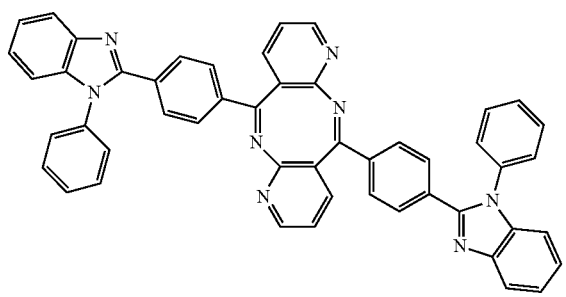
113
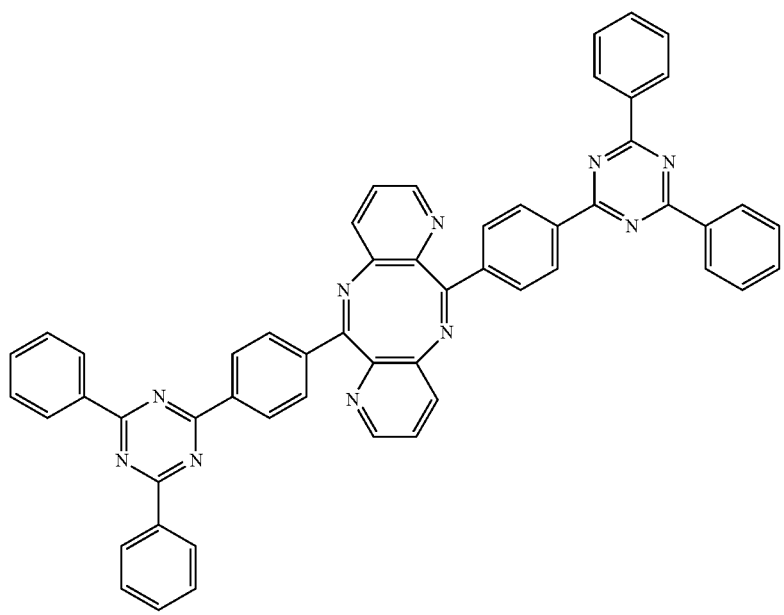

-continued
114
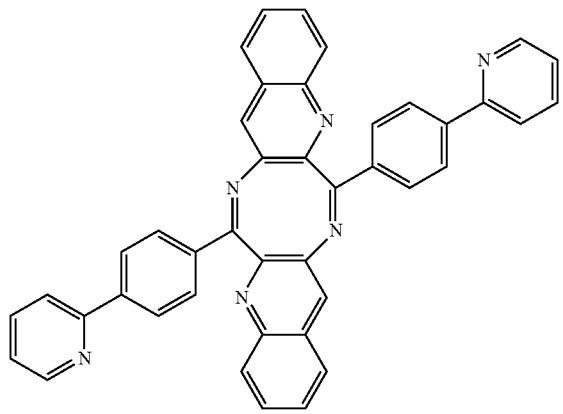
115
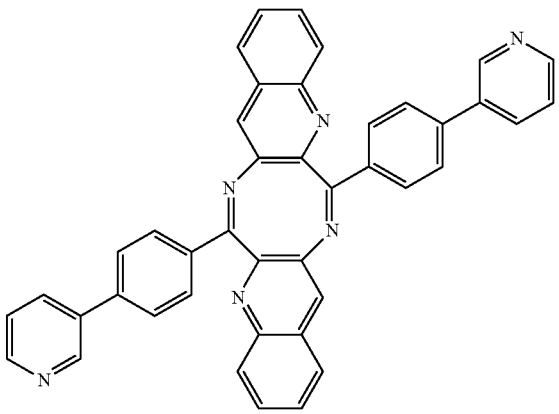
116
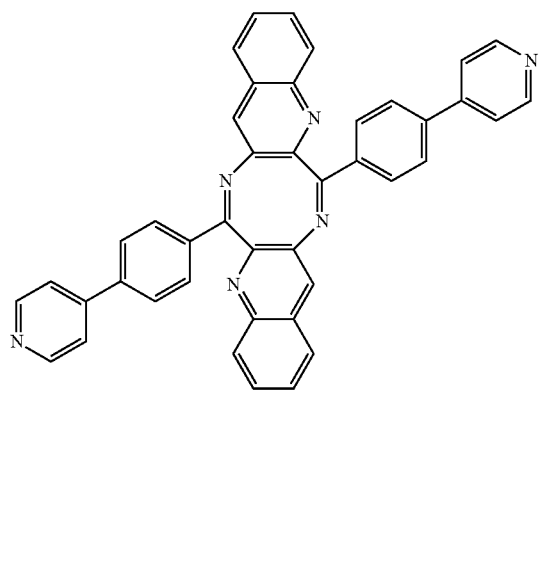
117
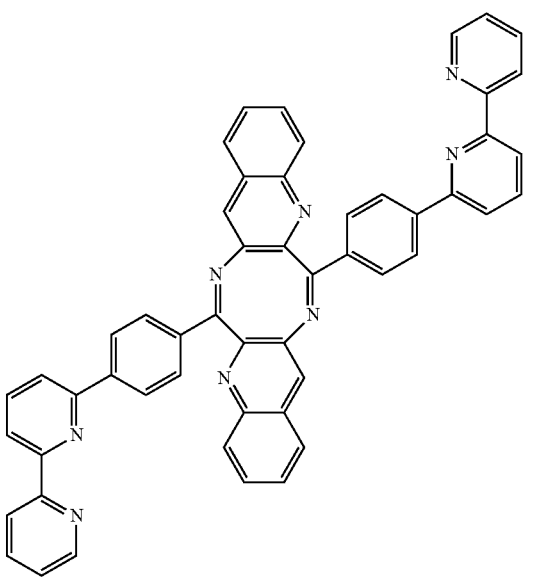
118
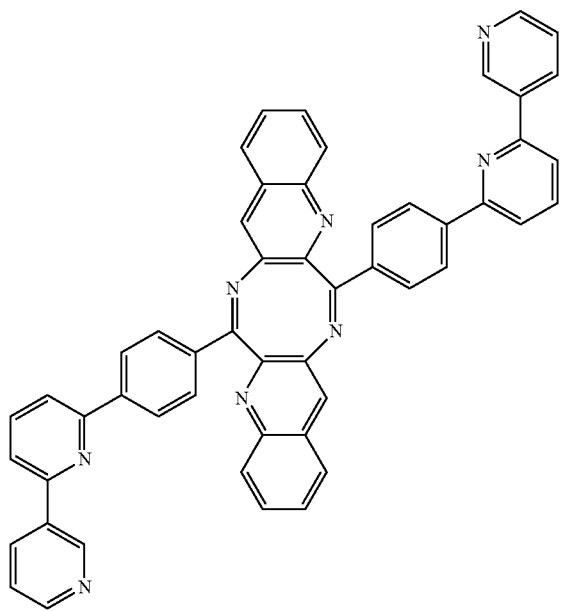
119
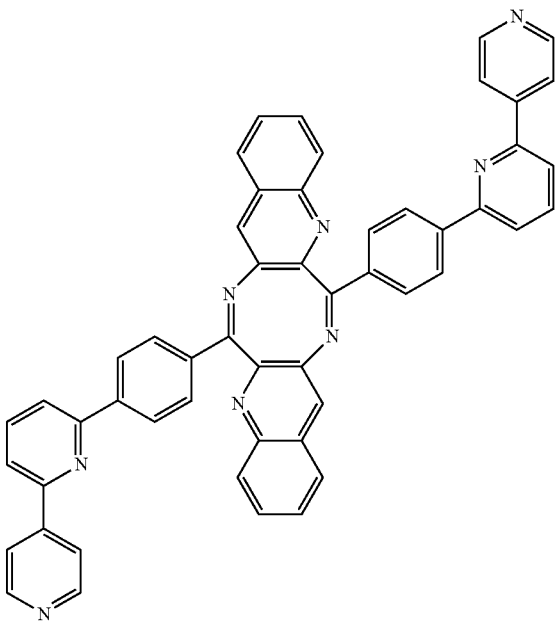

-continued
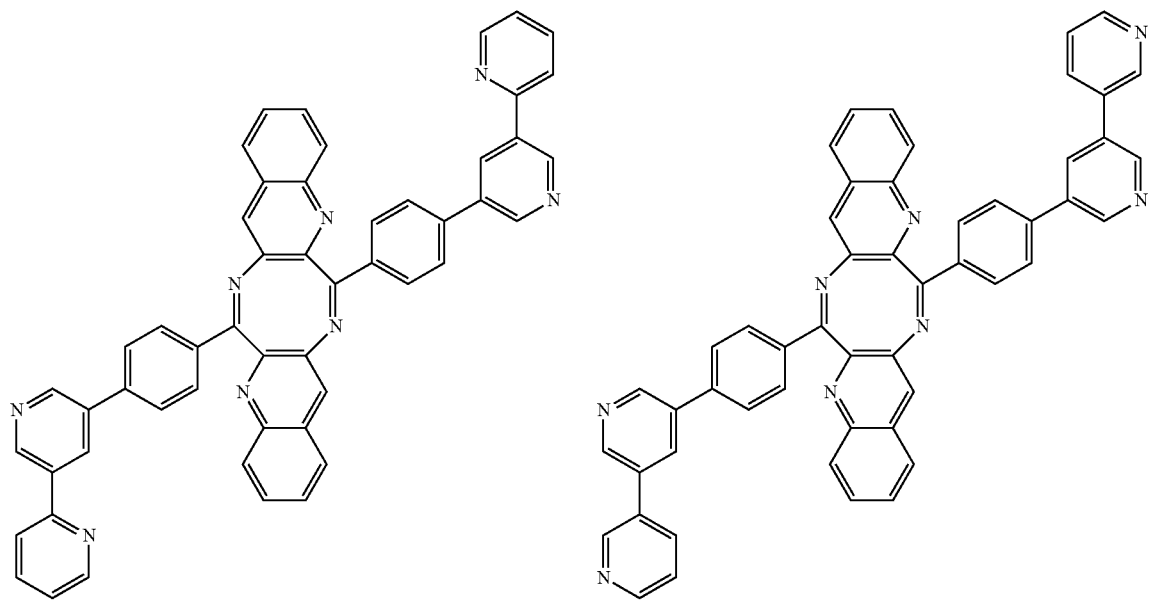
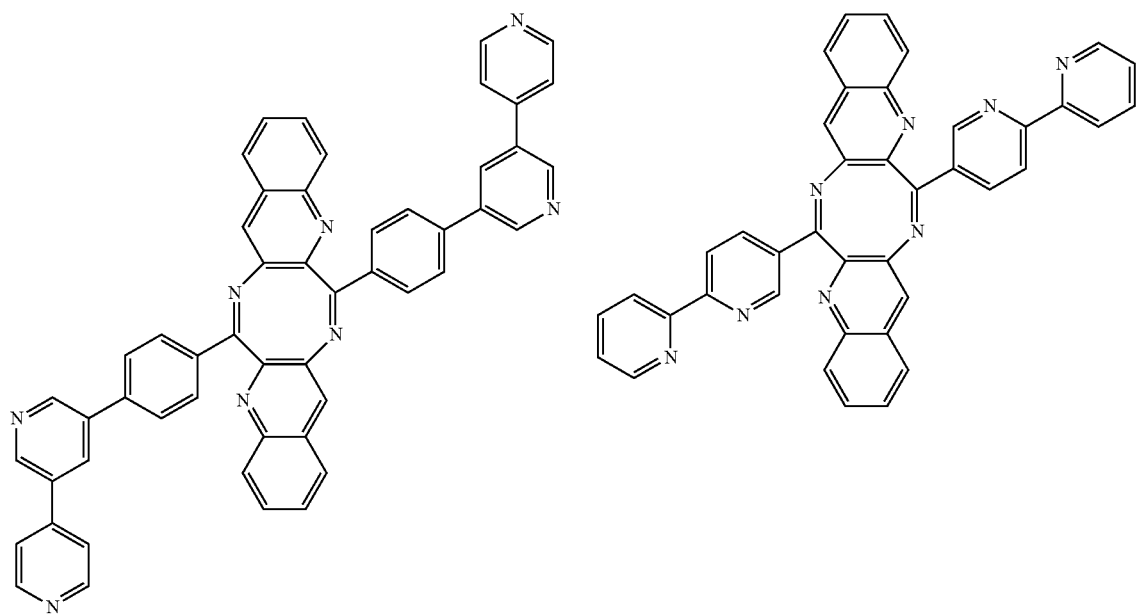

-continued
124
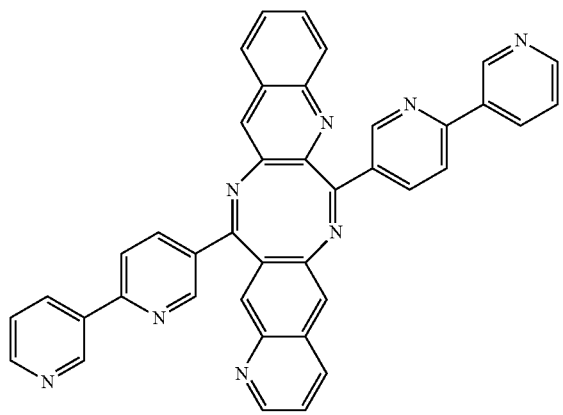
125
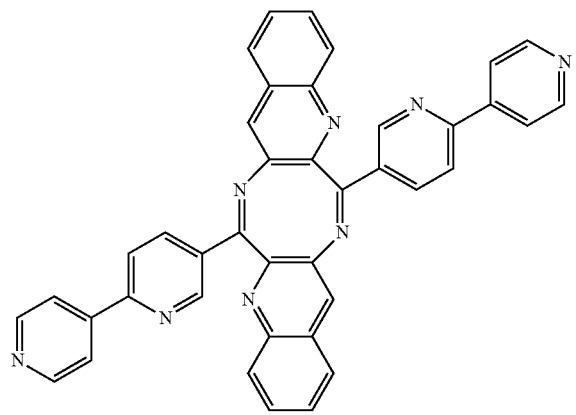
126
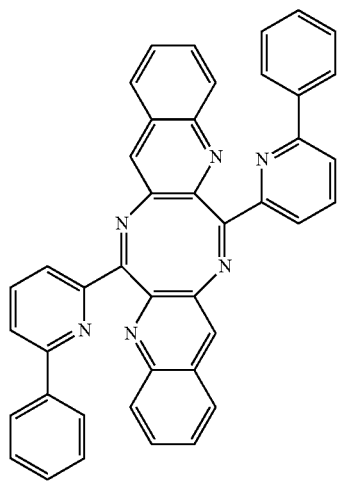
127
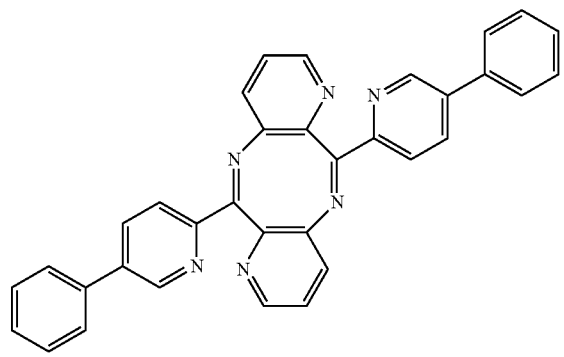
128
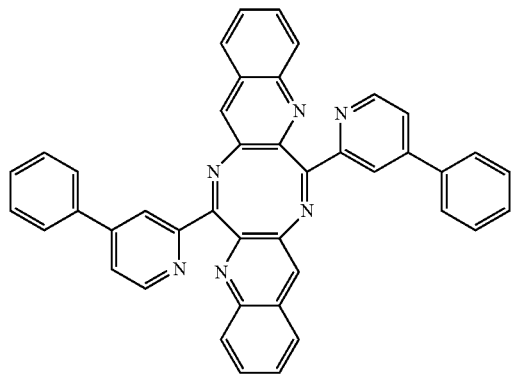
129
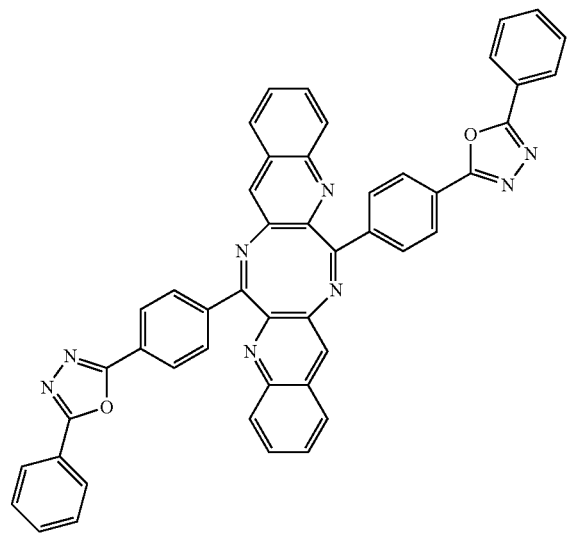

-continued
130
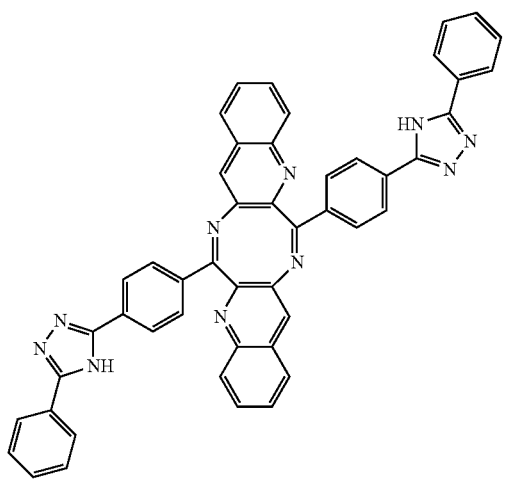
131
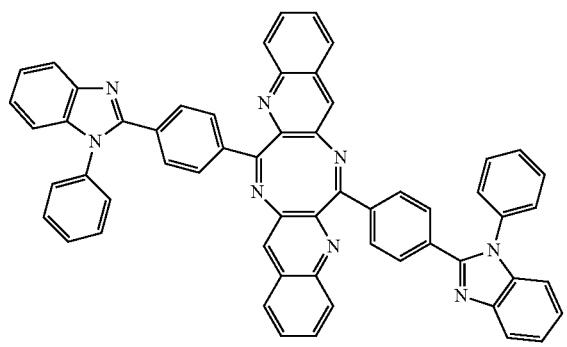
132
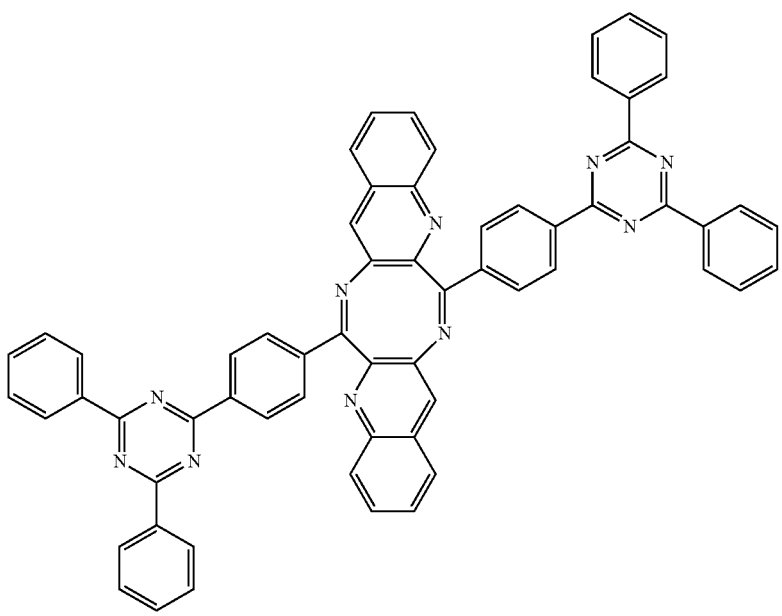
133
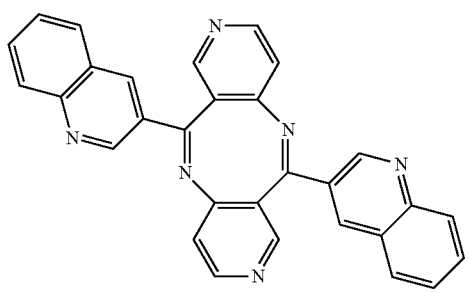
134
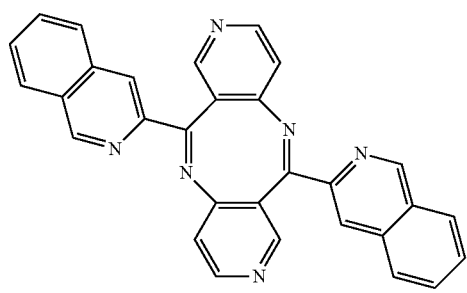

-continued
135 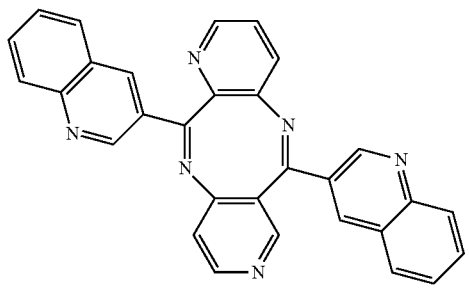
136 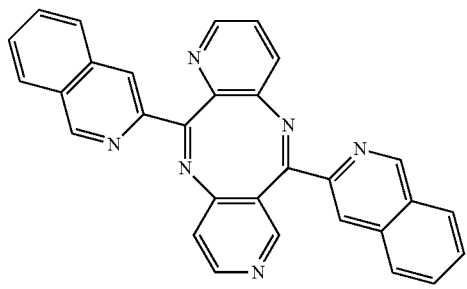
137 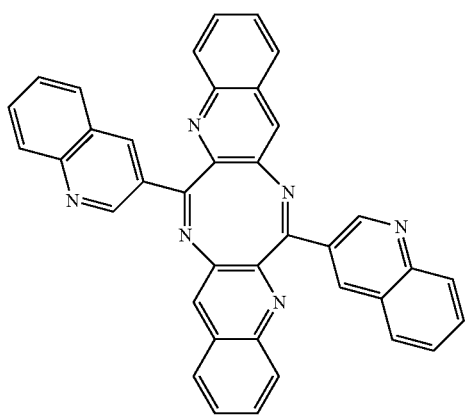
138 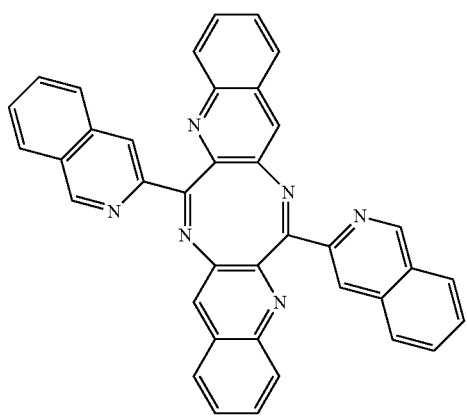
139 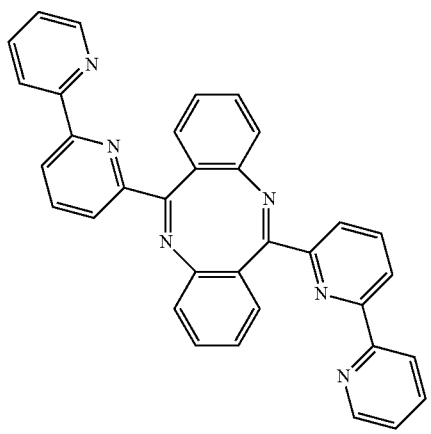
140 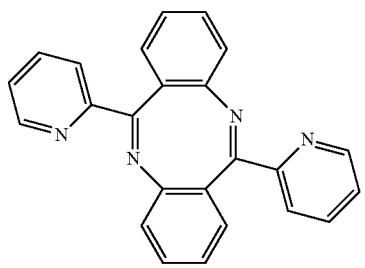
141 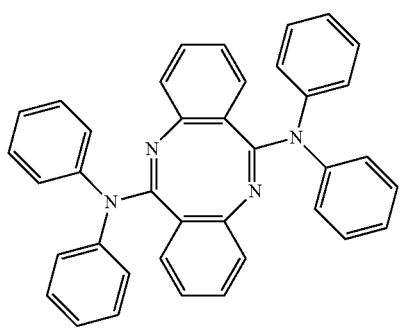
142 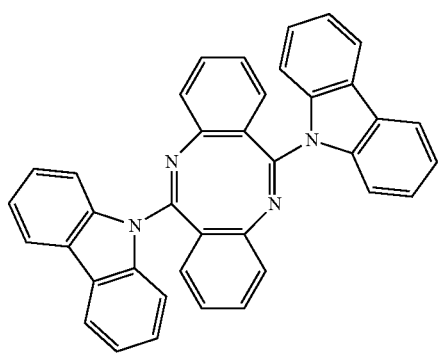

US 10,790,452 B2
-continued
143
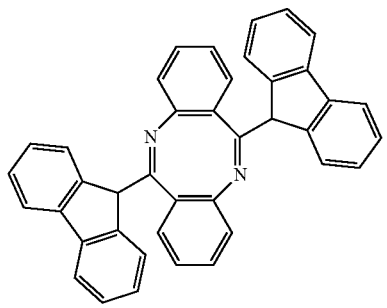
144
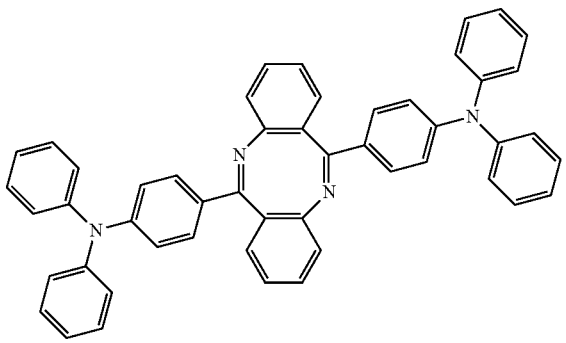
145
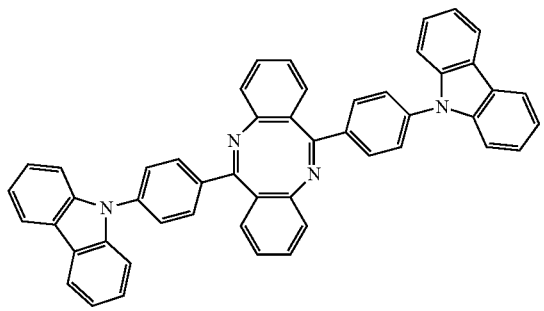
146
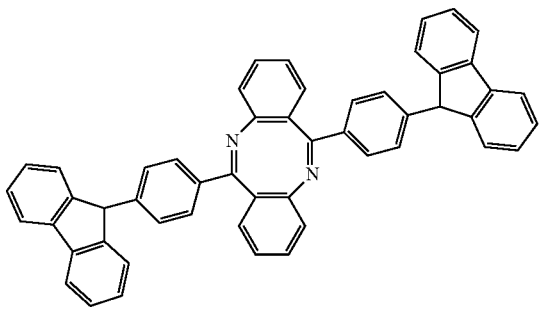
147
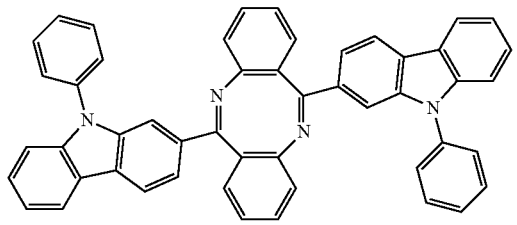
148
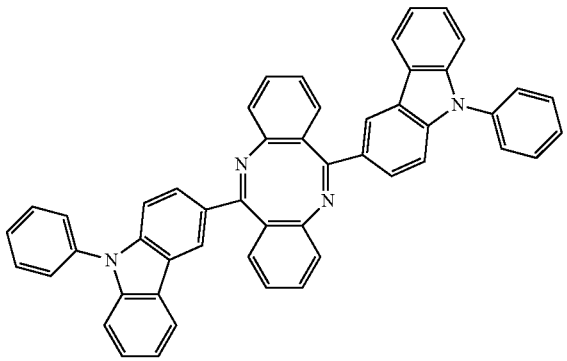
149
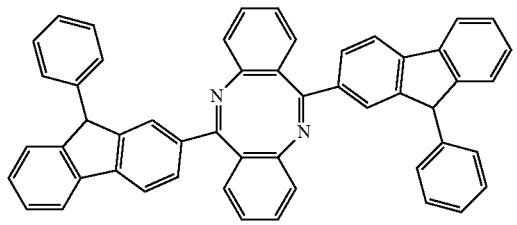
150
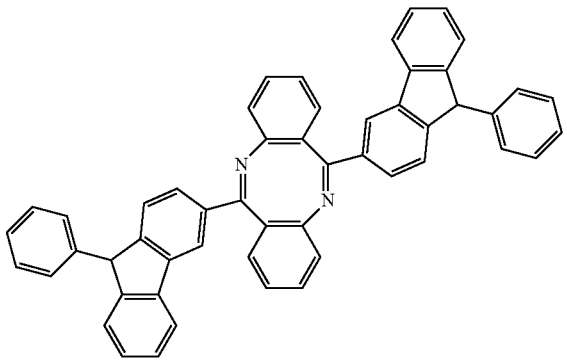

-continued
151
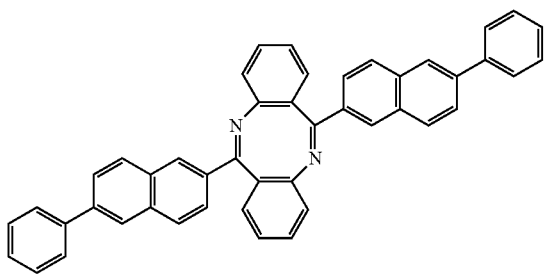
152
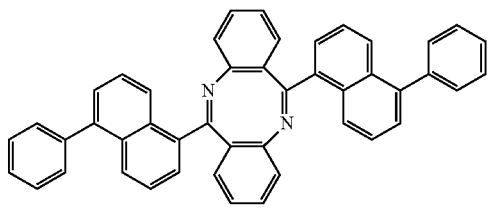
153
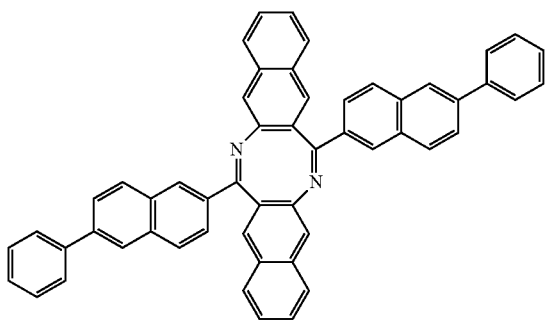
154
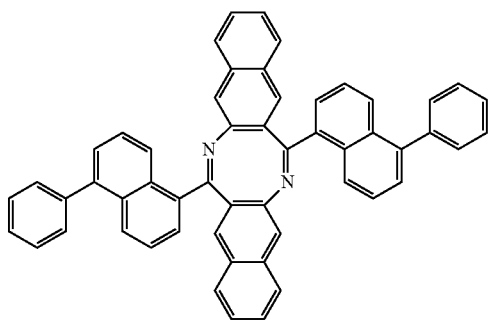
155
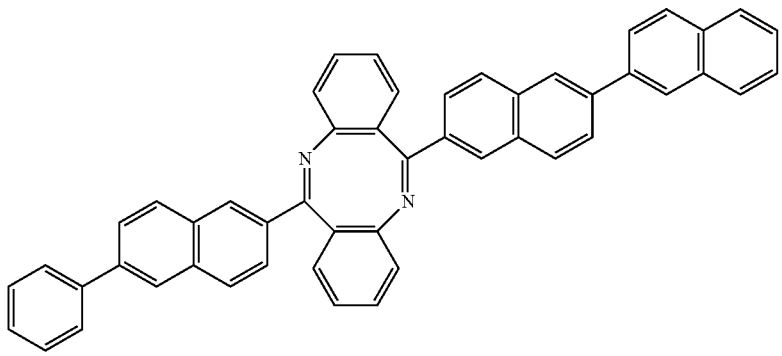
156
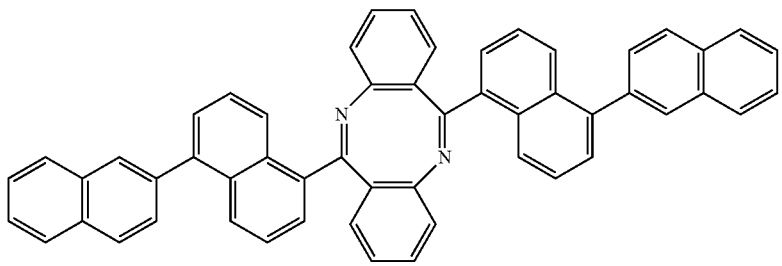

-continued
157
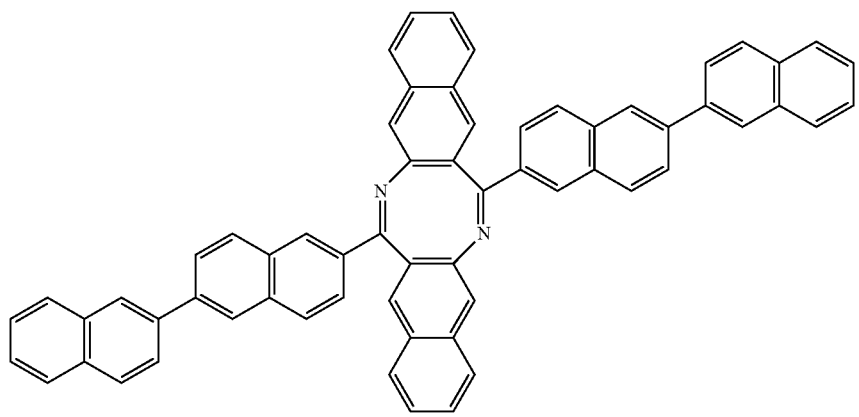
158
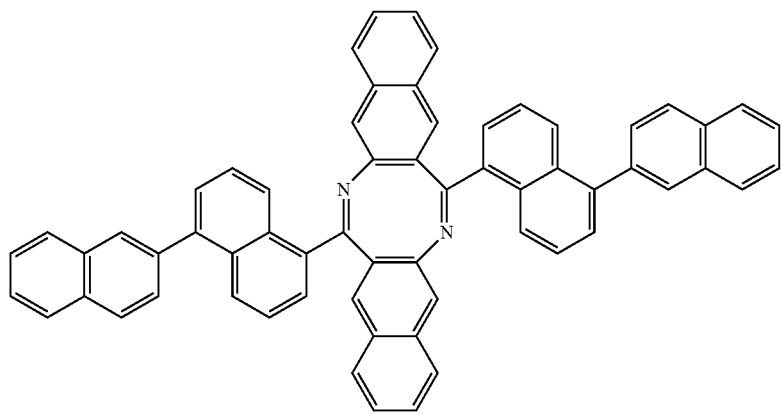
159 160
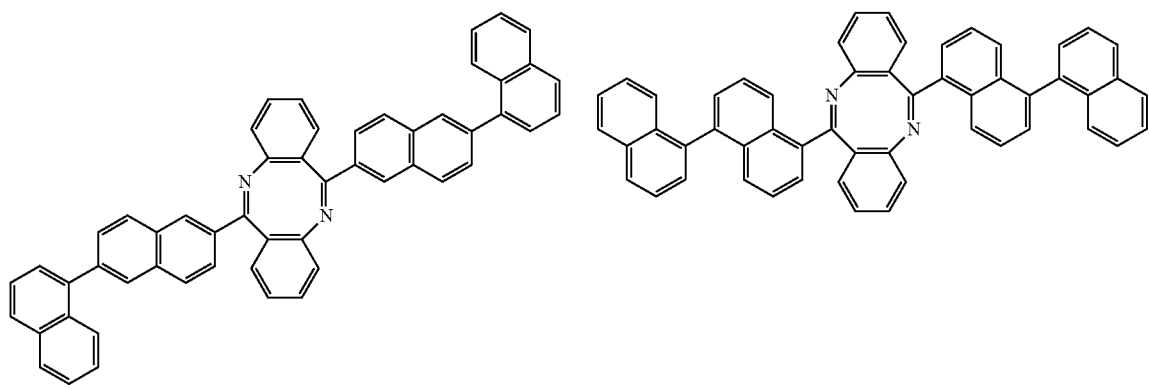
161
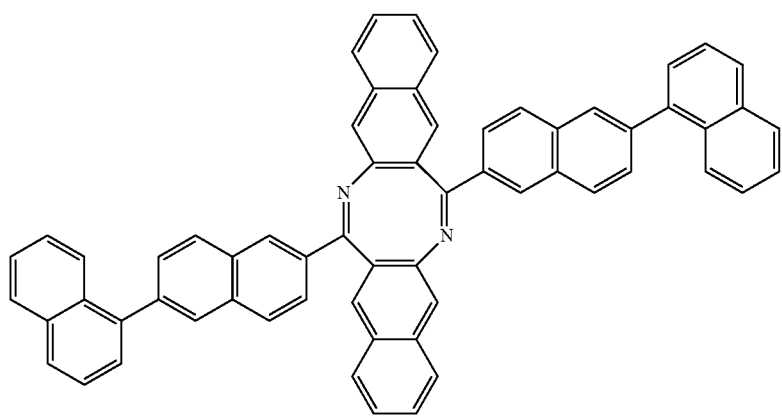

-continued
162
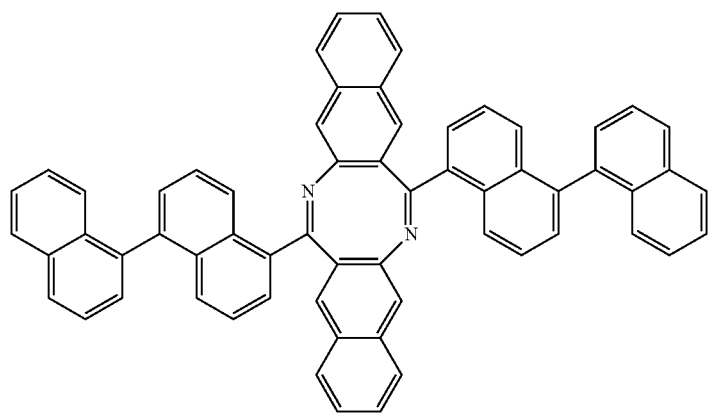
163
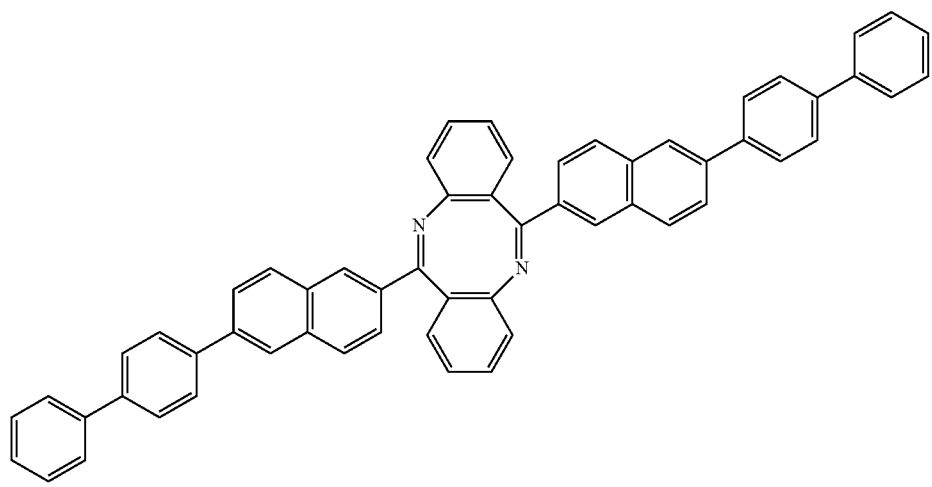
164
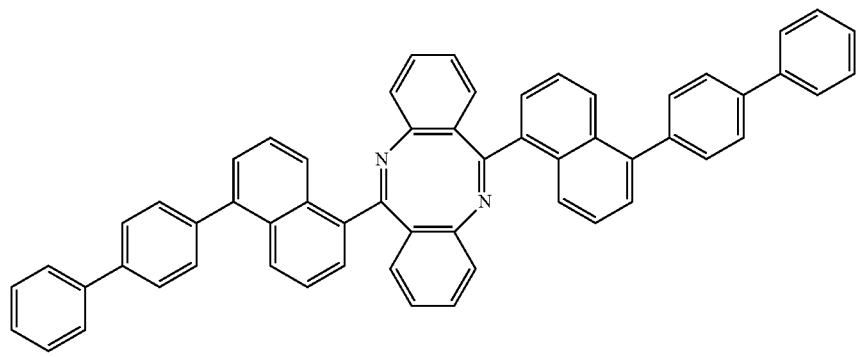

165
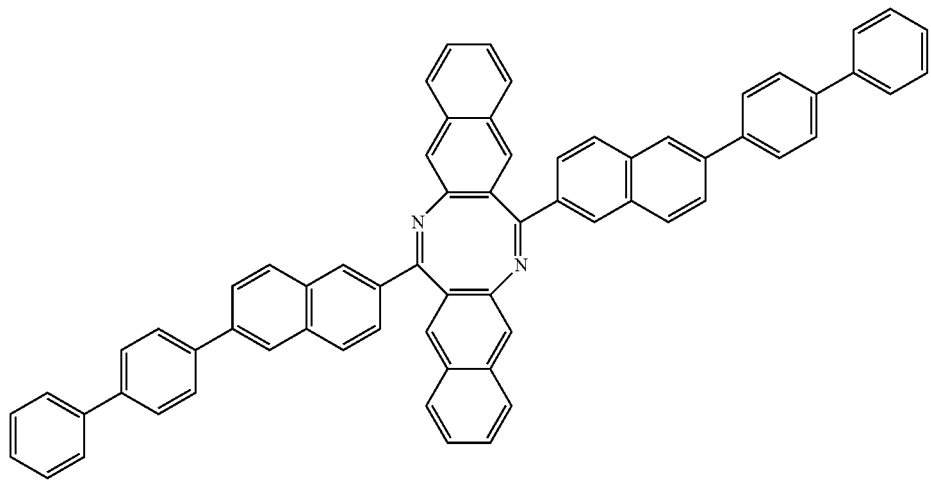
166
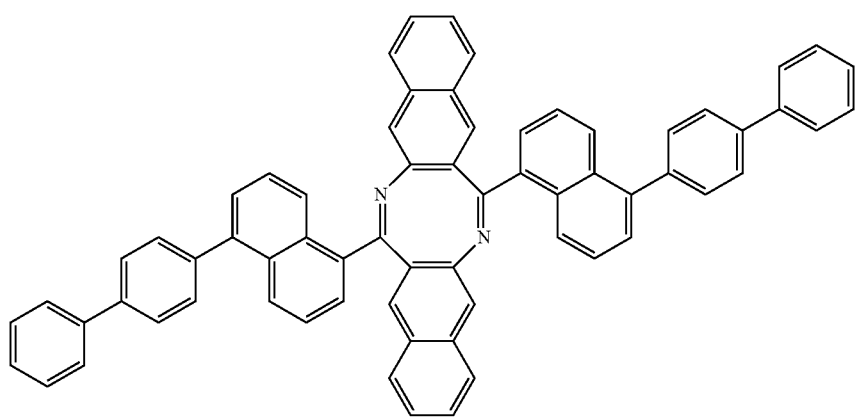
167
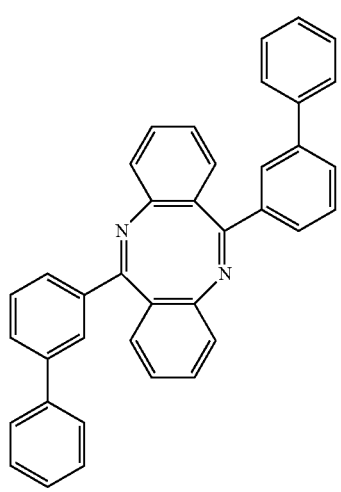
168
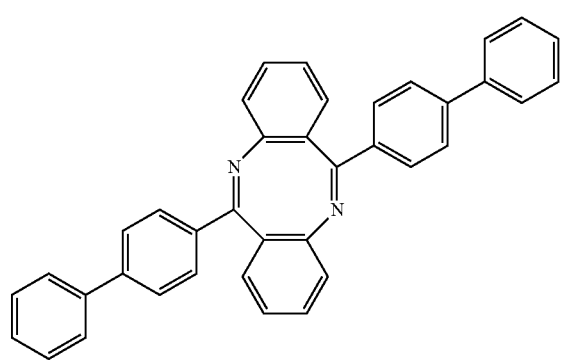

169
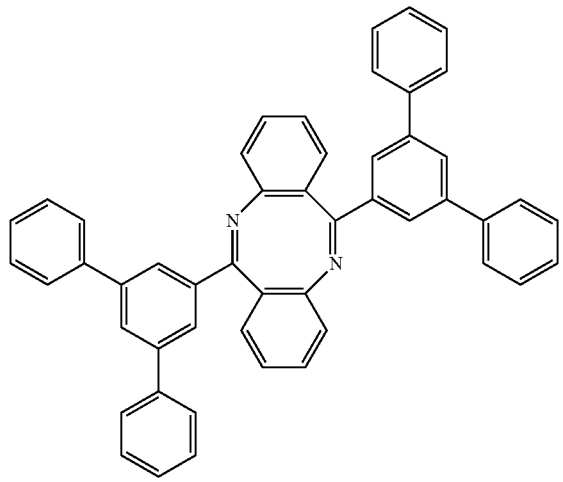
170
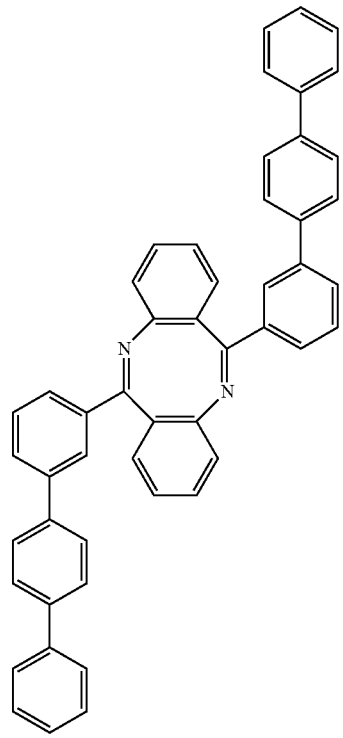
171
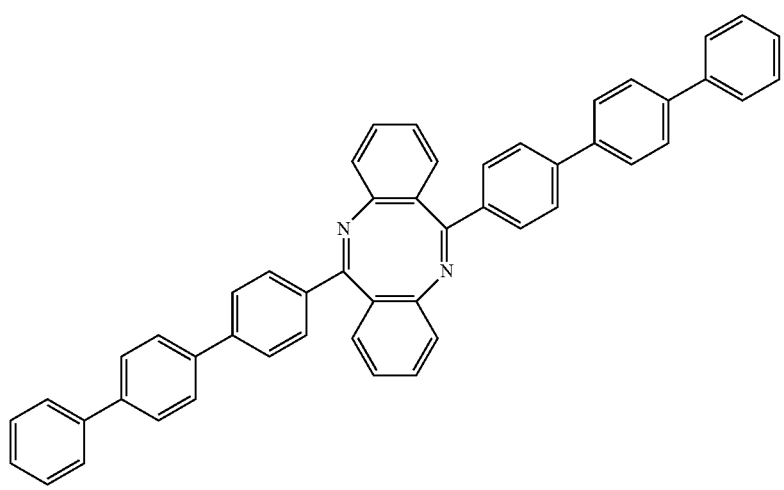

172
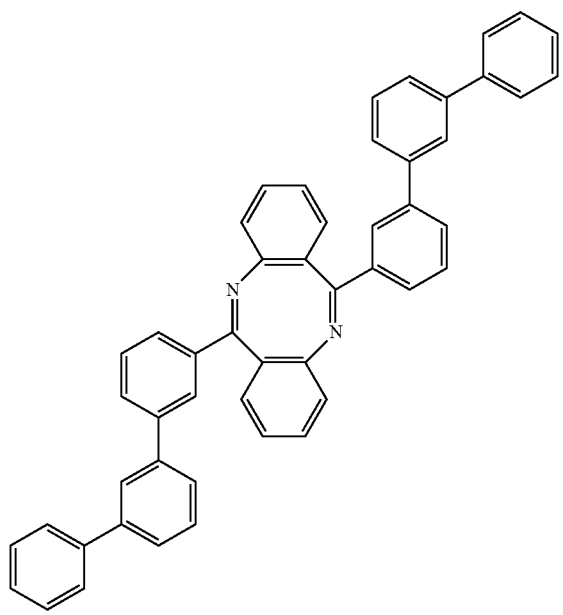
173
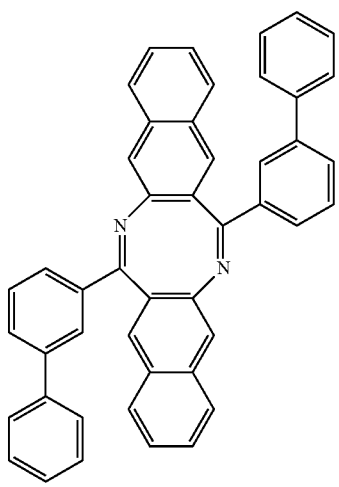
174
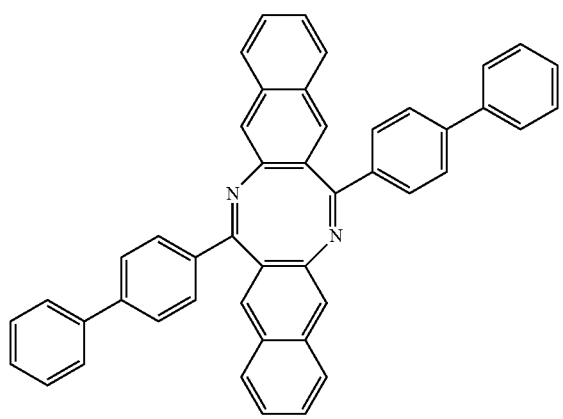
175
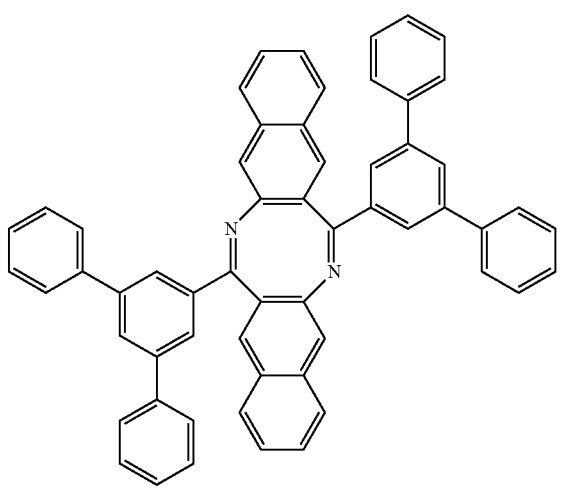

-continued
176
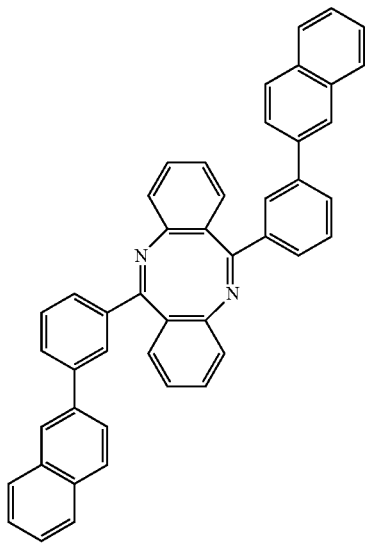
177
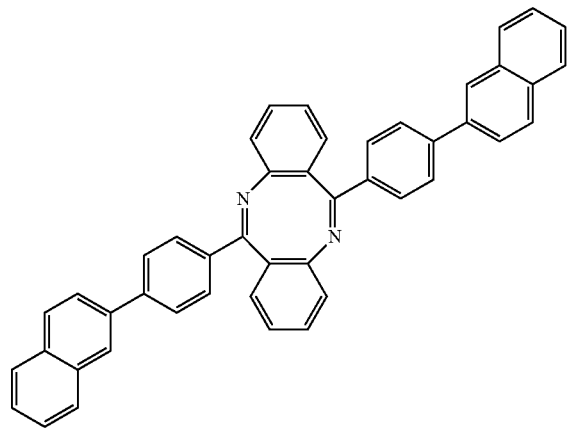
178
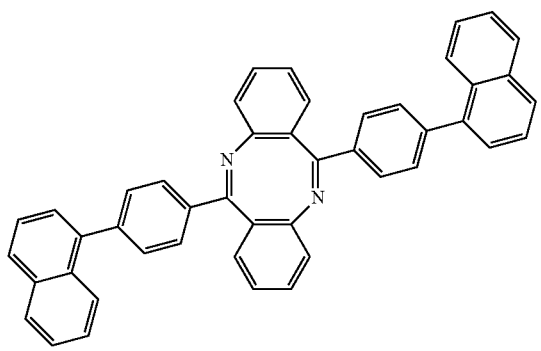
179
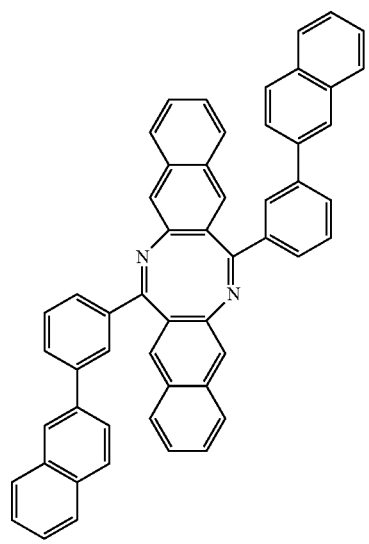
180
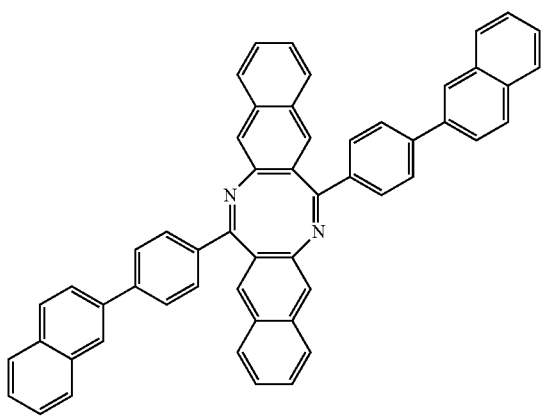
181
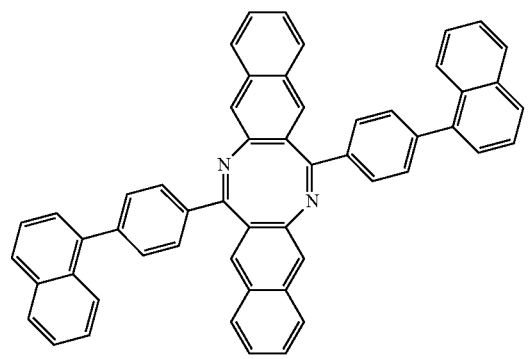

-continued
182
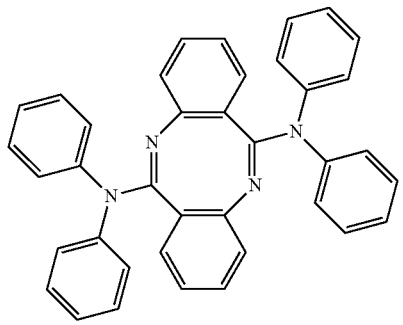
183
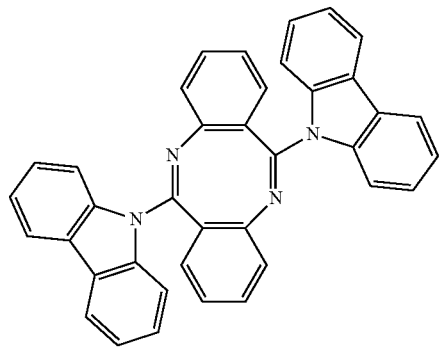
184
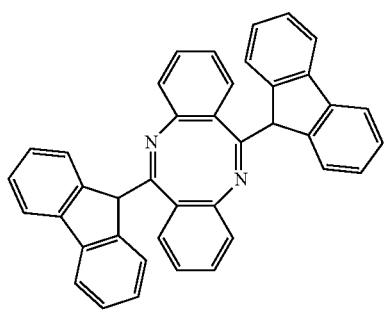
185
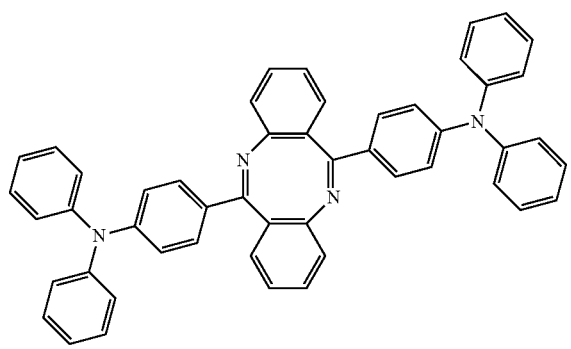
186
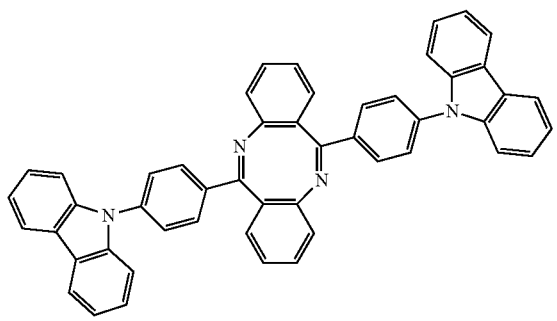
187
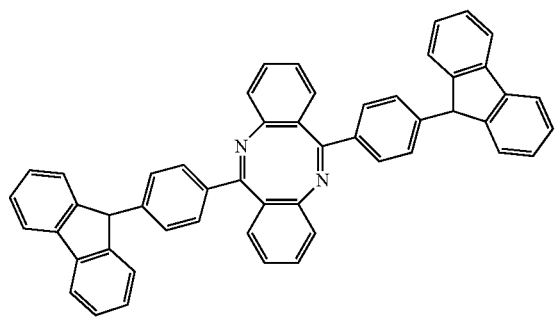
188
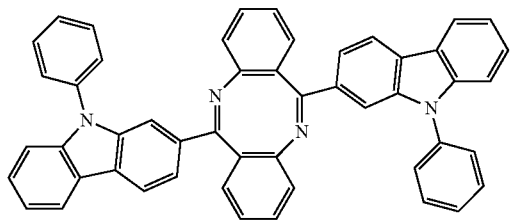
189
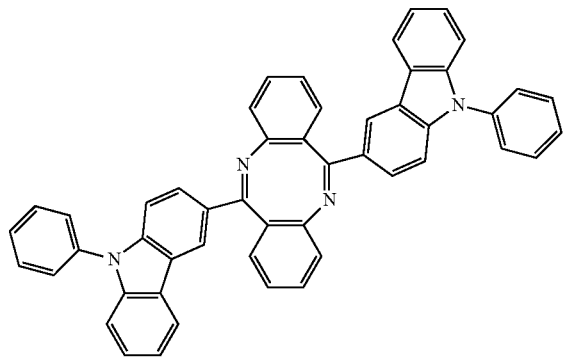

-continued
190
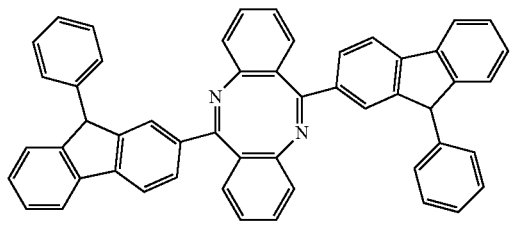
191
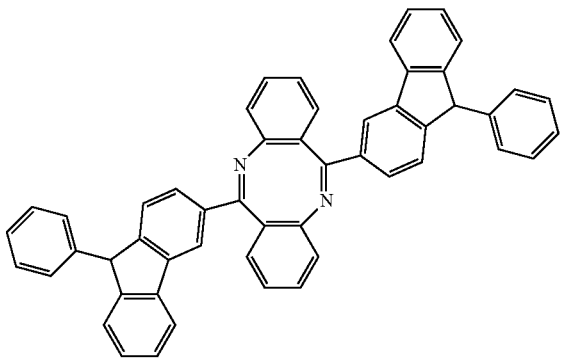
192
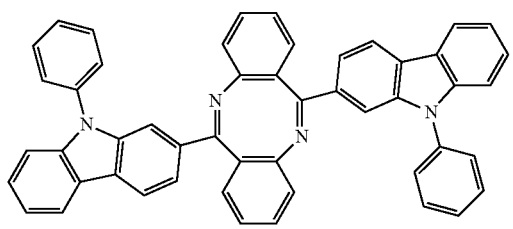
193
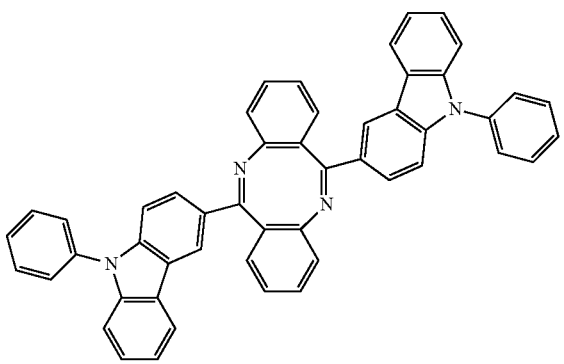
194
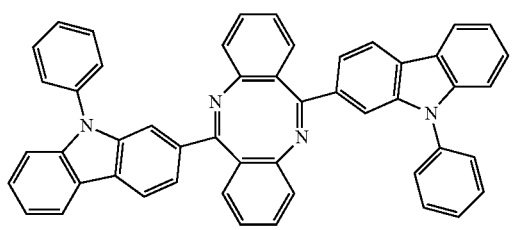
195
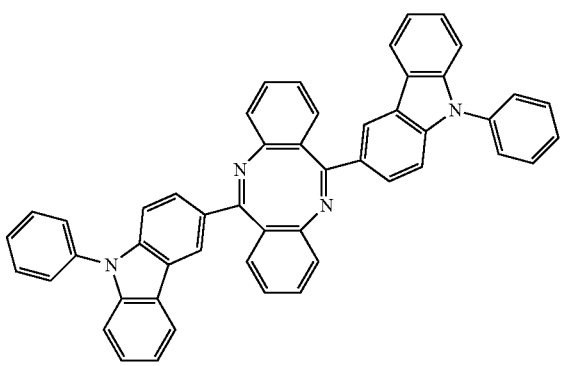
196
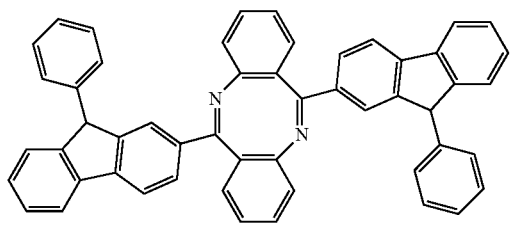
197
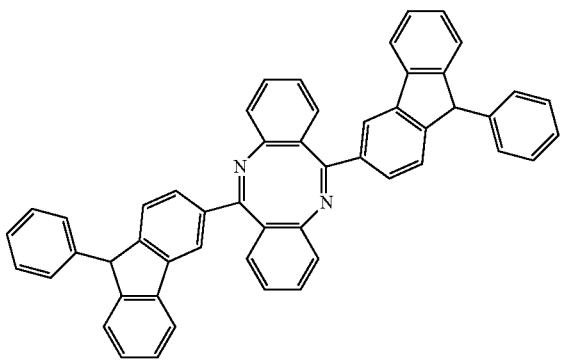

-continued
101
198
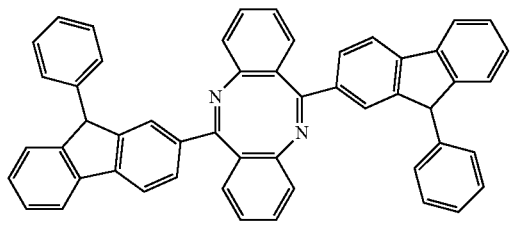
102
199
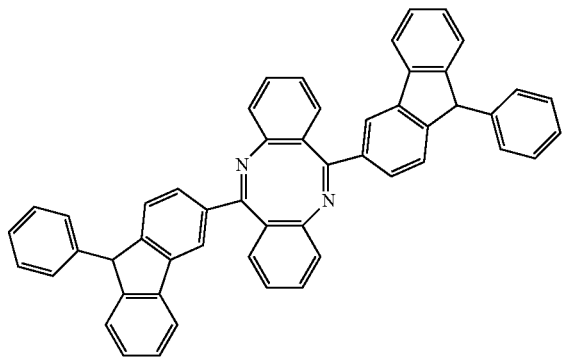
200
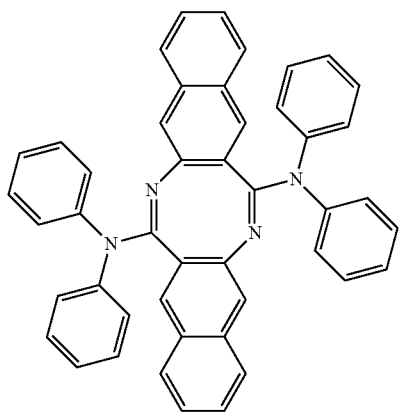
201
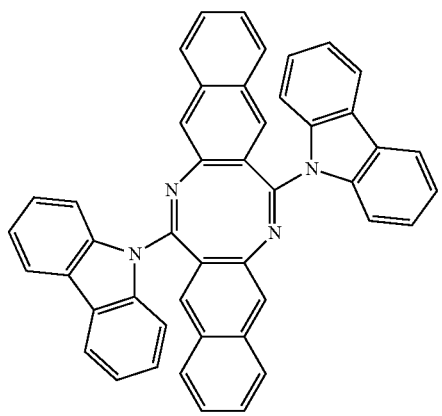
202
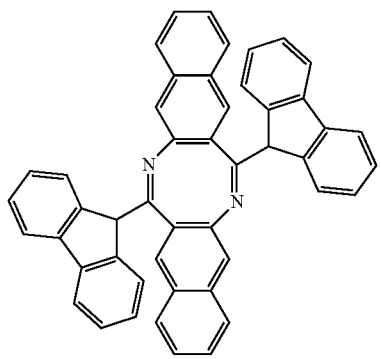
203
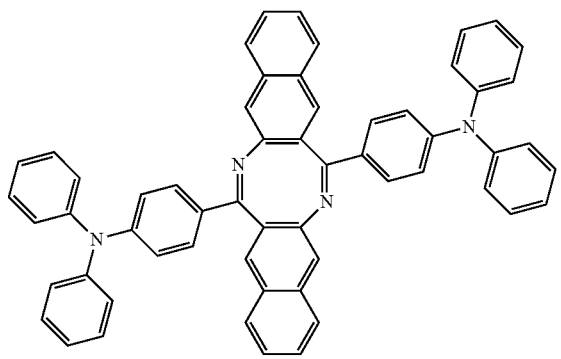
204
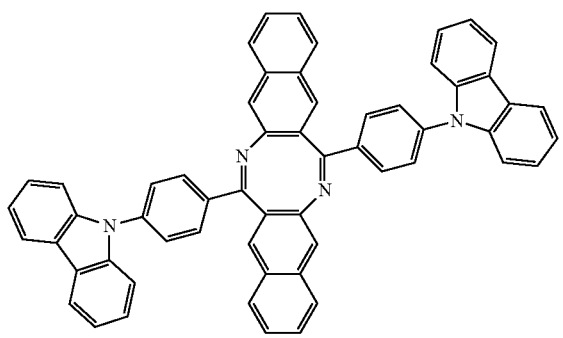
205
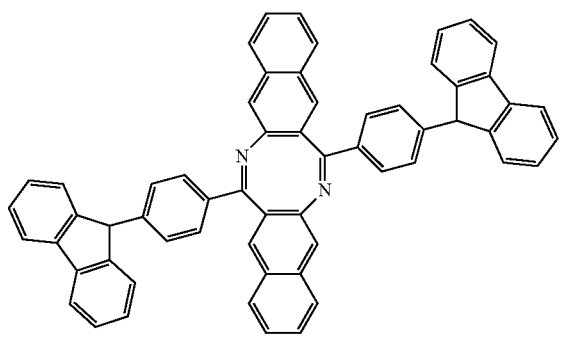

-continued
206
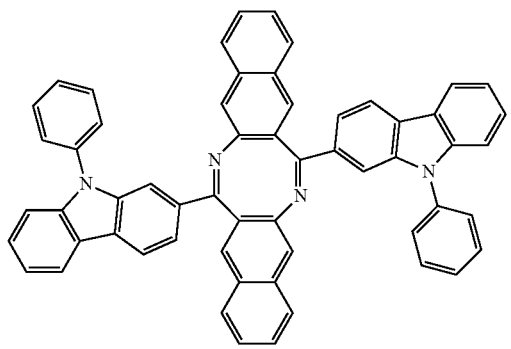
207
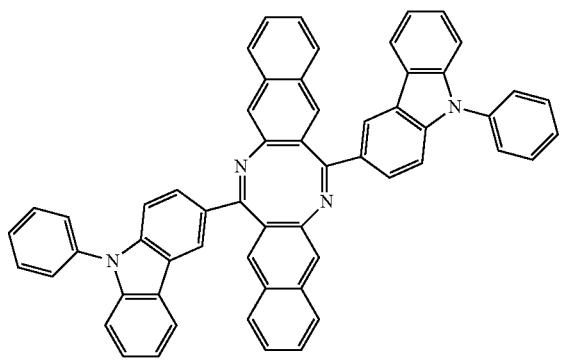
208
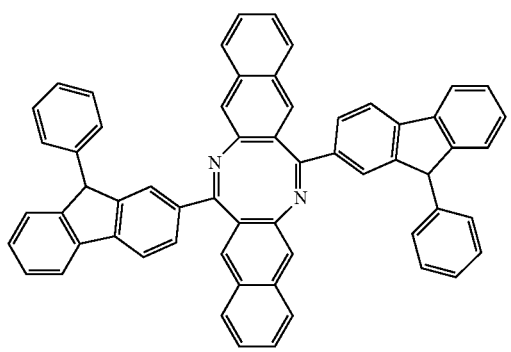
209
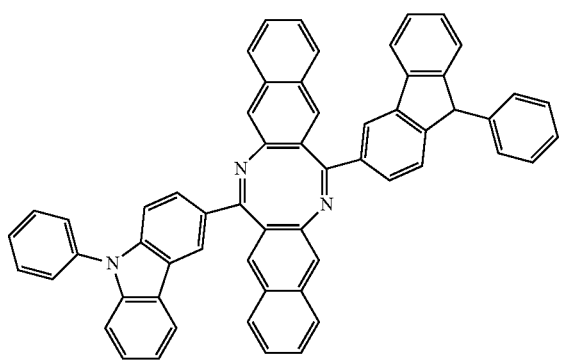
210
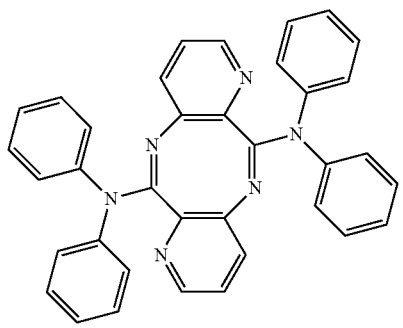
211
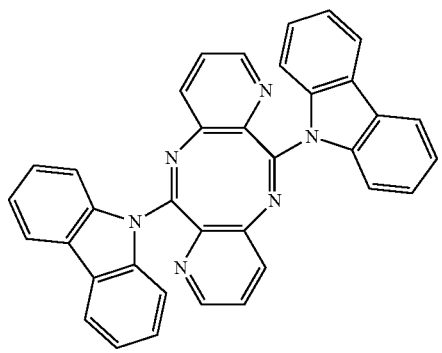
212
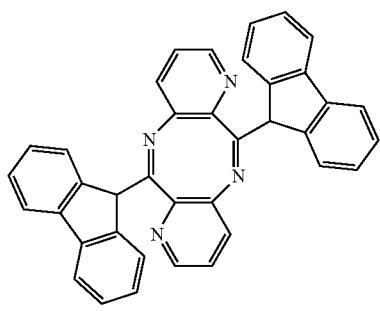
213
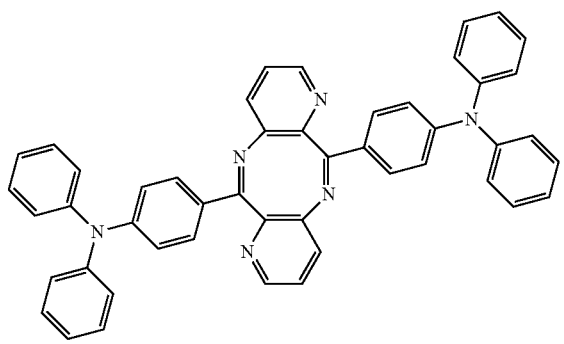

-continued
214 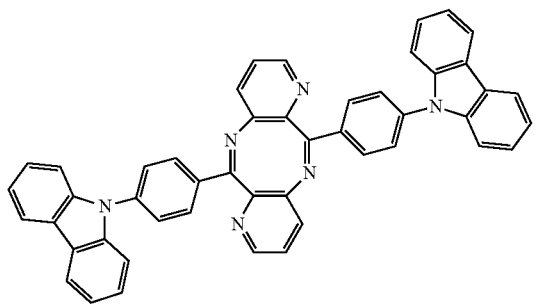
215 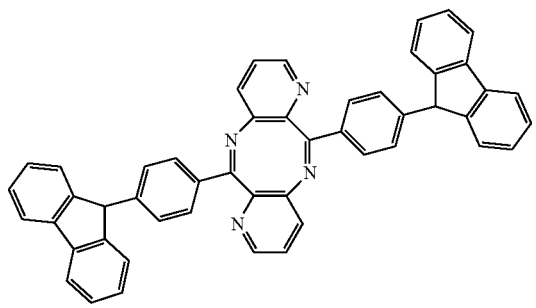
216 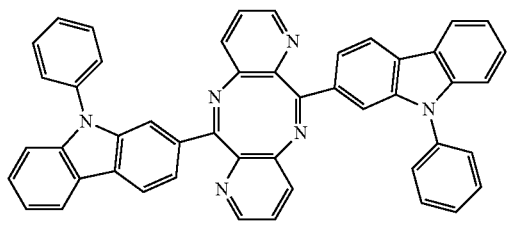
217 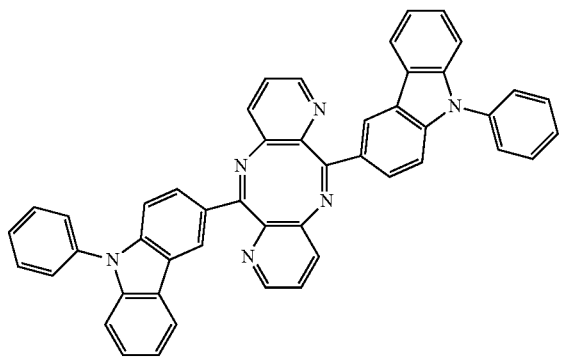
218 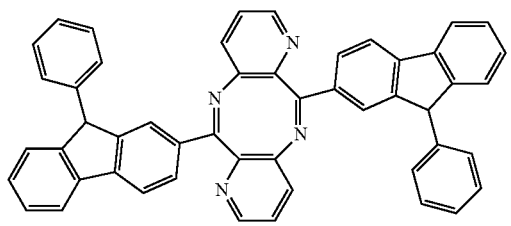
219 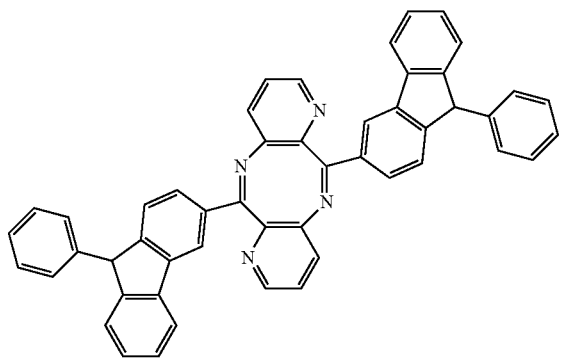
220 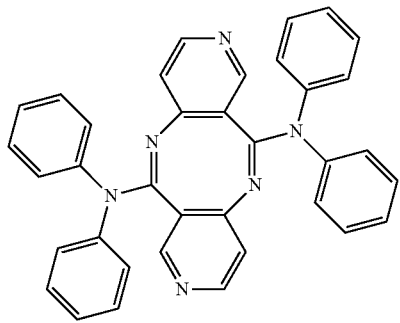
221 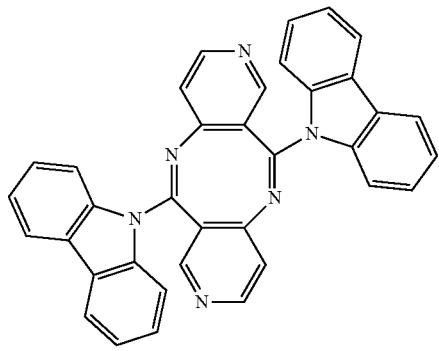

-continued
222
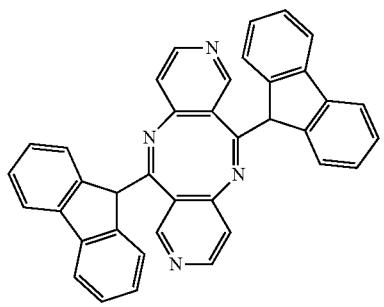
223
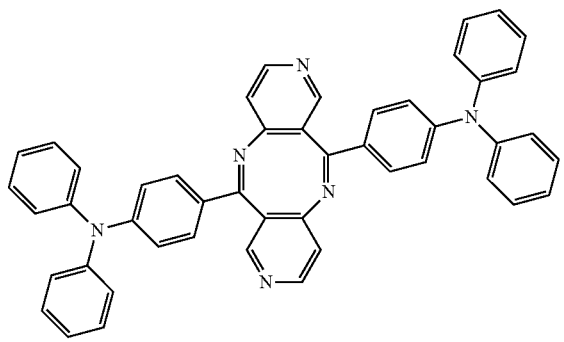
224
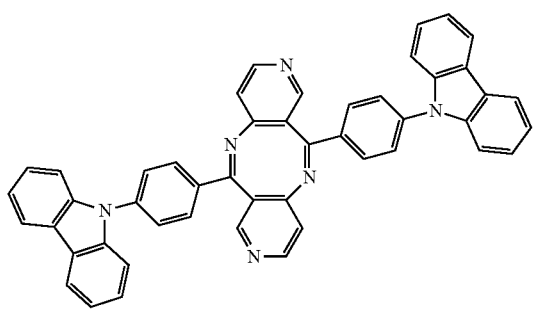
225
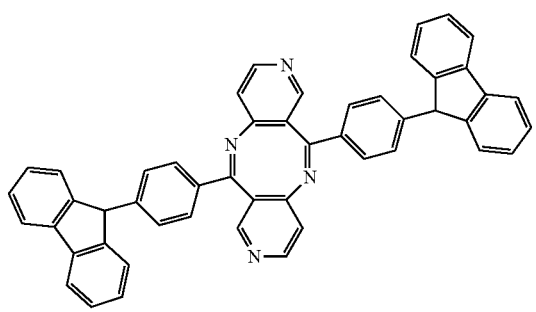
226
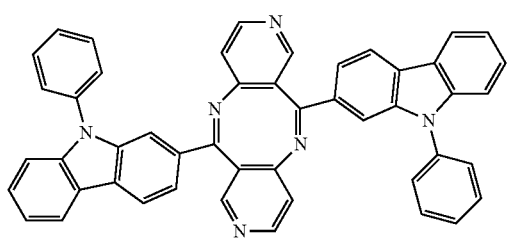
227
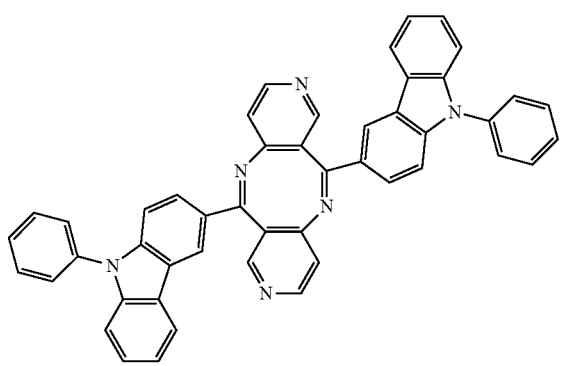
228
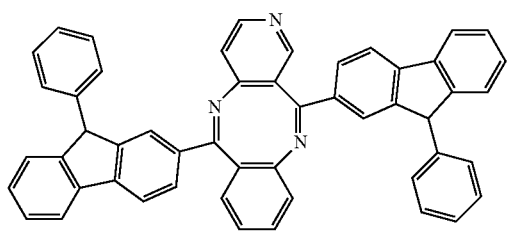
229
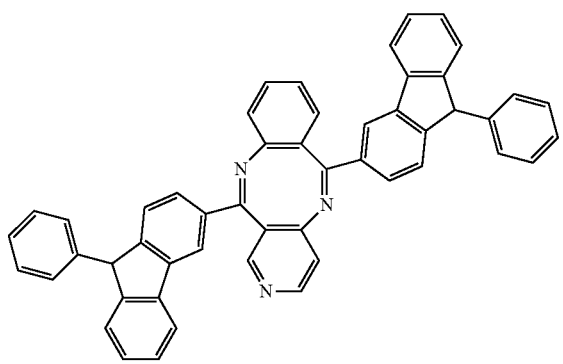

230
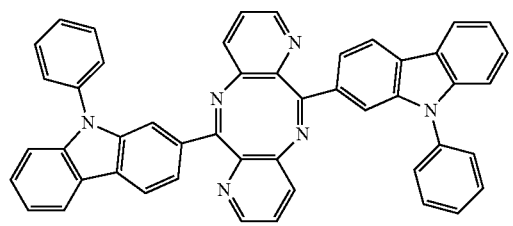
231
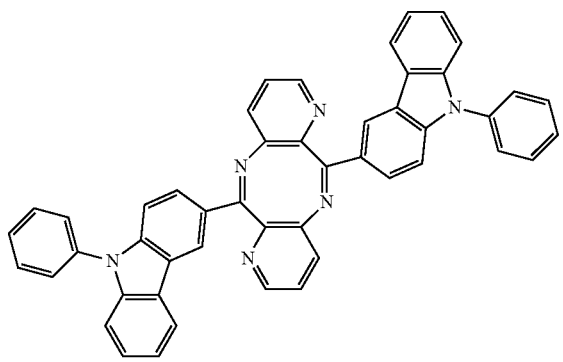
232
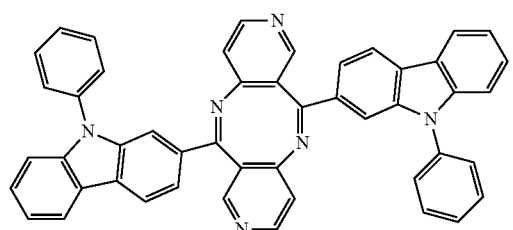
233
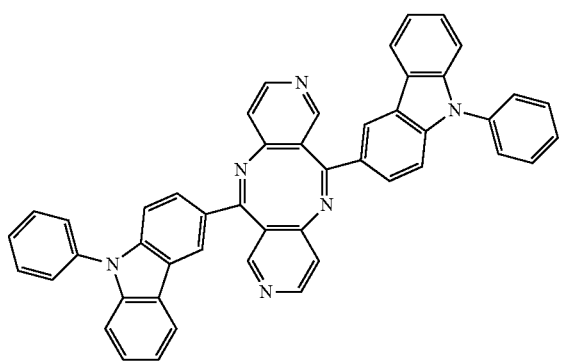
234
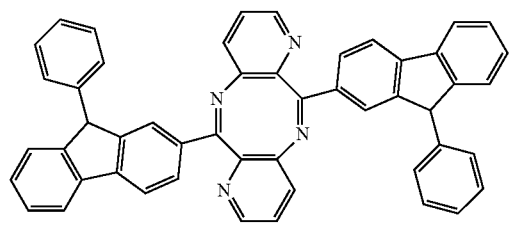
235
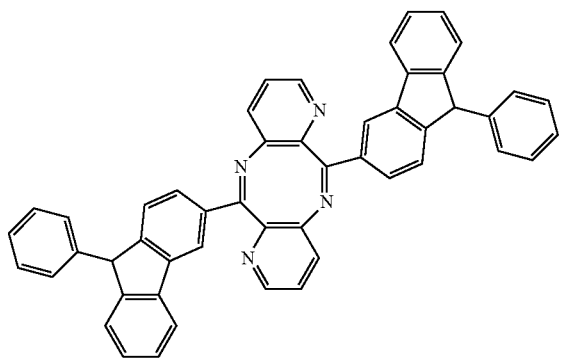
236
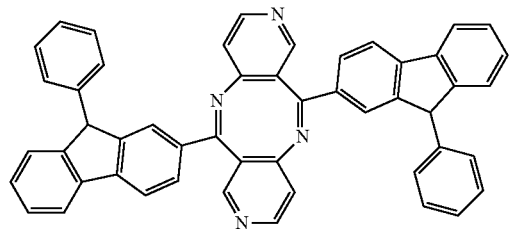
237
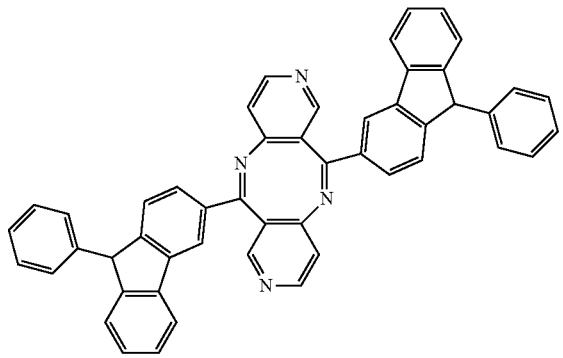

-continued
238
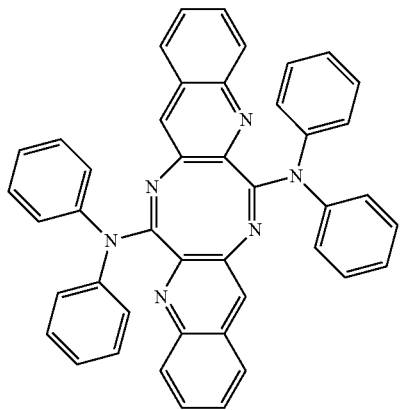
239
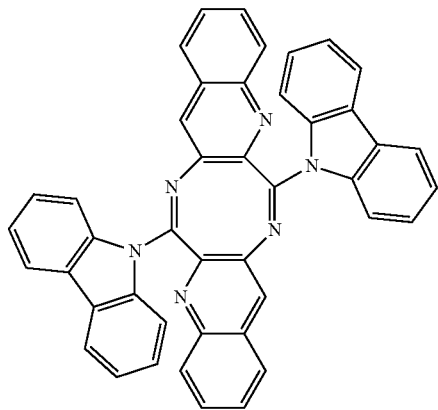
240
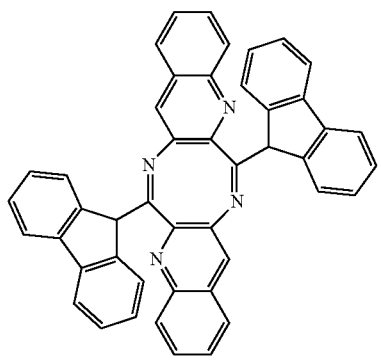
241
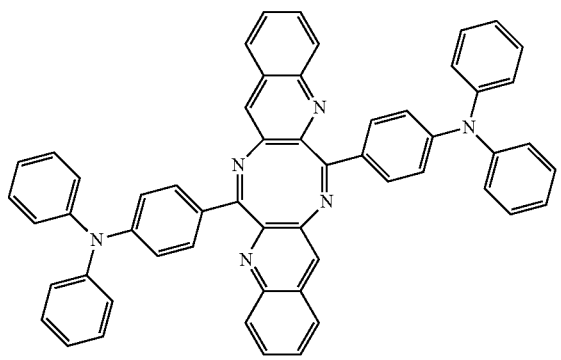
242
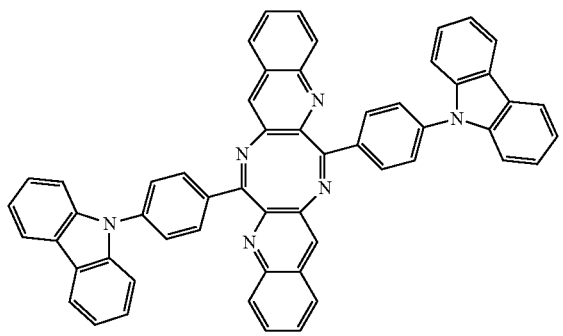
243
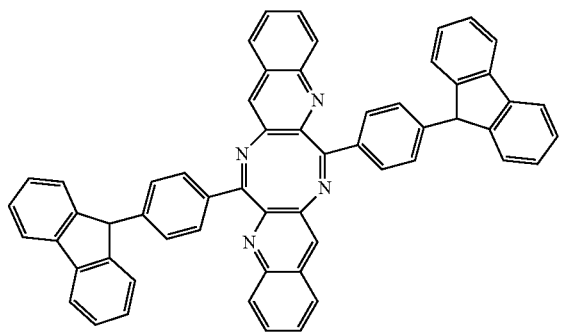
244
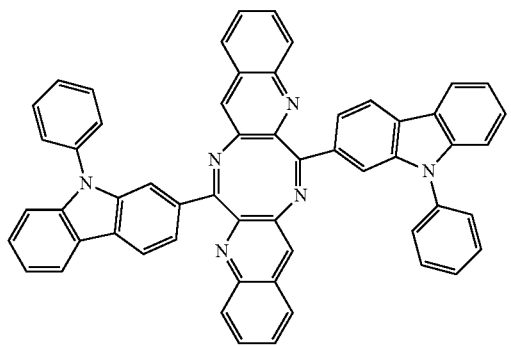
245
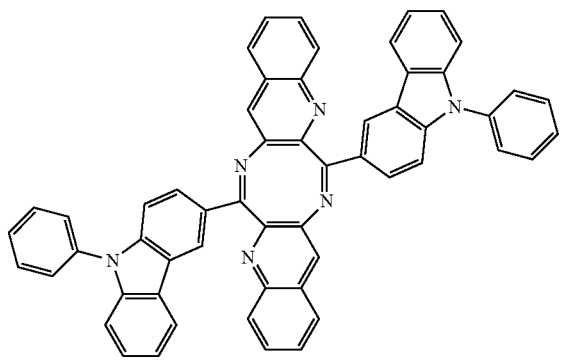

-continued

246

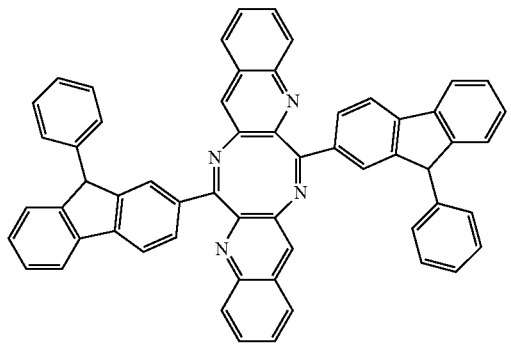

247

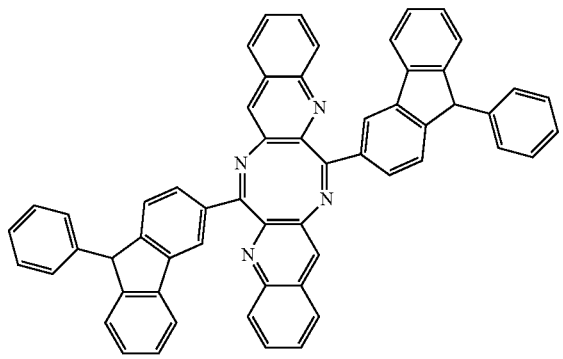

The antiaromatic compound represented by Formula 1 may have a nonplanar structure that is suitable for designing a structure in which a highest occupied molecular orbital (HOMO) energy level and a lowest unoccupied molecular orbital (LUMO) energy level do not overlap. In general, aromatic ring compounds have a perfect planar structure, and thus a substituent may cause less electrical change when formed into a thin film. However, antiaromatic compounds may undergo a large electrical change caused by a substituent when formed into a thin film due to the nonplanar structure thereof. In other words, a change in electrical characteristics of the antiaromatic compounds may be easily controllable with substituents. Due to the nonplanar structure, the antiaromatic compound represented by Formula 1 may have a lower crystallinity compared with aromatic ring compounds having a planar structure, and thus may be desired in terms of mass-production processibility. In general, highly crystalline compounds may cause unnecessary accumulation of materials or clogging of source during deposition processes.

Due to the ease of control of the electrical characteristics of the antiaromatic compound represented by Formula 1, an organic light-emitting device having a high efficiency and a high luminance may be implemented using (utilizing) the antiaromatic compound of Formula 1. In addition, due to the low crystallinity, the antiaromatic compound represented by Formula 1 may be desired in processibilty when used (utilized) to manufacture an organic light-emitting device.

Therefore, an organic light-emitting device using (utilizing) the antiaromatic compound represented by Formula 1 may have a low driving voltage, a high efficiency, and a high luminance.

The antiaromatic compound of Formula 1 may be synthesized using (utilizing) a suitable organic synthesis method. Methods of synthesizing the antiaromatic compound of Formula 1 may be understood by those of ordinary skill in the art based on the examples that will be described below.

The antiaromatic compound of Formula 1 may be used (utilized) between a pair of electrodes of an organic light-emitting device. For example, the antiaromatic compound of Formula 1 may be in an electron transport region, for example, in an electron transport layer.

According to another embodiment of the present disclosure, an organic light-emitting device includes a first electrode, a second electrode disposed opposite to the first electrode, and an organic layer disposed between the first electrode and the second electrode and including an emission layer, wherein the organic layer includes at least one of the antiaromatic compounds of Formula 1 described above.

As used herein, the expression "(the organic layer) includes at least one (or at least one of the) antiaromatic compound(s)" refers to the situation where "(the organic layer) includes one of the antiaromatic compounds of Formula 1, or at least two antiaromatic compounds of Formula 1."

In some embodiments, the organic layer may include only Compound 1 as the antiaromatic compound. In this regard, Compound 1 may be present in the emission layer of the organic light-emitting device. In some embodiments, the organic layer may include Compounds 1 and 2 as the antiaromatic compounds. In this regard, Compounds 1 and 2 may be present both in the same layer (for example, in the emission layer) or may be present in different layers (for example, in the emission layer and the electron transport layer, respectively).

The organic layer may include i) a hole transport region disposed between the first electrode and the emission layer, and including at least one of a hole injection layer, a hole transport layer, a buffer layer, and an electron blocking layer; and ii) an electron transport region disposed between the emission layer and the second electrode, and including at least one of a hole blocking layer, an electron transport layer, and an electron injection layer. The electron transport region may include the antiaromatic compound of Formula 1. For example, the electron transport region may include the electron transport layer, wherein the electron transport layer may include the antiaromatic compound of Formula 1.

As used herein, the term "organic layer" refers to a single layer and/or a plurality of layers disposed between the first and second electrodes of the organic light-emitting device. A material in the "organic layer" is not limited to an organic material.

Hereinafter, a structure of an organic light-emitting device according to an embodiment of the present disclosure and a method of manufacturing the same will now be described with reference to FIG. 1.

FIG. 1 is a schematic sectional view of an organic light-emitting device 10 according to an embodiment of the present disclosure. Referring to FIG. 1, the organic light-emitting device 10 includes a first electrode 110, an organic layer 150, and a second electrode 190.

A substrate may be disposed under the first electrode 110 or on the second electrode 190 in FIG. 1. The substrate may be a glass or transparent plastic substrate with good mechanical strength, thermal stability, transparency, surface smoothness, ease of handling, and/or water resistance.

For example, the first electrode 110 may be formed by depositing or sputtering a first electrode-forming material on the substrate 11. When the first electrode 110 is an anode, a material having a high work function may be used (utilized) as the first electrode-forming material to facilitate hole injection. The first electrode 110 may be a reflective electrode, a semi-transmissive electrode, or a transmissive electrode. Transparent and conductive materials (such as ITO, IZO, $SnO_2$, or ZnO) may be used (utilized) to form the first electrode. The first electrode 110 as a semi-transmissive electrode or a reflective electrode may be formed of at least one material selected from magnesium (Mg), aluminum (Al), aluminum-lithium (Al—Li), calcium (Ca), magnesium-indium (Mg—In), and magnesium-silver (Mg—Ag).

The first electrode 110 may have a single-layer structure or a multi-layer structure including a plurality of layers. For example, the first electrode 110 may have a three-layered structure of ITO/Ag/ITO, but is not limited thereto.

The organic layer 150 may be disposed on the first electrode 110. The organic layer 150 may include an emission layer (EML).

The organic layer 150 may include a hole transport region disposed between the first electrode and the EML, and an electron transport region between the EML and the second electrode.

For example, the hole transport region may include at least one of a hole injection layer (HIL), a hole transport layer (HTL), a buffer layer, and an electron blocking layer (EBL). For example, the electron transport layer may include at least one of a hole blocking layer (HBL), an electron transport layer (ETL), and an electron injection layer (EIL). However, embodiments of the present disclosure are not limited thereto.

The hole transport region may have a single-layered structure including a single material, a single-layered structure including a plurality of materials, or a multi-layered structure including a plurality of layers including different materials.

In some embodiments, the electron transport region may have a single-layered structure including a plurality of materials, or a multi-layered structure of HIL/HTL, HIL/HTL/buffer layer, HIL/buffer layer, HTL/buffer layer, or HIL/HTL/EBL, wherein these layers forming the multi-layered structure are sequentially disposed on the first electrode 110 in the order stated above. However, embodiments of the present disclosure are not limited thereto.

When the hole transport region includes an HIL, the HIL may be formed on the first electrode 110 by using (utilizing) any of a variety of suitable methods, for example, by using (utilizing) vacuum deposition, spin coating, casting, Langmuir-Blodgett (LB) deposition, inkjet printing, laser printing, laser induced thermal imaging (LITI), or the like.

When the HIL is formed using (utilizing) vacuum deposition, the deposition conditions may vary depending on the material that is used (utilized) to form the HIL and the structure of the HIL. For example, the deposition conditions may be selected from the following conditions: a deposition temperature of about 100° C. to about 500° C., a degree of vacuum of about $10^{-8}$ to about $10^{-3}$ torr, and a deposition rate of about 0.01 to 100 Å/sec.

When the HIL is formed using (utilizing) spin coating, the coating conditions may vary depending on the material that is used (utilized) to form the HIL and the structure of the HIL. For example, the coating conditions may be selected from the following conditions: a coating rate of about 2,000 rpm to about 5,000 rpm, and a heat treatment temperature of about 800° C. to about 200° C.

When the hole transport region includes an HTL, the HTL may be formed on the first electrode 110 or the HIL by using (utilizing) any of a variety of suitable methods, for example, by using (utilizing) vacuum deposition, spin coating, casting, Langmuir-Blodgett (LB) deposition, inkjet printing, laser printing, laser induced thermal imaging (LITI), or the like. When the HTL is formed using (utilizing) vacuum deposition or spin coating, the conditions for deposition and coating may be similar to the above-described deposition and coating conditions for forming the HIL, and accordingly will not be described in more detail.

In some embodiments, the hole transport region may include at least one of m-MTDATA, TDATA, 2-TNATA, NPB, β-NPB, TPD, Spiro-TPD, Spiro-NPB, α-NPB, TAPC, HMTPD, 4,4',4"-tris(N-carbazolyl)triphenylamine (TCTA), polyaniline/dodecylbenzene sulfonic acid (Pani/DBSA), poly(3,4-ethylenedioxythiophene)/poly(4-styrenesulfonate) (PEDOT/PSS), polyaniline/camphor sulfonic acid (Pani/CSA), polyaniline/poly(4-styrenesulfonate) (PANI/PSS), a compound represented by Formula 201, and a compound represented by Formula 202.

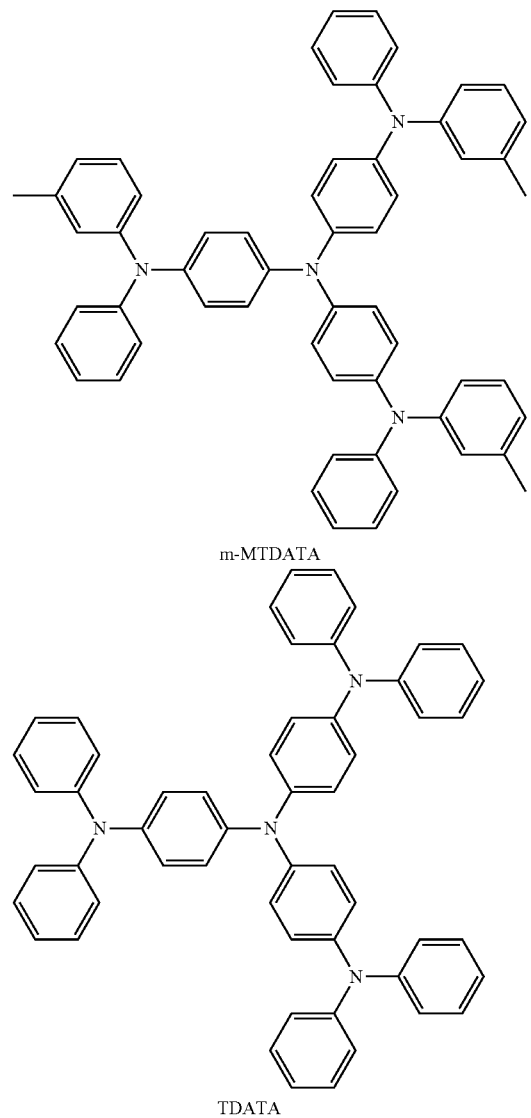

m-MTDATA

TDATA

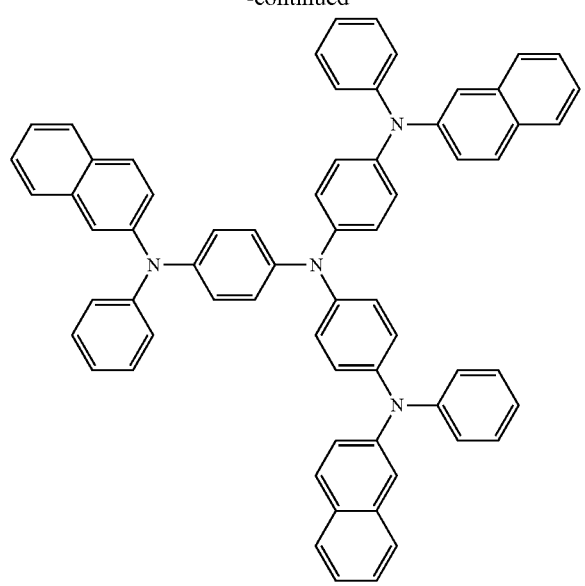
2-TNATA
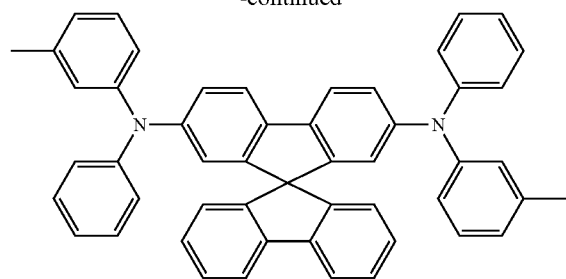
Spiro-TPD
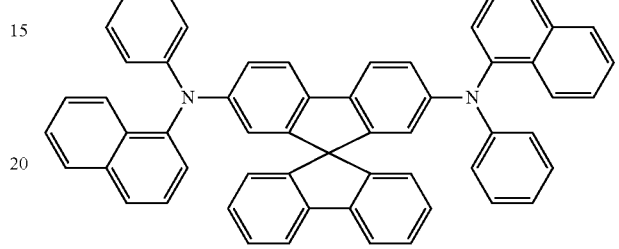
Spiro-NPB
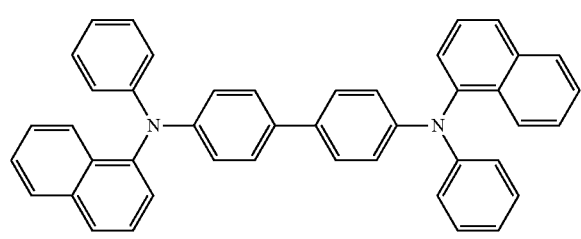
NPB
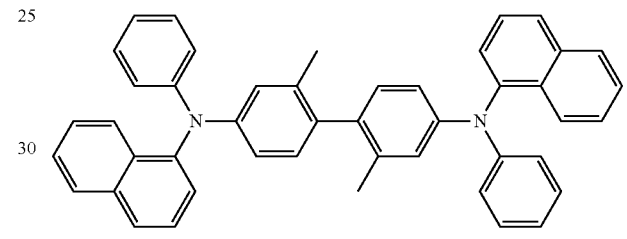
α-NPB
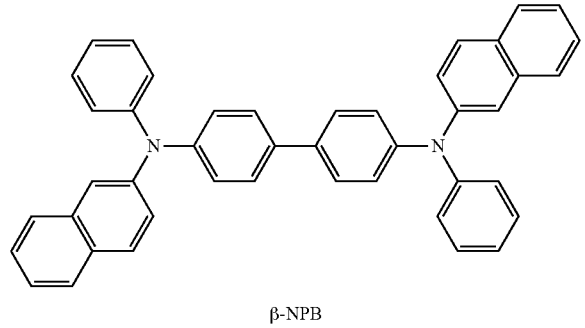
β-NPB
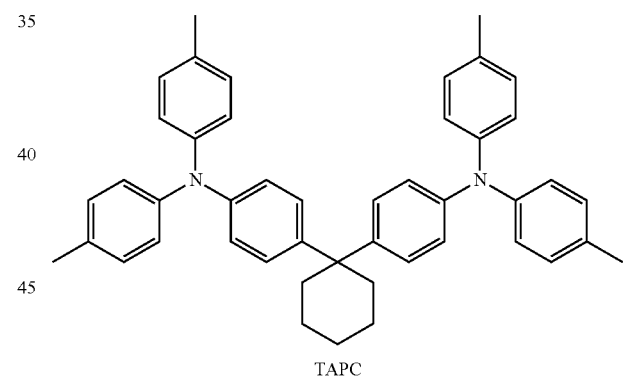
TAPC
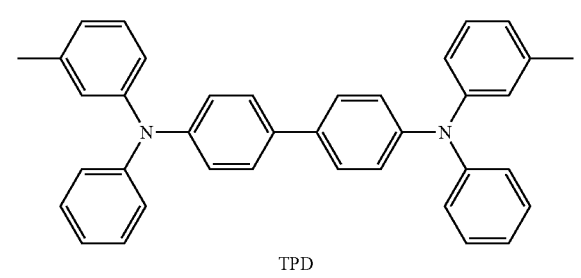
TPD
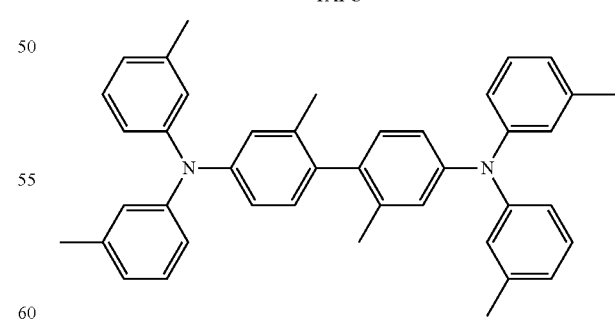
HMTPD
Formula 201
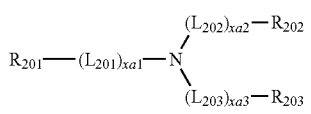

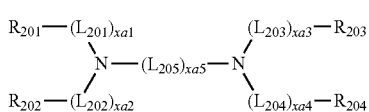

Formula 202

In Formulae 201 and 202, descriptions for $L_{201}$ to $L_{205}$ may be each independently the same as the descriptions for $L_1$ in Formula 1;

xa1 to xa4 may be each independently selected from 0, 1, 2, and 3;

xa5 may be selected from 1, 2, 3, 4, and 5; and descriptions for $R_{201}$ to $R_{205}$ may be each independently the same as the descriptions for $R_{11}$ described above.

For example, in Formulae 201 and 202, $L_{201}$ to $L_{205}$ may be each independently selected from:

a phenylene group, a naphthylene group, a fluorenylene group, a spiro-fluorenylene group, a fluorene group, a difluorene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group;

xa1 to xa4 may be each independently 0, 1, or 2;

xa5 may be 1, 2, or 3;

$R_{201}$ to $R_{205}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group. However, embodiments of the present disclosure are not limited thereto.

The compound of Formula 201 may be represented by Formula 201A:

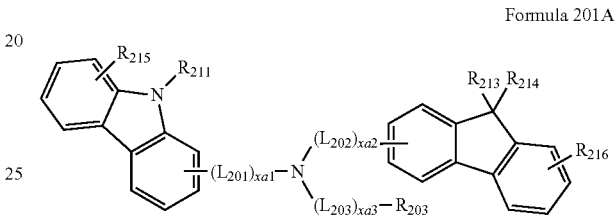

Formula 201A

For example, the compound of Formula 201 may be represented by Formula 201A-1, but is not limited thereto:

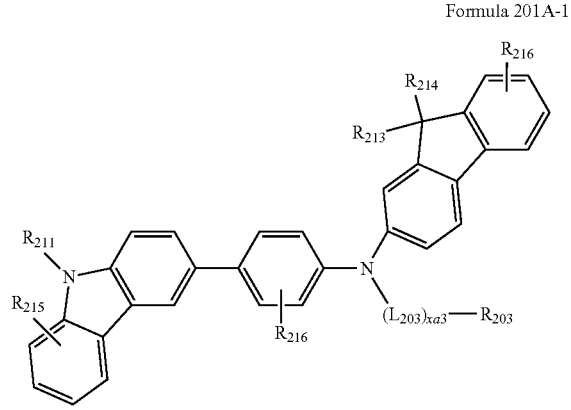

Formula 201A-1

The compound of Formula 202 may be represented by Formula 202A, but is not limited thereto:

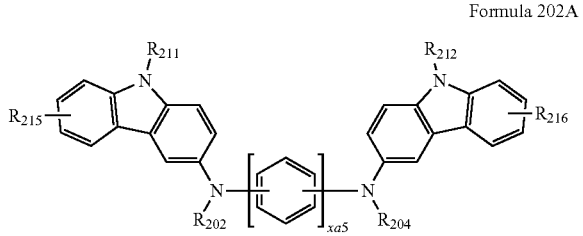

Formula 202A

In Formulae 201A, 201A-1, and 202A, descriptions for $L_{201}$ to $L_{203}$, xa1 to xa3, xa5, and $R_{202}$ to $R_{204}$ may be the same as those described in conjunction with Formula 201;

descriptions for $R_{211}$ may be the same as the descriptions for $R_{203}$ in Formula 201; and $R_{213}$ to $R_{216}$ may be each independently selected from a hydrogen atom, a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, $C_2$-$C_{60}$ alkenyl group, $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a non-aromatic condensed polycyclic group, and a non-aromatic condensed heteropolycyclic group.

For example, in Formulae 201A, 201A-1, and 202A, $L_{201}$ to $L_{203}$ may be each independently selected from:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{20}$ group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xa1 to xa3 may be each independently 0 or 1;

$R_{203}$, $R_{211}$, and $R_{212}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{213}$ and $R_{214}$ may be each independently selected from:

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{215}$ and $R_{216}$ may be each independently selected from:

a hydrogen atom, a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, and a phosphoric acid group or a salt thereof;

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and xa5 may be 1 or 2.

In Formulae 201A and 201A-1, $R_{213}$ and $R_{214}$ may be linked to each other to form a saturated or unsaturated ring.

The compound represented by Formula 201, and the compound represented by Formula 202 may be compounds HT1 to HT20 illustrated below, but they are not limited thereto.

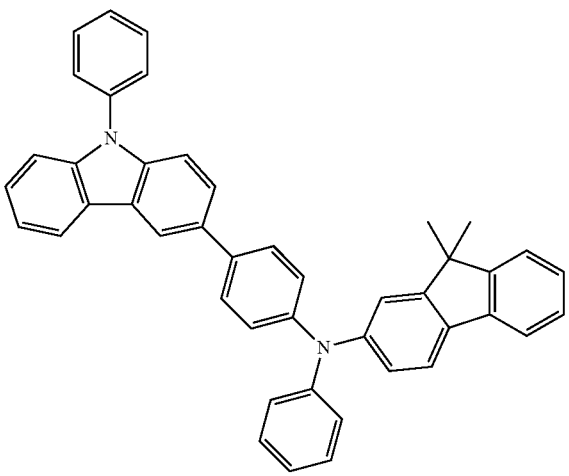

HT1

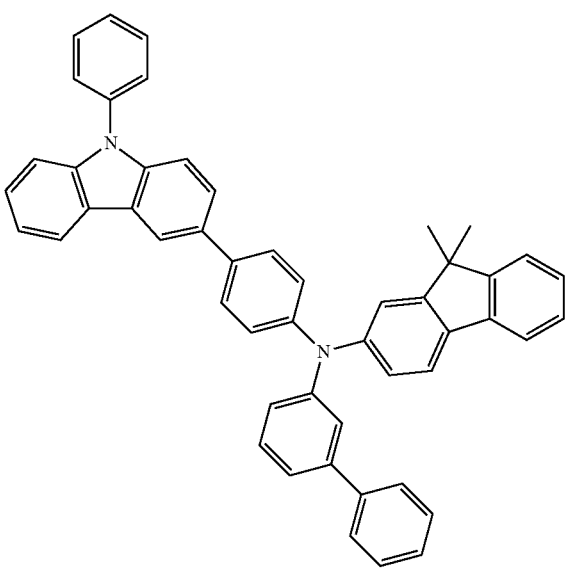

HT2

-continued
HT3
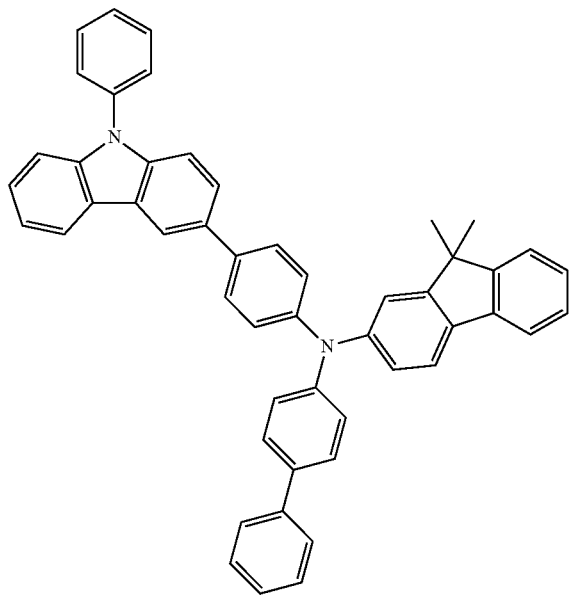
HT5
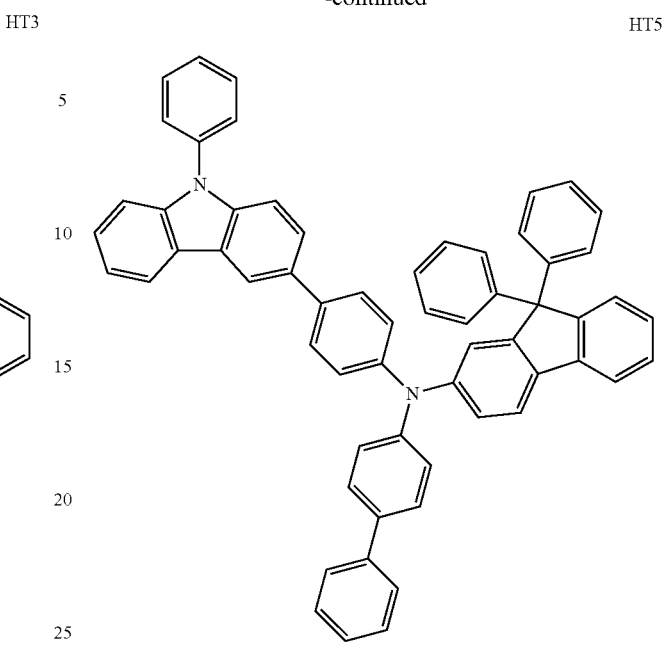
HT4
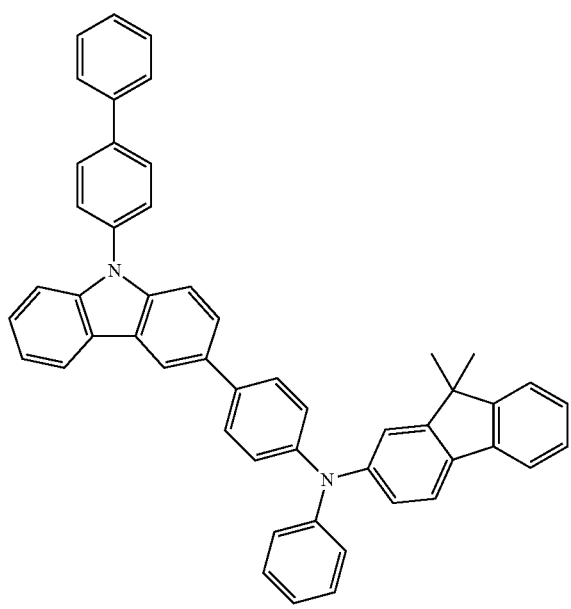
HT6

-continued
HT7
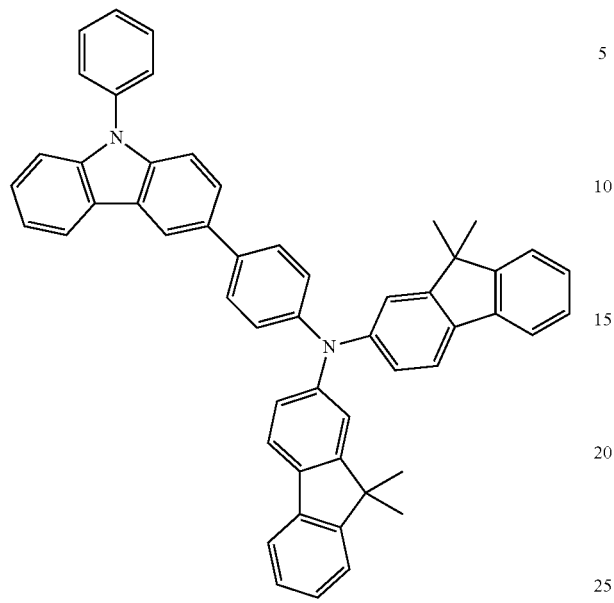
HT8
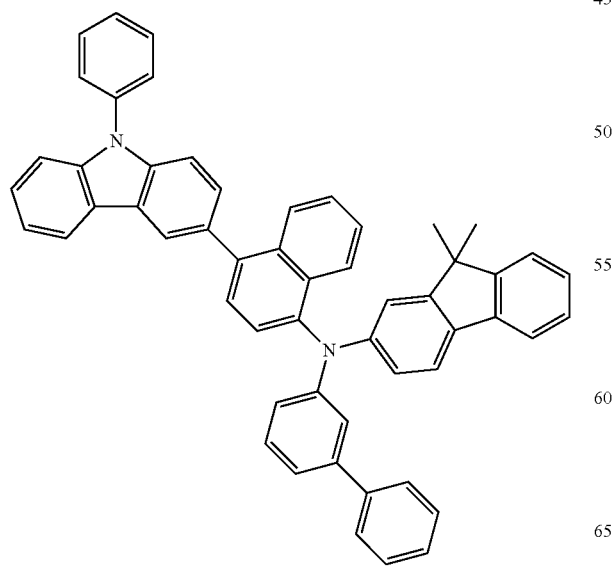
-continued
HT9
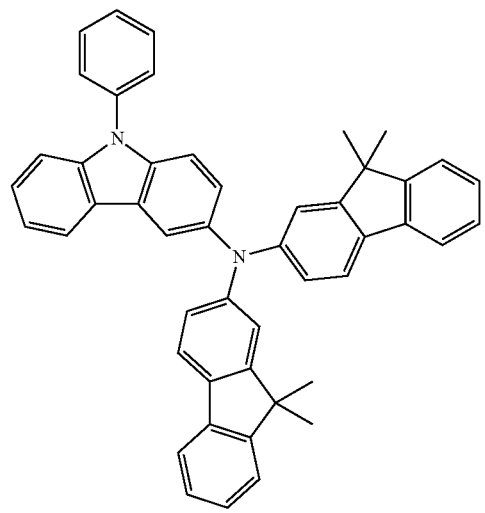
HT10
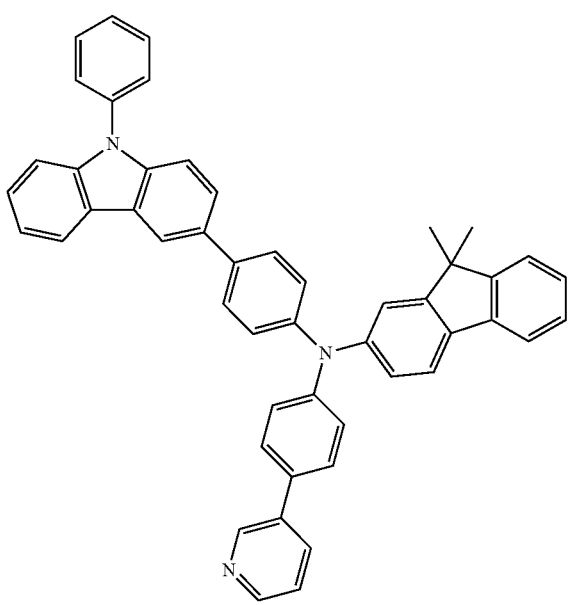

HT11
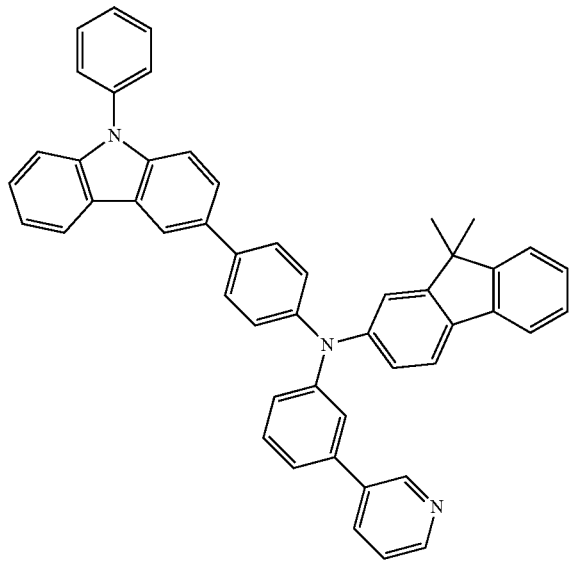
HT12
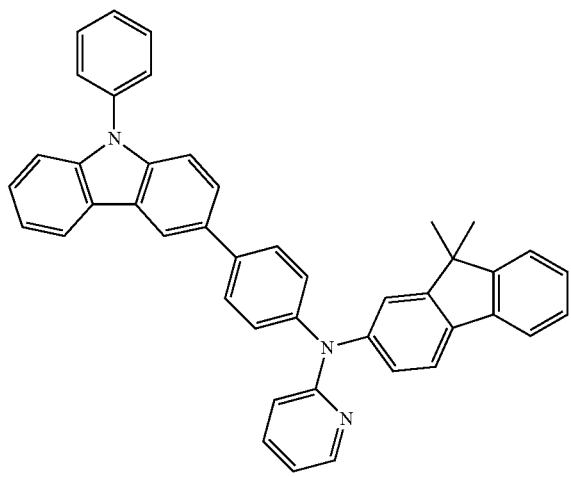
HT13
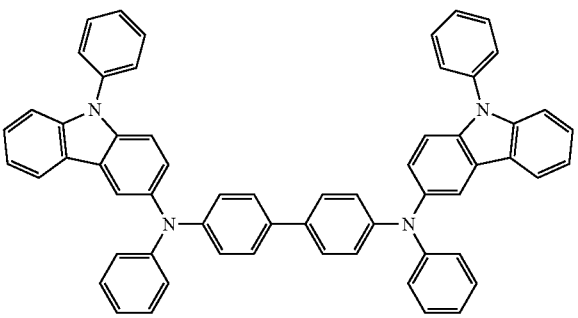
HT14
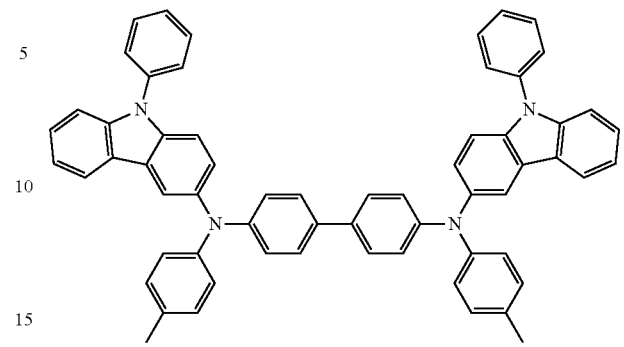
HT15
HT16
HT17
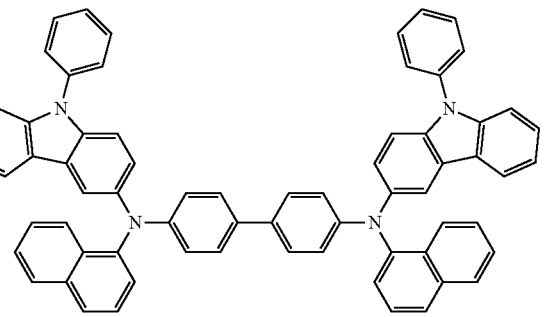

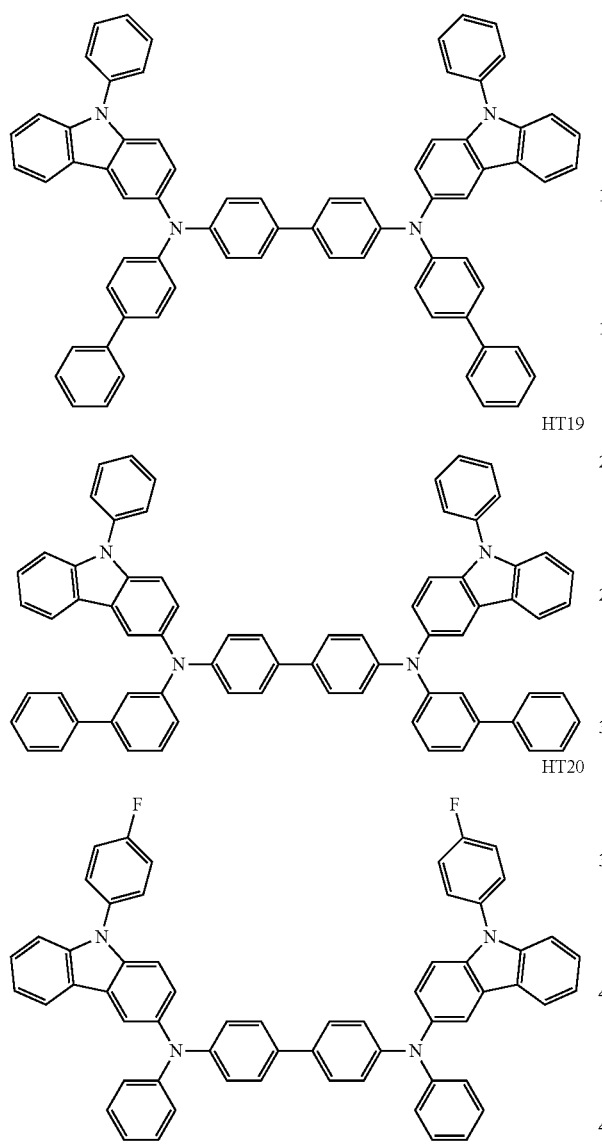

HT18

HT19

HT20

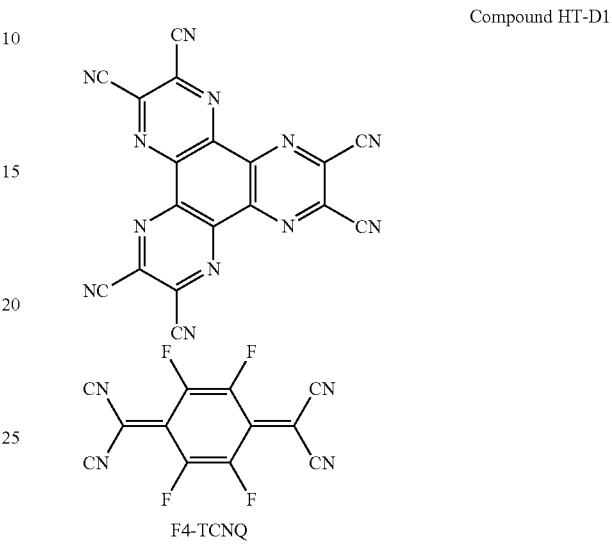

Compound HT-D1

F4-TCNQ

A thickness of the hole transport region may be from about 100 Å to about 10000 Å, and in some embodiments, from about 100 Å to about 1000 Å. When the hole transport region includes an HIL and an HTL, a thickness of the HIL may be from about 100 Å to about 10,000 Å, and in some embodiments, from about 100 Å to about 1,000 Å; and a thickness of the HTL may be from about 50 Å to about 2,000 Å, and in some embodiments, from about 100 Å to about 1,500 Å. In one embodiment, when the thicknesses of the hole transport region, the HIL, and the HTL are within these ranges, satisfactory hole transport characteristics are obtained without a substantial increase in driving voltage.

The hole transport region may further include a charge-generating material to improve the conductivity, in addition to the materials described above. The charge-generating material may be homogeneously or inhomogeneously dispersed in the hole transport region.

The charge-generating material may be, for example, a p-dopant. The p-dopant may be one of quinine derivatives, metal oxides, and compounds with a cyano group, but is not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-TCNQ), or the like; metal oxides such as tungsten oxide, molybdenum oxide, or the like; and Compound HT-D1.

The hole transport region may further include at least one of a buffer layer and an EBL, in addition to the HIL and HTL described above. The buffer layer may compensate for an optical resonance distance of light according to a wavelength of the light emitted from the EML, and thus may improve the light-emission efficiency. A material in the buffer layer may be any suitable material used (utilized) in the hole transport region. The EBL may reduce or block migration of electrons from the electron transport region into the EML.

The EML may be formed on the first electrode 110 or the hole transport region by using (utilizing) any of a variety of suitable methods, for example, by using (utilizing) vacuum deposition, spin coating, casting, Langmuir-Blodgett (LB) deposition, inkjet printing, laser printing, laser induced thermal imaging (LITI), or the like. When the EML is formed using (utilizing) vacuum deposition or spin coating, the deposition and coating conditions for forming the EML may be similar to the above-described deposition and coating conditions for forming the HIL, and accordingly will not be described in more detail When the organic light-emitting device 10 is a full color organic light-emitting device, the EML may be patterned into a red emission layer, a green emission layer, and a blue emission layer to correspond to individual subpixels, respectively. In some embodiments, the EML may have a structure in which a red emission layer, a green emission layer and a blue emission layer are stacked upon one another; or a structure including a mixture of a red light-emitting material, a green light-emitting material, and a blue light-emitting material, and thus may emit white light.

The EML may include a host and a dopant.

The host may include at least one selected from TPBi, TBADN, ADN (also referred to as "DNA"), CBP, CDBP, and TCP:

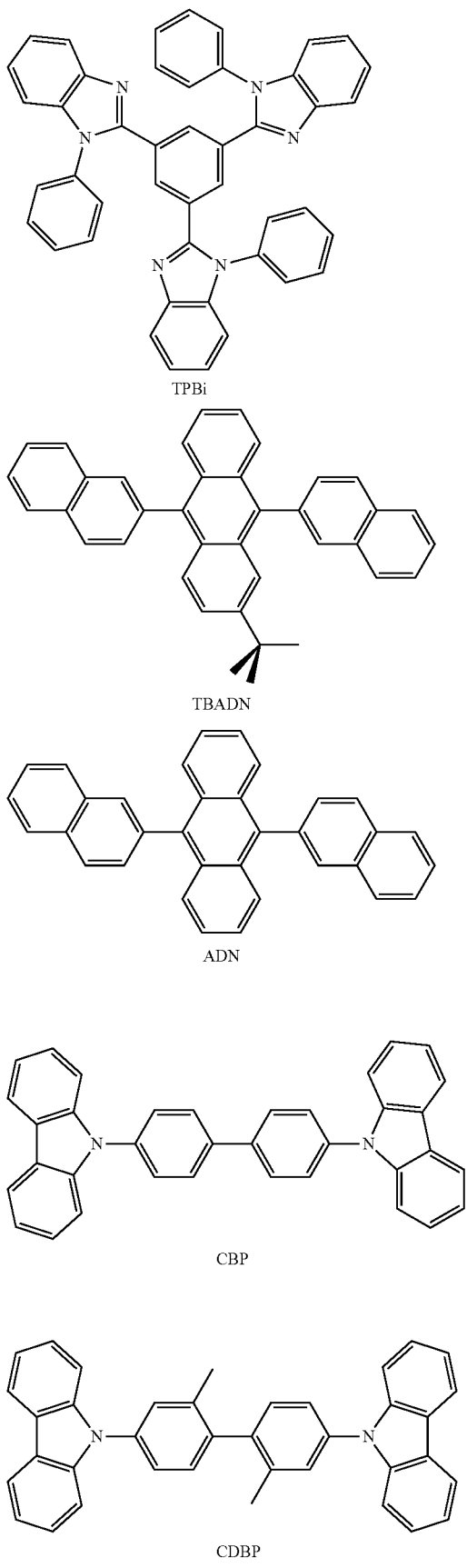

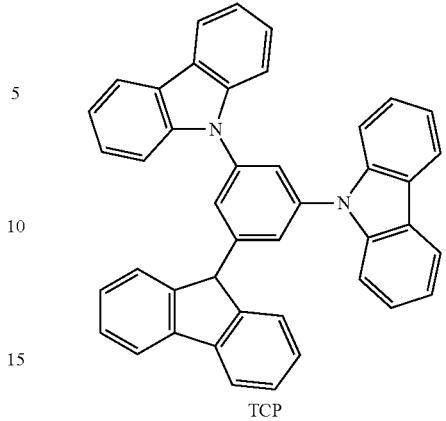

In some embodiments, the host may include a compound represented by Formula 301.

$$Ar_{301}\text{-}[(L_{301})_{xb1}\text{-}R_{301}]_{xb2}$$ Formula 301

In Formula 301, $Ar_{301}$ may be selected from:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene;

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one selected from a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a non-aromatic condensed polycyclic group, a non-aromatic condensed heteropolycyclic group, and —Si($Q_{301}$)($Q_{302}$)($Q_{303}$) (where $Q_{301}$ to $Q_{303}$ may be each independently selected from a hydrogen atom, a $C_1$-$C_{60}$ alkyl group, $C_2$-$C_{60}$ alkenyl group, a $C_6$-$C_{60}$ aryl group, and $C_2$-$C_{60}$ heteroaryl group);

descriptions for $L_{301}$ may be the same as the descriptions for $L_{201}$ in Formula 201;

$R_{301}$ may be selected from:

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xb1 may be selected from 0, 1, 2, and 3; and xb2 may be selected from 1, 2, 3, and 4.

For example, in Formula 301, $L_{301}$ may be selected from:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, each substituted with at least one selected from a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and $R_{301}$ may be selected from:

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one selected from a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group. However, embodiments of the present disclosure are not limited thereto.

For example, the host may include a compound represented by Formula 301A:

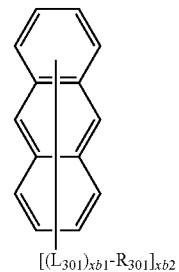

Formula 301A $[(L_{301})_{xb1}\text{-}R_{301}]_{xb2}$

Substituents in Formula 301A may be the same as those defined above herein.

The compound of Formula 301 may include at least one of Compounds H1 to H42, but is not limited thereto:

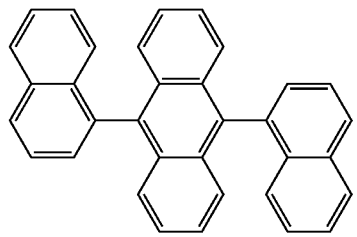

H1

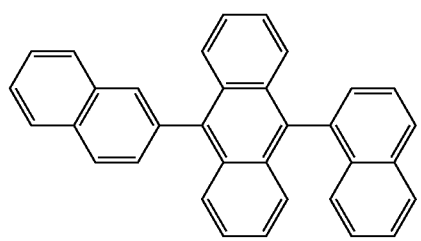

H2

H3
H4
H5
H6
H7
H8
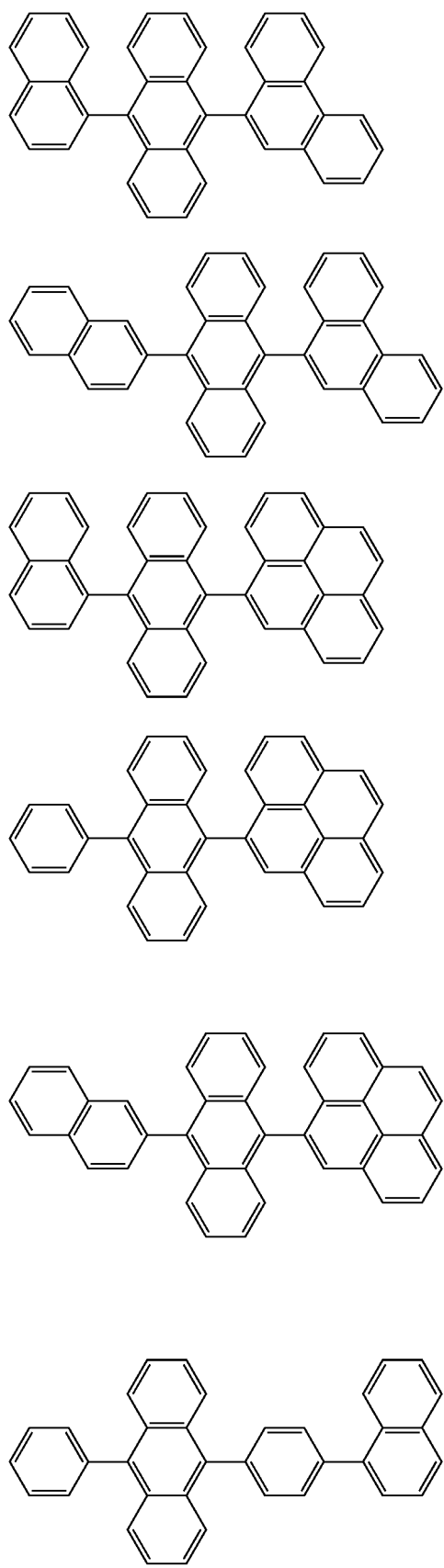
H9
H10
H11
H12
H13
H14
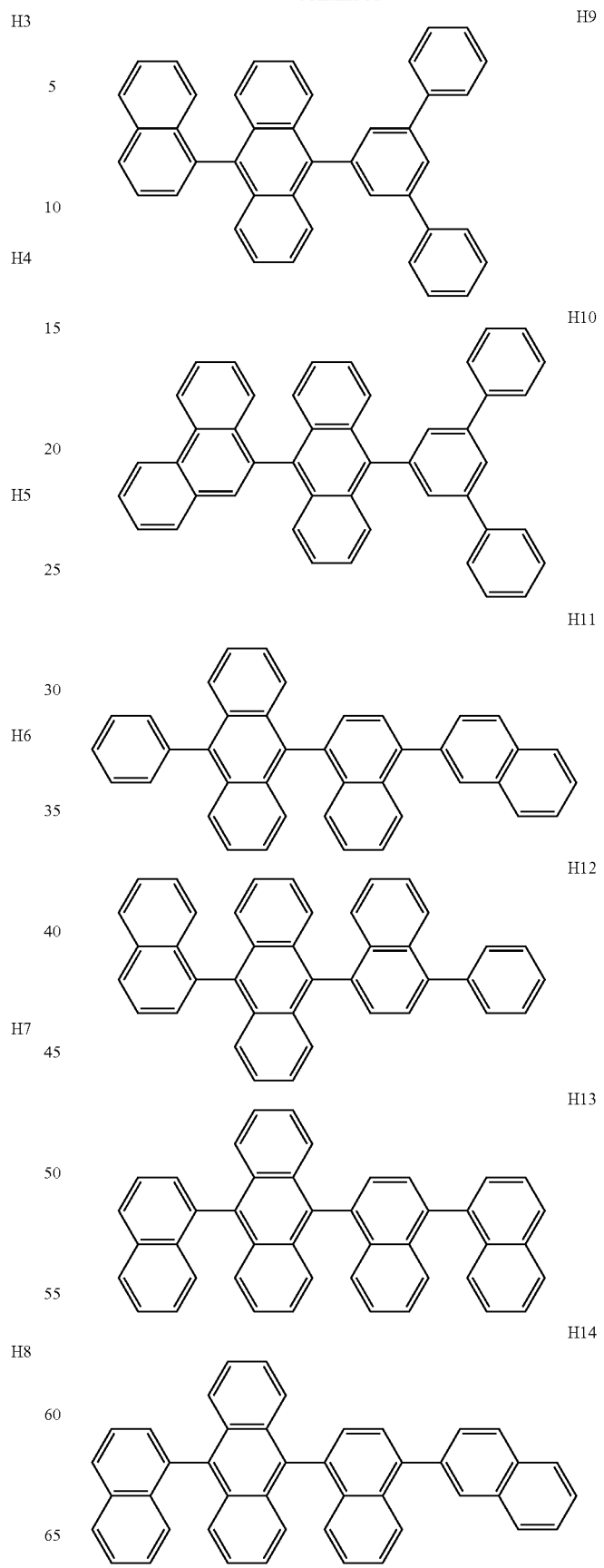

H15
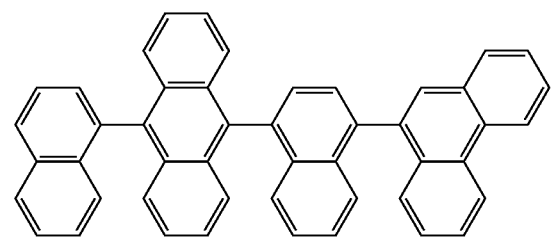
H16
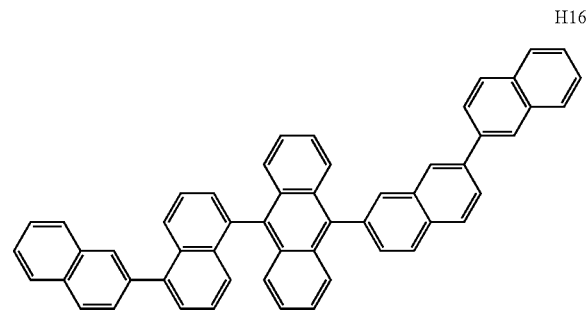
H17
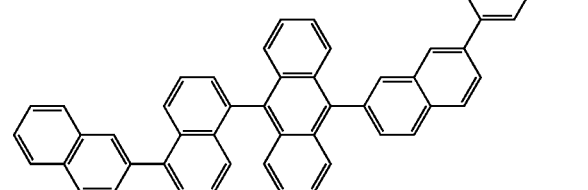
H18
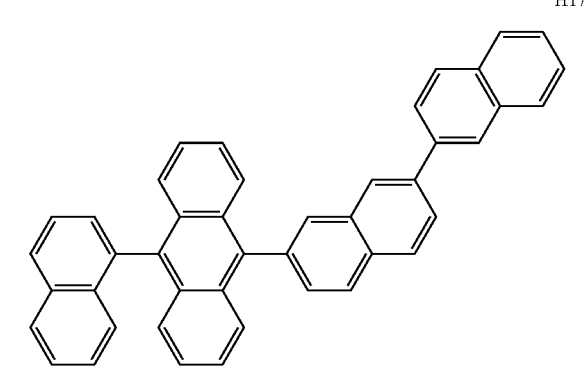
H19
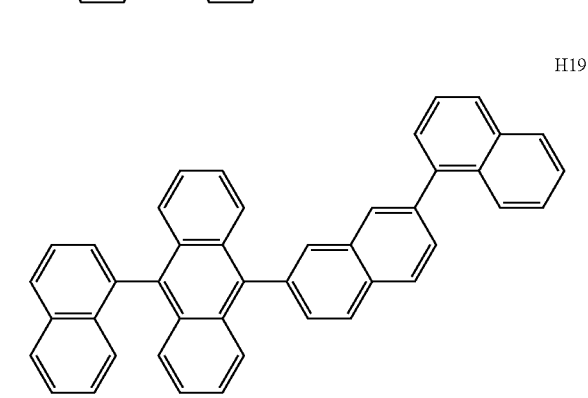
H20
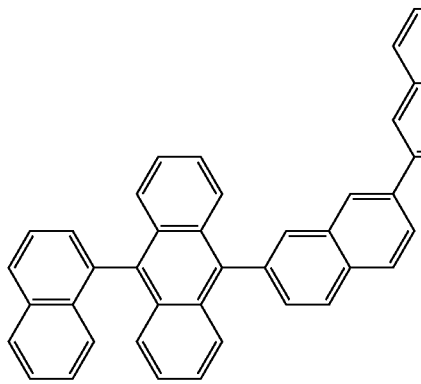
H21
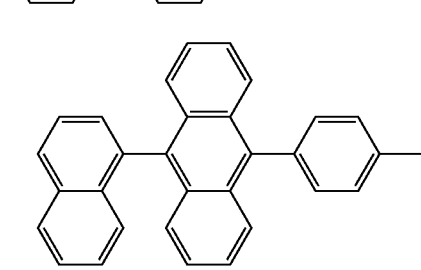
H22
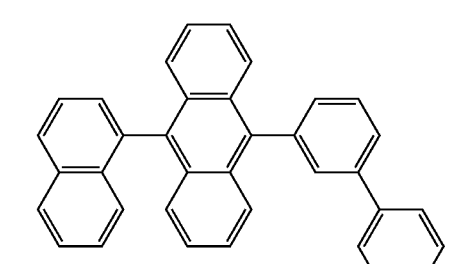
H23
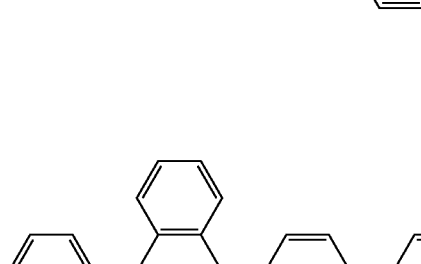
H24
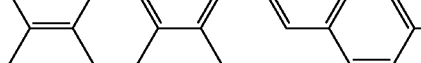

-continued
H25
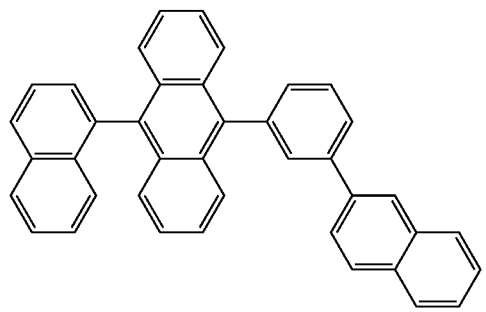
H26
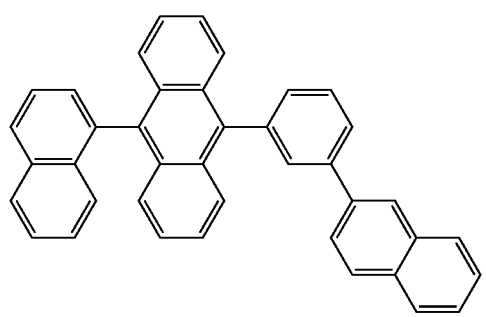
H27
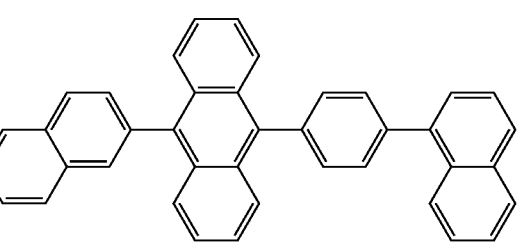
H28
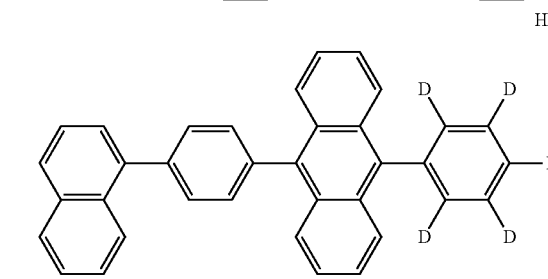
H29
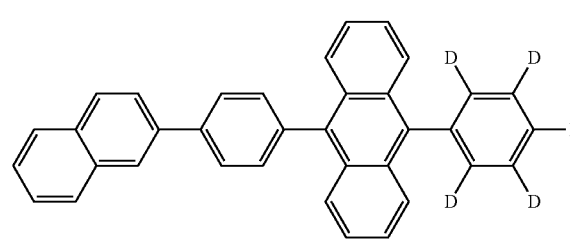
H30
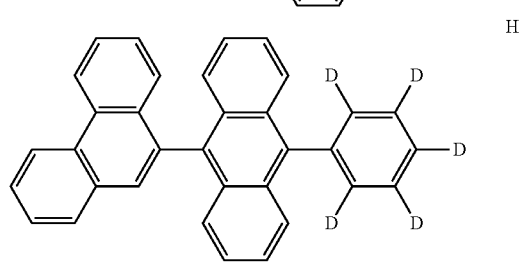
-continued
H31
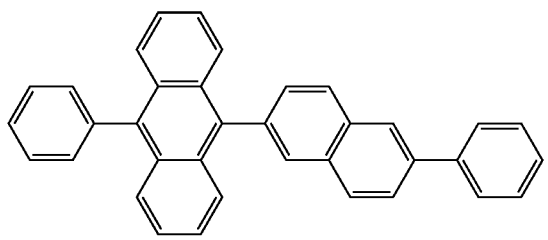
H32
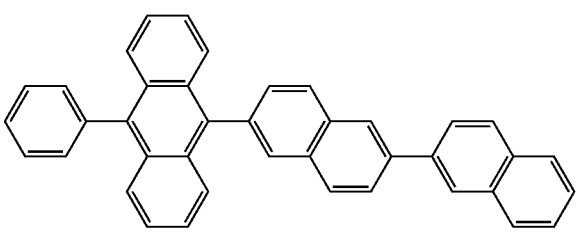
H33
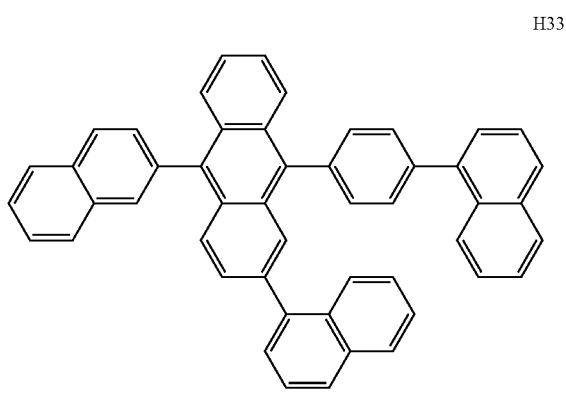
H34
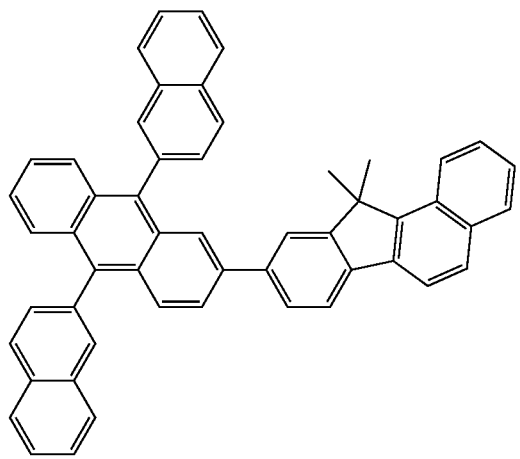

143
-continued
H35
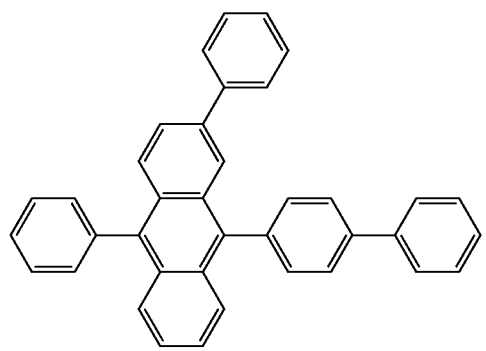
H36
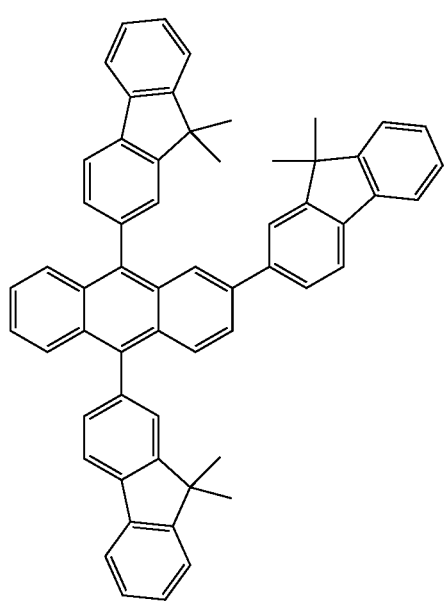
H37
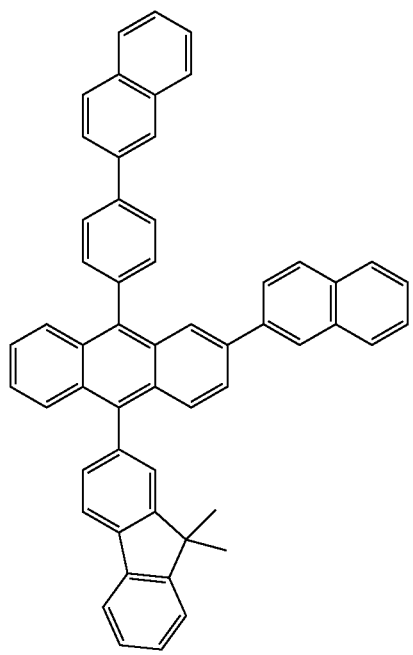
144
-continued
H38
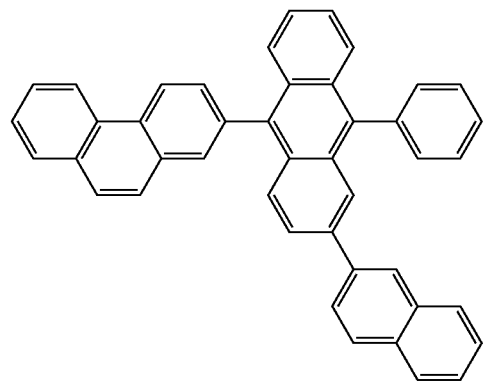
H39
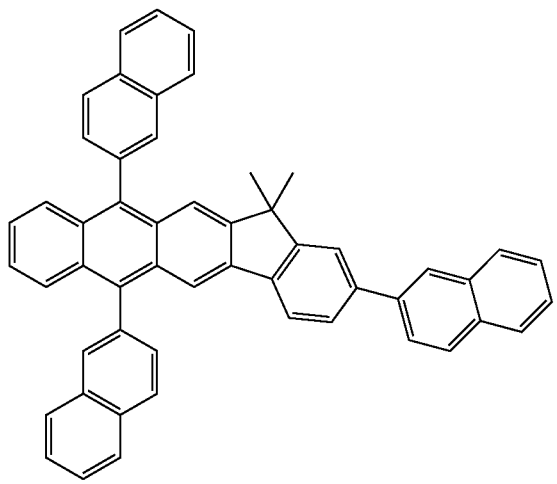
H40
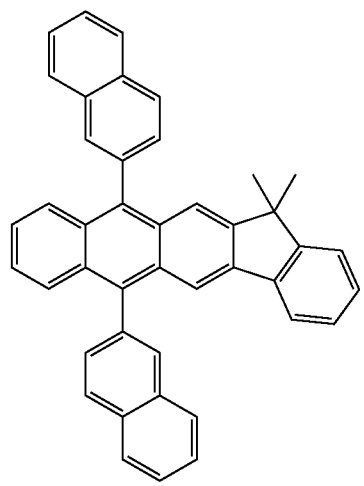

H41
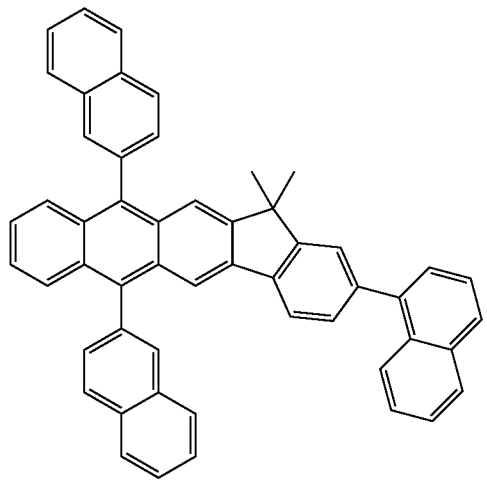
H42
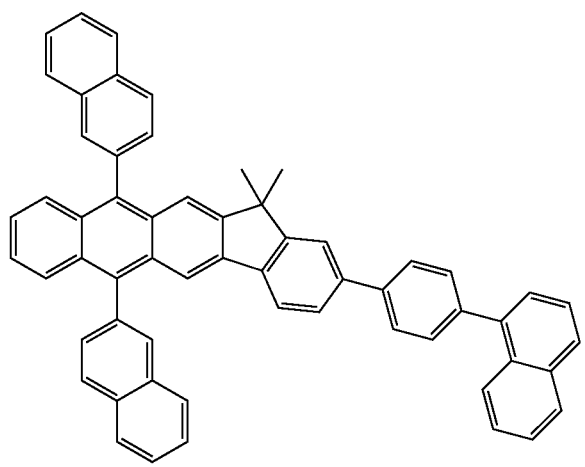
H44
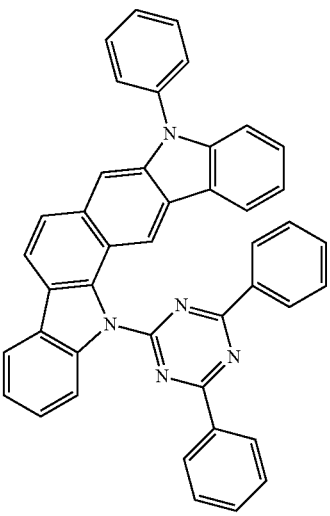
H45
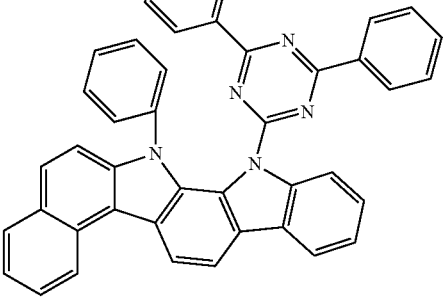
In some embodiments, the host may include at least one of Compounds H43 to H49, but is not limited thereto:
H43
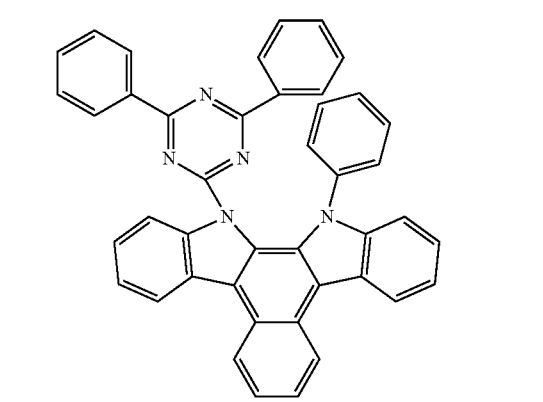
H46
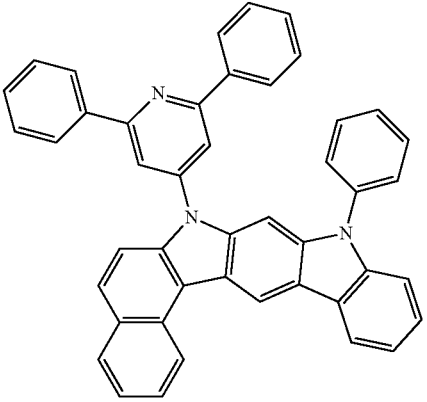

H47

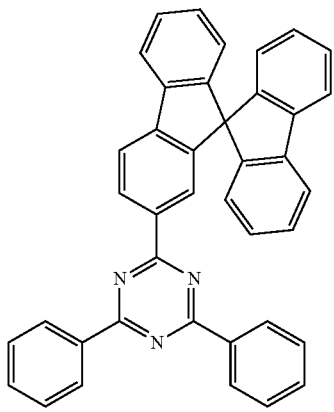

H48

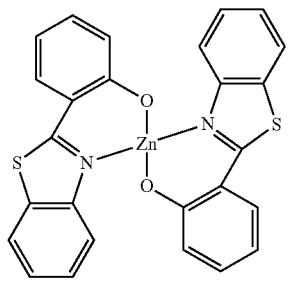

H49

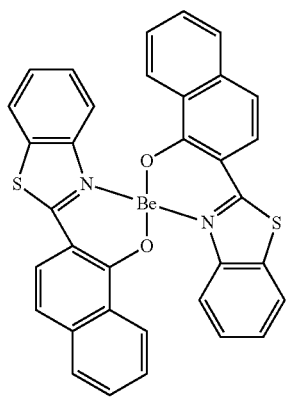

The dopant may include at least one of a fluorescent dopant and a phosphorescent dopant.

The phosphorescent dopant may include an organometallic complex represented by Formula 401:

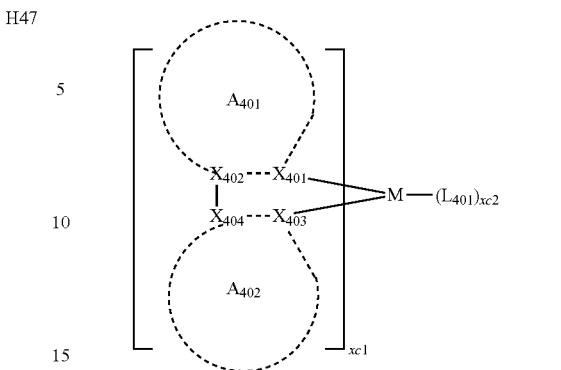

Formula 401

In Formula 401,

M may be selected from iridium (Ir), platinum (Pt), osmium (Os), titanium (Ti), zirconium (Zr), hafnium (Hf), europium (Eu), terbium (Tb), and thulium (Tm);

$X_{401}$ to $X_{404}$ may be each independently a nitrogen or a carbon;

rings $A_{401}$ and $A_{402}$ may be each independently selected from a substituted or unsubstituted benzene, a substituted or unsubstituted naphthalene, a substituted or unsubstituted fluorene, a substituted or unsubstituted spiro-fluorene, a substituted or unsubstituted indene, a substituted or unsubstituted pyrrole, a substituted or unsubstituted thiophene, a substituted or unsubstituted furan, a substituted or unsubstituted imidazole, a substituted or unsubstituted pyrazole, a substituted or unsubstituted thiazole, a substituted or unsubstituted isothiazole, a substituted or unsubstituted oxazole, a substituted or unsubstituted isoxazole, a substituted or unsubstituted pyridine, a substituted or unsubstituted pyrazine, a substituted or unsubstituted pyrimidine, a substituted or unsubstituted pyridazine, a substituted or unsubstituted quinoline, a substituted or unsubstituted isoquinoline, a substituted or unsubstituted benzoquinoline, a substituted or unsubstituted quinoxaline, a substituted or unsubstituted quinazoline, a substituted or unsubstituted carbazole, a substituted or unsubstituted benzoimidazole, a substituted or unsubstituted benzofuran, a substituted or unsubstituted benzothiophene, a substituted or unsubstituted isobenzothiophene, a substituted or unsubstituted benzoxazole, a substituted or unsubstituted isobenzoxazole, a substituted or unsubstituted triazole, a substituted or unsubstituted oxadiazole, a substituted or unsubstituted triazine, a substituted or unsubstituted dibenzofuran, and a substituted or unsubstituted dibenzothiophene;

at least one substituent of the substituted benzene, the substituted naphthalene, the substituted fluorene, the substituted spiro-fluorene, the substituted indene, the substituted pyrrole, the substituted thiophene, the substituted furan, the substituted imidazole, the substituted pyrazole, the substituted thiazole, the substituted isothiazole, the substituted oxazole, the substituted isoxazole, the substituted pyridine, the substituted pyrazine, the substituted pyrimidine, the substituted pyridazine, the substituted quinoline, the substituted isoquinoline, the substituted benzoquinoline, the substituted quinoxaline, the substituted quinazoline, the substituted carbazole, the substituted benzoimidazole, the substituted benzofuran, the substituted benzothiophene, the substituted isobenzothiophene, the substituted benzoxazole, the substituted isobenzoxazole, the substituted triazole, the substituted oxadiazole, the substituted triazine, the substituted dibenzofuran, and the substituted dibenzothiophene may be selected from:

a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, $C_2$-$C_{60}$ alkenyl group, a $C_2$-$C_{60}$ alkynyl group, a $C_1$-$C_{60}$ alkoxy group;

a $C_1$-$C_{60}$ alkyl group, $C_2$-$C_{60}$ alkenyl group, $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_3$-$C_{10}$ group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, $C_2$-$C_{60}$ heteroaryl group, a non-aromatic condensed polycyclic group, —N($Q_{401}$)($Q_{402}$), —Si($Q_{403}$)($Q_{404}$)($Q_{405}$), and —B($Q_{406}$)($Q_{407}$), a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, $C_2$-$C_{60}$ heteroaryl group, and a non-aromatic condensed polycyclic group, each substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, $C_2$-$C_{60}$ alkenyl group, $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, $C_2$-$C_{60}$ heteroaryl group, a non-aromatic condensed polycyclic group, —N($Q_{411}$)($Q_{412}$), —Si($Q_{413}$)($Q_{414}$)($Q_{415}$), and —B($Q_{416}$)($Q_{417}$); and —N($Q_{421}$)($Q_{422}$), —Si($Q_{423}$)($Q_{424}$)($Q_{425}$), and —B($Q_{426}$)($Q_{427}$);

$L_{401}$ may be an organic ligand;
xc1 may be 1, 2, or 3; and
xc2 may be 0, 1, 2, or 3.

$Q_{401}$ to $Q_{407}$, $Q_{411}$ to $Q_{417}$ and $Q_{421}$ to $Q_{427}$ may be each independently selected from a hydrogen atom, a $C_1$-$C_{60}$ alkyl group, a $C_2$-$C_{60}$ alkenyl group, a $C_6$-$C_{60}$ aryl group, and $C_2$-$C_{60}$ heteroaryl group.

For example, in Formula 401, $L_{401}$ may be a monovalent, divalent, or trivalent organic ligand. For example, $L_{401}$ in Formula 401 may be selected from a halogen ligand (for example, Cl or F), a diketone ligand (for example, acetylacetonate, 1,3-diphenyl-1,3-propanedionate, 2,2,6,6-tetramethyl-3,5-heptanedionate, or hexafluoroacetonate), a carboxylic acid ligand (for example, picolinate, dimethyl-3-pyrazolecarboxylate, or benzoate), a carbon monoxide ligand, an isonitrile ligand, a cyano ligand, and a phosphorous ligand (for example, phosphine or phosphite). However, embodiments of the present disclosure are not limited thereto.

When $A_{401}$ in Formula 401 has at least two substituent groups, the at least two substituent groups of $A_{401}$ may be linked to each other to form a saturated or unsaturated ring.

When $A_{402}$ in Formula 401 has at least two substituent groups, the at least two substituent groups of $A_{402}$ may be linked to each other to form a saturated or unsaturated ring.

When xc1 in Formula 401 is 2 or greater, a plurality of ligands

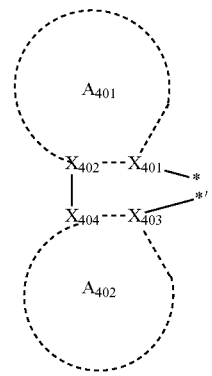

in Formula 401 may be identical to or different from each other. When xc1 in Formula 401 is 2 or greater, $A_{401}$ and $A_{402}$ may be linked to $A_{401}$ and $A_{402}$ of another adjacent ligand, respectively, directly or via a linking group (for example, a $C_1$-$C_5$ alkylene group, —N(R')— (where R' is a $C_1$-$C_{10}$ alkyl group or a $C_6$-$C_{20}$ aryl group), or C(=O)—).

The phosphorescent dopant may include at least one of Compounds PD1 to PD74, but is not limited thereto.

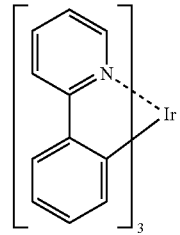

PD1

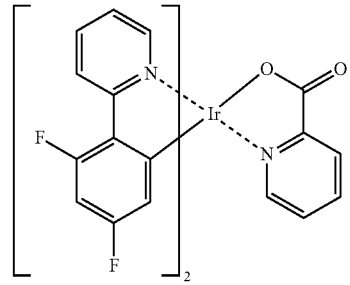

PD2

PD3 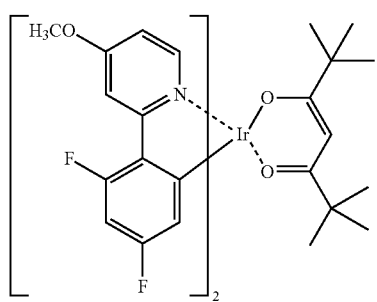
PD4 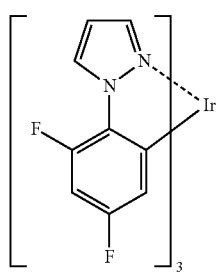
DP5 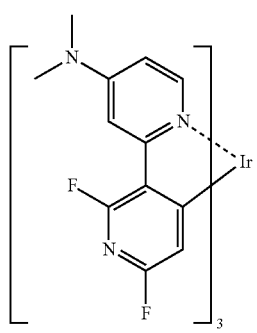
PD6 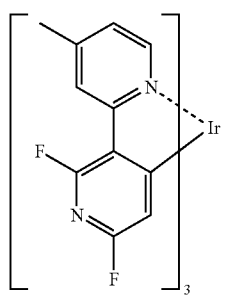
PD7 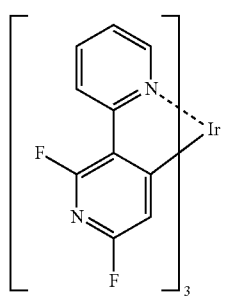
PD8 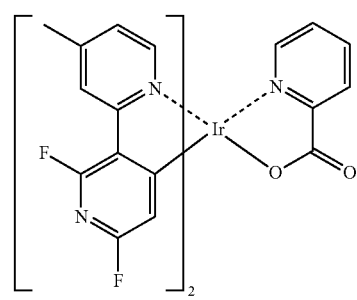
PD9 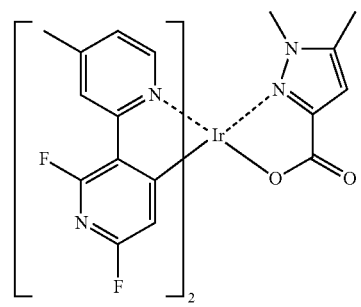
PD10 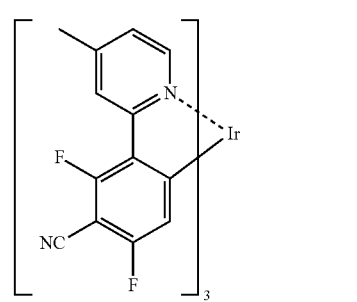
PD11 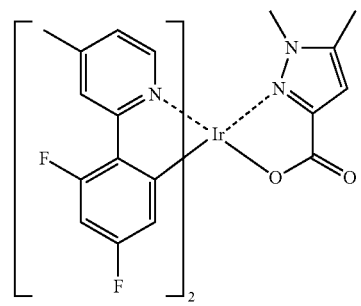
PD12 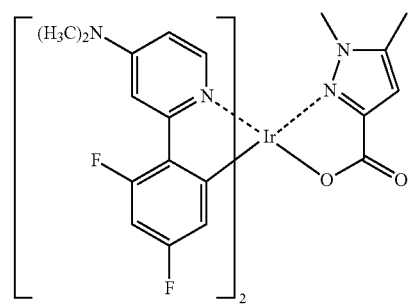

PD13
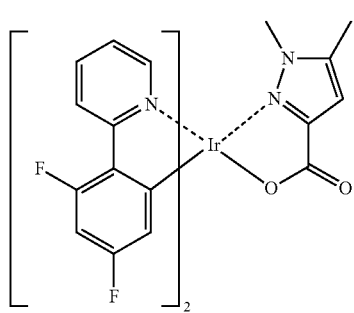
PD14
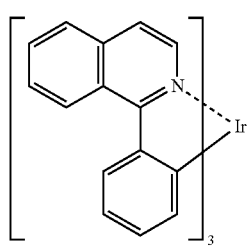
PD15
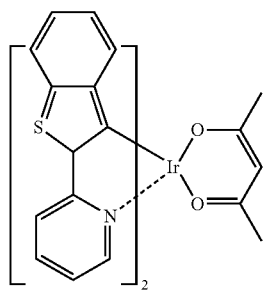
PD16
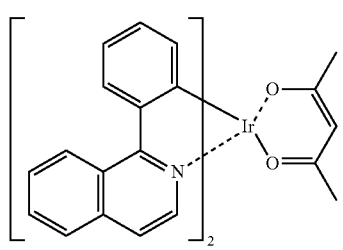
PD17
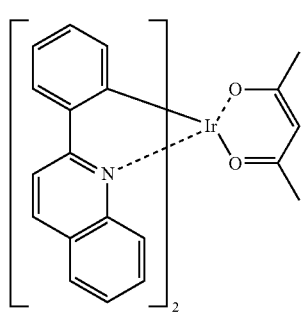
PD18
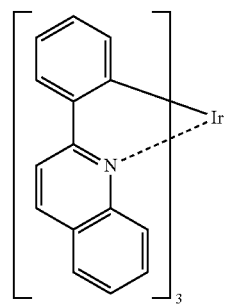
PD19
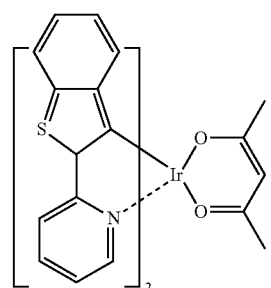
PD20
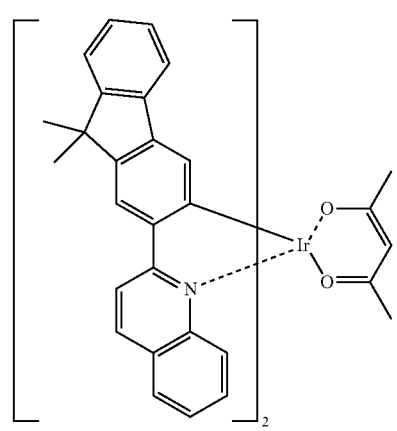
PD21
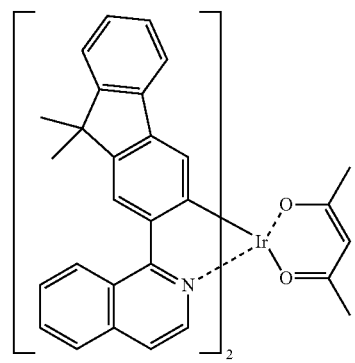
PD22
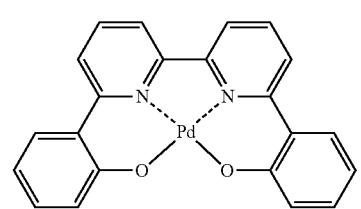

PD23 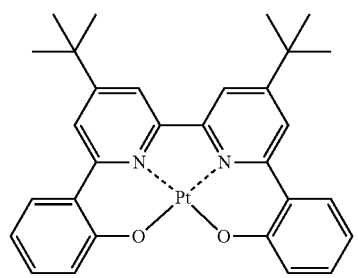
PD24 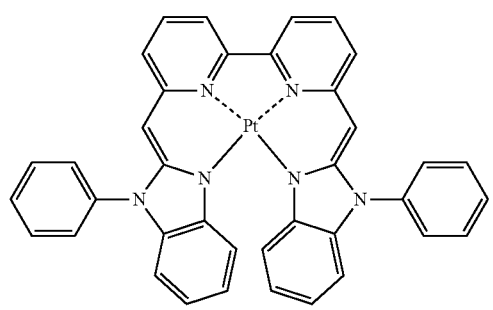
PD25 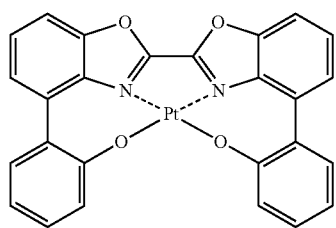
PD26 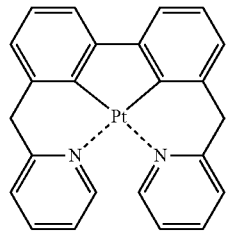
PD27 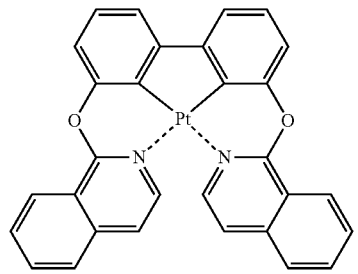
PD28 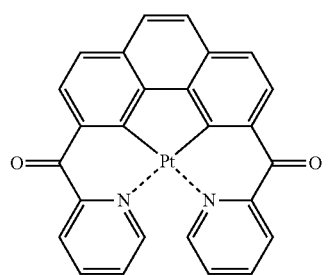
PD29 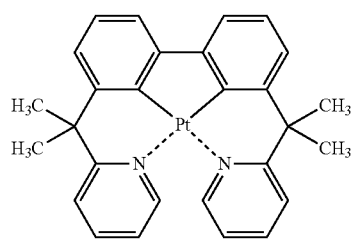
PD30 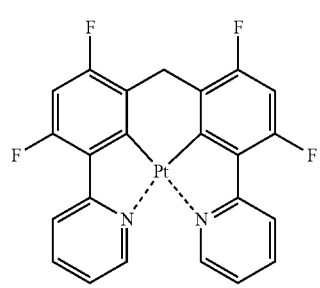
PD31 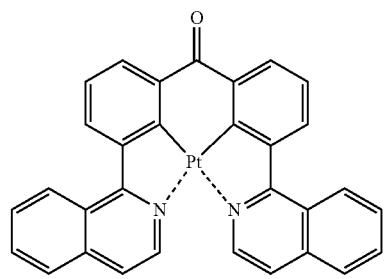
PD32 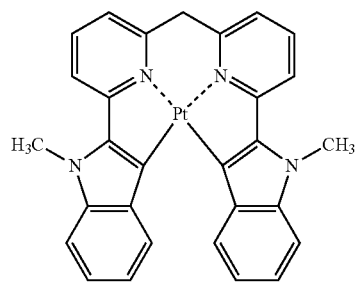
PD33 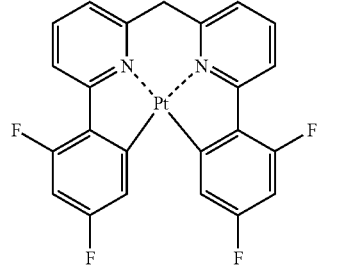
PD34 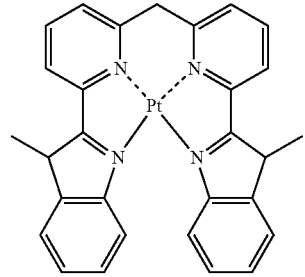

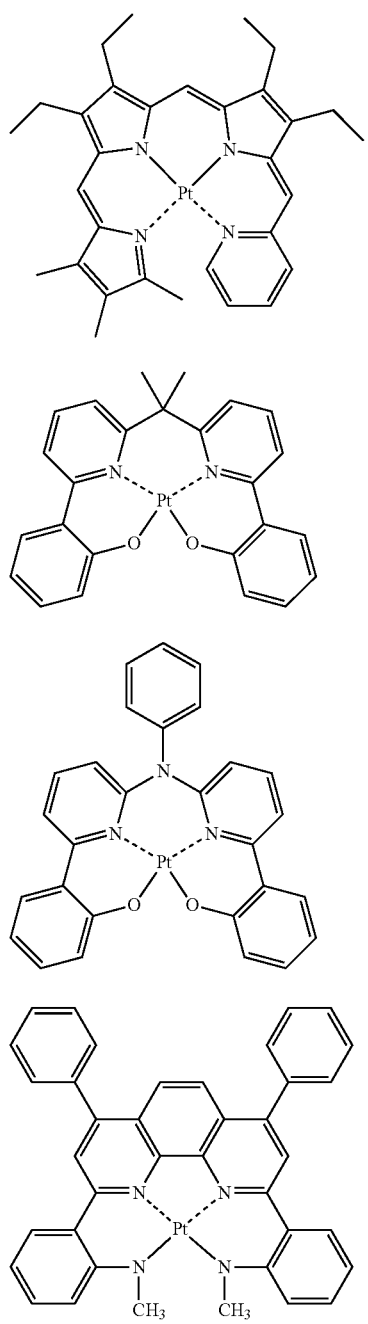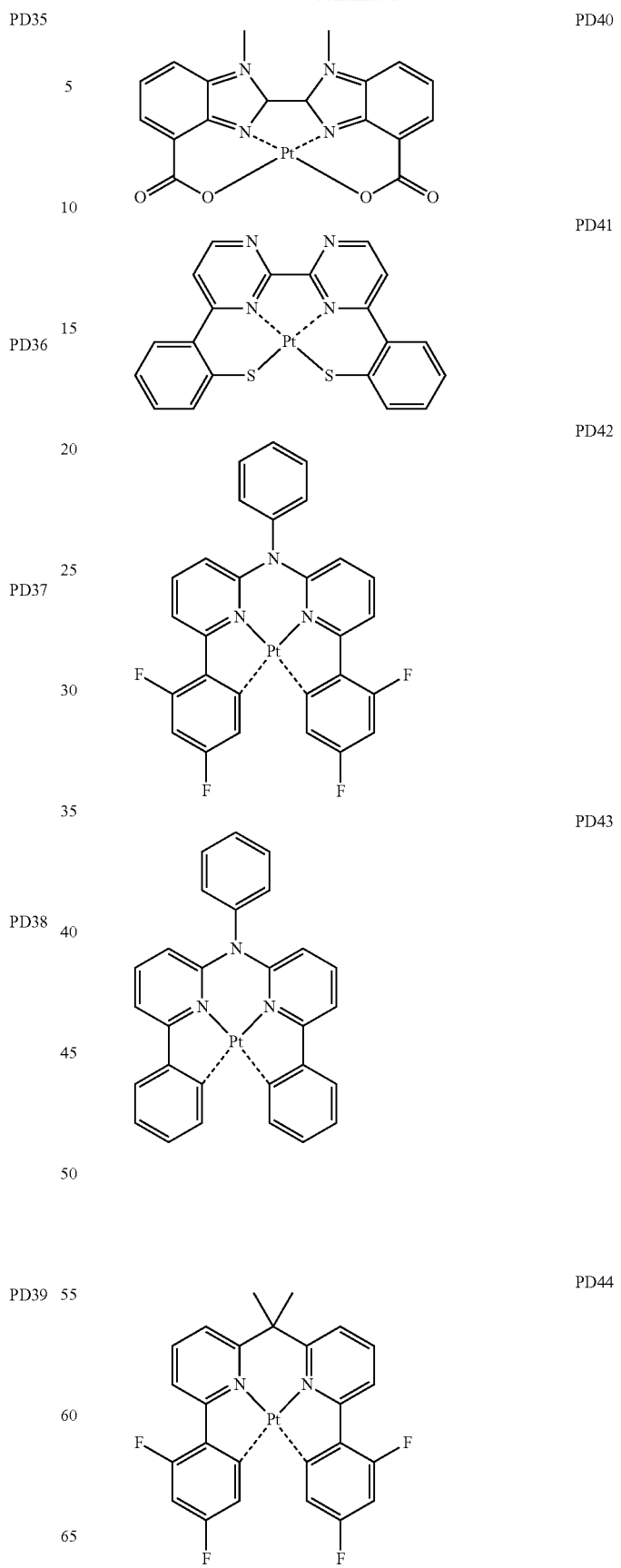

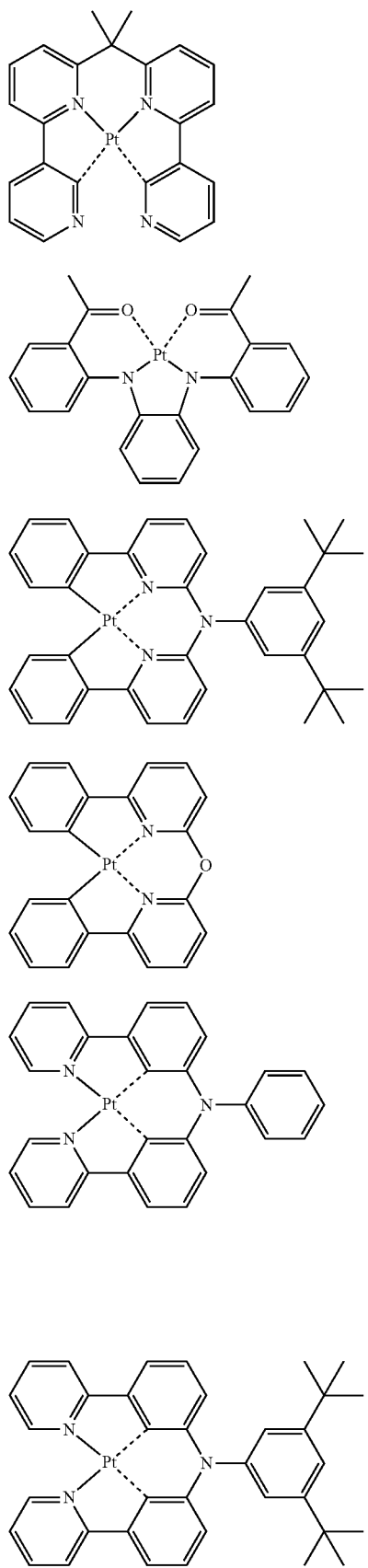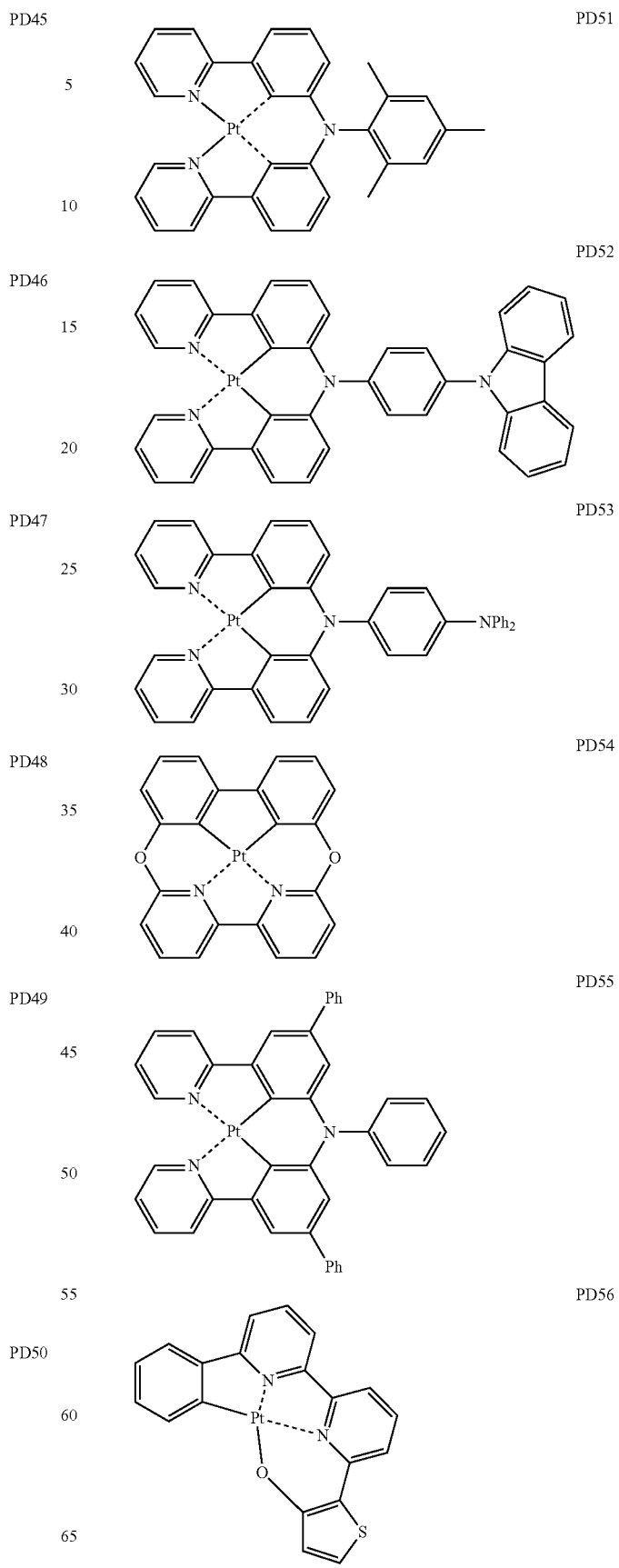

-continued
PD57
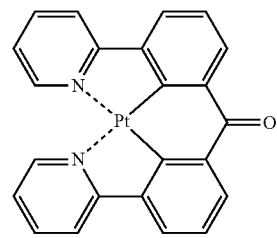
PD58
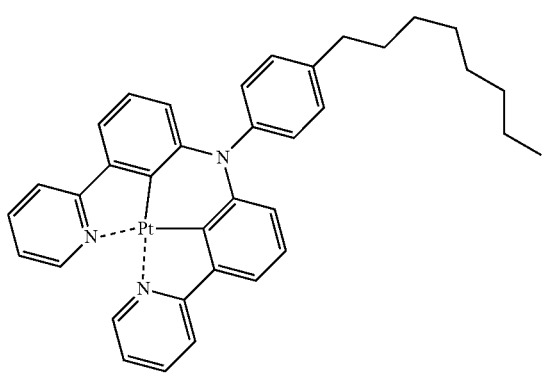
PD59
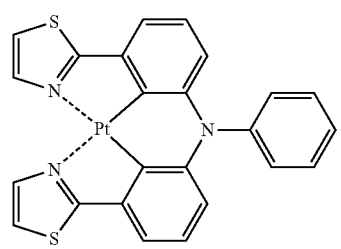
PD60
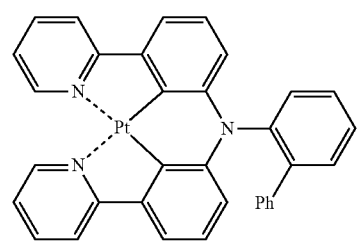
PD61
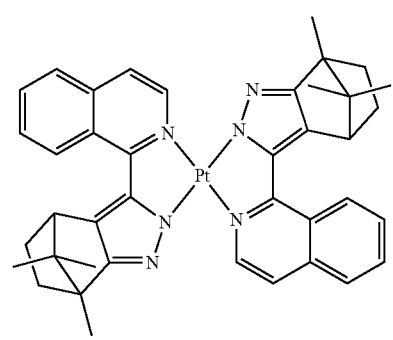
-continued
PD62
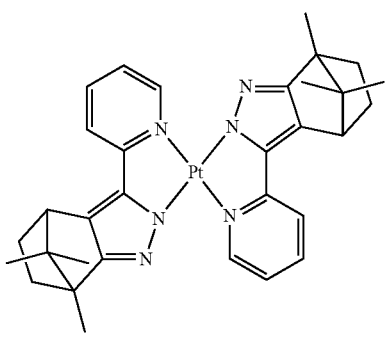
PD63
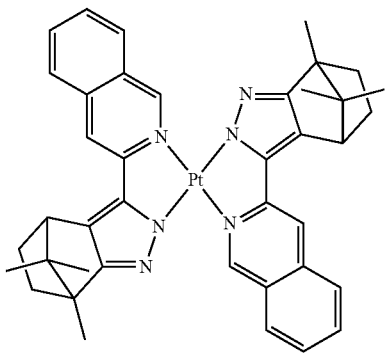
PD64
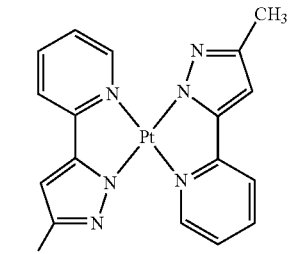
PD65
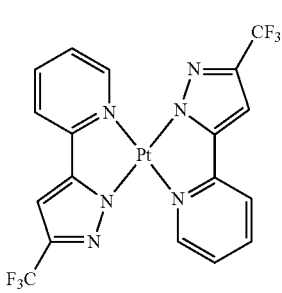
PD66
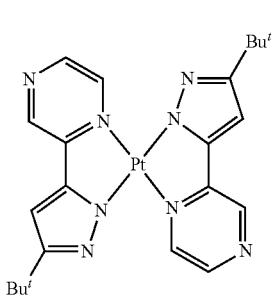

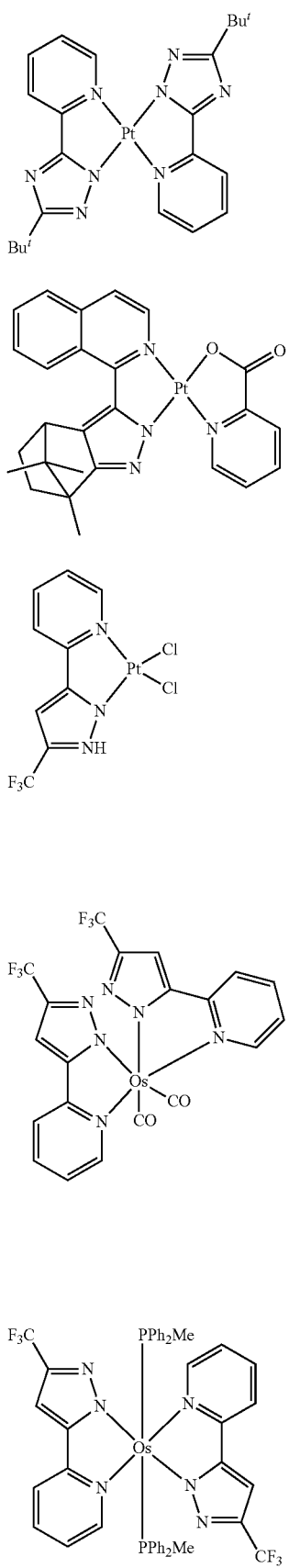
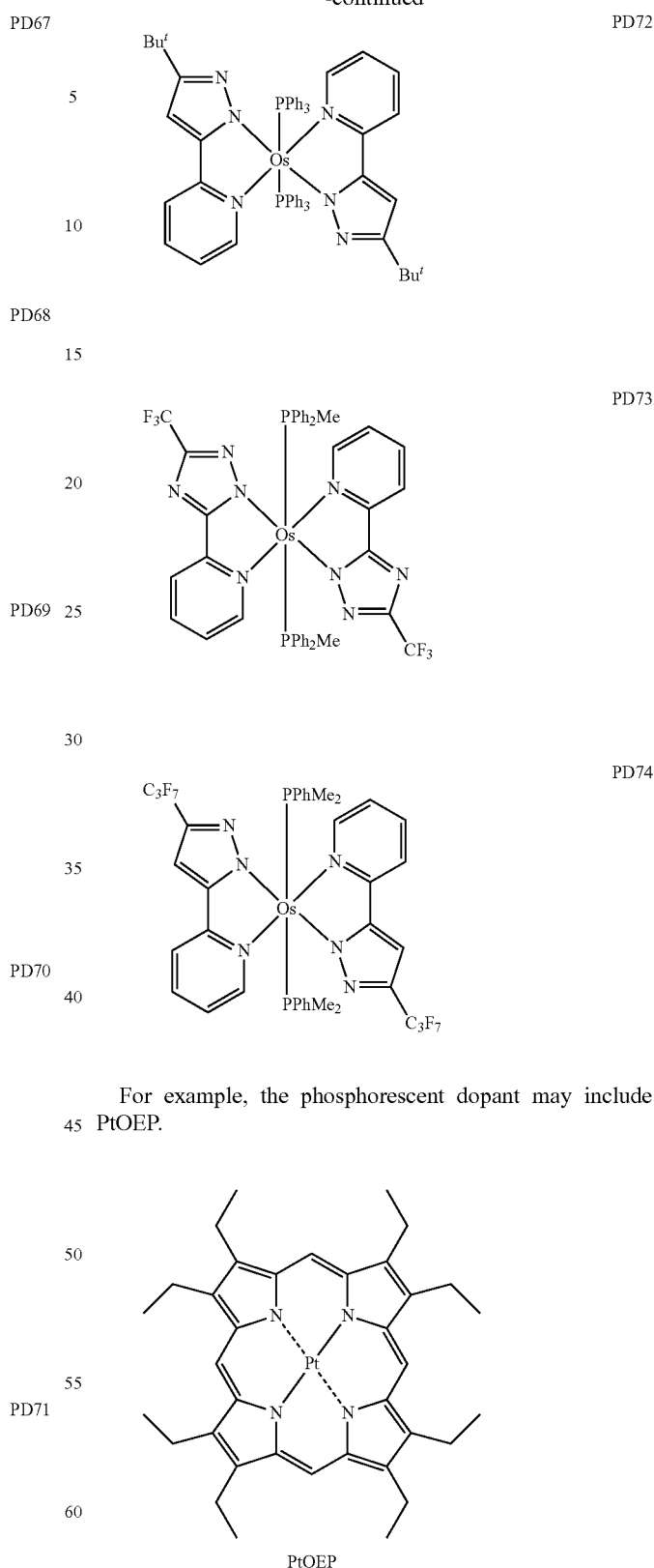
For example, the phosphorescent dopant may include PtOEP.
For example, the fluorescent dopant may further include at least one of DPAVBi, BDAVBi, TBPe, DCM, DCJTB, Coumarin 6, and C545T.

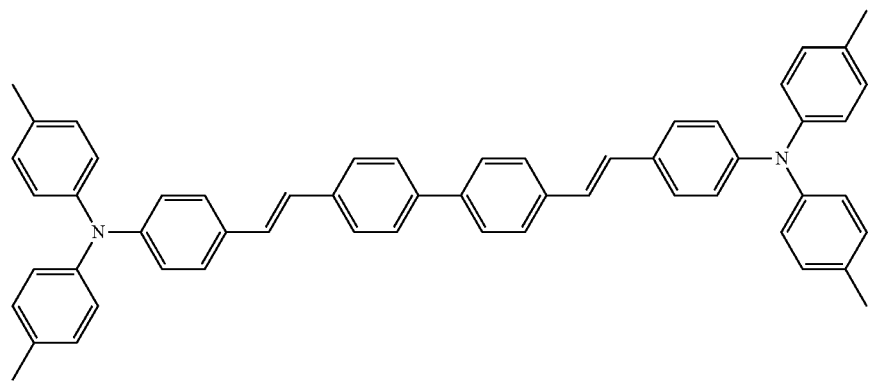
DPAVBi
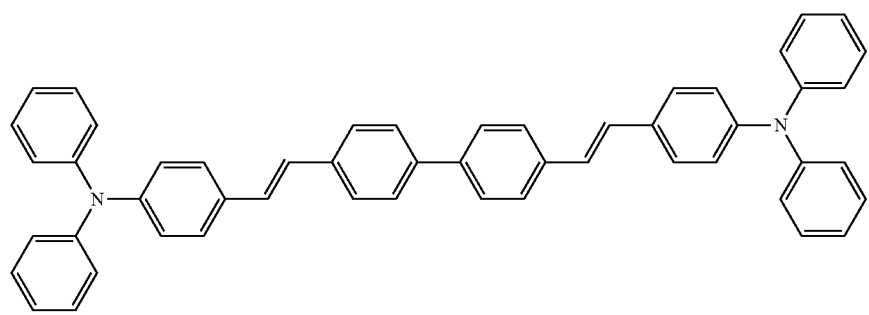
BDAVBi
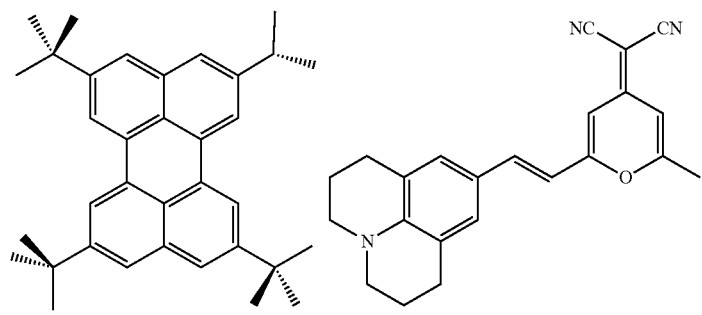
TBPe  DCM
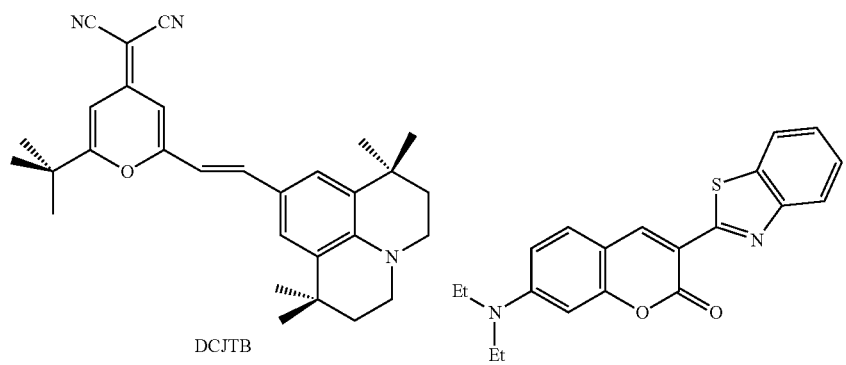
DCJTB  Coumarin 6

-continued

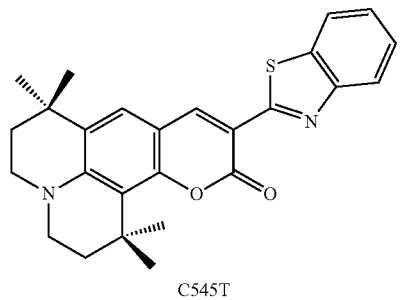

C545T

For example, the fluorescent dopant may include a compound represented by Formula 501.

$$Ar_{501}\left[-(L_{503})_{xd3}\left\langle\begin{array}{l}(L_{501})_{xd1}-R_{501}\\(L_{502})_{xd2}-R_{502}\end{array}\right]_{xd4}\right.$$ Formula 501

In Formula 501, $Ar_{501}$ may be selected from:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene;

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one selected from a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a non-aromatic condensed polycyclic group, and —Si($Q_{501}$)($Q_{502}$)($Q_{503}$) (where $Q_{501}$ to $Q_{503}$ may be each independently selected from a hydrogen atom, a $C_1$-$C_{60}$ alkyl group, a $C_2$-$C_{60}$ group, a $C_6$-$C_{60}$ aryl group, and a $C_2$-$C_{60}$ heteroaryl group);

descriptions for $L_{501}$ to $L_{503}$ may be each independently the same as the descriptions for $L_{201}$ defined herein;

$R_{501}$ and $R_{502}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, a triazinyl group, a dibenzofuranyl group, and a dibenzothiophenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and a dibenzofuranyl group, and a dibenzothiophenyl group, each substituted with at least one selected from a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group;

xd1 to xd3 may be each independently selected from 0, 1, 2, and 3; and xb4 may be selected from 1, 2, 3, and 4.

For example, the fluorescent dopant may include at least one of Compounds FD1 to FD8.

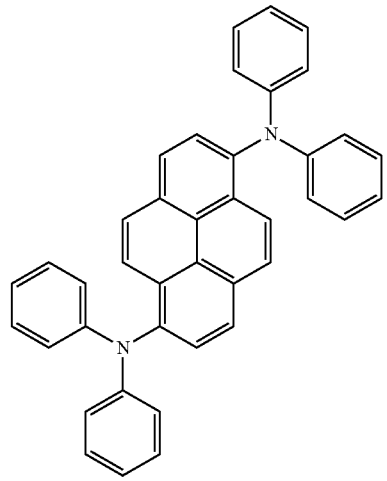

FD1

-continued
FD2
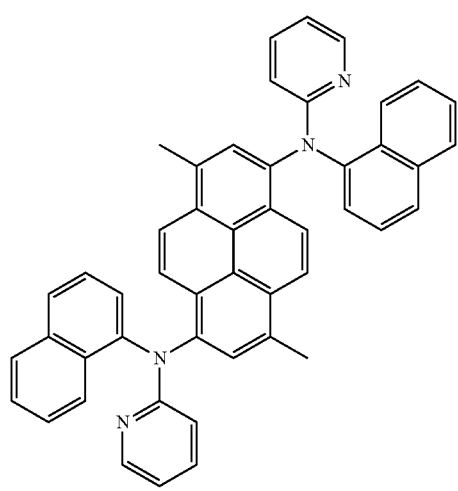
FD4
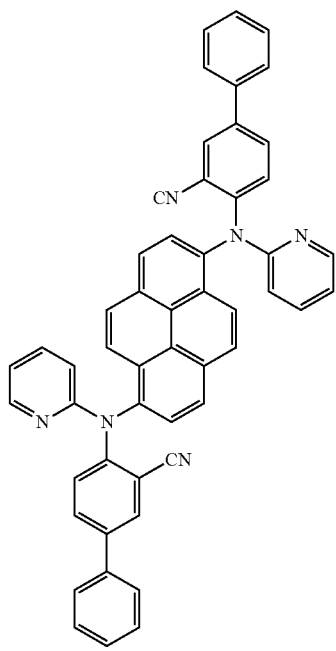
FD5
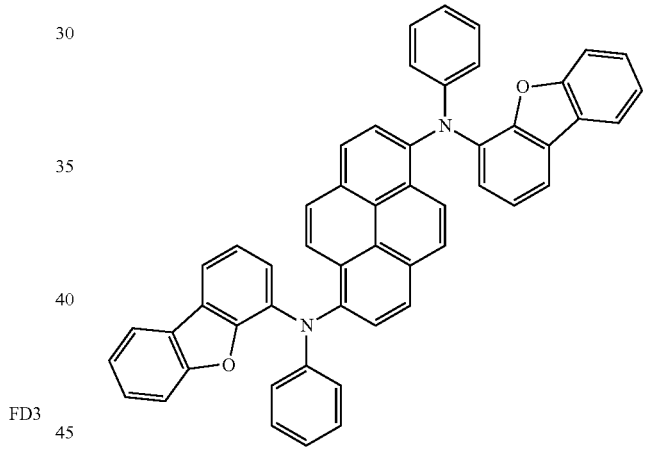
FD3
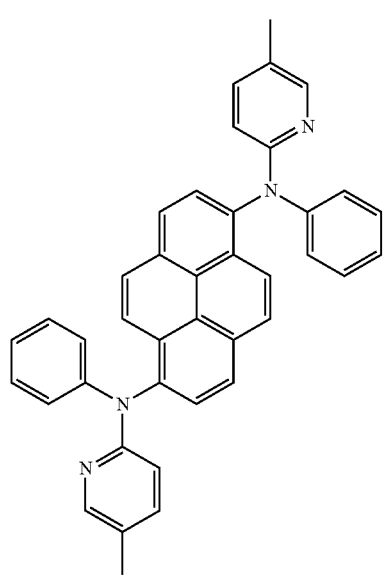
FD6
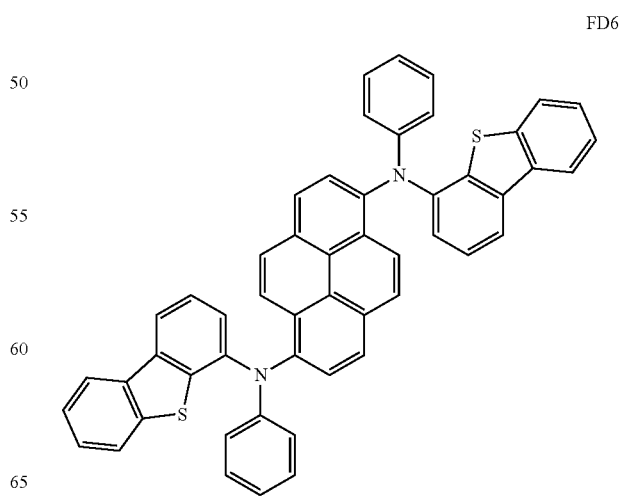

-continued

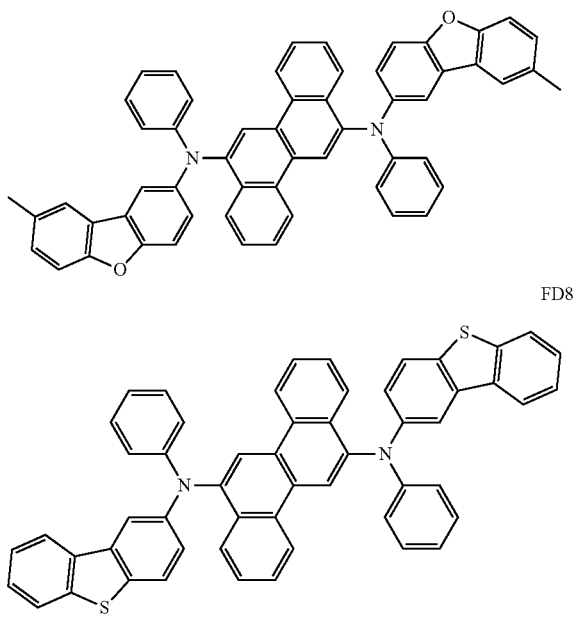
FD7

FD8

An amount of the dopant in the EML may be from about 0.01 parts to about 15 parts by weight based on 100 parts by weight of the host, but is not limited to this range.

The thickness of the EML may be about 100 Å to about 1000 Å, and in some embodiments, may be from about 200 Å to about 600 Å. In one embodiment, when the thickness of the EML is within these ranges, the EML has good light emitting ability without a substantial increase in driving voltage.

Next, the electron transport region may be disposed on the EML.

The electron transport region may include at least one of an HBL, an ETL, and an EIL. However, embodiments of the present disclosure are not limited thereto.

In some embodiments, the electron transport region may have a structure including an ETL/EIL, or an HBL/ETL/EIL, wherein the layers forming a structure of the electron transport region may be sequentially stacked on the EML in the order stated above. However, embodiments of the present disclosure are not limited thereto.

In some embodiments, the organic layer 150 of the organic light-emitting device 10 may include the electron transport region between the EML and the second electrode 190, and the antiaromatic compound of Formula 1 may be in the electron transport region.

The electron transport region may include an HBL. When the EML includes a phosphorescent dopant, the HBL may reduce or prevent diffusion of triplet excitons or holes into the ETL from the EML.

When the electron transport region includes an HBL, the HBL may be formed on the EML by using (utilizing) any of a variety of suitable methods, for example, by using (utilizing) vacuum deposition, spin coating, casting, Langmuir-Blodgett (LB) deposition, inkjet printing, laser printing, laser induced thermal imaging (LITI), or the like. When the HBL is formed using (utilizing) vacuum deposition or spin coating, the deposition and coating conditions for forming the HBL may be similar to the above-described deposition and coating conditions for forming the HIL, and accordingly will not be described in more detail.

For example, the HBL may include at least one of BCP below and Bphen below. However, embodiments of the present disclosure are not limited thereto.

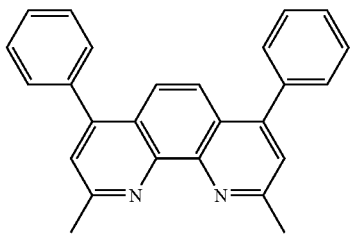
BCP

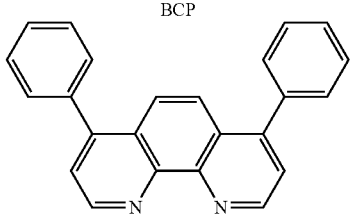
Bphen

A thickness of the HBL may be from about 20 Å to about 1,000 Å, and in some embodiments, from about 30 Å to about 300 Å. In one embodiment, when the thickness of the HBL is within these ranges, the HBL has improved hole blocking ability without a substantial increase in driving voltage.

The electron transport region may include an ETL. The ETL may be formed on the EML or the HBL by using (utilizing) any of a variety of suitable methods, for example, by using (utilizing) vacuum deposition, spin coating, casting, Langmuir-Blodgett (LB) deposition, inkjet printing, laser printing, laser induced thermal imaging (LITI), or the like. When the ETL is formed using (utilizing) vacuum deposition or spin coating, the deposition and coating conditions for forming the ETL may be similar to the above-described deposition and coating conditions for forming the HIL, and accordingly will not be described in more detail.

In some embodiments, the organic layer 150 of the organic light-emitting device may include an electron transport region between the EML and the second electrode 190, wherein the electron transport region may include an ETL, and the ETL may include the antiaromatic compound of Formula 1.

The ETL may further include at least one of BCP, Bphen Alq$_3$, Balq, TAZ, and NTAZ, in addition to the antiaromatic compound of Formula 1.

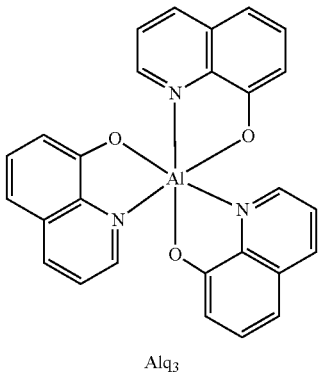
Alq$_3$

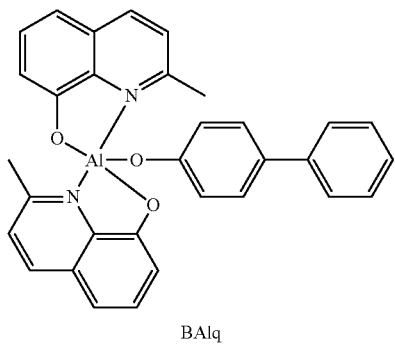

BAlq

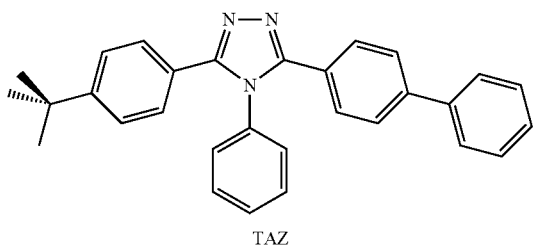

TAZ

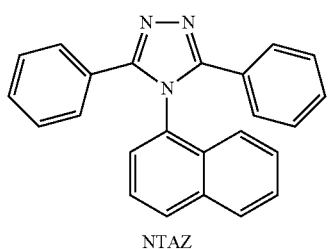

NTAZ

A thickness of the ETL may be from about 100 Å to about 1,000 Å, and in some embodiments, from about 150 Å to about 500 Å. In one embodiment, when the thickness of the ETL is within these ranges, the ETL has satisfactory electron transporting ability without a substantial increase in driving voltage.

In some embodiments the ETL may further include a metal-containing material, in addition to the above-described materials.

The metal-containing material may include a lithium (Li) complex. Non-limiting examples of the Li complex are compound ET-D1 below (lithium quinolate (LiQ)), or compound ET-D2.

ET-D1

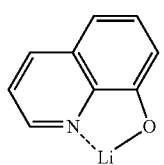

ET-D2

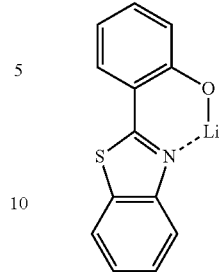

The electron transport region may include an EIL that may facilitate injection of electrons from the second electrode 190.

The EIL may be formed on the ETL by using (utilizing) any of a variety of suitable methods, for example, by using (utilizing) vacuum deposition, spin coating, casting, Langmuir-Blodgett (LB) deposition, inkjet printing, laser printing, laser induced thermal imaging (LITI), or the like. When the EIL is formed using (utilizing) vacuum deposition or spin coating, the deposition and coating conditions for forming the EIL may be similar to the above-described deposition and coating conditions for forming the HIL, and accordingly will not be described in more detail.

The EIL may include at least one selected from LiF, NaCl, CsF, $Li_2O$, BaO, and LiQ.

A thickness of the EIL may be from about 1 Å to about 100 Å, and in some embodiments, from about 3 Å to about 90 Å. In one embodiment, when the thickness of the EIL is within these ranges, the EIL has satisfactory electron injection ability without a substantial increase in driving voltage.

The second electrode 190 may be disposed on the organic layer 150, as described above. The second electrode 190 may be a cathode as an electron injecting electrode. A material for forming the second electrode 190 may be a metal, an alloy, an electrically conductive compound, which have a low-work function, or a mixture thereof. Non-limiting examples of materials for forming the second electrode 190 are lithium (Li), magnesium (Mg), aluminum (Al), aluminum-lithium (Al—Li), calcium (Ca), magnesium-indium (Mg—In), and magnesium-silver (Mg—Ag). In some embodiments, a material for forming the second electrode 190 may be ITO or IZO. The second electrode 190 may be a reflective electrode, a semi-transmissive electrode, or a transmissive electrode.

Although the organic light-emitting device of FIG. 1 is described above, embodiments of the present disclosure are not limited thereto.

As used herein, a $C_1$-$C_{60}$ alkyl group refers to a linear or branched aliphatic hydrocarbon monovalent group having 1 to 60 carbon atoms. Non-limiting examples of the $C_1$-$C_{60}$ alkyl group include a methyl group, an ethyl group, a propyl group, an isobutyl group, a sec-butyl group, a tert-butyl group, a pentyl group, an iso-amyl group, and a hexyl group. A $C_1$-$C_{60}$ alkylene group refers to a divalent group having the same structure as the $C_1$-$C_{60}$ alkyl.

As used herein, a $C_1$-$C_{60}$ alkoxy group refers to a monovalent group represented by —$OA_{101}$ (where $A_{101}$ is a $C_1$-$C_{60}$ alkyl group as described above). Non-limiting examples of the $C_1$-$C_{60}$ alkoxy group are a methoxy group, an ethoxy group, and an isopropyloxy group.

As used herein, a $C_2$-$C_{60}$ alkenyl group refers to a hydrocarbon group including at least one carbon double bond in the middle or terminal of the $C_2$-$C_{60}$ alkyl group. Non-limiting examples of the $C_2$-$C_{60}$ alkenyl group are an ethenyl group, a propenyl group, and a butenyl group. A $C_2$-$C_{60}$ alkylene group refers to a divalent group having the same structure as the $C_2$-$C_{60}$ alkenyl group.

As used herein, $C_2$-$C_{60}$ alkynyl group refers to a hydrocarbon group including at least one carbon triple bond in the middle or terminal of the $C_2$-$C_{60}$ alkyl group. Non-limiting examples of the $C_2$-$C_{60}$ alkynyl group are an ethynyl group and a propynyl group. A $C_2$-$C_{60}$ alkynylene group used herein refers to a divalent group having the same structure as the $C_2$-$C_{60}$ alkynyl group.

As used herein, a $C_3$-$C_{10}$ cycloalkyl group refers to a monovalent, monocyclic hydrocarbon group having 3 to 10 carbon atoms. Non-limiting examples of the $C_3$-$C_{10}$ group are a cyclopropyl group, a cyclobutyl group, a cyclopentyl group, a cyclohexyl group, and a cycloheptyl group. A $C_3$-$C_{10}$ cycloalkylene group refers to a divalent group having the same structure as the $C_3$-$C_{10}$ cycloalkyl group.

As used herein, a $C_3$-$C_{10}$ heterocycloalkyl group refers to a monovalent monocyclic group having 3 to 10 carbon atoms in which at least one hetero atom selected from N, O, P, and S is included as a ring-forming atom. Non-limiting examples of the $C_3$-$C_{10}$ heterocycloalkyl group are a tetrahydrofuranyl group and a tetrahydrothiophenyl group. A $C_3$-$C_{10}$ heterocycloalkylene group refers to a divalent group having the same structure as the $C_3$-$C_{10}$ heterocycloalkyl group.

As used herein, a $C_3$-$C_{10}$ cycloalkenyl group refers to a monovalent monocyclic group having 3 to 10 carbon atoms that includes at least one double bond in the ring but does not have aromaticity. Non-limiting examples of the $C_3$-$C_{10}$ cycloalkenyl group are a cyclopentenyl group, a cyclohexenyl group, and a cycloheptenyl group. A $C_3$-$C_{10}$ cycloalkenylene group refers to a divalent group having the same structure as the $C_3$-$C_{10}$ cycloalkenyl group.

As used herein, a $C_3$-$C_{10}$ heterocycloalkenyl group refers to a monovalent monocyclic group having 3 to 10 carbon atoms that includes at least one double bond in the ring and in which at least one hetero atom selected from N, O, P, and S is included as a ring-forming atom. Non-limiting examples of the $C_3$-$C_{10}$ group are a 2,3-hydrofuranyl group and a 2,3-hydrothiophenyl group. A $C_3$-$C_{10}$ heterocycloalkenylene group used herein refers to a divalent group having the same structure as the $C_3$-$C_{10}$ heterocycloalkenyl group.

As used herein, a $C_6$-$C_{60}$ aryl group refers to a monovalent, aromatic carbocyclic aromatic group having 6 to 60 carbon atoms, and a $C_6$-$C_{60}$ arylene group refers to a divalent, aromatic carbocyclic group having 6 to 60 carbon atoms. Non-limiting examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group include at least two rings, the rings may be fused to each other.

As used herein, a $C_2$-$C_{60}$ heteroaryl group refers to a monovalent, aromatic carbocyclic aromatic group having 2 to 60 carbon atoms in which at least one hetero atom selected from N, O, P, and S is included as a ring-forming atom. A $C_2$-$C_{60}$ group refers to a divalent, aromatic carbocyclic group having 2 to 60 atoms in which at least one hetero atom selected from N, O, P, and S is included as a ring-forming atom. Non-limiting examples of the $C_2$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_2$-$C_{60}$ heteroaryl and the $C_2$-$C_{60}$ heteroarylene include at least two rings, the rings may be fused to each other.

As used herein, a $C_6$-$C_{60}$ aryloxy group refers to a group represented by —$OA_{102}$ (where $A_{102}$ is a $C_6$-$C_{60}$ aryl group as described above), and a $C_6$-$C_{60}$ arylthio group refers to a group represented by —$SA_{103}$ (where $A_{103}$ is a $C_6$-$C_{60}$ aryl group as described above).

As used herein, a monovalent non-aromatic condensed polycyclic group refers to a monovalent group having at least two rings condensed to each other, in which only carbon atoms are exclusively included as ring-forming atoms and the entire molecule has non-aromaticity. A non-limiting example of the monovalent non-aromatic condensed polycyclic group is a fluorenyl group. A divalent non-aromatic condensed polycyclic group refers to a divalent group having the same structure as the monovalent non-aromatic condensed polycyclic group.

As used herein, a monovalent non-aromatic condensed heteropolycyclic group refers to a monovalent group having at least two rings condensed to each other, in which carbon atoms and at least one hetero atom selected from N, O, P, and S are the ring-forming atoms and the entire molecule has non-aromaticity. A non-limiting example of the monovalent non-aromatic condensed heteropolycyclic group is a carbazolyl group. A divalent non-aromatic condensed heteropolycyclic group refers to a divalent group having the same structure as the monovalent non-aromatic condensed heteropolycyclic group.

The acronym "Ph" used herein refers to phenyl, the acronym "Me" used herein refers to methyl, the acronym "Et" used herein refers to ethyl, and the acronym "ter-Bu" or "zBu" used herein refers to tert-butyl.

One or more embodiments of the present disclosure, which include condensed cyclic compounds, and organic light-emitting devices including the same, will now be described in more detail with reference to the following examples. However, these examples are only for illustrative purposes and are not intended to limit the scope of the one or more embodiments of the present disclosure. In the following synthesis example, the expression that "'B' instead of 'A' was used (utilized)" means that the amounts of 'B' and 'A' were the same in equivalent amounts.

EXAMPLES

Synthesis Example 1

Synthesis of Compound 1

Synthesis of Intermediate 1-(1)

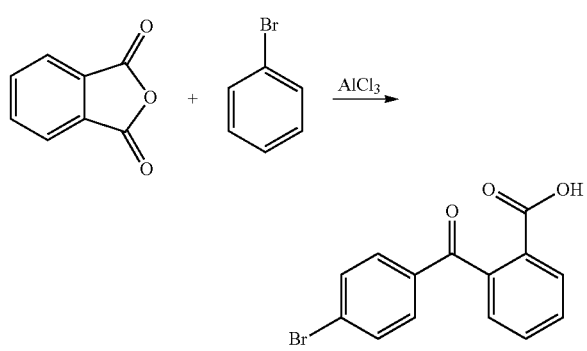

1-(1)

10 g (67.52 mmol) of phthalic anhydride, 8.54 mL (81.02 mmol) of bromobenzene, and 18.14 g (135.04 mmol) of AlCl₃ were added into a high-pressure reactor, and stirred at about 180° C. for about 1 hour. Ice water was added to the resulting mixture to terminate the reaction, followed by extraction with dichloromethane. The resulting organic layer was separated and then washed with 10% aqueous sulfuric acid solution. After adding a saturated Na₂CO₃ solution into the organic layer, an aqueous layer was separated and then neutralized with 10% aqueous sulfuric acid solution, followed by extraction with dichloromethane. The resulting organic layer was separated and then dried with anhydrous MgSO₄, followed by evaporation under reduced pressure to remove the solvent, and recrystallization with ethyl acetate to obtain 12.7 g of Intermediate 1-(1) as a white solid (Yield: 66%).

IR (KBr, cm-1): 3193-3298 (O—H), 3020-2970 (sp3 C—H), 1665 (C=O), 1598 (C=O);

1H-NMR (300 MHz, CDCl3, ppm): δ 8.11 (dd, 1H, J=0.2 Hz, J=0.2 Hz), 7.70 (ddd, 1H, J=0.2 Hz, J=0.2 Hz, J=0.2 Hz), 7.61 (dd, 1H, J=0.25 Hz, J=0.25 Hz), 7.57 (s, 4H), 7.36 (dd, 1H, J=0.2 Hz, J=0.2 Hz);

13C-NMR (300 MHz, CDCl3, ppm): δ 135.84, 133.47, 131.82, 130.73, 127.65;

EI, MS m/z (%): 304 (100, M+)

Synthesis of Intermediate 1-(3)

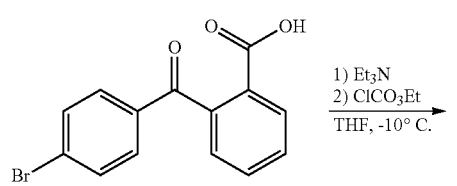

1-(1)

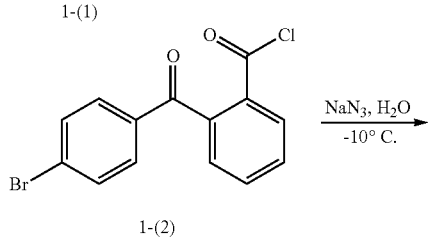

1-(2)

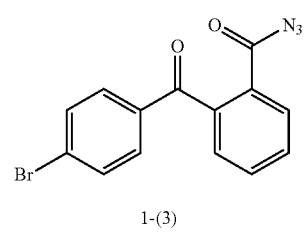

1-(3)

12 g (40 mmol) of Intermediate 1-(1) was dissolved in 160 mL of tetrahydrofuran (THF) in a 2-necked round-bottom flask, and the temperature of the reaction flask was maintained at about −10° C. After slowly adding 6.1 mL (44 mmol) of triethylamine to the reaction solution, 6.96 mL (44 mmol) of ethyl chloroformate was slowly added thereto and stirred at about −10° C. for about 1 hour. 3.12 g (44 mmol) of sodium azide dissolved in 110 mL of distilled water was slowly added to the reaction solution and stirred at about −10° C. for about 3 hours. After termination of the reaction, the reaction solution was evaporated under reduced pressure to remove the solvent (THF). The remaining aqueous layer was extracted with dichloromethane. The resulting organic layer was separated and then dried with anhydrous MgSO₄, followed by evaporation under reduced pressure to remove the solvent, and to obtain 12.75 g of Intermediate 1-(3). This Intermediate 1-(3) was used (utilized) for the next reaction without purification.

Synthesis of Intermediate 1-(4)

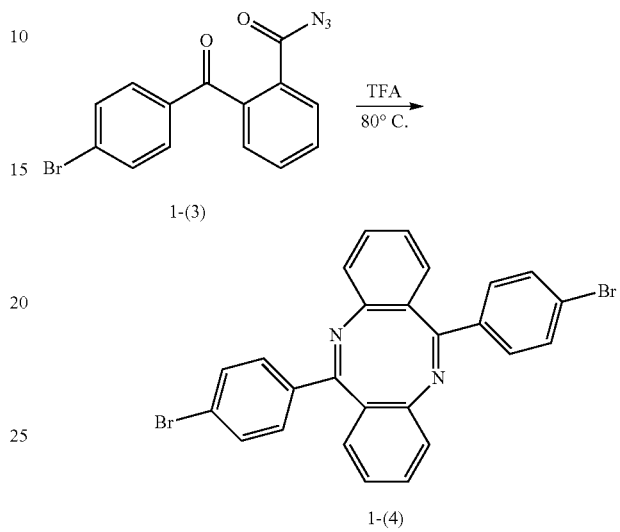

1-(4)

12.75 g (38.62 mmol) of Intermediate 1-(3) was dissolved in 19 mL of trifluoro acetic acid and 19 mL of acetic acid in a 2-necked round-bottom flask, and then stirred at about 80° C. After 2 hours, the reaction mixture was cooled down to room temperature, a saturated Na₂CO₃ solution was added thereto for neutralization, followed by extraction with dichloromethane. The resulting organic layer was separated and then dried with anhydrous MgSO₄, followed by evaporation under reduced pressure to remove the solvent, drying, and recrystallization with ethyl acetate to obtain 3.59 g of Intermediate 1-(4) as a yellow solid (Yield: 36%).

IR (KBr, cm-1): 2983-3081 (sp2=C—H), 1625 (C=N), 1583 (C=C), 1425 (C=C), 1392 (C—N);

1H-NMR (300 MHz, CDCl3, ppm): δ 7.64 (d, 4H, J=2.9 Hz), 7.47 (d, 4H, J=2.9 Hz), 7.34 (q, 2H, J=5.1 Hz), 7.03 (d, 4H, J=2.6 Hz), 6.95 (d, 2H, J=2.5 Hz);

13C-NMR (300 MHz, CDCl3, ppm): δ 156.36, 153.19, 146.78, 136.67, 129.74, 129.19, 128.69, 128.49, 127.26, 122.41, 117.00;

EI, MS m/z (%): 516 (100, M+)

Synthesis of Intermediate 1-(5)

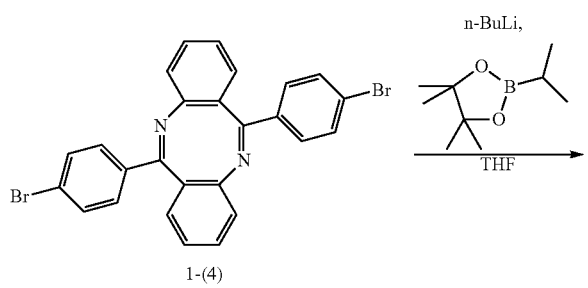

1-(4)

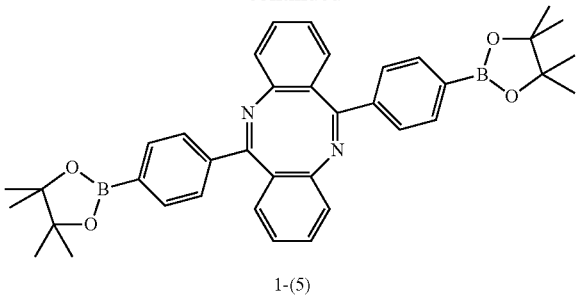

1-(5)

2 g (3.88 mmol) of Intermediate 1-(4) was dissolved in 20 mL of THF in a 2-necked round-bottom flask, and the temperature of the reaction vessel flask was cooled down to about −78° C. 4.66 mL (11.64 mmol) of n-BuLi (2.5 M in hexane) was slowly added thereto and stirred at the same temperature for 1 hour. 2.36 mL (11.64 of 2-isopropyl-4,4,5,5-tetramethyl-1,3,2-dioxaborolane was added thereto and stirred at about −78° C. for about 1 hour, and then at room temperature for about 12 hours. The reaction mixture was evaporated under reduced pressure, and separated with column chromatography (hexane:ethyl acetate=4:1 by v/v) to obtain 2.3 g of Intermediate 1-(5) as a white solid (Yield: 97%).

Synthesis of Compound 1

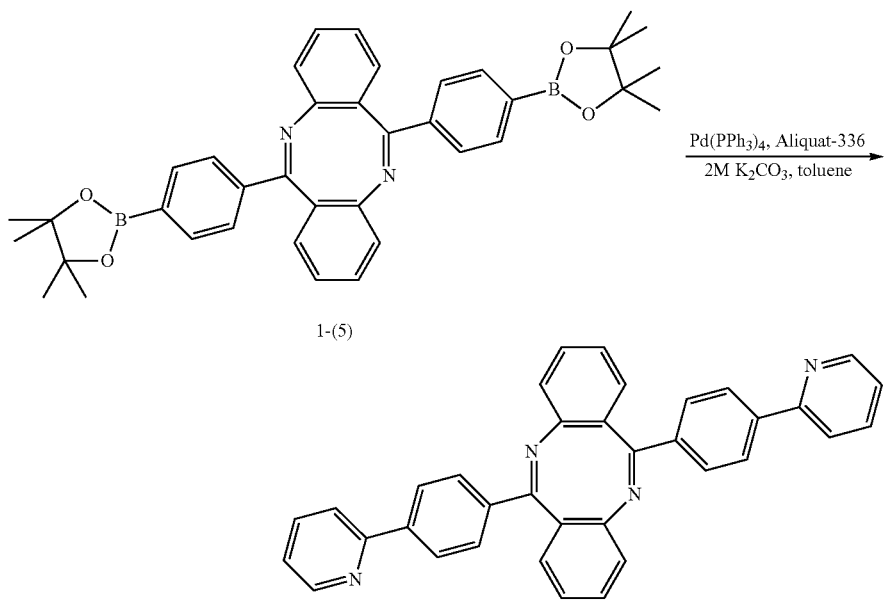

and separation by column chromatography (hexane:ethyl acetate=2:1 by v/v) to obtain 1.3 g of Compound 1 as a yellow solid (Yield: 67%).

IR (KBr, cm-1): 3006-3050 (sp2=C—H), 1619 (C=N), 1585 (C=C), 1465 (C=C), 1402 (C—N);

1H-NMR (300 MHz, CDCl3, ppm): δ 8.71 (tt, 2H, J=0.9 Hz, J=0.9 Hz), 8.00 (dd, 4H, J=0.6 Hz, J=0.6 Hz), 7.90 (dd, 4H, J=0.6 Hz, J=0.6 Hz), 7.77-7.74 (m, 4H), 7.37 (ddd, 2H, J=0.7 Hz, J=0.7 Hz, J=0.7 Hz), 7.27-7.23 (m, 2H), 7.11-7.03 (m, 6H);

13C-NMR (300 MHz, CDCl3, ppm): δ 156.59, 156.34, 149.79, 151.75, 136.74, 131.93, 129.88, 129.73, 129.15, 127.58, 126.69, 120.98, 188.44, 114.79;

EI, MS m/z (%): 512 (100, M+)

Synthesis Example 2

Synthesis of Compound 2

Synthesis of Intermediate 2-(1)

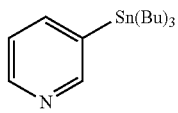

8-(1)

2 g (3.88 mmol) of Intermediate I-(5), 0.9 mL (9.43 mmol) of 2-bromopyridine, 5.65 mL (11.31 mmol) of 2M K2CO3, 0.068 mL (0.15 mmol) of Aliquat®336, and toluene were mixed in a 2-necked round-bottom flask. After degassing, 0.35 g (0.3 mmol) of Pd(PPh3)4 was added thereto, and stirred at about 80° C. for about 24 hours. Excess water was added to terminate the reaction, followed by extraction with dichloromethane. The resulting organic layer was separated and then dried with anhydrous MgSO4, followed by evaporation under reduced pressure to remove the solvent, drying, 0.5 mL (5.19 mmol) of 3-bromopyridine was dissolved in 25 mL of Et2O in a 2-necked round-bottom flask, and the temperature of the flask was cooled down to about −78° C. 3.89 mL (6.23 mmol) of n-BuLi (1.6 M in hexane) was slowly added thereto and stirred at the same temperature for 3 hours. After adding 1.55 mL (5.71 of tributyltin chloride, the resulting reaction mixture was stirred at about −78° C. for about 30 minutes and then at room temperature for about 12 hours, followed by adding a saturated aqueous NH4Cl solution, and extraction with Et2O. The resulting organic layer was separated and then dried with anhydrous MgSO4, followed by evaporation under reduced pressure to remove the solvent, and separation by column chromatography (hexane:ethyl acetate=9:1 by v/v) to obtain 1.58 g of Intermediate 2-(1) as transparent oil (Yield: 83%).

Synthesis of Compound 2

1 g (1.94 mmol) of Intermediate 1-(4), 1.6 g (4.26 mmol) of Intermediate 8-(1), and 0.08 g (0.04 mmol) of Pd(PPh$_3$)$_4$ were dissolved in 10 mL of toluene in a 2-necked round-bottom flask, and stirred at about 80° C. for 3 days. Excess water was added to terminate the reaction, followed by extraction with dichloromethane. The resulting organic layer was separated and then dried with anhydrous MgSO$_4$, followed by evaporation under reduced pressure to remove the solvent, and separation by column chromatography (hexane:ethyl acetate=1:1 by v/v) to obtain 0.43 g of Compound 1 as a yellow solid (Yield: 44%).

IR (KBr, cm-1): 3027-3052 (sp2=C—H), 1619 (C=N), 1600 (C=C), 1475 (C=C), 1392 (C—N);

1H-NMR (300 MHz, CDCl3, ppm): δ 8.85 (s, 2H), 8.60 (d, 2H, J=3.6 Hz) 7.88 (q, 6H, J=7.1 Hz) 7.57 (d, 4H, J=8.7 Hz) 7.37 (q, 4H, J=5.6 Hz) 7.11-7.02 (m, 6H, J=6.3 Hz);

13C-NMR (300 MHz, CDCl3, ppm): δ 169.02, 164.56, 164.02, 151.84, 148.25, 140.38, 137.66, 135.82, 134.40, 130.21, 129.84, 127.48, 127.04, 126.90, 126.63, 125.54, 123.62, 123.58, 120.99, 118.69;

EI, MS m/z (%): 512 (100, M+)

Synthesis Example 3

Synthesis of Compound 18

Synthesis of Intermediate 18-(2)

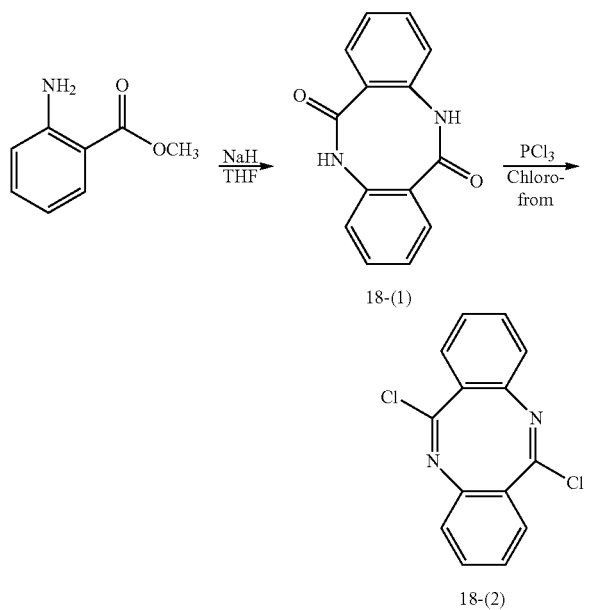

After 20 g (0.13 mol) of methyl 2-aminobenzoate was put into a 500 mL of flask and then dissolved with THF, 6 g (0.26 mol) of sodium hydride was added thereto. The resulting mixture was stirred at about 50° C. for about 48 hours, 0.1M HCl was added thereto to terminate the reaction, followed by extraction with dichlorimethane. The resulting organic layer was separated, and dried under reduced pressure to remove the solvent. The residue was washed with water and methanol, and dried for about 24 hours to obtain 23 g of Intermediate 18-(1) (Yield: 75%).

1H NMR (300 MHz, DMSO), δ (ppm): δ 10.20 (s, 2H), 7.32 (m, 6H), 7.07 (d, 2H).

13C NMR (300 MHz, DMSO), δ (ppm): 126.13, 127.68, 128.59, 130.95, 135.18, 169.69.

IR: V max (cm-1), 3400 (—N—H), 3168, 3041 (=C—H), 1647 (—C=O), 1499 1443, 1400, 1070, 1140 (—C=C).

After dissolving 5 g (0.02 mol) of Intermediate 18-(1) in chloroform, 11 g (0.05 mol) of PCl$_5$ was added thereto. After stirring the mixture at about 100° C. for about 24 hours, water was added to the mixture to terminate the reaction, followed by extraction with ethyl acetate, and drying under reduced pressure to remove the solvent, thereby obtaining 5 g of Intermediate 18-(2) (Yield: 55%).

1H-NMR (300 MHz, CD2Cl2): δ 7.41-7.36 (m, 4H), 7.19 (t, 2H), 7.01-6.98 (m, 2H).

13C NMR (300 MHz, CD2Cl2), δ (ppm): 155.93, 145.32, 131.58, 127.00, 125.36, 121.78.

Synthesis of Intermediate 18-(3)

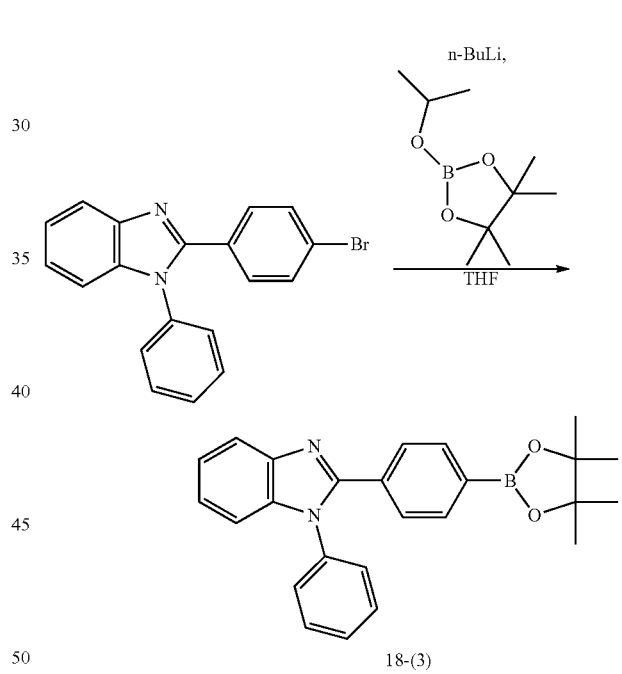

4 g (0.011 mol) of 2-(4-bromophenyl)-1-phenyl-1H-benzo[d]imidazole was put into a 250 mL flask, and dissolved with THF. 6 mL (0.013 mol) of n-BuLi was slowly added thereto at about −78° C., and the temperature was maintained for about 1 hour. 3 g (0.013 mol) of 2-isopropoxy-4,4,5,5-tetramethyl-1,3,2-dioxaborolane was slowly added thereto at about −78° C., and reacted at room temperature for about 12 or longer. Water was added to terminate the reaction, followed by extraction with ethyl acetate, and purification to obtain 3 g of Intermediate 18-(3) (Yield: 66%).

1H NMR (300 MHz, CDCl3): δ 7.9 (d, 1H), 7.77 (d, 2H), 7.60-7.52 (m, 2H), 7.50 (d, 3H). 7.37-7.26 (m, 5H), 1.35 (s, 12H).

Synthesis of Compound 18

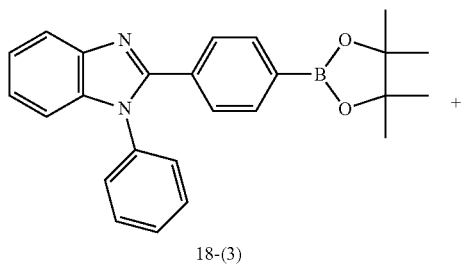

18-(3)

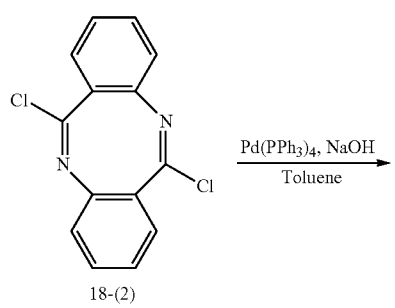

18-(2)

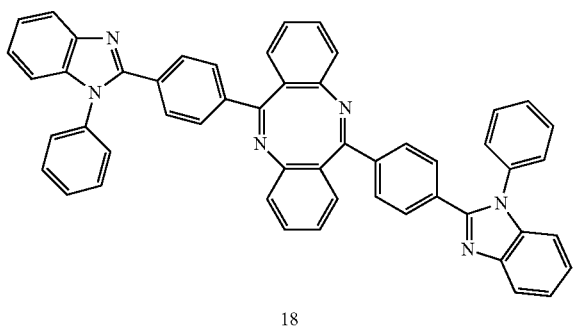

18

1 g (5 mmol) of Intermediate 18-(2) and 4 g (10 mmol) of Intermediate 18-(3) were dissolved in 50 mL of toluene in a 100-mL 3-necked round-bottom flask by using (utilizing) a torch. 10 mL of 2M NaOH was added thereto and stirred for about 30 while supplying nitrogen thereto. After adding 0.4 g (0.40 mmol) of Pd(PPh$_3$)$_4$ and a temperature increase to about 100° C., the mixture was stirred for about 24 hours. The mixture was cooled down to room temperature, and 2M HCl was added thereto to terminate the reaction, followed by extraction with ethyl acetate. The resulting organic layer was dried using (utilizing) anhydrous MgSO$_4$, and the solvent was removed using (utilizing) a rotary evaporator, followed by separation by column chromatography (hexane:ethyl acetate=10:1 by v/v), and recrystallization with ethyl acetate and ethanol to obtain 1.5 g of Compound 18 (Yield; 70%).

1H-NMR (300 MHz, CD2Cl2): δ 7.86-7.84 (m, 2H), 7.72-7.60 (m, 4H), 7.55-7.53 (m, 10H), 7.40-7.25 (m, 12H), 7.10-6.99 (m, 6H).

13C NMR (300 MHz, CD2Cl2), δ (ppm): 167.80, 151.72, 150.00, 149.03, 130.86, 130.34, 130.22, 129.24, 128.82, 127.52, 127.09, 126.95, 125.73, 121.12.

Synthesis Example 4

Synthesis of Compound 139

Synthesis of Intermediate 139-(1)

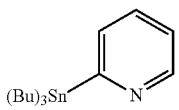

139-(1)

1.5 mL (15.57 mmol) of 2-bromopyridine was dissolved in 15 mL of THF in a 2-necked round-bottom flask, and the temperature of the flask was cooled down to about −78° C. 11.67 mL (18.69 mmol) of n-BuLi (1.6 M in hexane) was slowly added thereto and stirred at the same temperature for about 2 hours. After adding 4.65 mL (17.13 mmol) of tributyltin chloride, the resulting reaction mixture was stirred at about −78° C. for about 30 minutes and then at room temperature for about 12 hours, followed by adding a saturated aqueous NH$_4$Cl solution, and extraction with diethyl ether. The resulting organic layer was separated and then dried with anhydrous MgSO$_4$, followed by evaporation under reduced pressure to remove the solvent, drying, and separation by column chromatography (hexane:ethyl acetate=9:1 by v/v) to obtain 3.23 g of Intermediate 139-(1) as transparent oil (Yield: 93%).

Synthesis of Intermediate 139-(2)

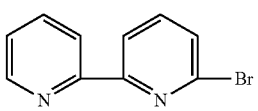

139-(2)

1.5 g (6.33 mmol) of 2,6-dibromopyridine, 3.48 g (9.48 mmol) of Intermediate 139-(1), and 0.15 g (0.06 mmol) of Pd(PPh$_3$)$_4$ were dissolved in 15 mL of toluene in a 2-necked round-bottom flask, and stirred at about 80° C. for about 24 hours. After evaporation under reduced pressure to remove the solvent, the resulting residue was dissolved in dichloromethane, followed by extraction with 6M HCl. The aqueous layer was separated and collected, and ammonia water was added thereto, followed by extraction with dichloromethane. The resulting organic layer was separated and then dried with anhydrous MgSO$_4$, followed by evaporation under reduced pressure to remove the solvent, by drying, and by separation with column chromatography (hexane:ethyl acetate=5:1 by v/v) to obtain 0.9 g of Intermediate 139-(2) as white solid (Yield: 61%).

1H-NMR (300 MHz, CDCl3, ppm): δ 8.68 (tt, 1H, J=1 Hz, J=0.6 Hz), 8.41 (dd, 2H, J=9 Hz, J=9 Hz), 7.84 (ttt, 1H, J=0.6 Hz, J=0.5 Hz, J=0.6 Hz), 7.69 (t, 1H, J=7.65 Hz), 7.51 (t, 1H, J=3.9 Hz), 7.35 (q, 1H, J=4.5 Hz);

13C-NMR (300 MHz, CDCl3, ppm): δ 156.21, 155.78, 149.30, 143.28, 141.05, 137.87, 125.88, 123.24, 123.52, 120.64;

EI, MS m/z (%): 234 (100, M+)

Synthesis of Intermediate 139-(3)

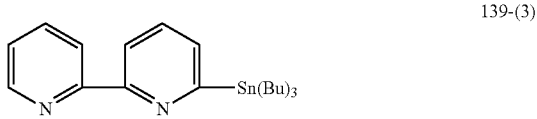

0.9 g (3.81 mmol) of Intermediate 139-(2) was dissolved in 15 mL of THF in a 2-necked round-bottom flask, and the temperature of the reaction flask was cooled down to about −78° C. 1.74 mL (2.82 mmol) of n-BuLi (1.6 M in hexane) was slowly added thereto and stirred at the same temperature for 1 hour. After adding 4.65 mL (17.13 mmol) of tributyltin chloride, the resulting reaction mixture was stirred at about −78° C. for about 30 minutes and then at room temperature for about 12 hours, followed by adding a saturated aqueous NH$_4$Cl solution, and extraction with ethyl acetate. The resulting organic layer was separated and then dried with anhydrous MgSO$_4$, followed by evaporation under reduced pressure to remove the solvent, drying, and separation by column chromatography (hexane:ethyl acetate=5:1 by v/v) to obtain 0.75 g of Intermediate 139-(3) as transparent oil (Yield: 45%).

Synthesis of Compound 139

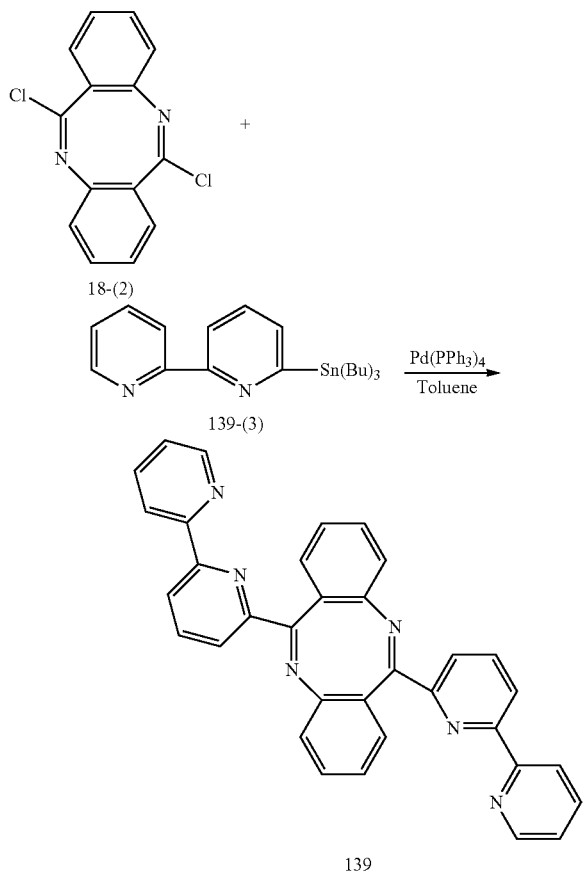

0.2 g (0.8 mmol) of Intermediate 18-(2), 0.75 g (1.5 mmol) of Intermediate 139-(3), and 0.04 g (0.04 mmol) of Pd(PPh$_3$)$_4$ were dissolved in 2 mL of toluene in a 2-necked round-bottom flask, and stirred at about 80° C. for about 24 hours. Excess water was added to terminate the reaction, followed by extraction with dichloromethane. The resulting organic layer was separated and then dried with anhydrous MgSO$_4$, followed by evaporation under reduced pressure to remove the solvent, drying, and separation by column chromatography (hexane:ethyl acetate=5:1 by v/v) to obtain 0.16 g of Compound 16 as yellow solid (Yield: 43%).

1H-NMR (300 MHz, CDCl3, ppm): δ 8.86 (t, 1H, J=1, 2 Hz), 8.62 (q, 1H, J=2.1 Hz) 7.90 (t, 2H, J=4.3 Hz) 7.70 (q, 2H, J=21.1 Hz) 7.39-7.33 (m, 6H) 7.09-7.01 (m, 8H);

13C-NMR (300 MHz, CDCl3, ppm): δ 163.93, 159.77, 151.80, 140.32, 129.41, 128.22, 126.96, 123.63, 123.45, 120.99, 120.88, 116.92;

EI, MS m/z (%): 514 (100, M+)

Synthesis Example 5

Synthesis of Compound 140

Synthesis of Intermediate 20-(1)

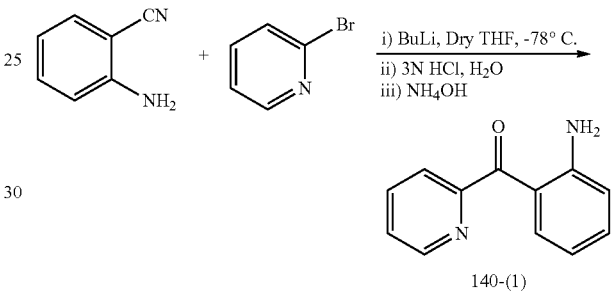

5.57 mL (5.84 mmol, 2.3 eq) of 2-bromopyridine and 50 mL of purified toluene were put into a 100-mL 1-necked-round-bottom flask, and stirred in an argon atmosphere. The temperature of the resulting reaction mixture was cooled down to −78° C. by using (utilizing) a cooling bath (EtOAc/Liquid N2 bath), followed by adding 22.37 mL of n-BuLi (5.58 mmol, 2.5 M in hexane, 2.2 eq) thereto, and stirring in an argon atmosphere for about 30 minutes. 3 g (2.54 mmol, 1 eq) of 2-aminobenzonitrile dissolved in purified toluene (25 mL) was slowly added to the resulting reaction mixture and stirred for about 30 minutes. After a slow temperature increase to room temperature, the reaction mixture was stirred for about 2 hour, and termination of the reaction was identified by thin-layer chlomatography (TLC).

After 80 g of cracked ice was put into a 250-mL beaker, the reaction mixture was slowly added thereto while stirring, and then further stirred at room temperature for about 1 hour. After discarding the aqueous layer by using (utilizing) a separatory funnel, 40 mL of HCl was added to the remaining organic layer to obtain a salt form of the desired product, and then the aqueous layer including the same was collected. The collected aqueous layer was washed with 20 mL of toluene, followed by pH adjustment with NH$_4$OH (25% aqueous solution). The pH-adjusted aqueous layer was stirred for about 1 hour, and the resulting solid was filtered under reduced pressure, and washed with cold water (20 mL). The resulting yellow solid was purified by column chromatography (eluent; EtOAc) to obtain 3.80 g of Intermediate 140-(1) as a yellow solid compound (Yield: 75%).

mp 140-142° C.

1H NMR (300 MHz, CDCl3) δ 6.31 (bs, 2H, D2O exchangeable), 6.59-6.64 (m, 1H), 6.71-6.74 (m, 1H), 7.27-

7.33 (m, 1H), 7.40-7.45 (m, 1H), 7.64-7.67 (m, 1H), 7.76 (d, 1H, J=7.8 Hz), 7.84-7.89 (m, 1H), 8.71 (d, 1H, 4.7 Hz).

Synthesis of Compound 140

1 g (5.04 mmol, 1 eq) of Intermediate 140-(1) and 0.1 g (0.50 mmol, 0.1 eq) of p-toluenesulfonic acid were put into a 30-mL culture test tube, and the culture test tube was capped and stirred in a 150° C. oil bath for about 4 hours. The reaction mixture was cooled down to room temperature, and dissolved with 5 mL of dichloromethane. The reaction mixture was washed with water (20 mL×5 times), and the aqueous layer was collected, followed by extraction with dichloromethane (20 mL×2 times). The organic layer was collected, dried with anhydrous MgSO$_4$, and evaporated under reduced pressure. 3 mL of CH$_2$Cl$_2$ was added to the residue, followed by filtration under reduced pressure and further washing with 2 mL of CH$_2$Cl$_2$ to obtain 0.83 g of compound 140 as a yellow solid (Yield: 92%).

mp 214-216° C.

1H NMR (300 MHz, CDCl3) δ 7.02-7.09 (m, 6H), 7.25-7.35 (m, 4H), 7.64-7.70 (m, 2H), 7.97 (d, 2H, J=7.94 Hz), 8.64-8.66 (m, 2H).

13C NMR (75 MHz, CDCl3) δ 120.7, 123.6, 124.3, 124.9, 126.0, 127.8, 136.4, 149.5, 151.2, 155.3, 168.8. HRMS (m/z): [M]+ calcd for C24H16N4 360.1375. Found: 360.1375.

Synthesis Example 6

Synthesis of Compound 39

Synthesis of Intermediate 39-(1)

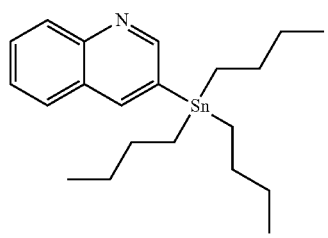

39-(1)

10 g (0.048 mol) of 3-bromoquinoline was put into a 250-mL flask, and dissolved with THF. 21 mL (0.052 mol) of n-BuLi was slowly added to the mixture at about −78° C., and the temperature was maintained for about 1 hour. 19 g (0.057 mol) of tributyltin chloride was slowly added thereto at about −78° C., and reacted at room temperature for about 12 hours or longer. Water was added thereto to terminate the reaction, followed by extraction with ethyl acetate to obtain 14 g of Intermediate 39-(1) (Yield: 70%).

1H NMR (300 MHz, CDCl3): δ 8.95-8.94 (d, 1H), 8.25 (s, 1H), 8.10-807 (m, 1H), 7.81-7.77 (m, 1H), 7.73-7.67 (m, 1H), 7.54-7.51 (m, 1H), 1.63-1.54 (m, 6H), 1.41-1.35 (m, 6H), 1.21-1.16 (m, 6H), 0.93-0.88 (m, 12H).

Synthesis of Compound 39

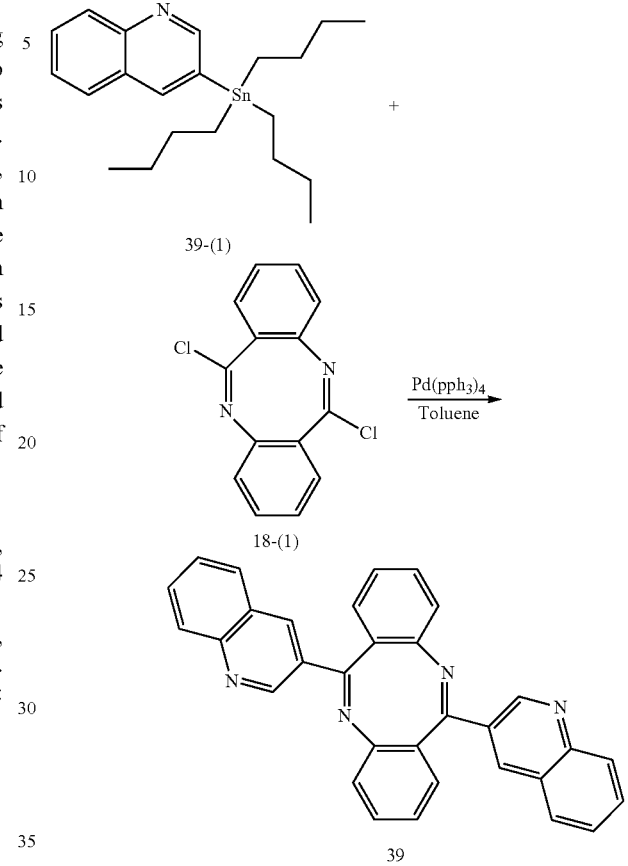

1 g (5 mmol) of Intermediate 39-(1), 4 g (10 mmol) of Intermediate 18-(1), and 0.2 g (0.2 mmol) of Pd(PPh$_3$)$_4$ were dissolved in 50 mL of toluene in a torch dried 100-mL 3-necked round-bottom flask. After a temperature increase to about 100° C., the resulting mixture was stirred for about 24 hours. The mixture was cooled down to room temperature, and water was added thereto to terminate the reaction, followed by extraction with ethyl acetate. The organic layer was collected, and dried using (utilizing) MgSO$_4$ to remove water. The remaining solvent was removed using (utilizing) a rotary evaporator, followed by drying and separation by column chromatography (hexane:ethyl acetate 10:1 by v/v), and recrystallization with ethyl acetate and ethanol to obtain 1.6 g of Compound 39 (Yield: 80%).

mp: 237° C.,

1H NMR (300 MHz, DMSO, ppm): 9.42 (s, 2H), 8.32 (s, 2H), 8.08-8.06 (m, 4H), 7.86-7.83 (t, 2H), 7.66-7.63 (t, 2H), 7.50-7.47 (m, 2H), 7.47-7.17 (m, 6H).

13C NMR (300 MHz, CD2Cl2), δ (ppm): 167.80, 151.72, 150.00, 149.03, 130.86, 130.34, 130.22, 129.24, 128.82, 127.52, 127.09, 126.95, 125.73, 121.12.

Example 1

An ITO/Ag/ITO anode was sonicated in isopropyl alcohol for about 5 minutes and pure water for about 5 minutes, and then cleaned by irradiation of ultraviolet rays for about 10 minutes and exposure to ozone. The resulting substrate was loaded into a vacuum deposition device.

After Compound A was deposited on the anode to form an HIL having a thickness of 600 Å, Compound B was deposited on the HIL to form an HTL having a thickness of about 550 Å, and then ADN (host) and Compound B (dopant) were co-deposited in a weight ratio of 200:3 on the HTL to form an EML having a thickness of about 200 Å. After Compound 1 and lithium quinolate (LiQ) were co-deposited in a weight ratio of 5:5 on the EML to form an ETL having a thickness of about 300 Å, LiQ was deposited on the ETL to form an EIL having a thickness of about 10 Å, and Mg and Ag were deposited in a weight ratio of 90:10 on the EIL to form a cathode having a thickness of about 120 Å, thereby manufacturing an organic light-emitting device.

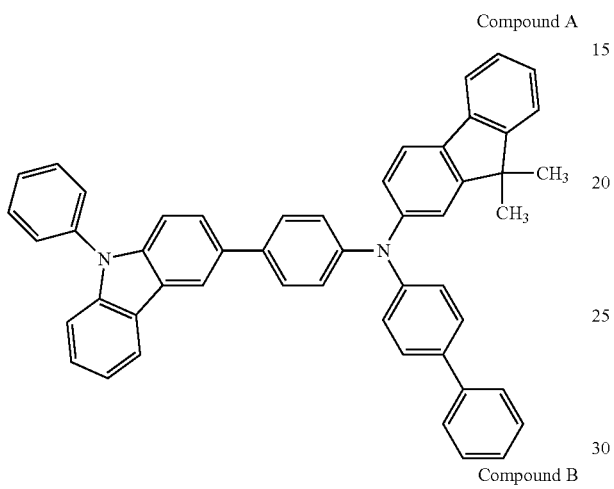

Compound A

Compound B

Example 2

An organic light-emitting device was manufactured in the same manner as in Example 1, except that Compound 2 instead of Compound 1 was used (utilized) to form the ETL.

Example 3

An organic light-emitting device was manufactured in the same manner as in Example 1, except that Compound 18 instead of Compound 1 was used (utilized) to form the ETL.

Example 4

An organic light-emitting device was manufactured in the same manner as in Example 1, except that Compound 139 instead of Compound 1 was used (utilized) to form the ETL.

Example 5

An organic light-emitting device was manufactured in the same manner as in Example 1, except that Compound 140 instead of Compound 1 was used (utilized) to form the ETL.

Example 6

An organic light-emitting device was manufactured in the same manner as in Example 6, except that Compound 114 instead of Compound 1 was used (utilized) to form the ETL.

Example 7

An organic light-emitting device was manufactured in the same manner as in Example 6, except that Compound 131 instead of Compound 1 was used (utilized) to form the ETL.

Comparative Example 1

An organic light-emitting device was manufactured in the same manner as in Example 1, except that $Alq_3$, instead of Compound 1, was used (utilized) to form the ETL.

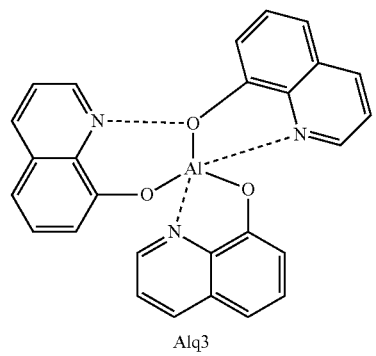

Alq3

Comparative Example 2

An organic light-emitting device was manufactured in the same manner as in Example 1, except that Compound C, instead of Compound 1, was used (utilized) to form the ETL.

Compound C

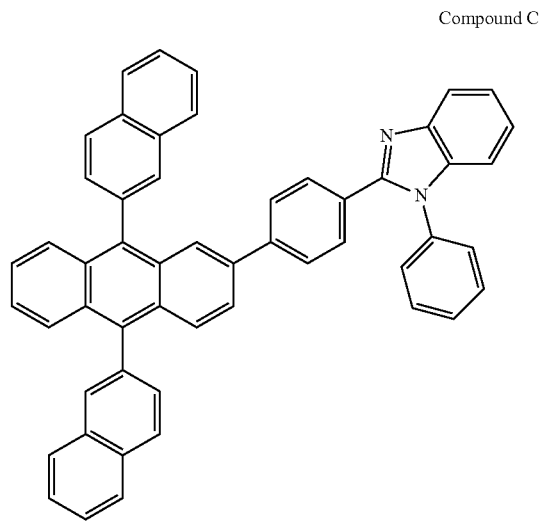 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1]

Evaluation Example 1

Driving voltages, current densities, luminances, efficiencies, and half-lifetimes of the organic light-emitting devices of Examples 1 to 7 and Comparative Examples 1 and 2 were evaluated using (utilizing) a Kethley Source-Measure Unit (SMU 236) and a PR650 (Spectroscan) Source Measurement Unit (available from Photo Research, Inc.). The results are shown in Table 1.

TABLE 1

| Example | ETL | Driving voltage (V) | Current density (mA/cm²) | Luminance (cd/m²) | Efficiency (cd/A) | CIE_x | CIE_y |
|---|---|---|---|---|---|---|---|
| Example 1 | Compound 1 | 5.2 | 12.5 | 600 | 6.2 | 0.137 | 0.055 |
| Example 2 | Compound 2 | 5.5 | 9.2 | 600 | 6.5 | 0.140 | 0.055 |
| Example 3 | Compound 18 | 5.1 | 9.1 | 600 | 6.7 | 0.139 | 0.055 |
| Example 4 | Compound 139 | 5.8 | 10.3 | 600 | 5.8 | 0.136 | 0.050 |
| Example 5 | Compound 140 | 5.7 | 11.3 | 600 | 5.3 | 0.145 | 0.050 |
| Example 6 | Compound 114 | 5.1 | 9.2 | 600 | 6.5 | 0.139 | 0.051 |
| Example 7 | Compound 131 | 5.6 | 9.1 | 600 | 6.6 | 0.141 | 0.057 |
| Comparative Example 1 | Alq$_3$ | 7.7 | 21.8 | 600 | 3.2 | 0.141 | 0.060 |
| Comparative Example 2 | Compound C | 5.2 | 21.4 | 600 | 2.8 | 0.139 | 0.053 |

Referring to Table 1, the organic light-emitting devices of Examples 1 to 7 were found to have improved driving voltages, improved current densities, improved luminances, improved efficiencies, and improved half-lifetimes, compared to those of the organic light-emitting devices of Comparative Examples 1 and 2.

Evaluation Example 2

Compounds 1, 2, and 18 were analyzed by UV spectroscopy, photoluminescence (PL) spectroscopy, cyclic voltammetry (CV), thermogravimetry (TGA), and differential scanning calorimetry (DSC). The results are shown in FIGS. 2 to 14 and Tables 2 to 4

TABLE 2

| | UV-vis. $\lambda_{max}$ (nm) | | PL $\lambda_{em.\,max}$ (nm) | | $E_g$ (eV) | LU-MO (eV) | HO-MO (eV) | $T_d$ (°C.) | $T_m$ (°C.) |
|---|---|---|---|---|---|---|---|---|---|
| | solution | film | solution | film | | | | | |
| Compound 1 | 298 | 300 | 433 | 452 | 3.02 | −3.62 | −6.04 | 295 | 156 |

TABLE 3

| | UV-vis. $\lambda_{max}$ (nm) | | PL $\lambda_{em.\,max}$ (nm) | | $E_g$ (eV) | LU-MO (eV) | HO-MO (eV) | $T_d$ (°C.) | $T_m$ (°C.) |
|---|---|---|---|---|---|---|---|---|---|
| | solution | film | solution | film | | | | | |
| Compound 2 | 289 | 295 | 543 | 545 | 3.32 | −3.52 | −6.84 | 299 | |

TABLE 4

| | UV-vis. $\lambda_{max}$ (nm) | | PL $\lambda_{em.\,max}$ (nm) | | $E_g$ (eV) | LU-MO (eV) | HO-MO (eV) | $T_d$ (°C.) | $T_m$ (°C.) |
|---|---|---|---|---|---|---|---|---|---|
| | solution | film | solution | film | | | | | |
| Compound 18 | 323 | 328 | — | — | 3.12 | −2.84 | −5.96 | 438 | — |

As described above, according to the one or more of the above embodiments of the present disclosure, an organic light-emitting device including an antiaromatic compound of Formula 1 may have a high efficiency and improved lifetime characteristics.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present disclosure have been described with reference to the figures, it will be understood by those of ordinary skill in the art that various changes in form and details may be made therein without departing from the spirit and scope of the present disclosure as defined by the following claims, and equivalents thereof.

What is claimed is:

1. An antiaromatic compound represented by Formula 1:

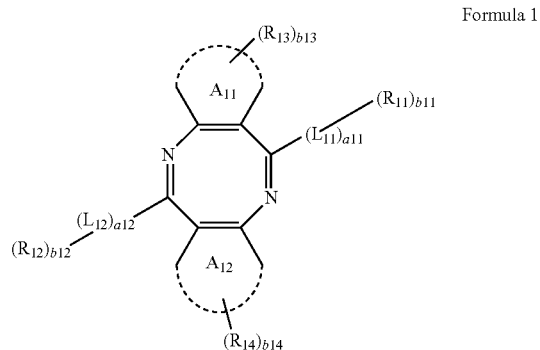

Formula 1 wherein, in Formula 1, $A_{11}$ and $A_{12}$ are each independently selected from a benzene, a naphthalene, a phenanthrene, an anthracene, a triphenylene, a pyrene, a chrysene, a pyrrole, a furan, an imidazole, a pyrazole, a thiazole, an oxazole, a pyridine, a pyrazine, a pyrimidine, a pyridazine, an indole, a quinoline, an isoquinoline, a benzoquinoline, a naphthyridine, a quinoxaline, a quinazoline, a phenanthridine, an acridine, a phenanthroline, a phenazine, a benzimidazole, a benzofuran, a benzothiophene, a benzoxazole, a triazole, a triazine, a dibenzofuran, and a dibenzothiophene;

$L_{11}$ and $L_{12}$ are each independently a moiety selected from a first group of moieties, the first group of moieties comprising a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted non-aromatic condensed polycyclic group, and a substituted or unsubstituted non-aromatic condensed heteropolycyclic group;

at least one substituent of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted non-aromatic condensed polycyclic group, and the substituted non-aromatic condensed heteropolycyclic group is selected from:

a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group; and a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group, each substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group;

a11 and a12 are each independently selected from 0, 1, 2, 3, 4, 5 and 6;

R11 and R12 are each independently a moiety selected from a second group of moieties, the second group of moieties comprising a substituted or unsubstituted $C_6$-$C_{60}$ aryl group, a substituted or unsubstituted $C_1$-$C_{60}$ heteroaryl group, a substituted or unsubstituted non-aromatic condensed polycyclic group, a substituted or unsubstituted non-aromatic condensed heteropolycyclic group, -N($Q_{11}$)($Q_{12}$), -Si($Q_{13}$)($Q_{14}$)($Q_{15}$), and -P($Q_{16}$)($Q_{17}$);

$Q_{11}$ to $Q_{17}$ are each independently selected from a substituted or unsubstituted $C_6$-$C_{60}$ aryl group, and a substituted or unsubstituted $C_1$-$C_{60}$ heteroaryl group;

at least one substituent of the substituted $C_6$-$C_{60}$ aryl group, the substituted $C_1$-$C_{60}$ heteroaryl group, the substituted non-aromatic condensed polycyclic group, and the substituted non-aromatic condensed heteropolycyclic group is selected from:

a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a C1-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group; and a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group, each substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group;

b11 and b12 are each independently an integer selected from 1 to 3;

R13 and R14 are each independently selected from:

a hydrogen atom, a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group; and a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group, each substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group; and b13 and b14 are each independently selected from 1, 2, 3, 4, 5, 6, 7, 8, 9 and 10, wherein when $A_{11}$ and $A_{12}$ are each a benzene, and a11 is 0 and a12 is 0 in Formula 1, $R_{11}$ and $R_{12}$ are each independently selected from a substituted or unsubstituted $C_{10}$-$C_{60}$ aryl group, a substituted $C_5$-$C_{60}$ heteroaryl group, an unsubstituted $C_6$-$C_{60}$ heteroaryl group, a substituted or unsubstituted non-aromatic condensed polycyclic group, a substituted or unsubstituted non-aromatic condensed heteropolycyclic group, -N($Q_{11}$)($Q_{12}$), -Si($Q_{13}$)($Q_{14}$)($Q_{15}$), -P($Q_{16}$)($Q_{17}$), a11 or a12 is not 0 when at least one moiety selected from the first group of moieties is linked to at least one moiety selected from the second group of moieties at a corresponding position of $(L_{11})$a11-$(R_{11})$b11 or $(L_{12})$a12-$(R_{12})$b12, wherein when, $A_{11}$ and $A_{12}$ are each a benzene, and each of $R_{11}$ and $R_{12}$ is an unsubstituted phenyl group, each of a11 and a12 is independently selected from 1, 2, 3, 4, 5 and 6, and wherein when $A_{11}$ and $A_{12}$ are each a pyridine, and a11 is 0 and a12 is 0 in Formula 1, $R_{11}$ and $R_{12}$ are each independently selected from a substituted or unsubstituted $C_{10}$-$C_{60}$ aryl group, a substituted or unsubstituted $C_1$-$C_{60}$ heteroaryl group, a substituted or unsubstituted non-aromatic condensed polycyclic group, a substituted or unsubstituted non-aromatic condensed heteropolycyclic group, -N($Q_{11}$)($Q_{12}$), -Si($Q_{13}$)($Q_{14}$)($Q_{15}$), and -P($Q_{16}$)($Q_{17}$).

2. The antiaromatic compound of claim 1, wherein $A_{11}$ and $A_{12}$ are each independently selected from a benzene, a naphthalene, a phenanthrene, an anthracene, a triphenylene, a pyridine, a quinoline, an isoquinoline, a naphthyridine, a quinoxaline, and a quinazoline.

3. The antiaromatic compound of claim 1, wherein $L_{11}$ and $L_{12}$ are each independently selected from:

a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thienylene group, a furanylene group, a silolylene group, an imidazolylene group, a pyrazolylene group, a thiazolylene group, an isothiazolylene group, an oxazolylene group, an isooxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothienylene group, a benzosilolylene group, an isobenzothiazolylene group, a benzooxazolylene group, an isobenzooxazolylene group, a triazolylene group, a tetrazolylene group, an oxadiazolylene group, a triazinylene group, a dibenzofuranylene group, a dibenzothiophenylene group, a benzocarbazolyene group, a dibenzocarbazolyene group, and a dibenzosilolylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thienylene group, a furanylene group, a silolylene group, an imidazolylene group, a pyrazolylene group, a thiazolylene group, an isothiazolylene group, an oxazolylene group, an isooxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothienylene group, a benzosilolylene group, an isobenzothiazolylene group, a benzooxazolylene group, an isobenzooxazolylene group, a triazolylene group, a tetrazolylene group, an oxadiazolylene group, a triazinylene group, a dibenzofuranylene group, a dibenzothiophenylene group, a benzocarbazolyene group, a dibenzocarbazolyene group, and a dibenzosilolylene group, each substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coroneryl group, an ovarenyl group, a pyrrolyl group, a thienyl group, a furanyl group, a silolyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuryl group, a benzothienyl group, a benzosilolyl group, an isobenzothiazolyl group, a benzooxazolyl group, an isobenzooxazolyl group, a triazolyl group, a tetrazole group, an oxadiazolyl group, a triazinyl group, a dibenzofuranyl group, a dibenzothienyl group, a benzocarbazolyl group, a dibenzocarbazolyl group, and a dibenzosilolyl group.

4. An antiaromatic compound represented by Formula 1:

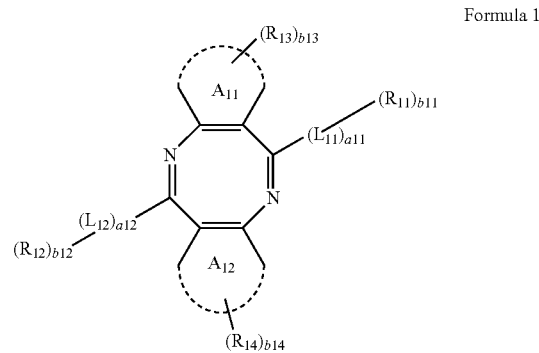

Formula 1 wherein, in Formula 1,
$A_{11}$ and $A_{12}$ are each independently selected from a benzene, a naphthalene, a phenanthrene, an anthracene, a triphenylene, a pyrene, a chrysene, a pyrrole, a furan, an imidazole, a pyrazole, a thiazole, an oxazole, a pyridine, a pyrazine, a pyrimidine, a pyridazine, an indole, a quinoline, an isoquinoline, a benzoquinoline, a naphthyridine, a quinoxaline, a quinazoline, a phenanthridine, an acridine, a phenanthroline, a phenazine, a benzimidazole, a benzofuran, a benzothiophene, a benzoxazole, a triazole, a triazine, a dibenzofuran, and a dibenzothiophene;
$L_{11}$ and $L_{12}$ are each independently a moiety selected from a first group of moieties, the first group of moieties comprising a substituted or unsubstituted $C_3$-$C_{10}$ cycloalkylene group, a substituted or unsubstituted heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted non-aromatic condensed polycyclic group, and a substituted or unsubstituted non-aromatic condensed heteropolycyclic group;
at least one substituent of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted non-aromatic condensed polycyclic group, and the substituted non-aromatic condensed heteropolycyclic group is selected from:
a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and $C_1$-$C_{60}$ alkoxy group;
a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group; and a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group, each substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group;

a11 and a12 are each independently selected from 0, 1, 2, 3, 4, 5 and 6;

R11 and R12 are each independently a moiety selected from a second group of moieties, the second group of moieties comprising a substituted or unsubstituted $C_6$-$C_{60}$ aryl group, a substituted or unsubstituted $C_1$-$C_{60}$ heteroaryl group, a substituted or unsubstituted non-aromatic condensed polycyclic group, a substituted or unsubstituted non-aromatic condensed heteropolycyclic group, -N($Q_{11}$)($Q_{12}$), -Si($Q_{13}$)($Q_{14}$)($Q_{15}$), and -P($Q_{16}$)($Q_{17}$);

$Q_{11}$ to $Q_{17}$ are each independently selected from a substituted or unsubstituted $C_6$-$C_{60}$ aryl group, and a substituted or unsubstituted $C_1$-$C_{60}$ heteroaryl group;

at least one substituent of the substituted $C_6$-$C_{60}$ aryl group, the substituted $C_1$-$C_{60}$ heteroaryl group, the substituted non-aromatic condensed polycyclic group, and the substituted non-aromatic condensed heteropolycyclic group is selected from:

a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group; and a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group;

b11 and b12 are each independently an integer selected from 1 to 3;

R13 and R14 are each independently selected from:

a hydrogen atom, a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group; and a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group, each substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group; and b13 and b14 are each independently selected from 1, 2, 3, 4, 5, 6, 7, 8, 9 and 10, wherein when $A_{11}$ and $A_{12}$ are each a benzene, and a11 is 0 and a12 is 0 in Formula 1, $R_{11}$ and $R_{12}$ are each independently selected from a substituted or unsubstituted $C_{10}$-$C_{60}$ aryl group, a substituted $C_5$-$C_{60}$ heteroaryl group, an unsubstituted $C_6$-$C_{60}$ heteroaryl group, a substituted or unsubstituted non-aromatic condensed polycyclic group, a substituted or unsubstituted non-aromatic condensed heteropolycyclic group, -N($Q_{11}$)($Q_{12}$), -Si($Q_{13}$)($Q_{14}$)($Q_{15}$), -P($Q_{16}$)($Q_{17}$), a11 or a12 is not 0 when at least one moiety selected from the first group of moieties is linked to at least one moiety selected from the second group of moieties at a corresponding position of ($L_{11}$)a11-($R_{11}$)b11 ($L_{12}$)a12-($R_{12}$)b12, wherein $L_{11}$ and $L_{12}$ are each independently a group represented by one of Formulae 3-1 to 3-32:

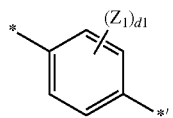

3-1

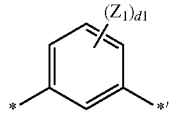

3-2

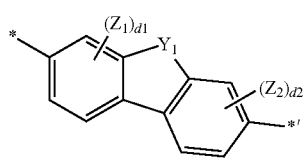

3-3

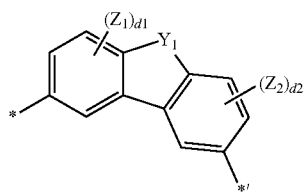

3-4

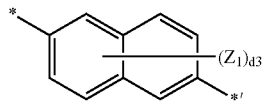

3-5

-continued

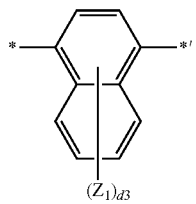

3-6

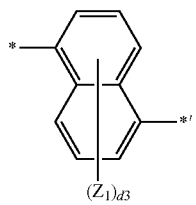

3-7

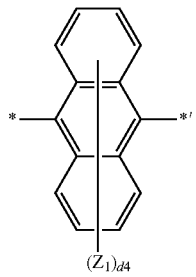

3-8

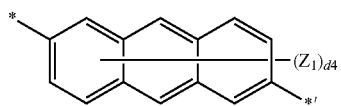

3-9

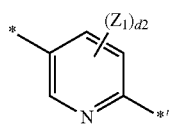

3-10

3-11

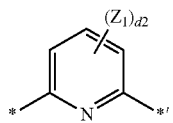

3-12

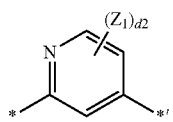

3-13

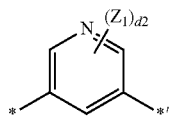

3-14

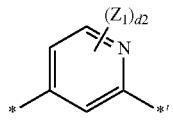

3-15

-continued

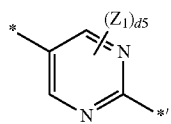 3-16

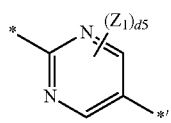 3-17

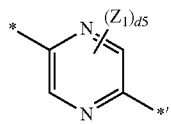 3-18

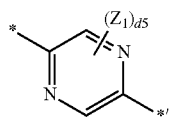 3-19

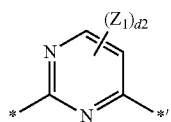 3-20

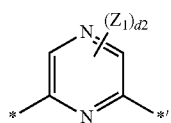 3-21

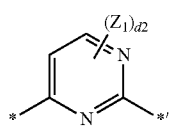 3-22

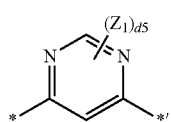 3-23

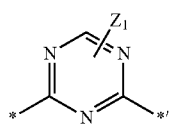 3-24

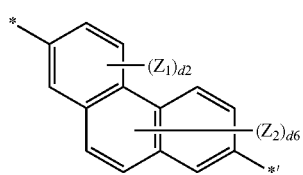 3-25

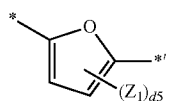 3-26

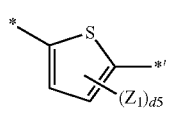 3-27

-continued

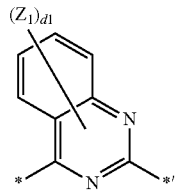 3-28

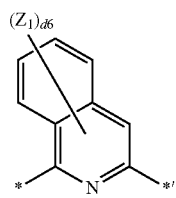 3-29

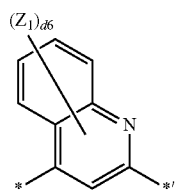 3-30

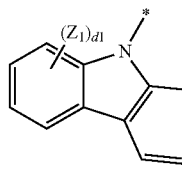 3-31

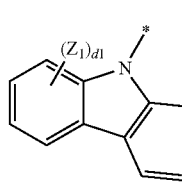 3-32 wherein, in Formulae 3-1 to 3-32, $Y_1$ is selected from $C(Q_{31})(Q_{32})$, $N(Q_{33})$, an oxygen atom, a sulfur atom, and $Si(Q_{34})(Q_{35})$;

$Q_{31}$ to $Q_{35}$ are each independently selected from a hydrogen atom, a deuterium atom, a $C_1$-$C_{20}$ alkyl group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$Z_1$ and $Z_2$ are each independently selected from a hydrogen atom, a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

d1 is an integer selected from 1 to 4;
d2 is an integer selected from 1 to 3;
d3 is an integer selected from 1 to 6;
d4 is an integer selected from 1 to 8;
d5 is 1 or 2;
d6 is an integer selected from 1 to 5; and
* and *' are each independently a binding site with another atom, and wherein when $A_{11}$ and $A_{12}$ are each a pyridine, and $a_{11}$ is 0 and a12 is 0 in Formula 1, $R_{11}$ and $R_{12}$ are each independently selected from a substituted or unsubstituted $C_{10}$-$C_{60}$ aryl group, a substituted or unsubstituted $C_1$-$C_{60}$ heteroaryl group, a substituted or unsubstituted non-aromatic condensed polycyclic group, a substituted or unsubstituted non-aromatic condensed heteropolycyclic group, -N($Q_{11}$)($C_{12}$), -Si($Q_{13}$)($Q_{14}$)($Q_{15}$), and -P($Q_{16}$)($Q_{17}$).

5. The antiaromatic compound of claim 1, wherein $L_{11}$ and $L_{12}$ are each independently a group represented by one of Formulae 4-1 to 4-10:

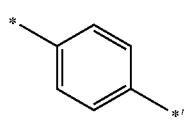
4-1

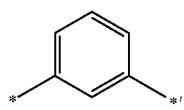
4-2

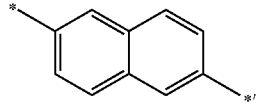
4-3

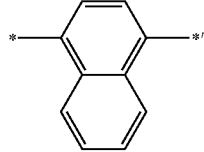
4-4

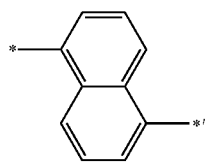
4-5

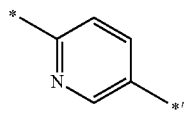
4-6

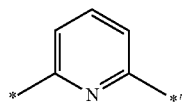
4-7

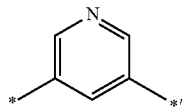
4-8

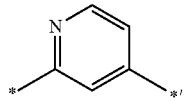
4-9

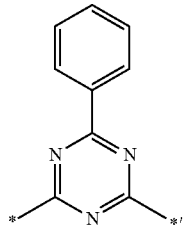
4-10 wherein, in Formulae 4-1 to 4-10, * and *' are each independently a binding site with another atom.

6. The antiaromatic compound of claim 1, wherein a11 and a12 are each independently 0 or 1.

7. The antiaromatic compound of claim 1, wherein $(L_{11})_{a11}$ and $(L_{12})_{a12}$ are each independently selected from a single bond and groups represented by Formulae 4-21 to 4-32:

4-21

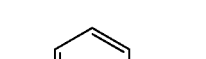
4-22

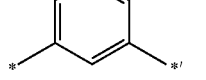
4-23

4-24

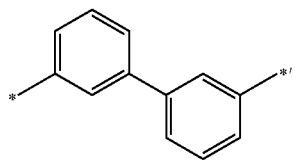
4-25

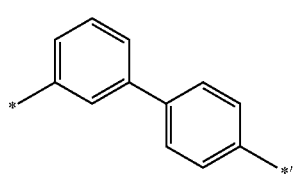
4-26

-continued

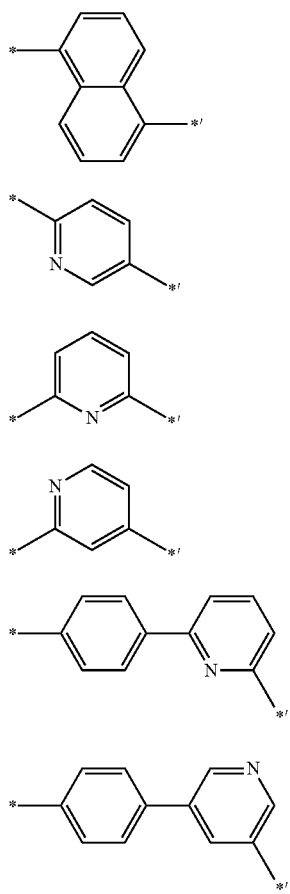

4-27

4-28

4-29

4-30

4-31

4-32 wherein, in Formulae 4-21 to 4-32, * and *' are each independently a binding site with another atom.

8. The antiaromatic compound of claim 1, wherein Ru and R12 are each independently selected from:

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuryl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, -N($Q_{11}$)($Q_{12}$), -Si($Q_{13}$)($Q_{14}$)($Q_{15}$), and -P($Q_{16}$)($Q_{17}$); and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovarenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuryl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group, each substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coroneryl group, an ovarenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuryl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group; and $Q_{11}$ to $Q_{17}$ are each independently selected from:

a phenyl group, a naphthyl group, a fluorenyl group, an anthracenyl group, a pyrenyl group, a pyridinyl group, a pyrazinyl group, a pyrimidinyl group, a pyridazinyl group, a quinolinyl group, an isoquinolinyl group, a carbazolyl group, and a triazinyl group; and a phenyl group, a naphthyl group, a fluorenyl group, an anthracenyl group, a pyrenyl group, a pyridinyl group, a pyrazinyl group, a pyrimidinyl group, a pyridazinyl group, a quinolinyl group, an isoquinolinyl group, a carbazolyl group, and a triazinyl group, each substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coroneryl group, an ovarenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuryl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group.

9. The antiaromatic compound of claim 1, wherein $R_{11}$ and $R_{12}$ are each independently selected from:

a phenyl group, a naphthyl group, an anthracenyl group, a phenanthrenyl group, a fluorenyl group, a pyridinyl group, a pyrazinyl group, an imidazole group, a benzimidazole group, a triazole group, a triazine group, an oxadiazolyl group, a quinolinyl group, an isoquinolinyl group, -N($Q_{11}$)($Q_{12}$), -Si($Q_{13}$)($Q_{14}$)($Q_{15}$), and -P($Q_{16}$)($Q_{17}$);

a phenyl group, a naphthyl group, an anthracenyl group, a phenanthrenyl group, a fluorenyl group, a pyridinyl group, a pyrazinyl group, an imidazole group, a benzimidazole group, a triazole group, a triazine group, an oxadiazolyl group, a quinolinyl group, and an isoquinolinyl group, each substituted with at least one selected from a deuterium atom, a halogen atom, a cyano group, a nitro group, a $C_1$-$C_{20}$ alkyl group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and $Q_{11}$ to $Q_{17}$ are each independently selected from:

a phenyl group, a naphthyl group, a fluorenyl group, a pyridinyl group, a carbazolyl group, and a triazinyl group; and a phenyl group, a naphthyl group, a fluorenyl group, a pyridinyl group, a carbazolyl group, and a triazinyl group, each substituted with at least one selected from a deuterium atom, a halogen atom, a cyano group, a nitro group, a $C_1$-$C_{20}$ alkyl group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

10. The antiaromatic compound of claim 1, wherein $R_{11}$ and $R_{12}$ are each independently selected from a group represented by Formulae 5-1 to 5-39:

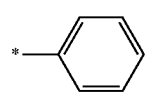

5-1

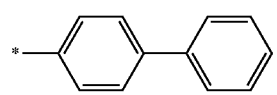

5-2

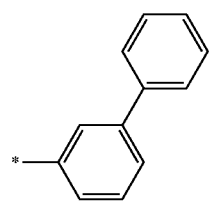

5-3

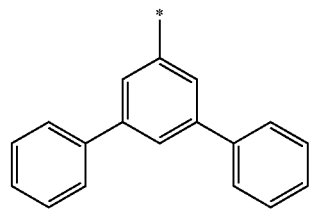

5-4

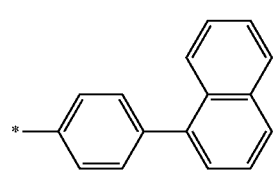

5-5

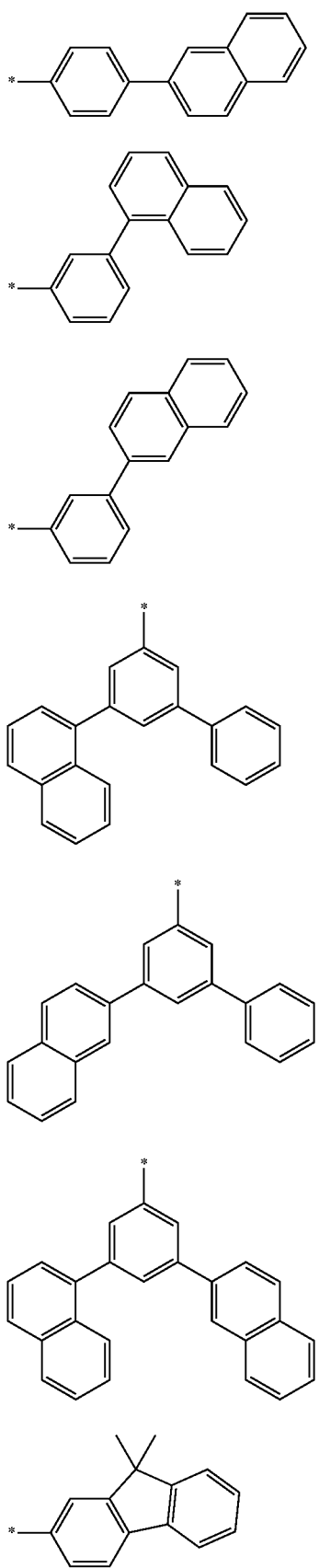
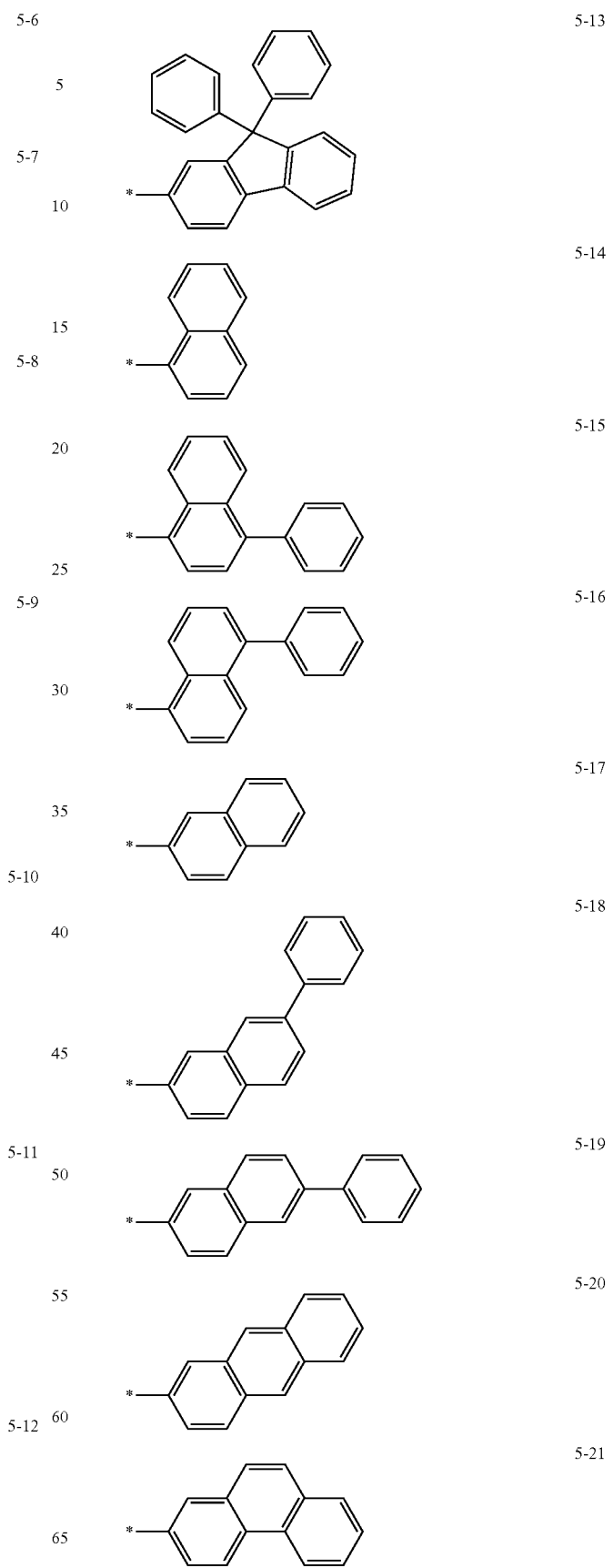

5-22 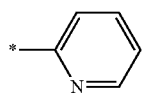
5-23 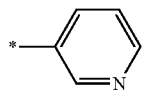
5-24 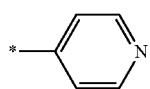
5-25 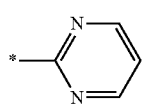
5-26 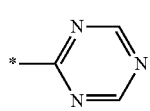
5-27 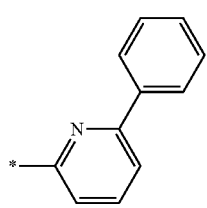
5-28 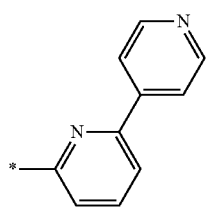
5-29 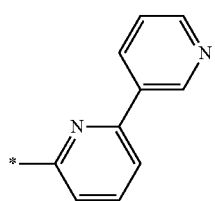
5-30 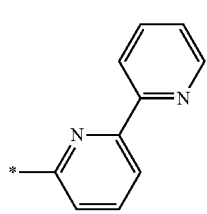
5-31 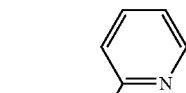
5-32 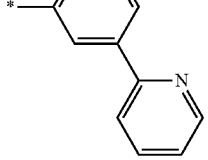
5-33 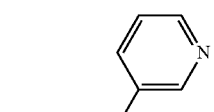
5-34 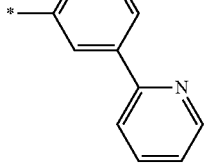
5-35 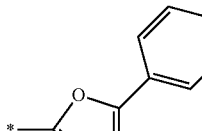
5-36 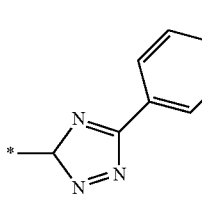

215
-continued

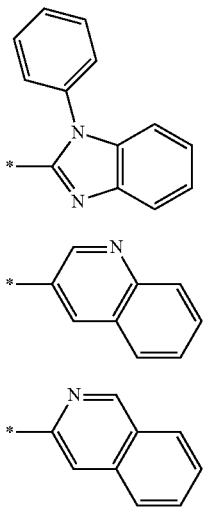

5-37

5-38

5-39 wherein, in Formulae 5-1 to 5-39,

* is each independently a binding site with another atom.

11. The antiaromatic compound of claim 1, wherein each of b11 and b12 is 1.

12. The antiaromatic compound of claim 1, wherein $R_{13}$ and $R_{14}$ are each independently selected from:

a hydrogen atom, a deuterium atom, a halogen atom, a cyano group, a nitro group, and a $C_1$-$C_{60}$ alkyl group;

a $C_1$-$C_{60}$ alkyl group substituted with at least one of a deuterium atom, a halogen atom, a cyano group, a nitro group, a $C_6$-$C_{60}$ aryl group, a $C_1$-$C_{60}$ heteroaryl group, a non-aromatic condensed polycyclic group, and a non-aromatic condensed heteropolycyclic group;

a $C_6$-$C_{60}$ aryl group, a $C_1$-$C_{60}$ heteroaryl group, a non-aromatic condensed polycyclic group, and a non-aromatic condensed heteropolycyclic group; and a $C_6$-$C_{60}$ aryl group, a $C_1$-$C_{60}$ heteroaryl group, a non-aromatic condensed polycyclic group, and a non-aromatic condensed heteropolycyclic group, each substituted with at least one of a deuterium atom, a halogen atom, a cyano group, a nitro group, a $C_1$-$C_{60}$ alkyl group, a $C_6$-$C_{60}$ aryl group, a $C_1$-$C_{60}$ heteroaryl group, a non-aromatic condensed polycyclic group, and a non-aromatic condensed heteropolycyclic group.

13. The antiaromatic compound of claim 1, wherein the antiaromatic compound is represented by one of Formulae 1A to 1E:

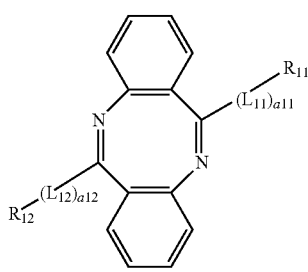

Formula 1A

216
-continued

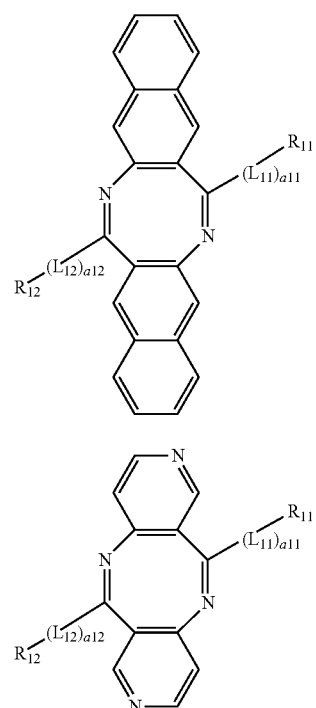

Formula 1B

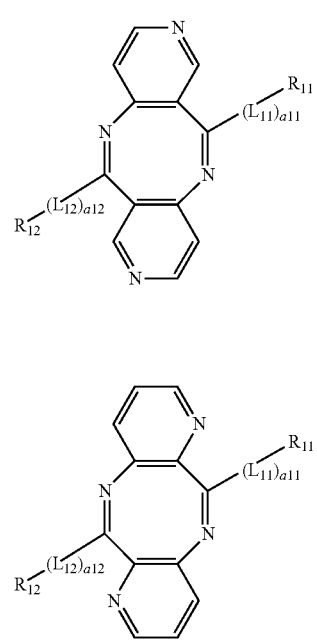

Formula 1C

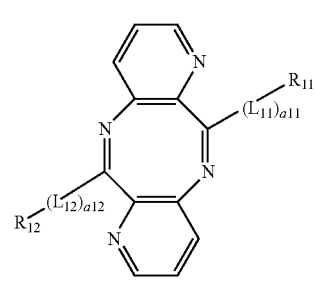

Formula 1D

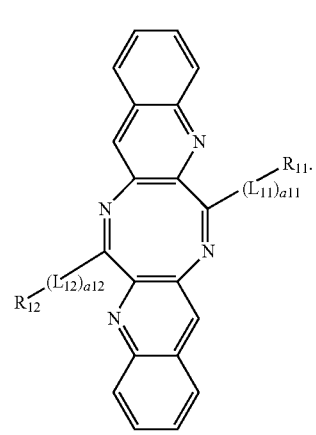

Formula 1E

14. The antiaromatic compound of claim 1, wherein the antiaromatic compound is represented by one of Formulae 1A to 1E:

Formula 1A
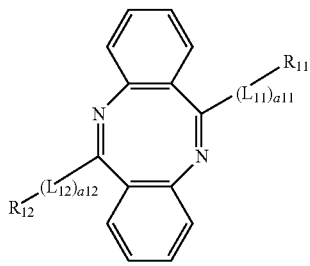
Formula 1B
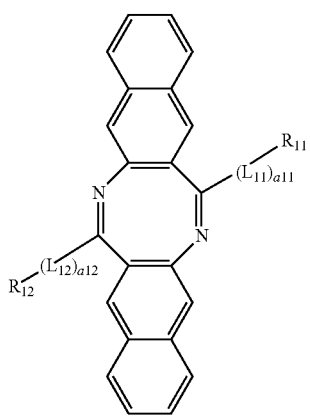
Formula 1C
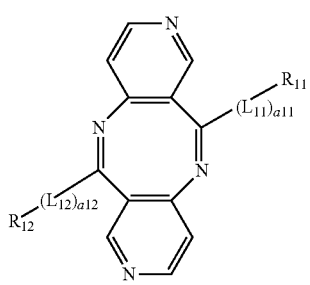
Formula 1D
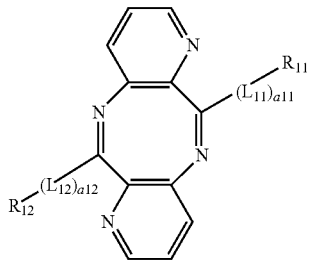
Formula 1E
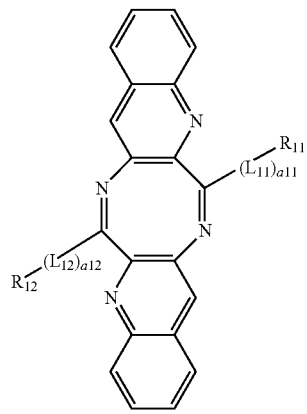
wherein, in Formulae 1A to 1E,
$L_{11}$ and $L_{12}$ are each independently a group represented by one of Formulae 4-1 to 4-10;
4-1
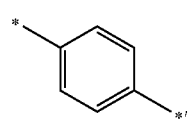
4-2
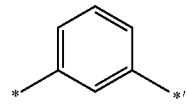
4-3
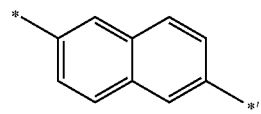
4-4
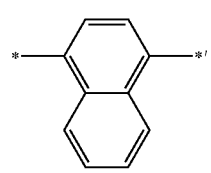
4-5
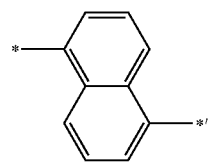
4-6
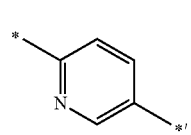
4-7
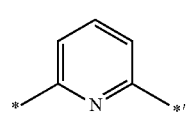

4-8
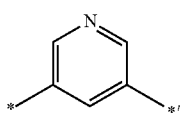
4-9
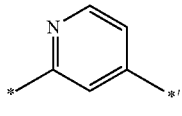
4-10
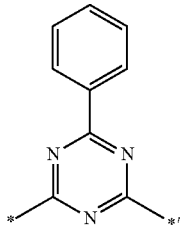
wherein, in Formulae 4-1 to 4-10,
* and *' are each independently a binding site with another atom;
$a_{11}$ and $a_{12}$ are each independently 0 or 1;
$R_{11}$ and $R_{12}$ are each independently a group represented by one of Formulae 5-1 to 5-39; wherein when $a_{11}$ is 0 and $a_{12}$ is 0 in Formula 1A, $R_{11}$ and $R_{12}$ are each independently a group represented by one of Formulae 5-2 to 5-21 and 5-27 to 5-39:
5-1
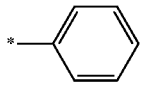
5-2
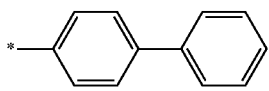
5-3
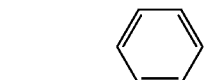
5-4
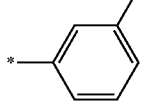
5-5
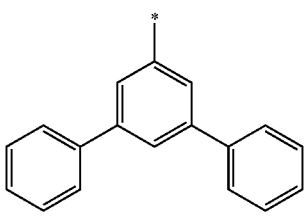
5-6
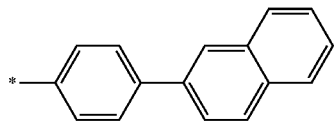
5-7
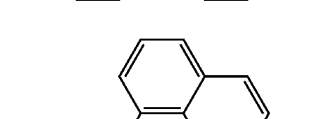
5-8
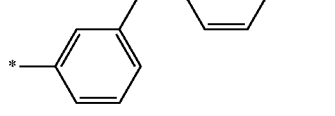
5-9
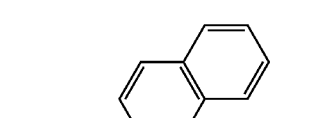
5-10
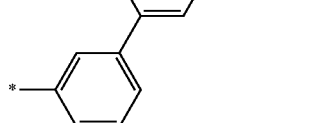
5-11
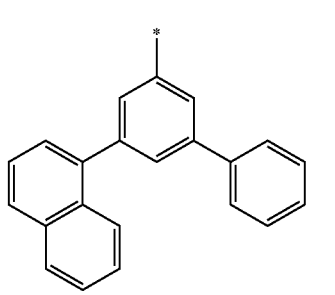
5-12
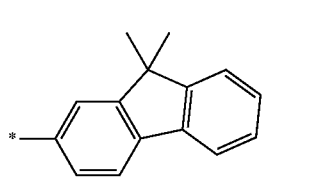

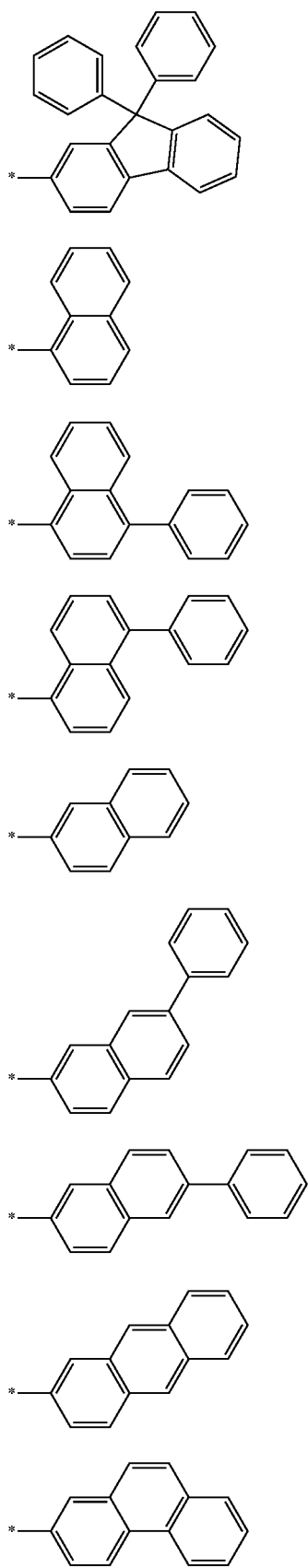
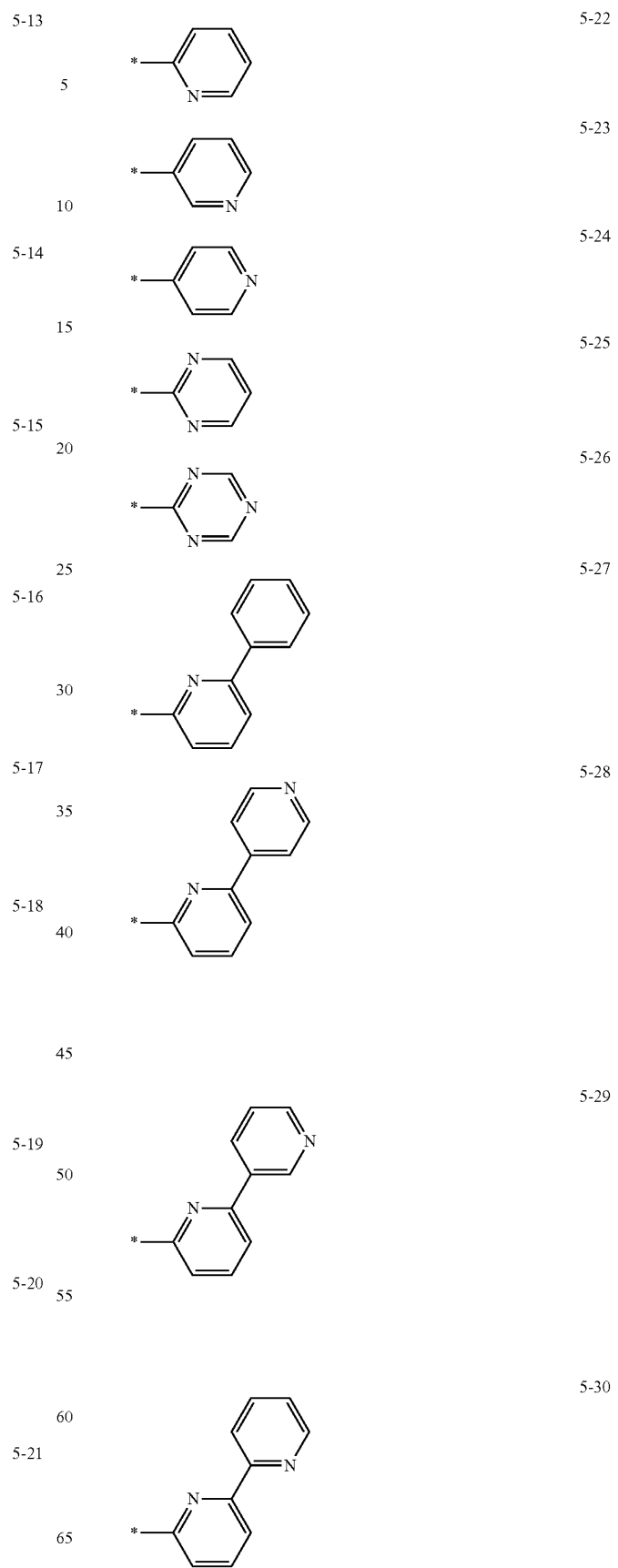

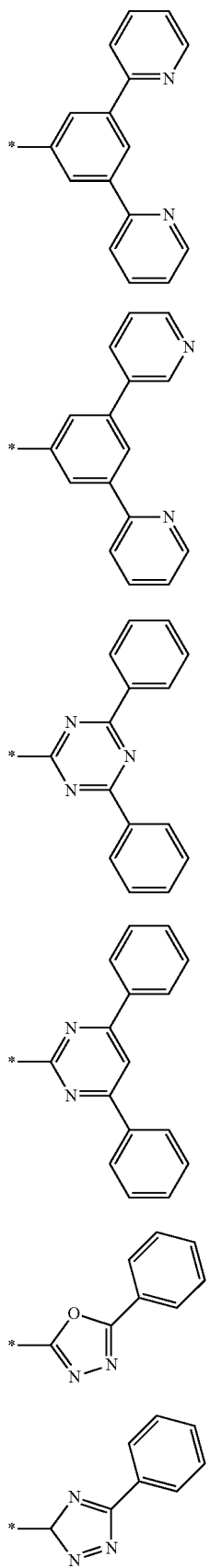
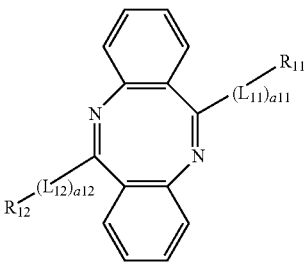
wherein, Formulae 5-1 to 5-39,
* is each independently a binding site with another atom.
15. The antiaromatic compound of claim 1, wherein the antiaromatic compound is represented by one of Formulae 1A to 1E:
Formula 1A
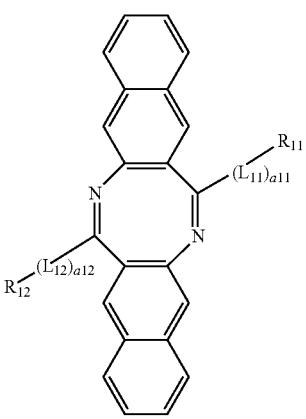
Formula 1B Formula 1C

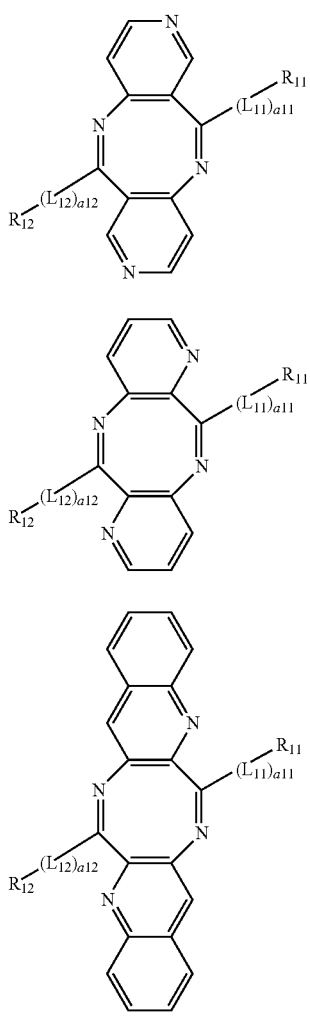

Formula 1D

Formula 1E wherein, in Formulae 1A and 1B, $L_{11}$ and $L_{12}$ are each independently a group represented by one of Formulae 4-1 to 4-10:

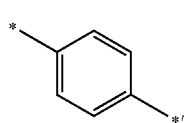

4-1

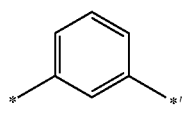

4-2

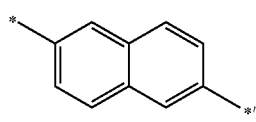

4-3

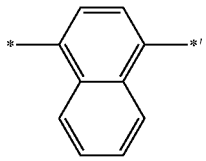

4-4

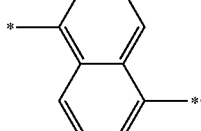

4-5

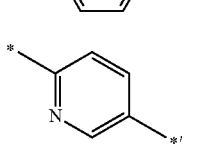

4-6

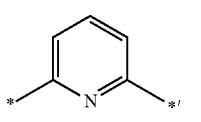

4-7

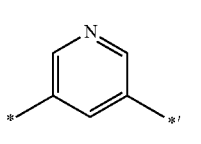

4-8

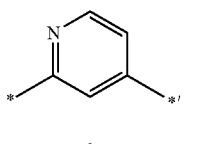

4-9

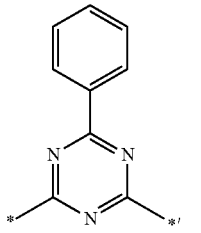

4-10 wherein, in Formulae 4-1 to 4-10,
* and *' are each independently a binding site with another atom;
$a_{11}$ and $a_{12}$ are each independently 0 or 1; and
$R_{11}$ and $R_{12}$ are each independently a group represented by one of Formulae 5-22 to 5-39; wherein when a11 is 0 and a12 is 0 in Formula 1A, $R_{11}$ and $R_{12}$ are each independently a group represented by one of Formulae 5-27 to 5-39:

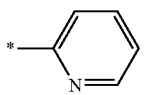

5-22

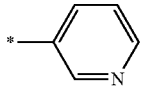

5-23

-continued
5-24
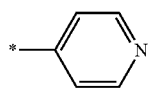
5-25
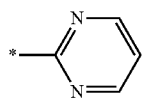
5-26
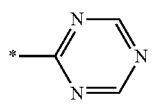
5-27
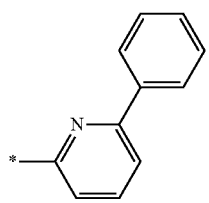
5-28
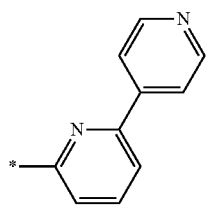
5-29
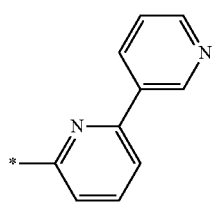
5-30
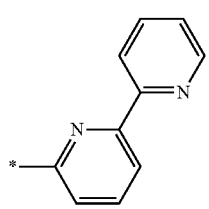
5-31
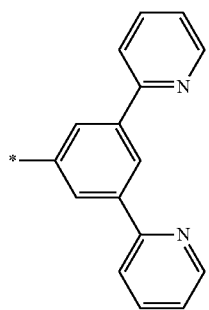
-continued
5-32
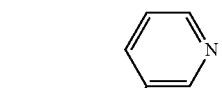
5-33
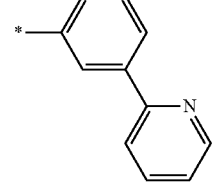
5-34
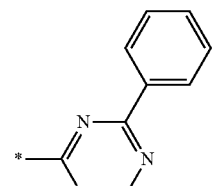
5-35
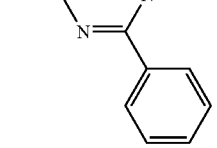
5-36
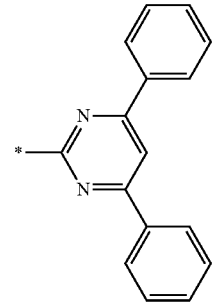
5-37
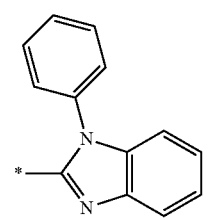

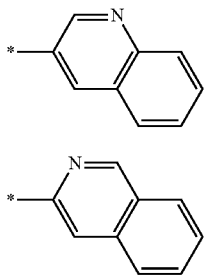
5-38

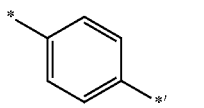
5-39 wherein, in Formulae 5-22 to 5-39, * is each independently a binding site with another atom; and in Formulae 1C to 1E, $L_{11}$ and $L_{12}$ are each independently a group represented by one of Formulae 4-1 to 4-5:

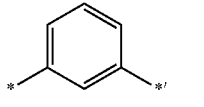
4-1

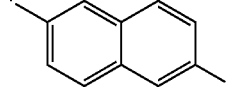
4-2

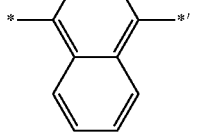
4-3

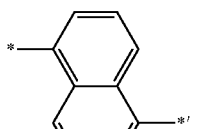
4-4

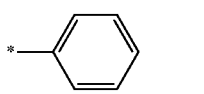
4-5 wherein, in Formulae 4-1 to 4-5,

* and *' are each independently a binding site with another atom;

a11 and a12 are each independently 0 or 1; and $R_{11}$ and $R_{12}$ are each independently a group represented by one of Formulae 5-1 to 5-21:

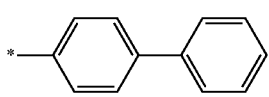
5-1

5-2

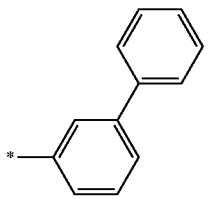
5-3

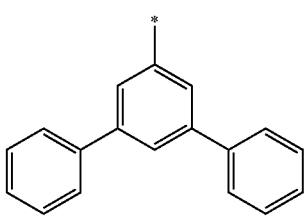
5-4

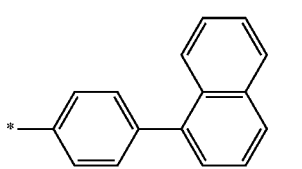
5-5

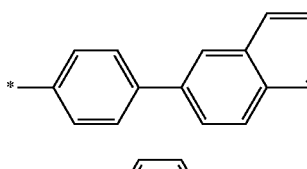
5-6

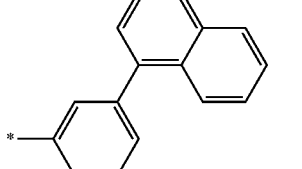
5-7

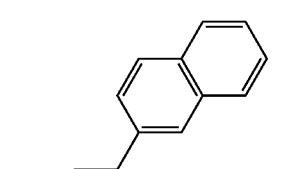
5-8

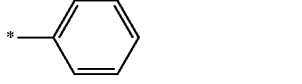
5-9

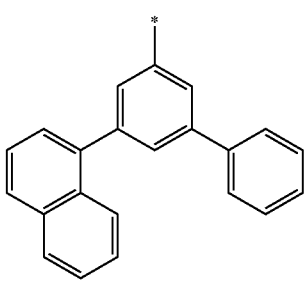

5-10 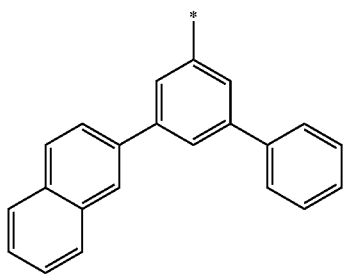
5-11 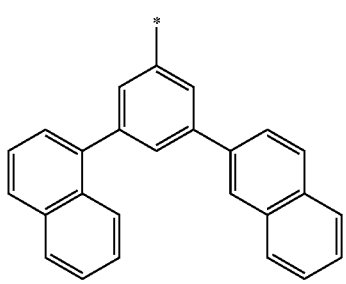
5-12 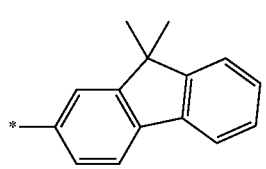
5-13 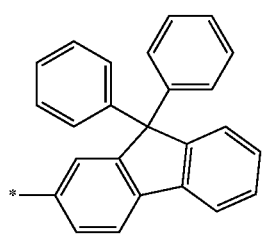
5-14 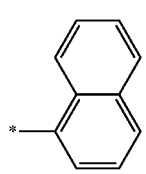
5-15 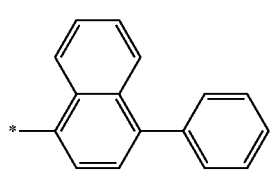
5-16 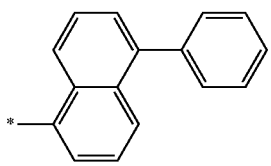
5-17 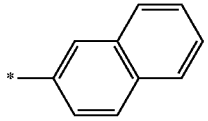
5-18 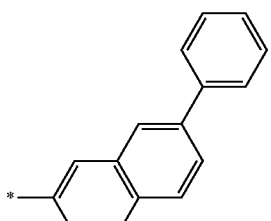
5-19 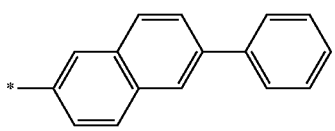
5-20 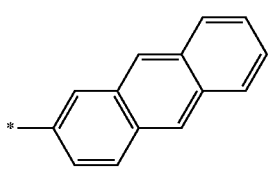
5-21 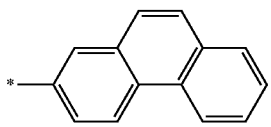
wherein, in Formulae 5-1 to 5-21, * is each independently a binding site with another atom.
16. The antiaromatic compound of claim 1, wherein the antiaromatic compound is selected from one of the following compounds 1 to 139, 141 to 181, and 200 to 247:

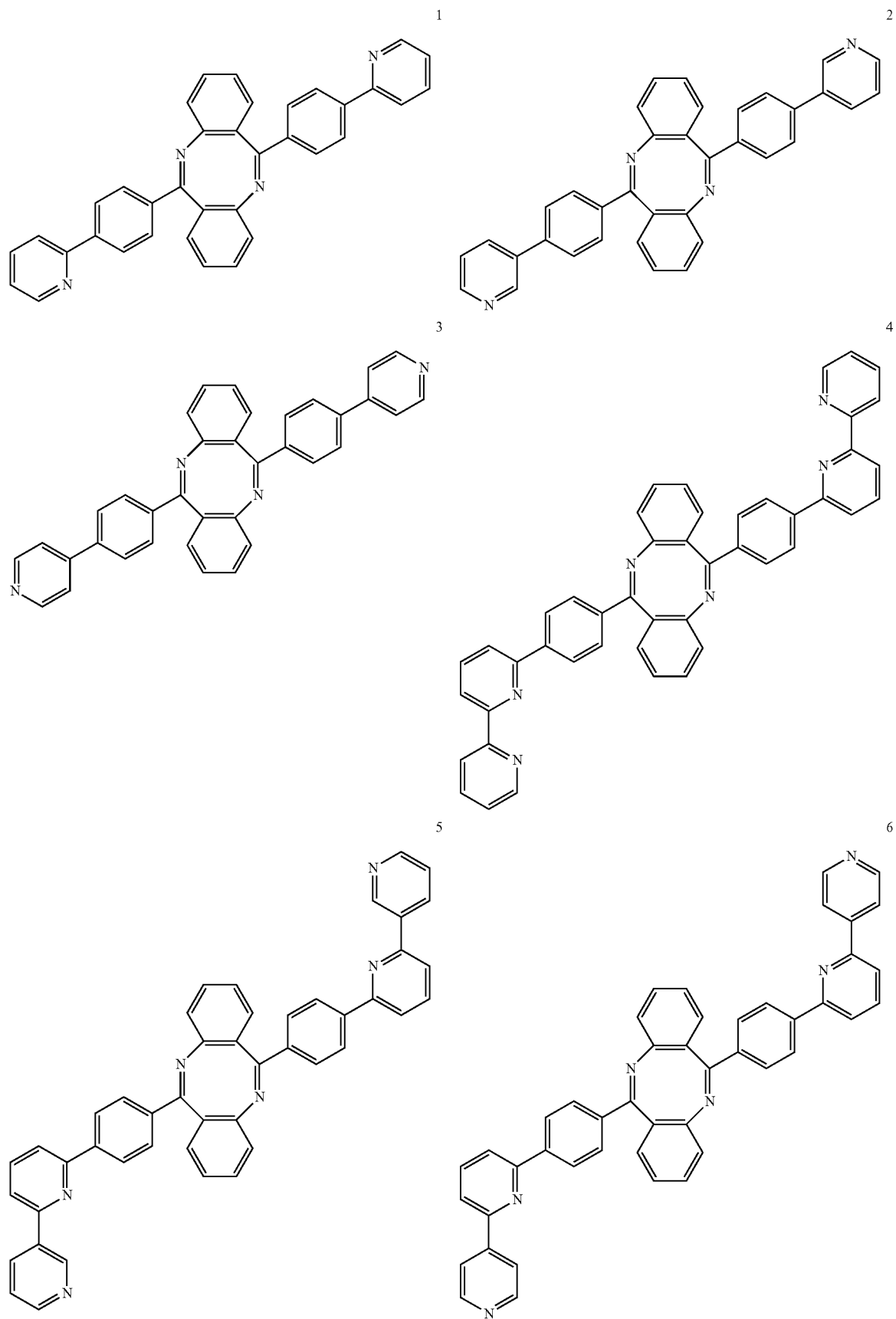

-continued
7
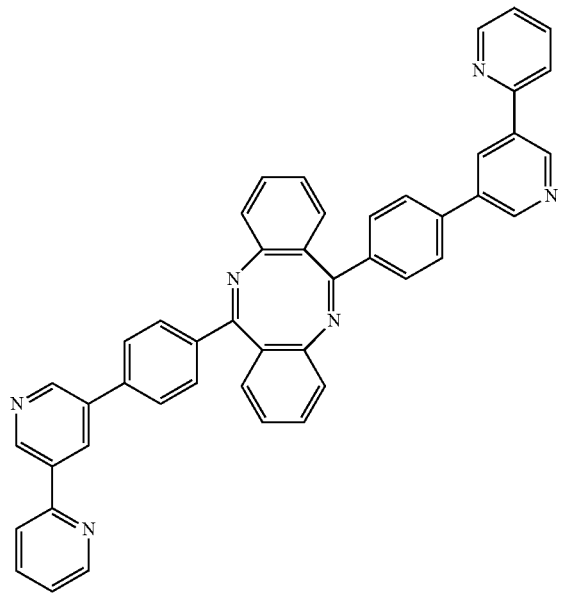
8
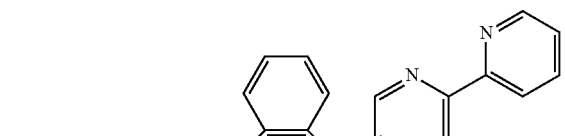
9
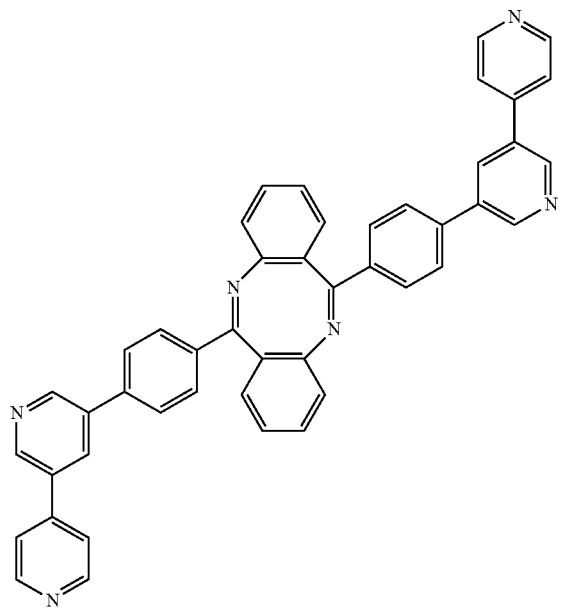
10
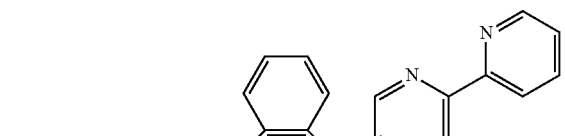
11
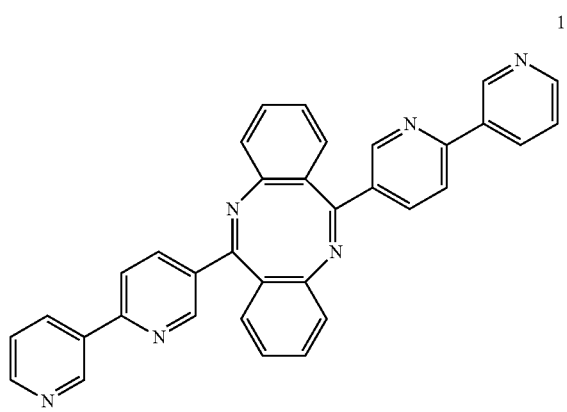
12
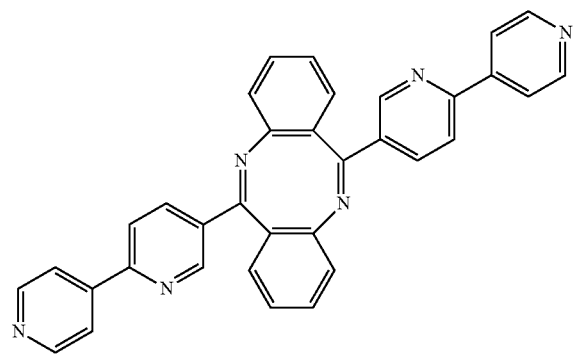

-continued
13
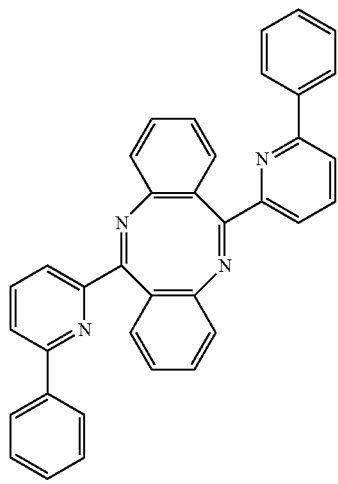
14
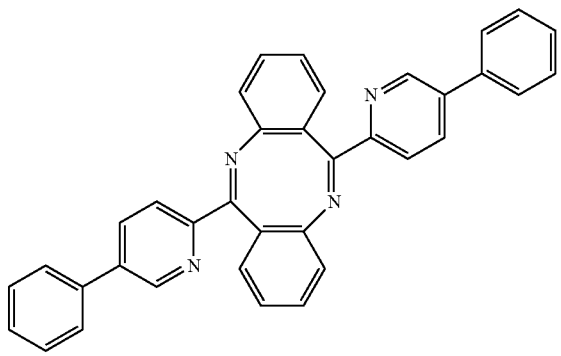
15
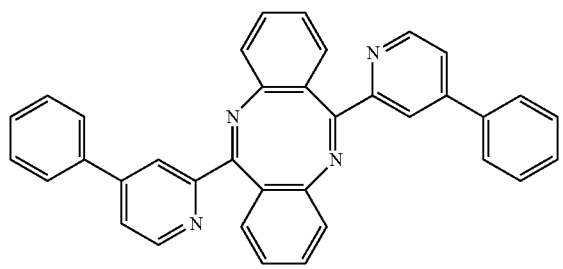
16
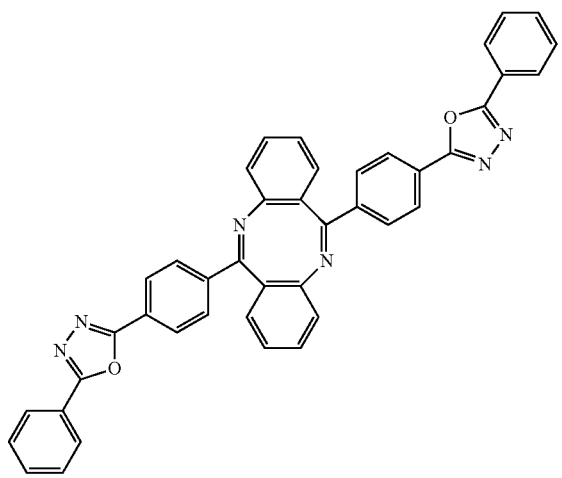
17
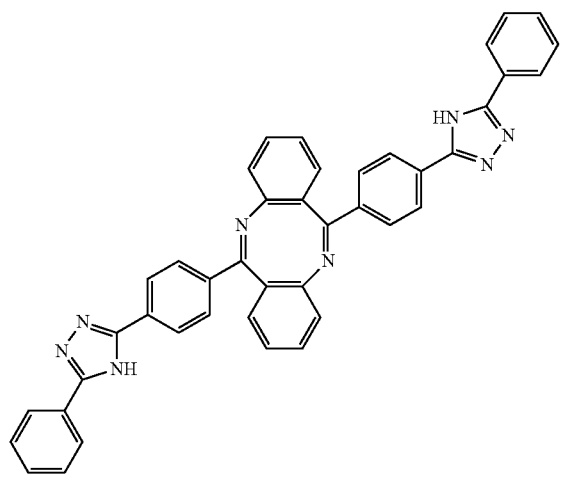
18
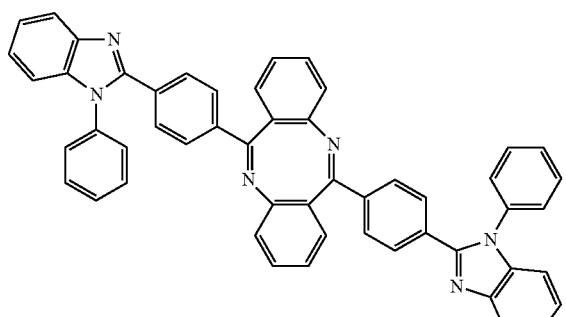

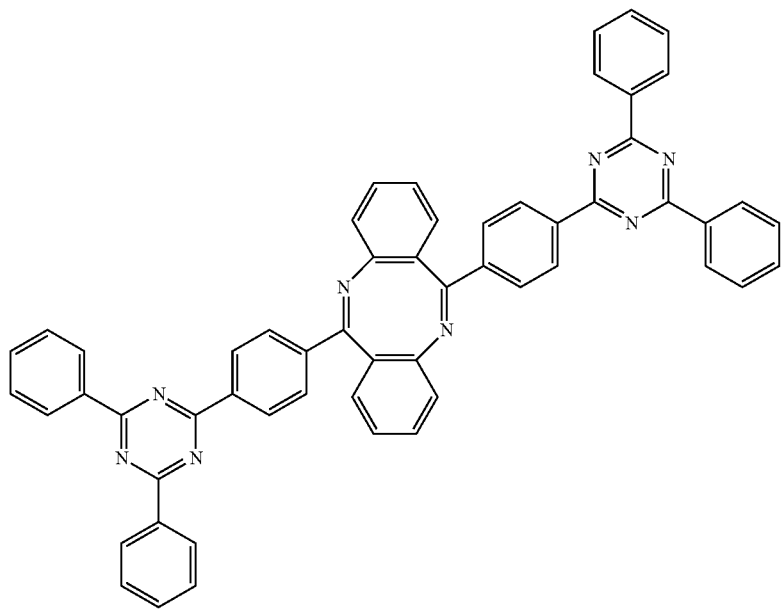
19
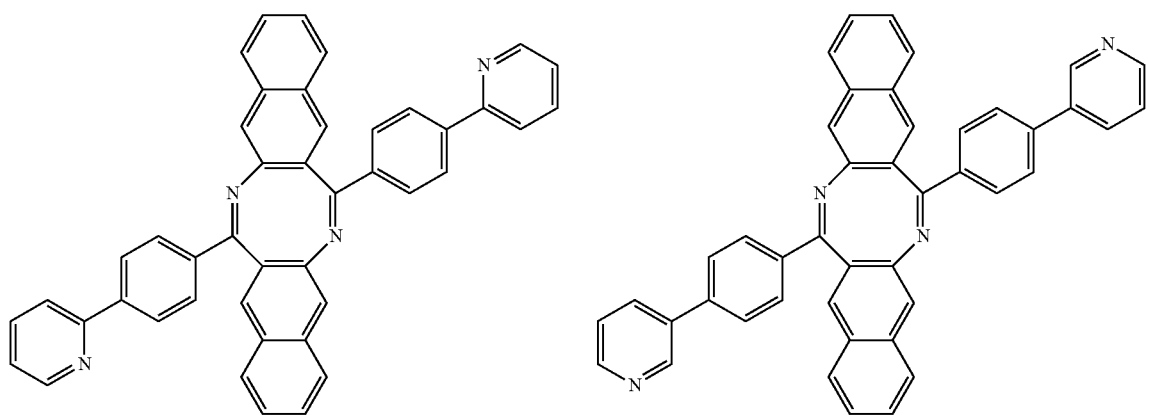
20 21
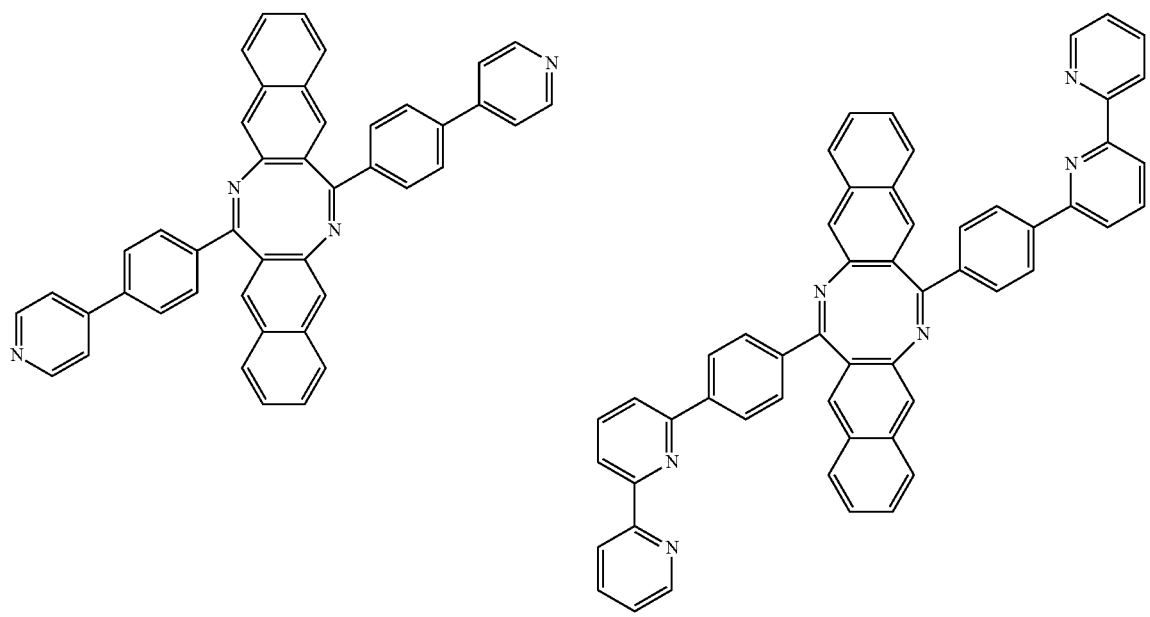
22 23

-continued
24
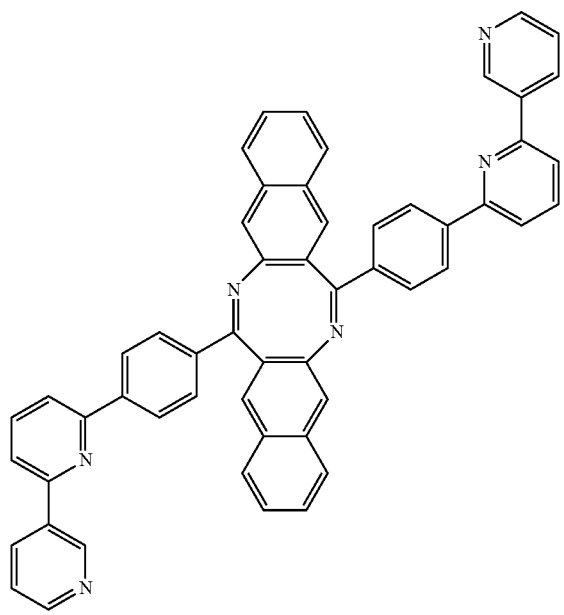
25
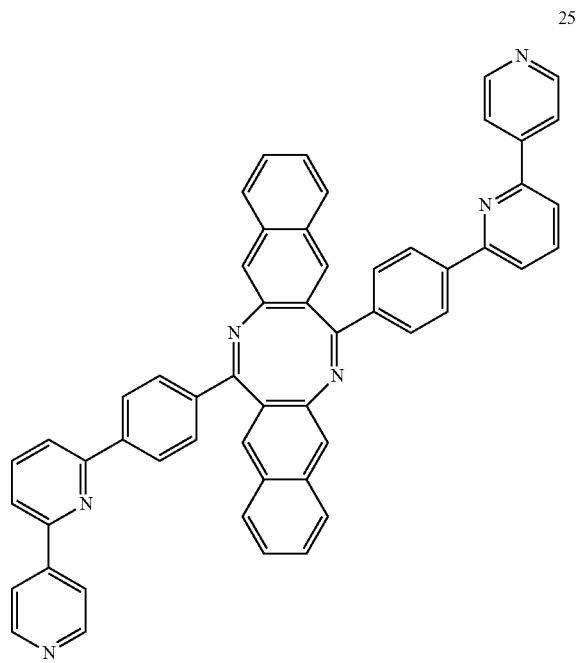
26
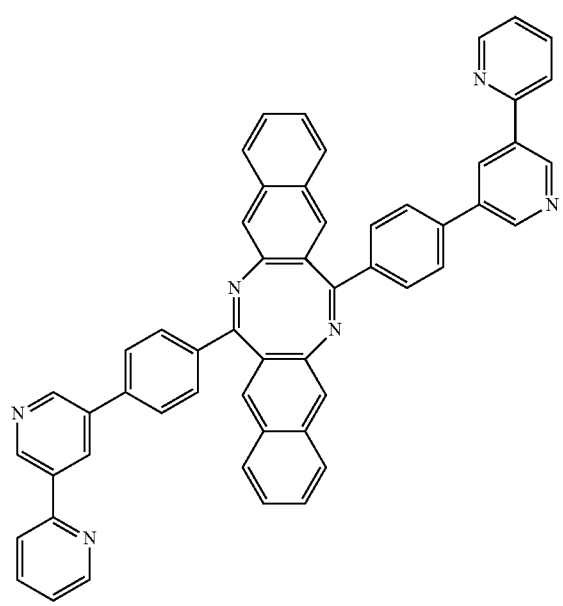
27
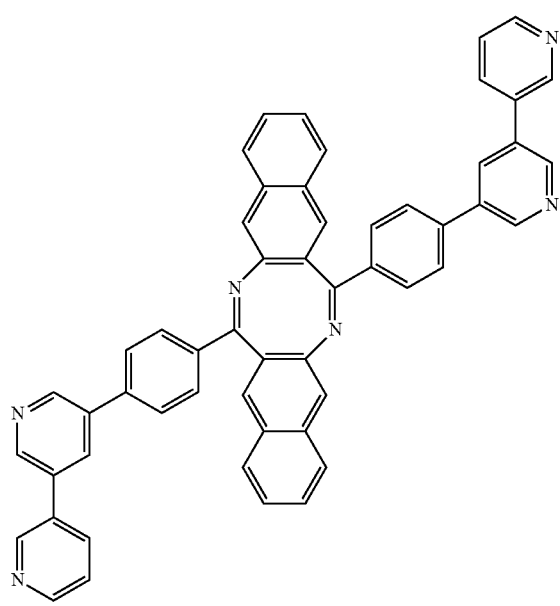

-continued
28
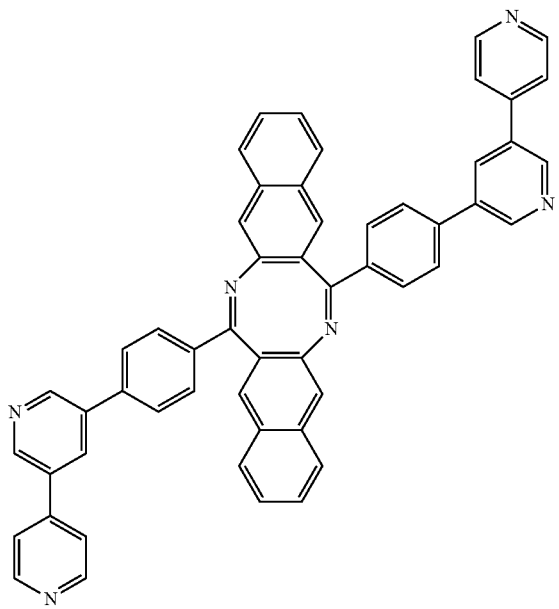
29
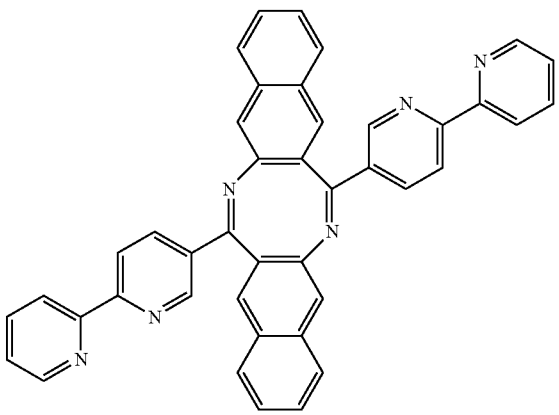
30
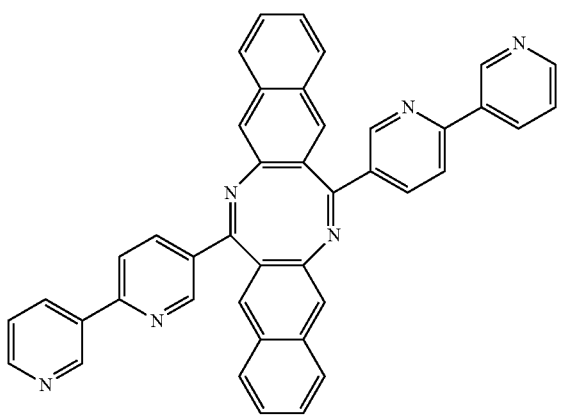
31
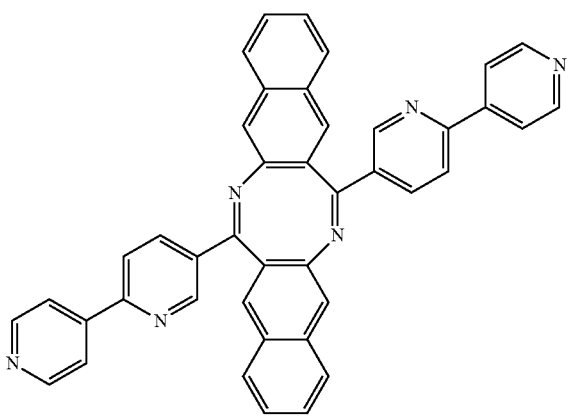
32
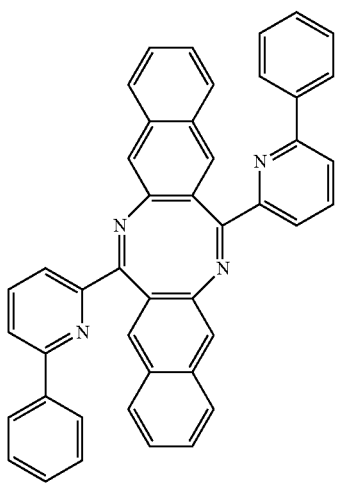
33
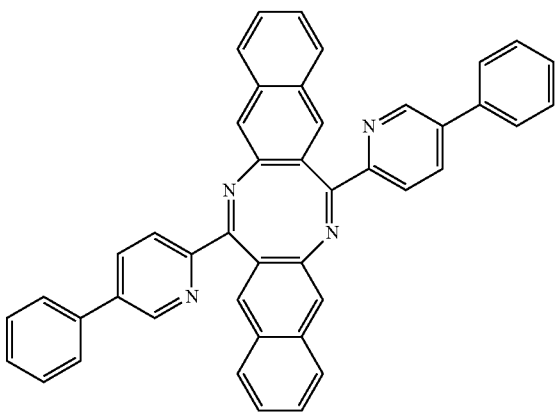

34
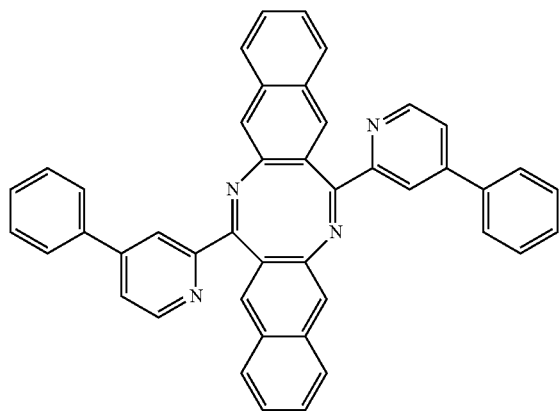
35
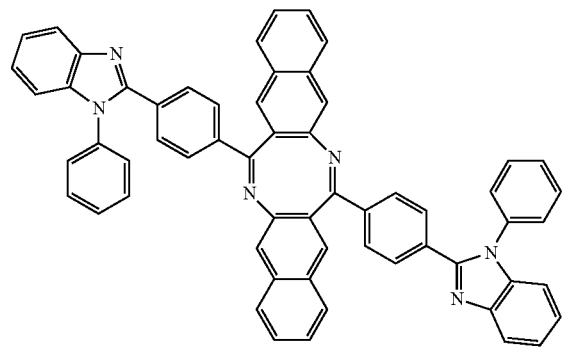
36
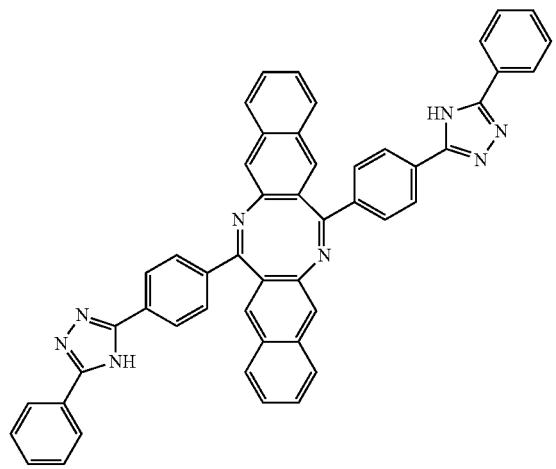
37
38
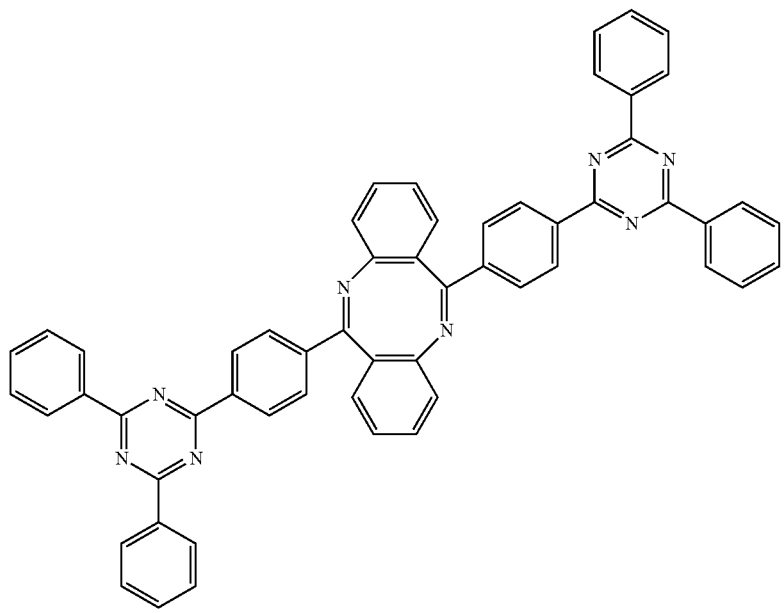

-continued
39
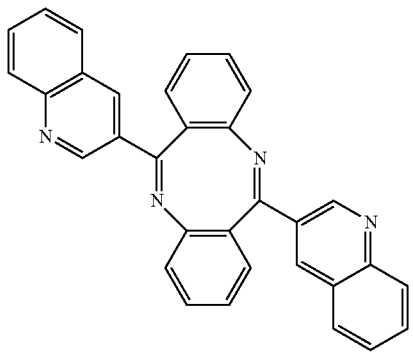
40
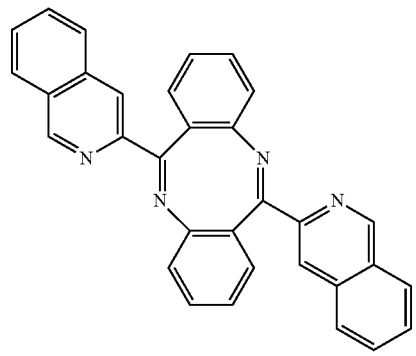
41
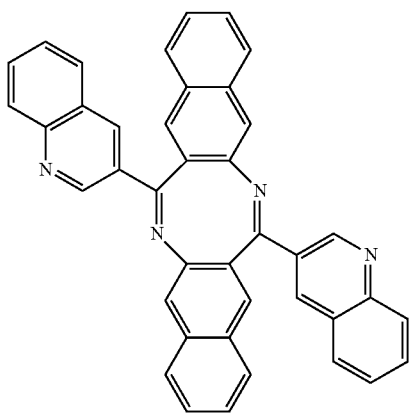
42
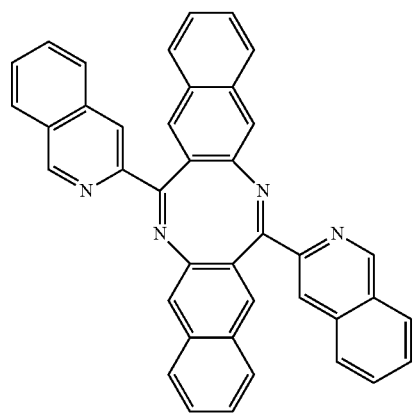
43
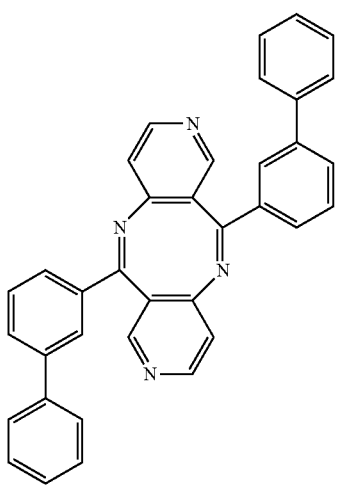
44
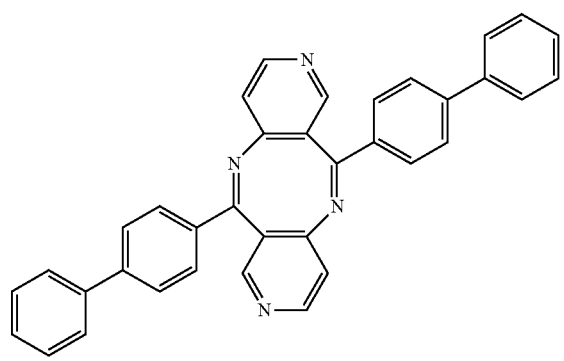

-continued
45
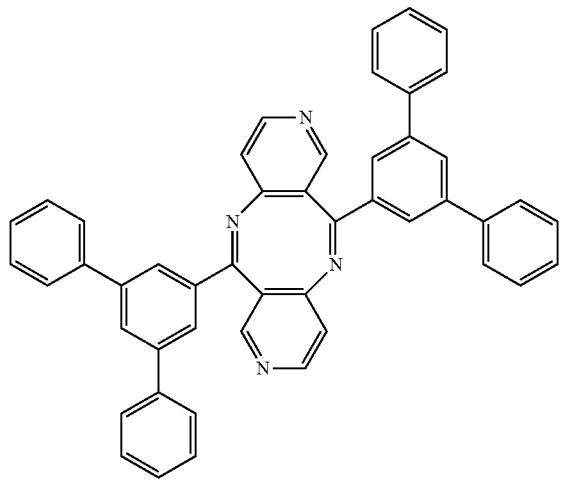
46
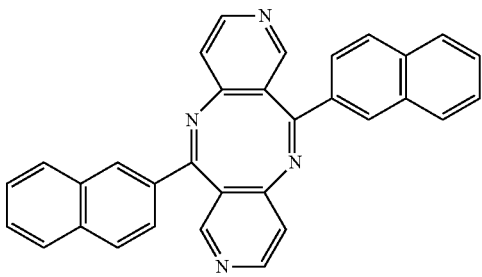
47
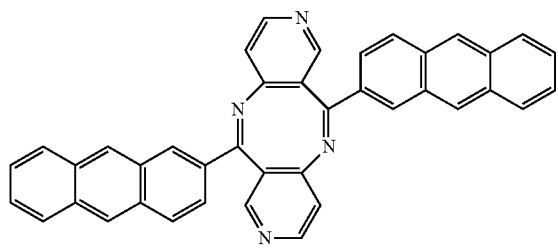
48
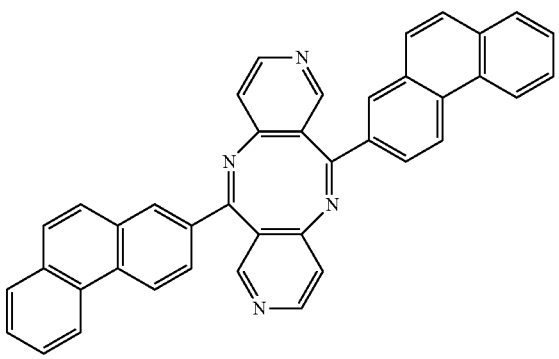
49
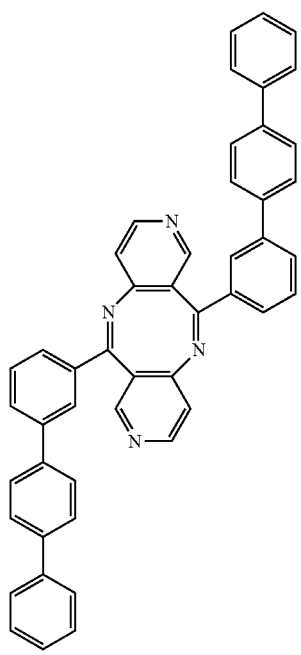

-continued
50
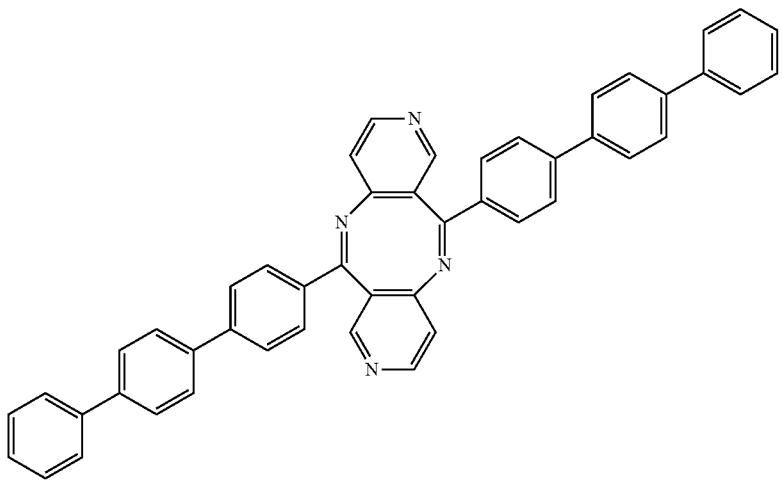
51
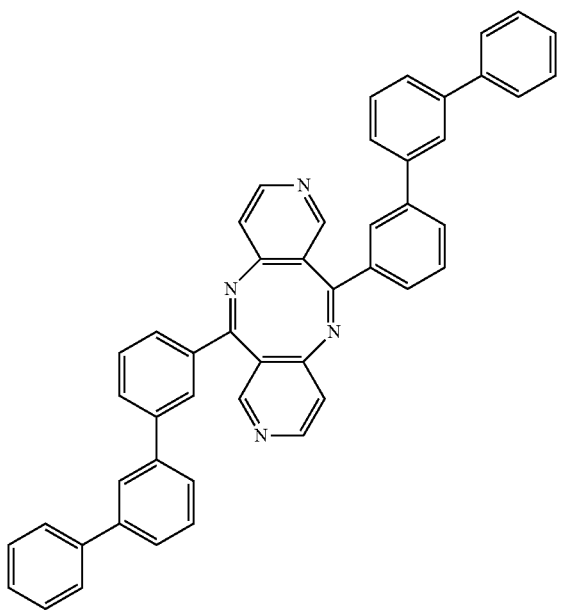
52
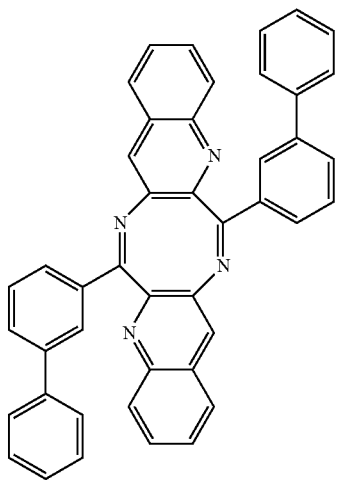
53
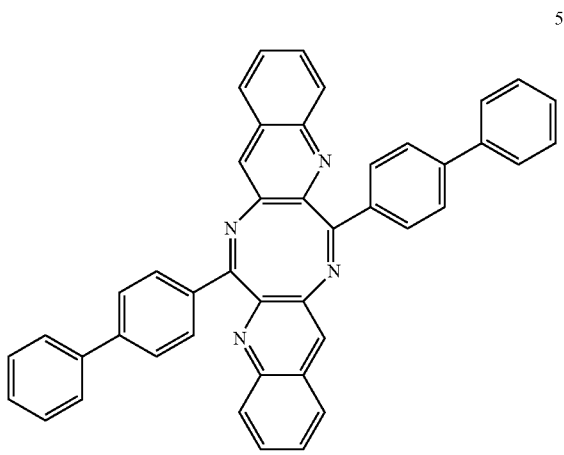
54
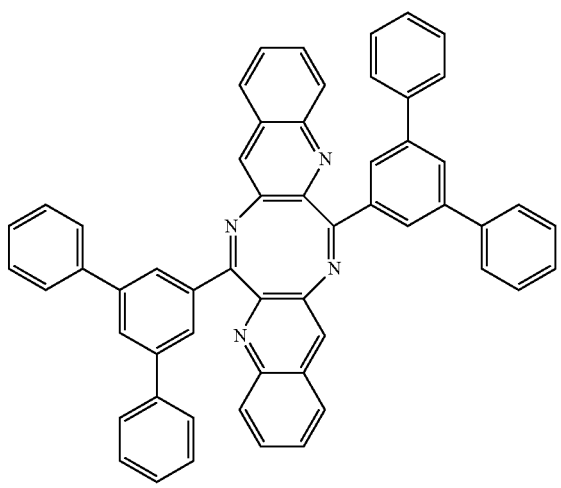

-continued
55
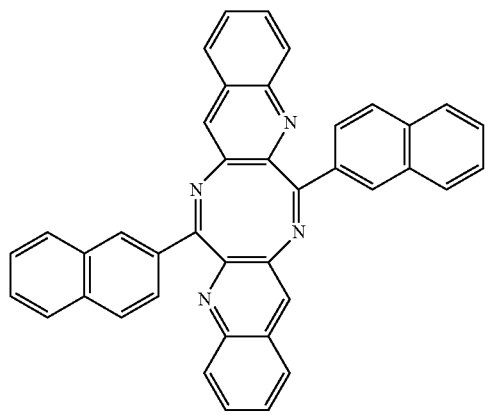
56
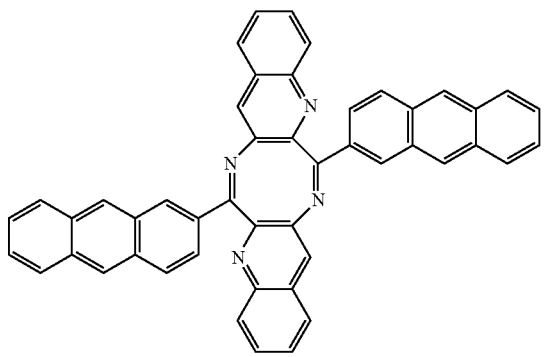
57
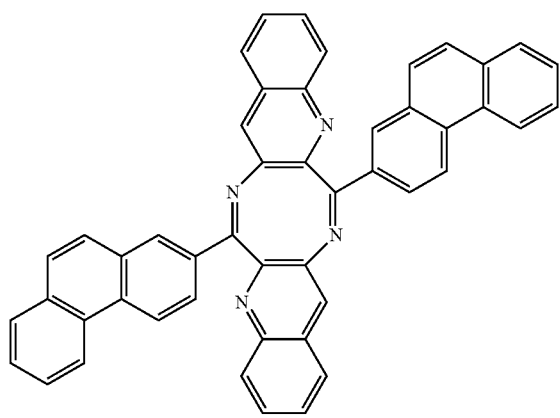
58
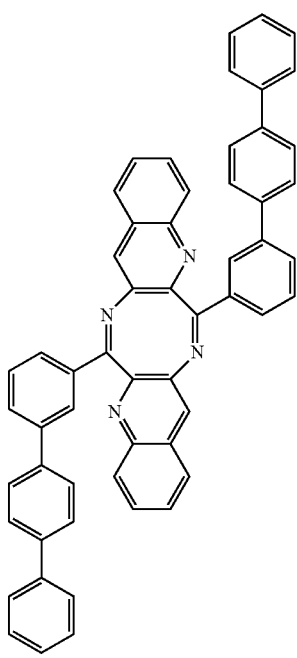
59
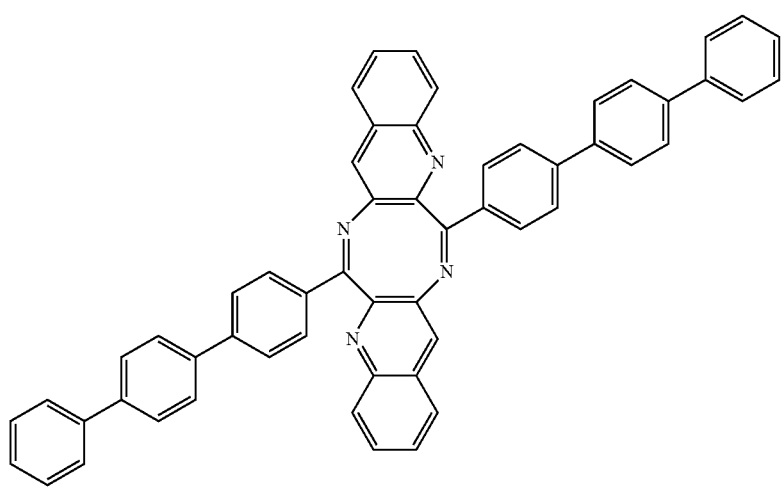

-continued
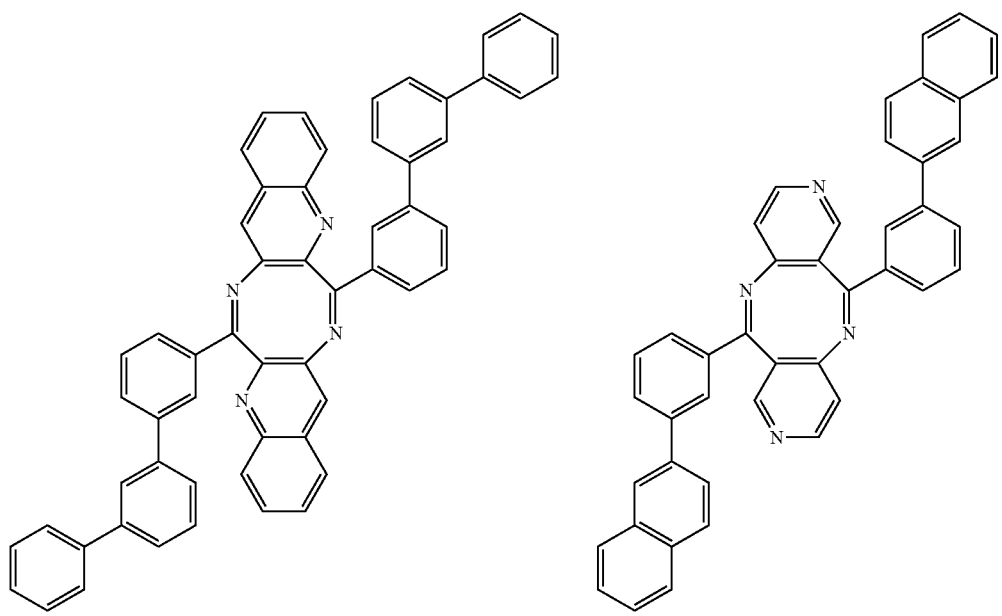
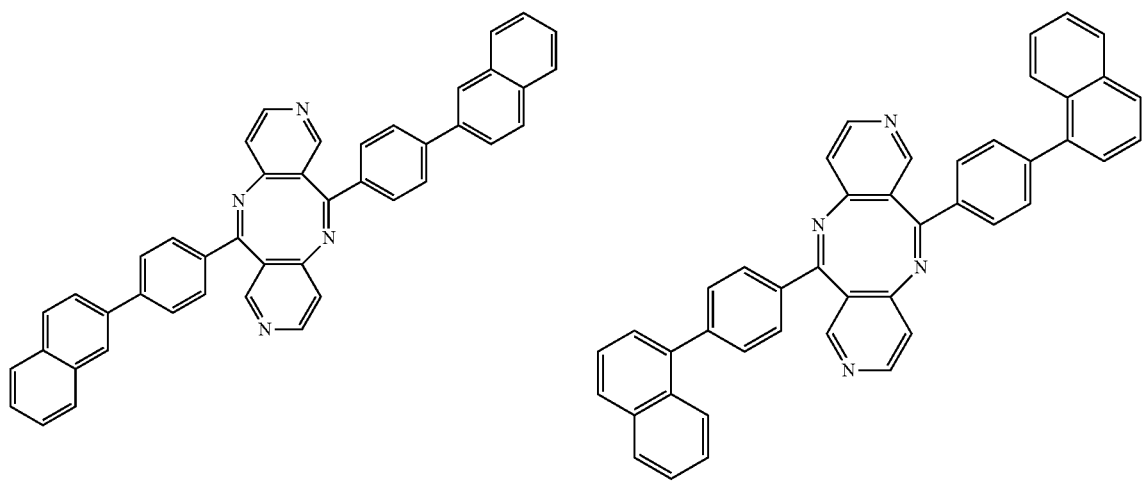
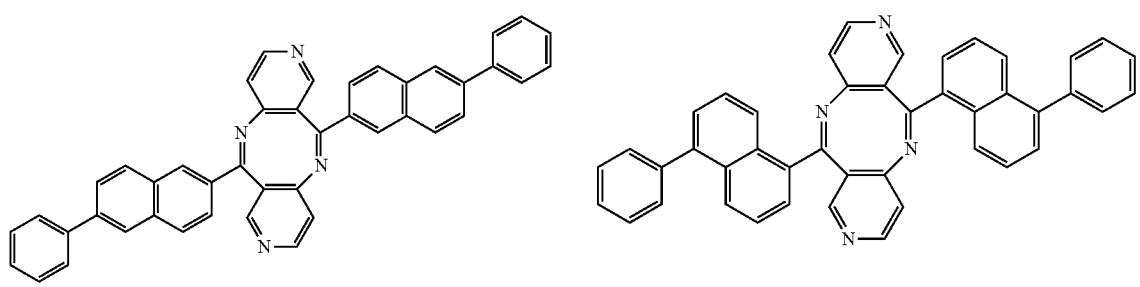

66
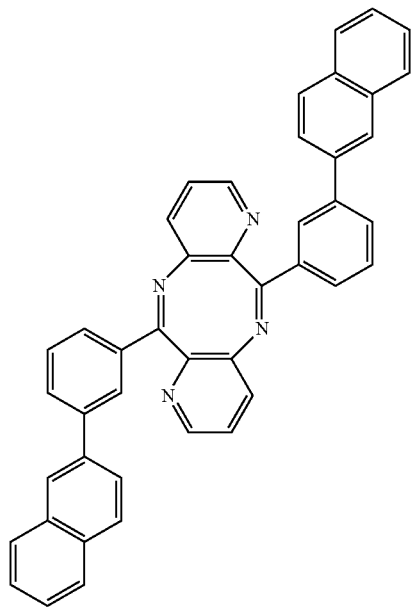
67
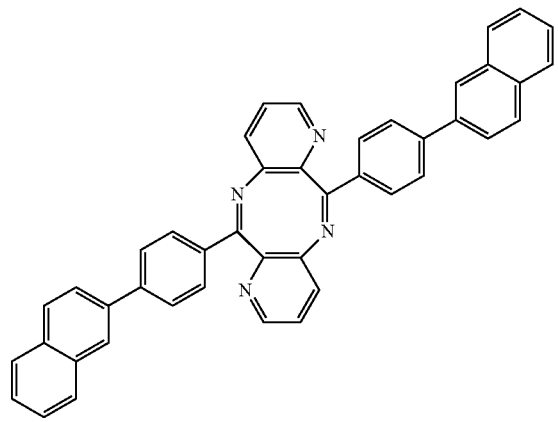
68
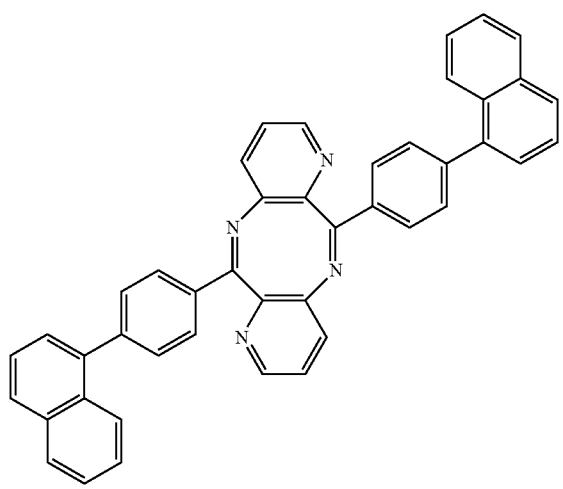
69
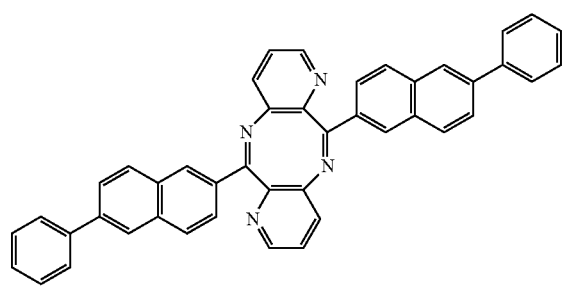

-continued
70
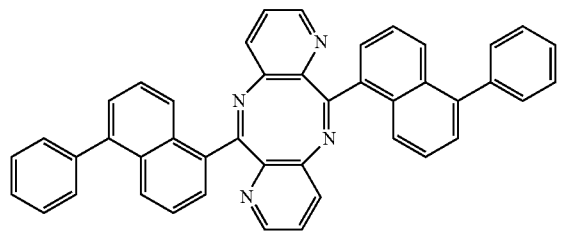
71
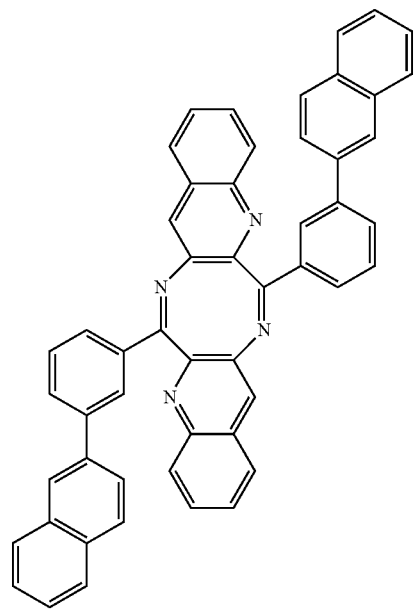
72
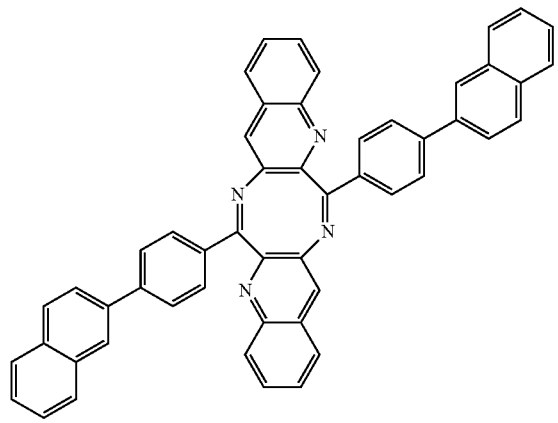
73
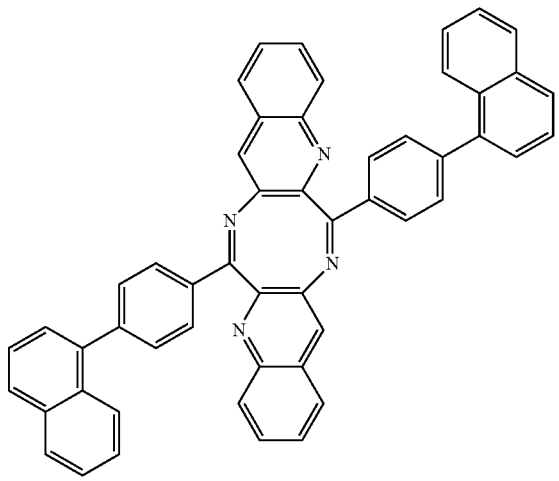
74
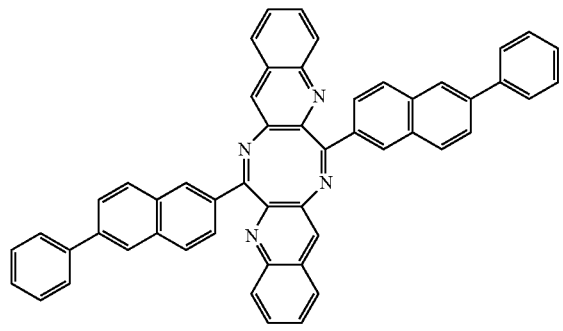
75
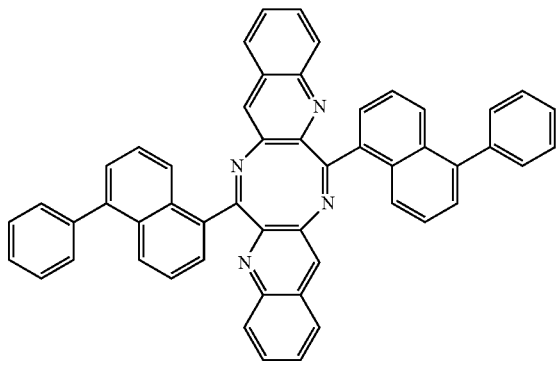

-continued
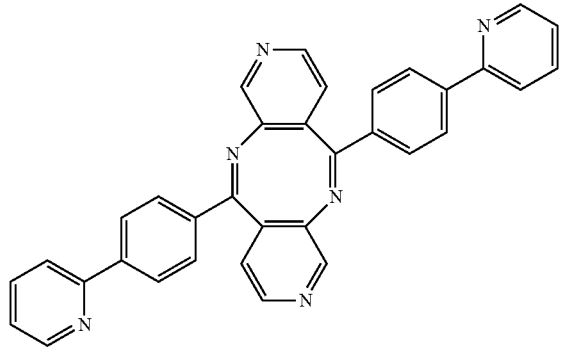
76
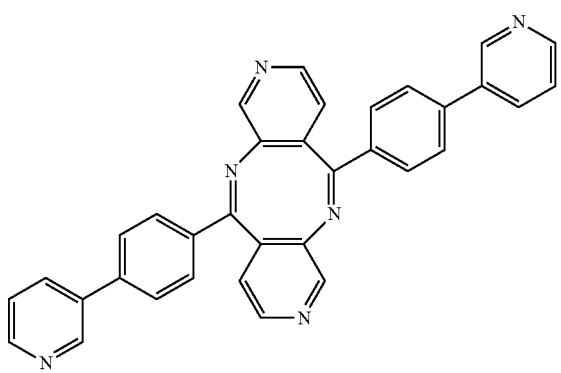
77
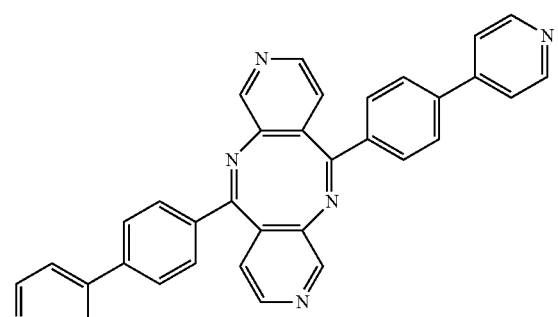
78
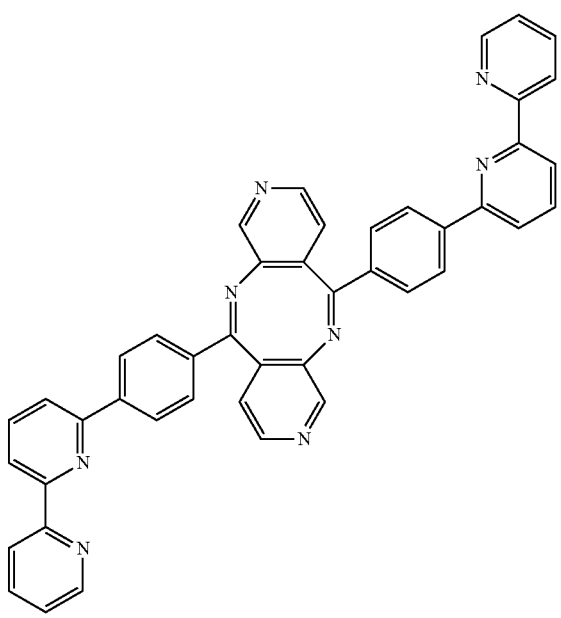
79
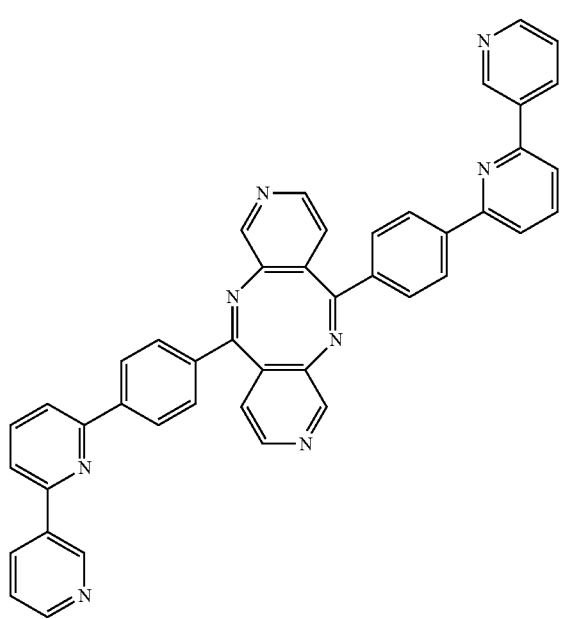
80
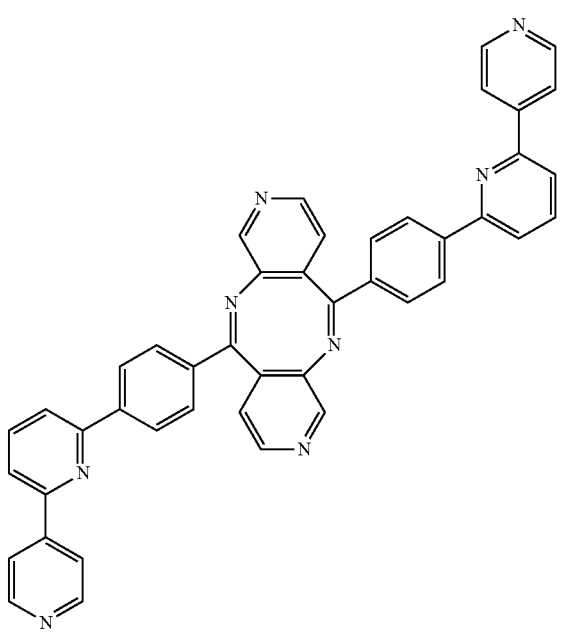
81

-continued
82
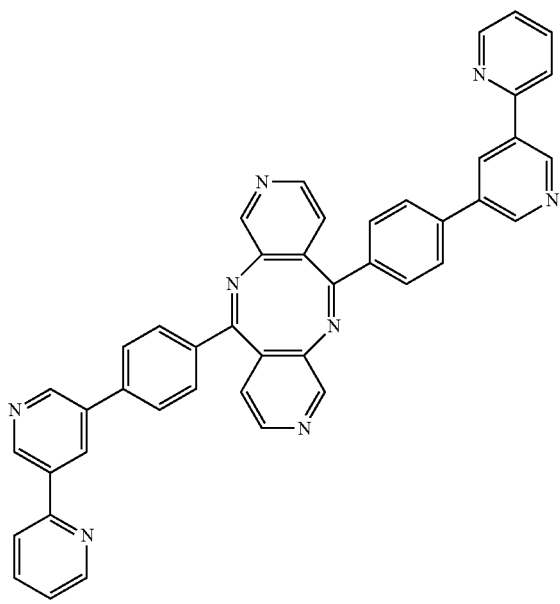
83
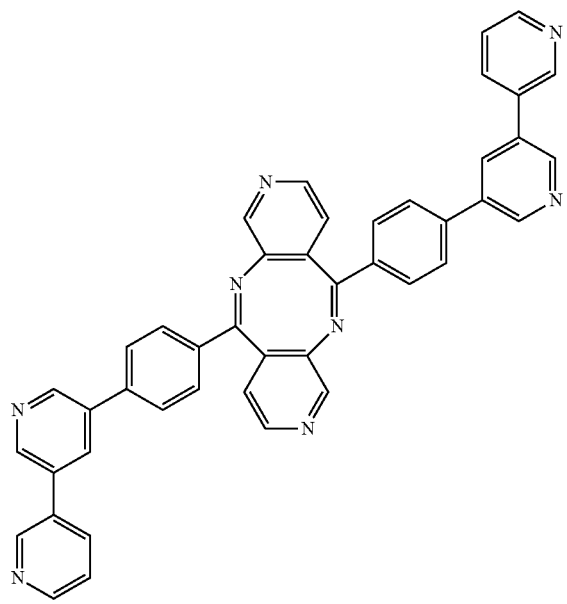
84
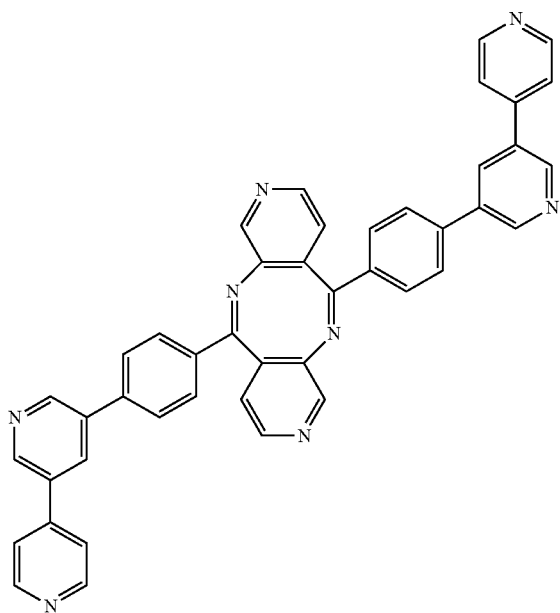
85
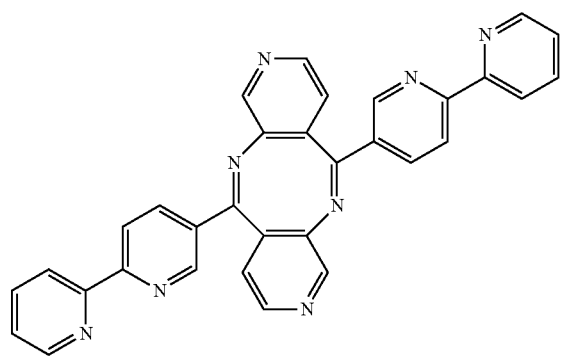
86
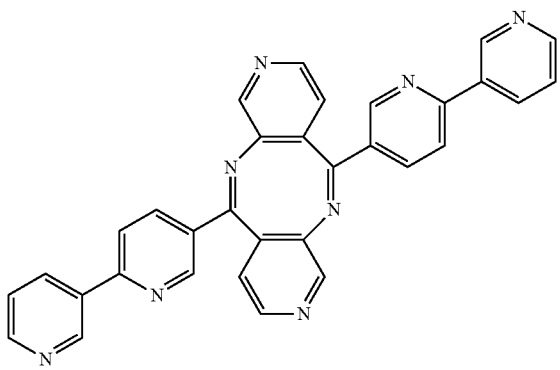
87
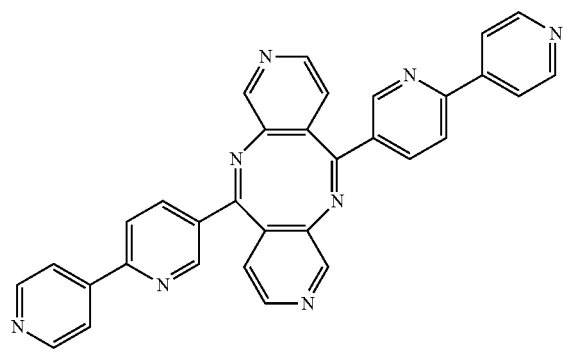

88
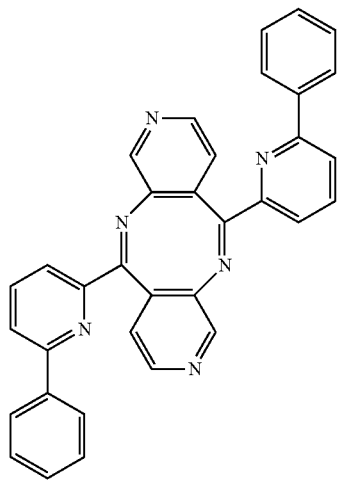
89
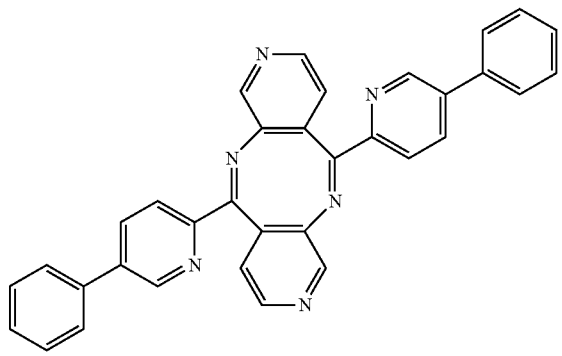
90
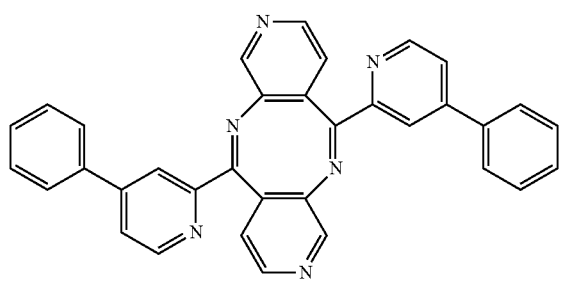
91
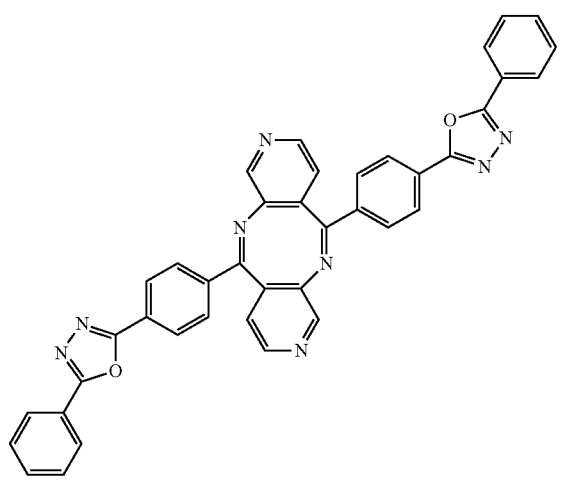
92
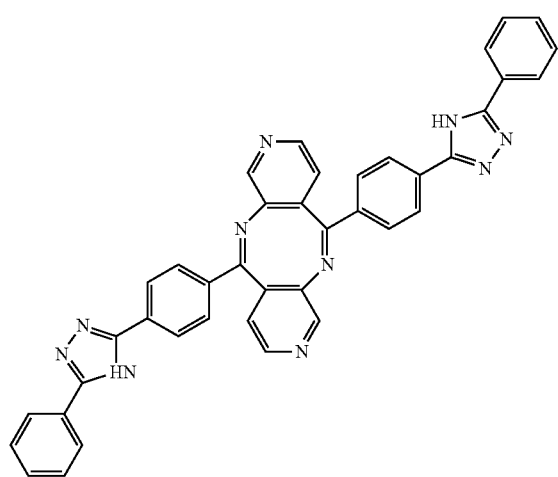
93
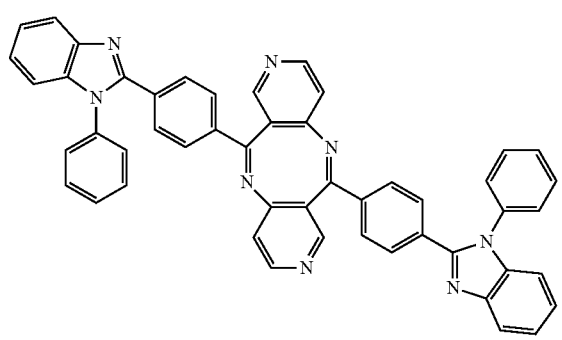

94
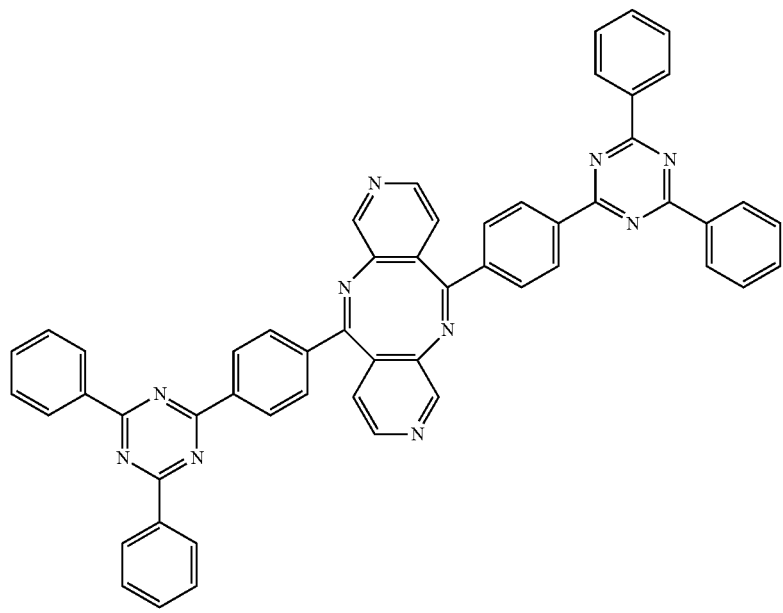
95
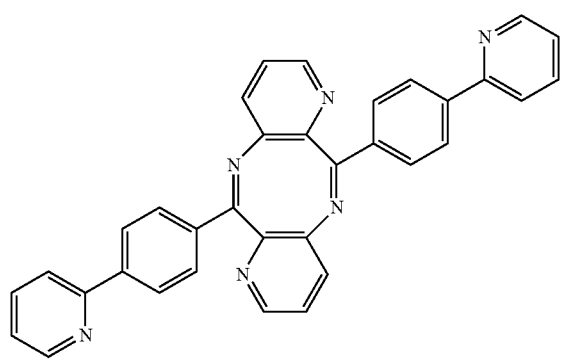
96
97
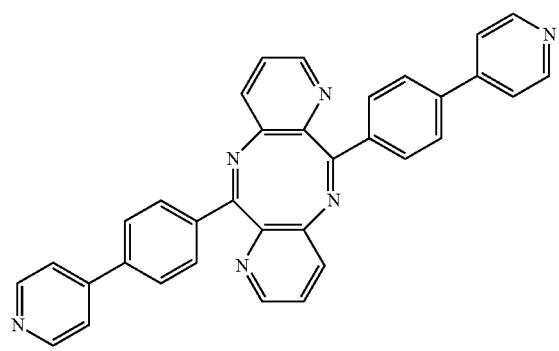
98
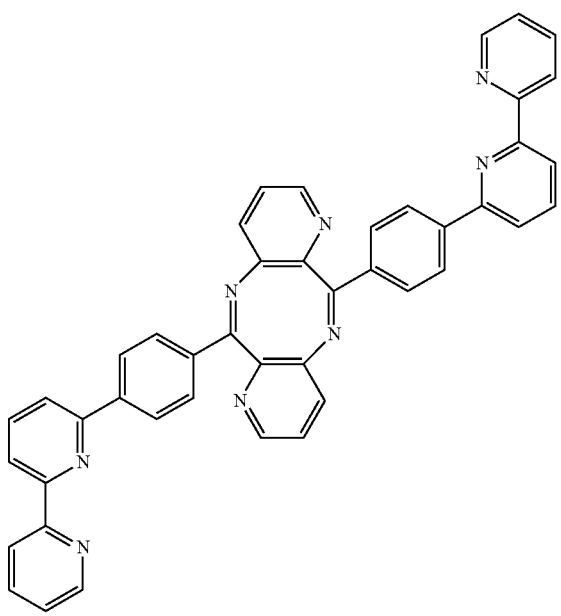

-continued
99
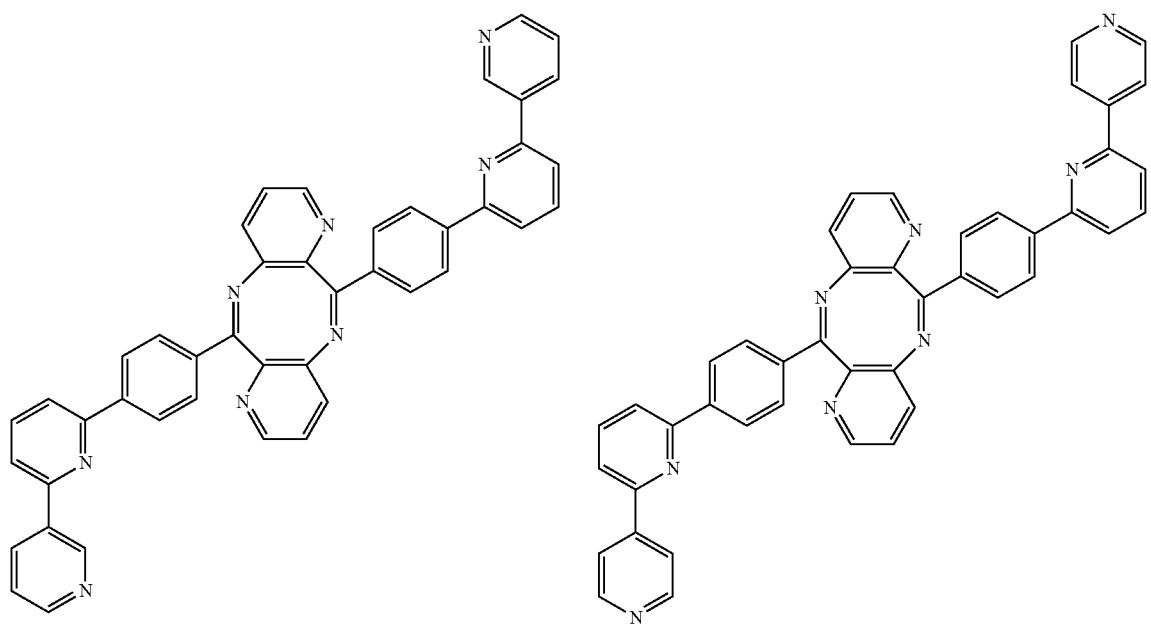
100
101
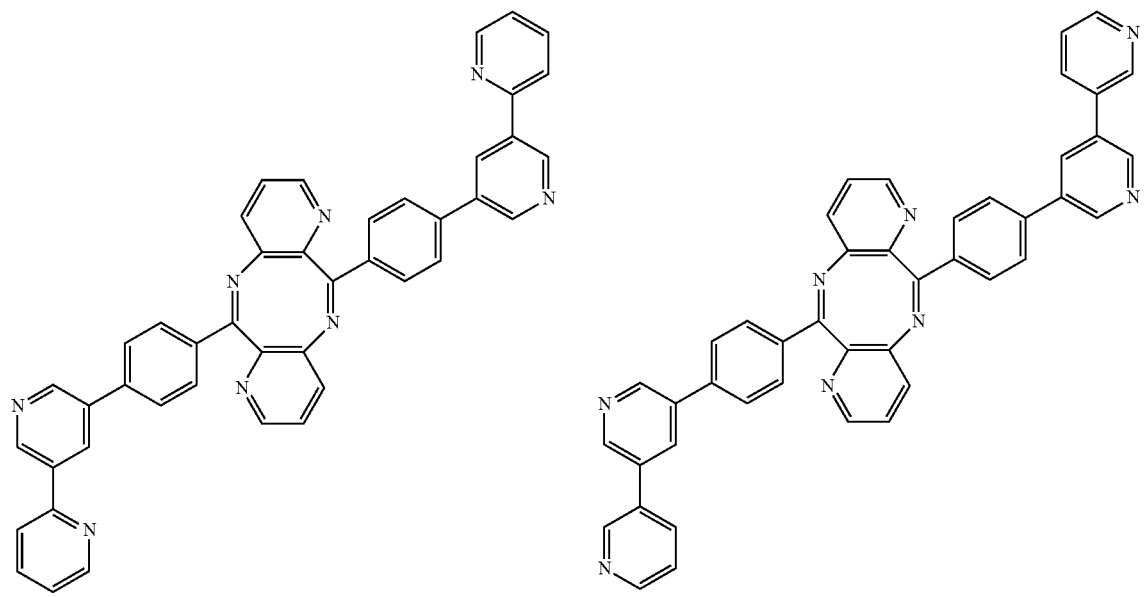
102

-continued
103
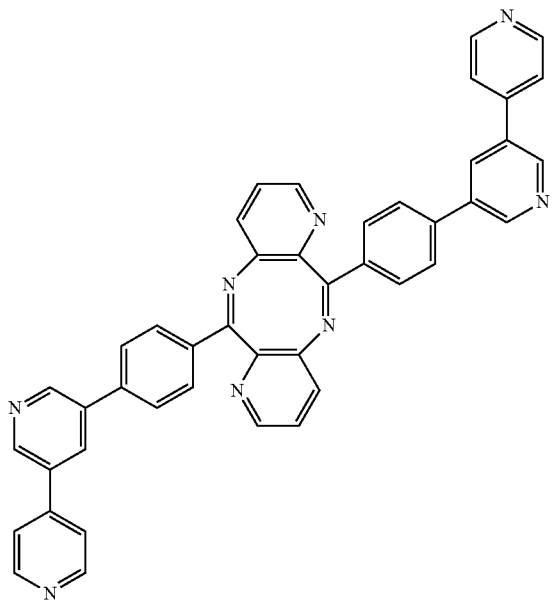
104
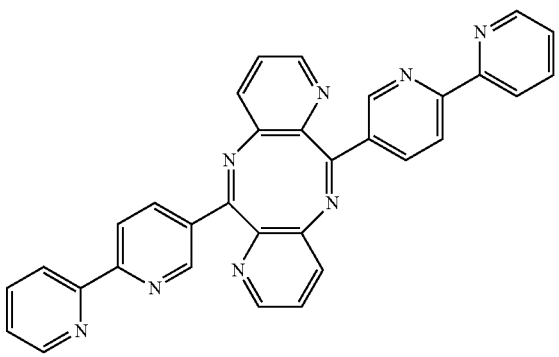
105
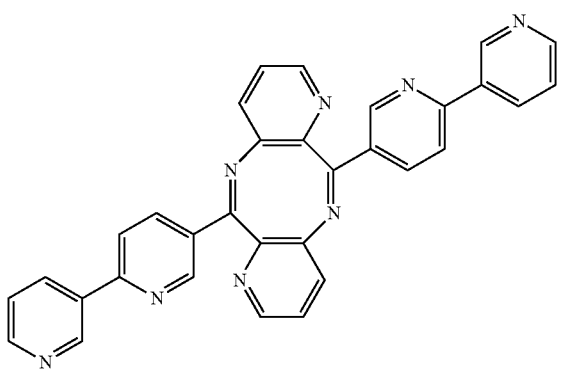
106
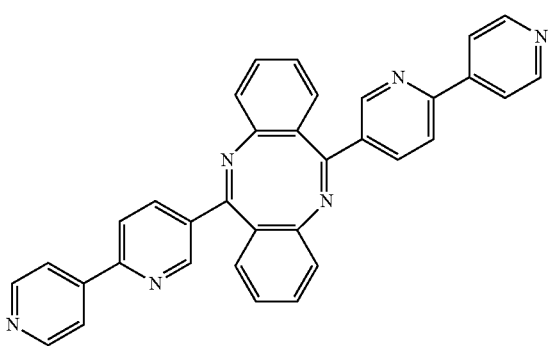
107
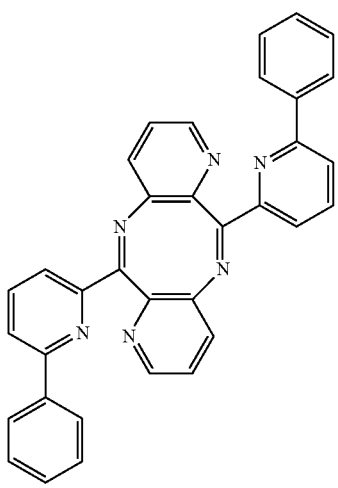
108
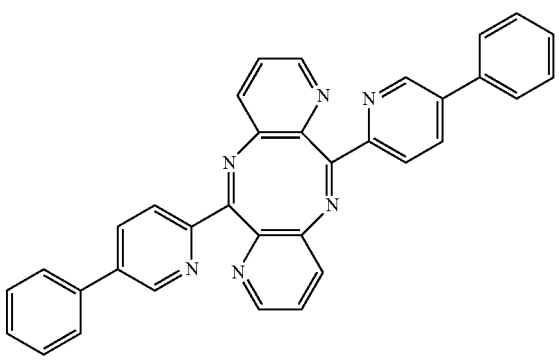

-continued
109
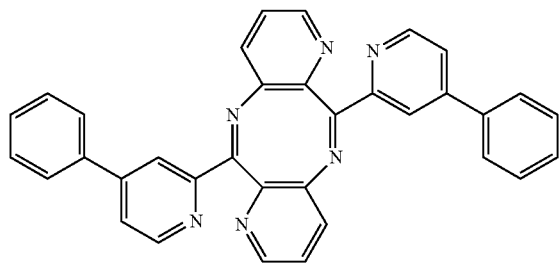
110
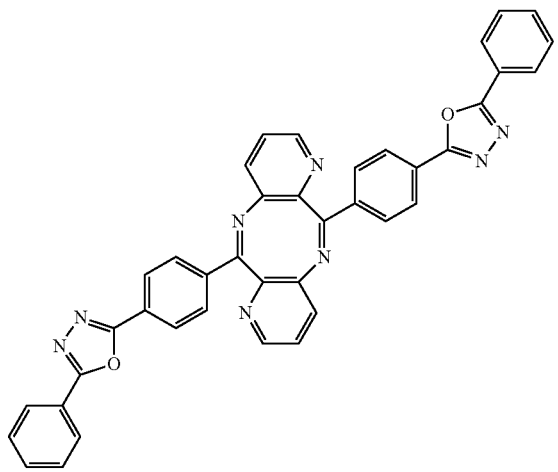
111
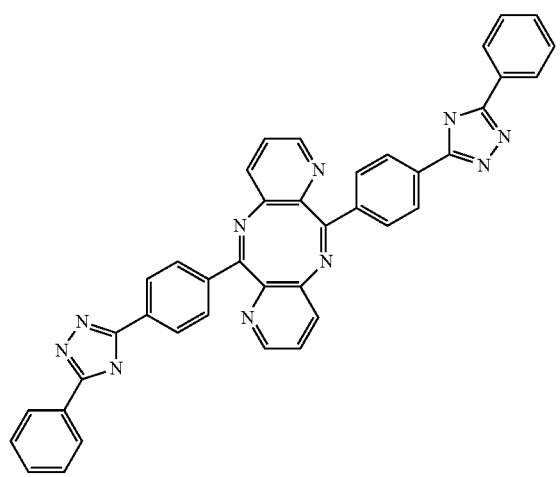
112
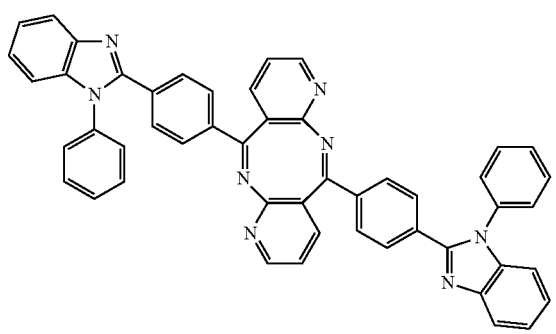
113
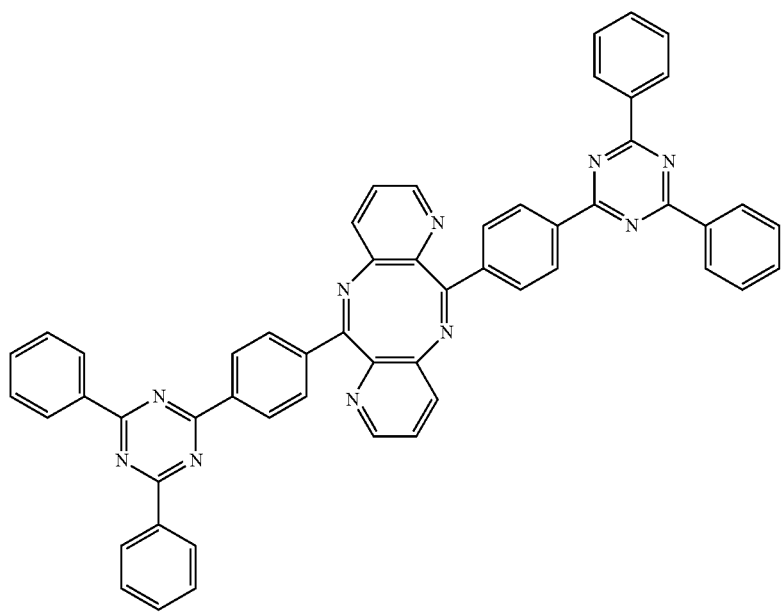

-continued
114
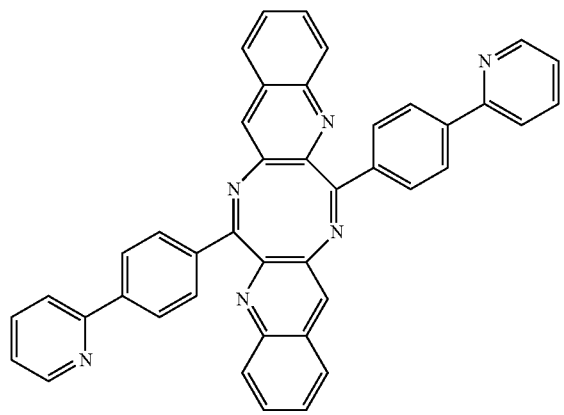
115
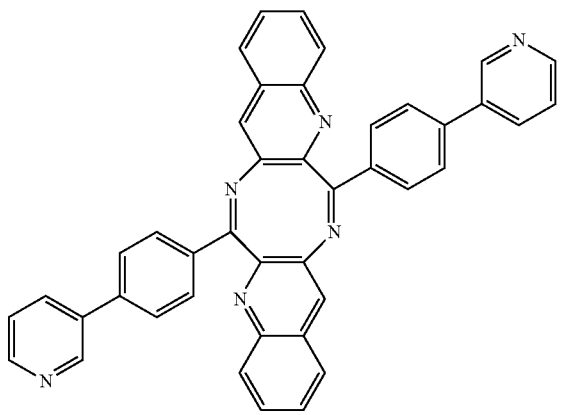
116
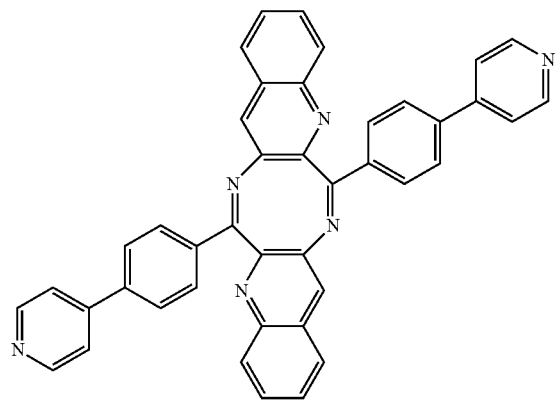
117
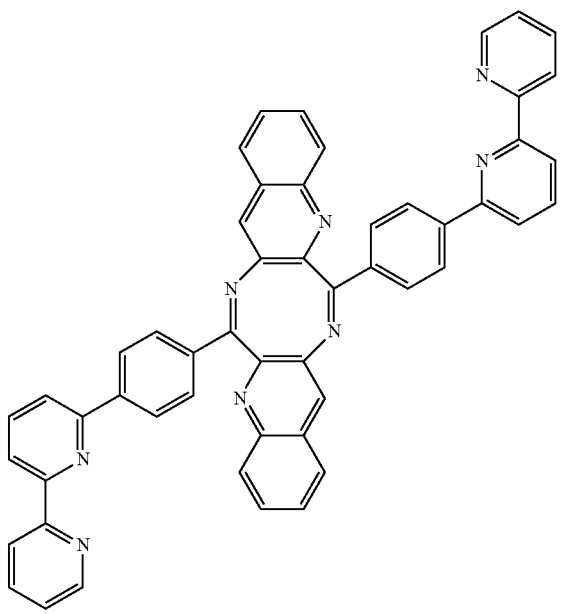

-continued
118
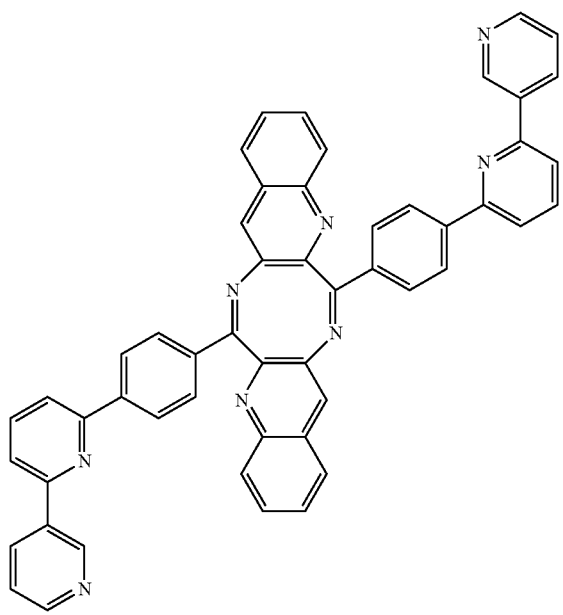
119
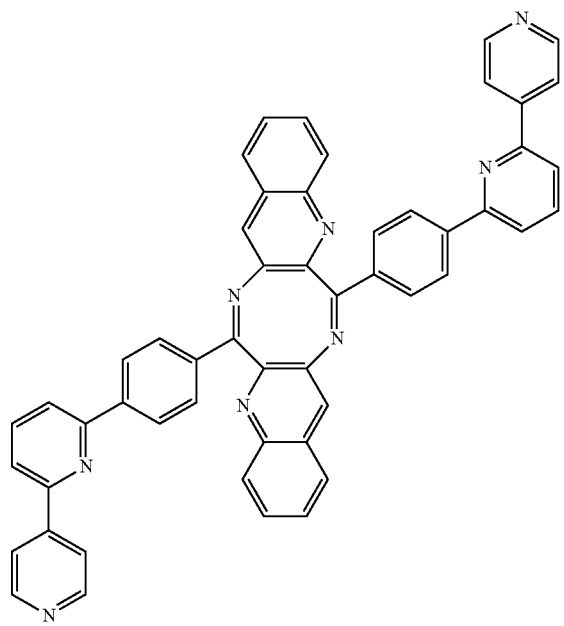
120
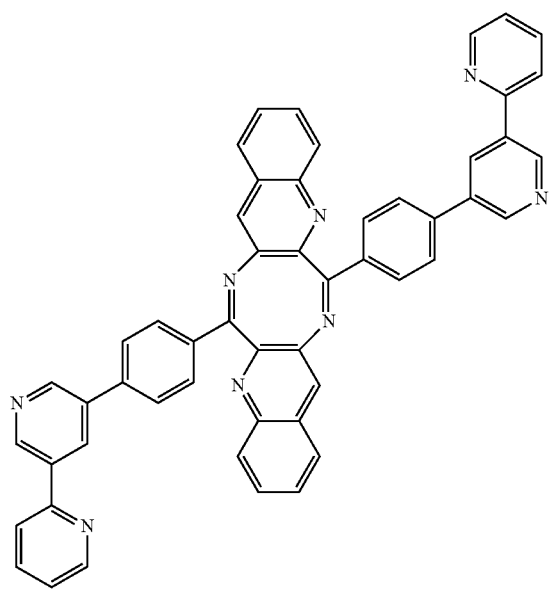
121
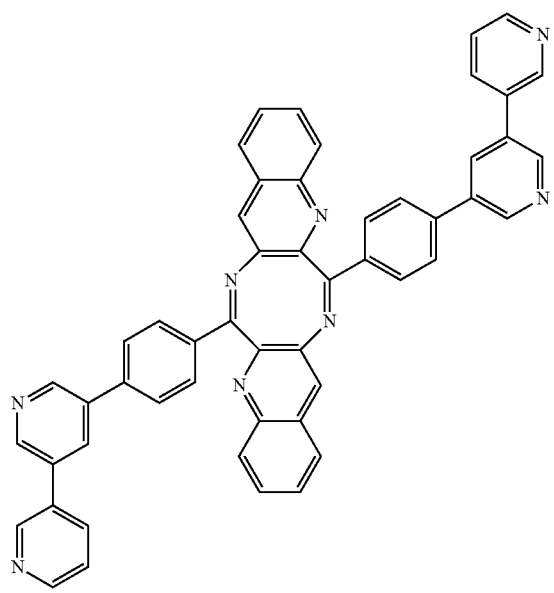

122
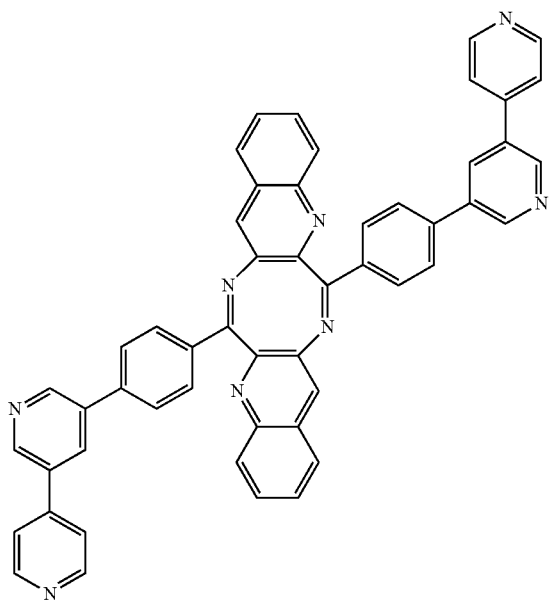
123
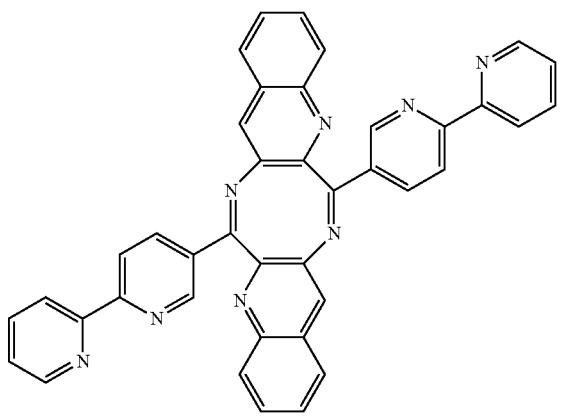
124
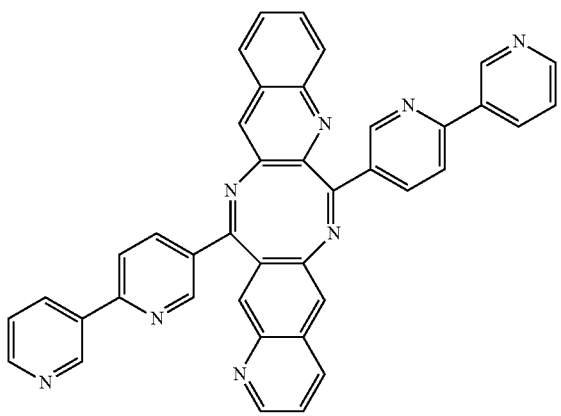
125
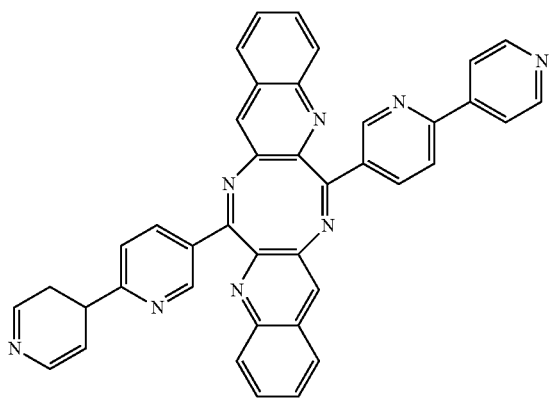
126
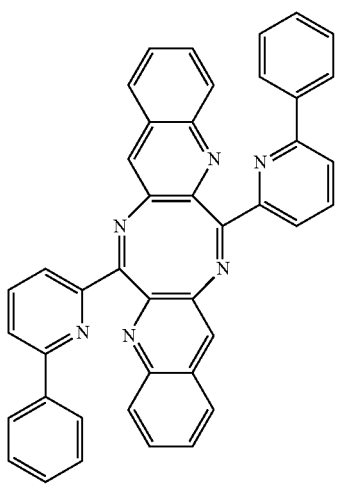
127
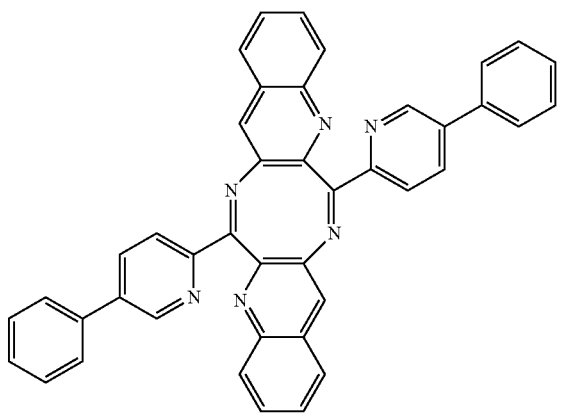

-continued
128
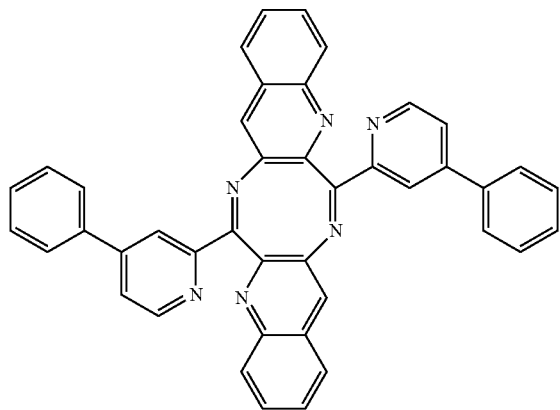
129
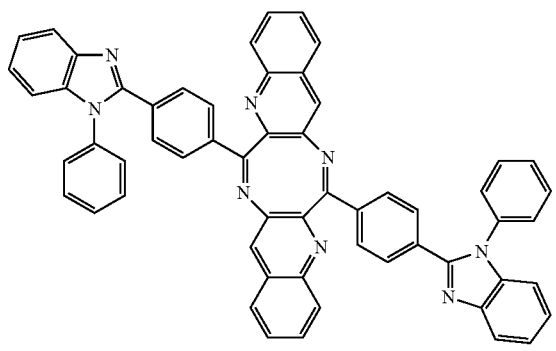
130
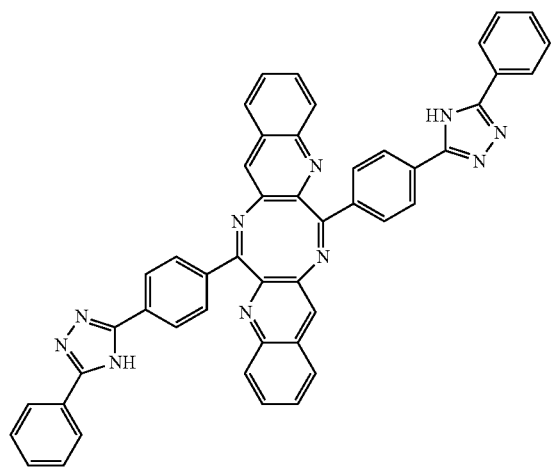
131
132
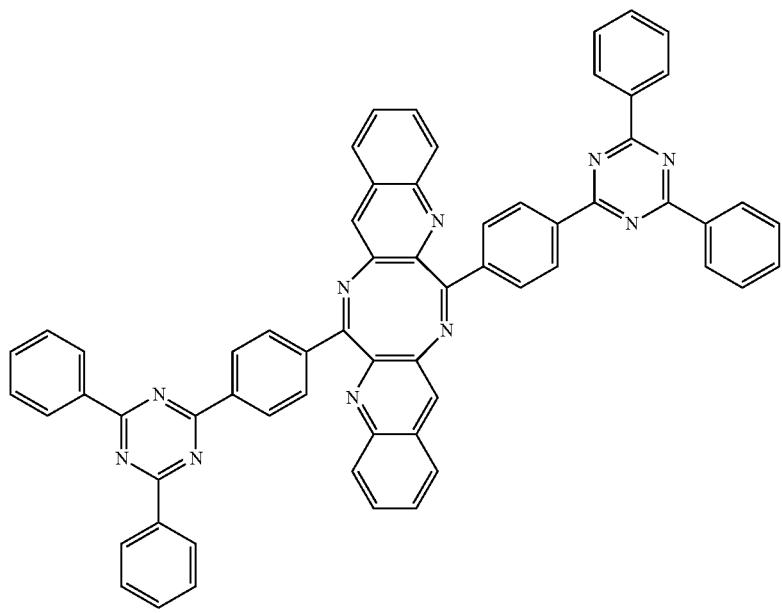

-continued
| | |
|---|---|
| 133 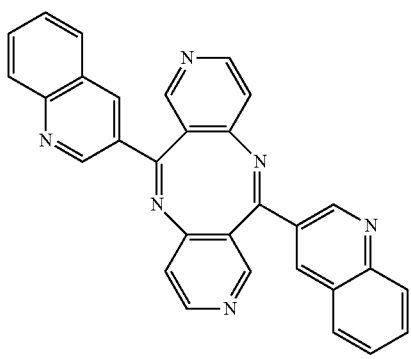 | 134 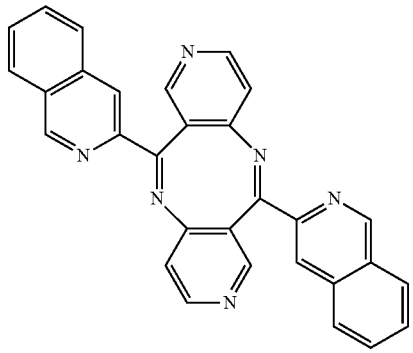 |
| 135 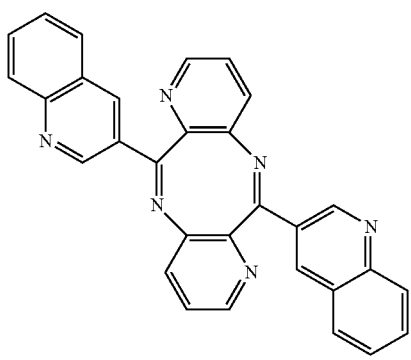 | 136 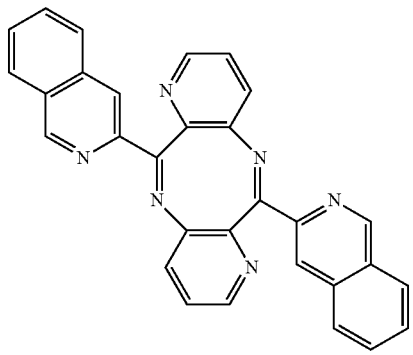 |
| 137 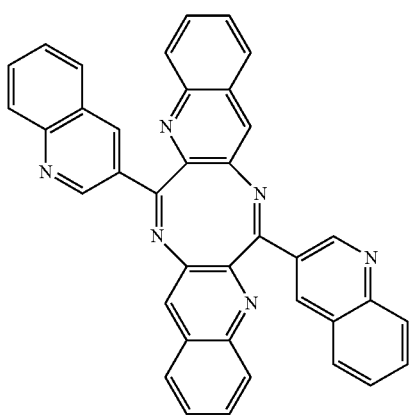 | 138 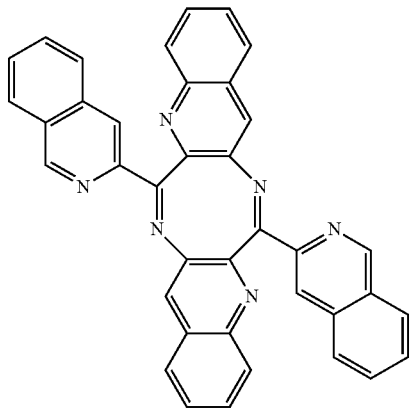 |
| 139 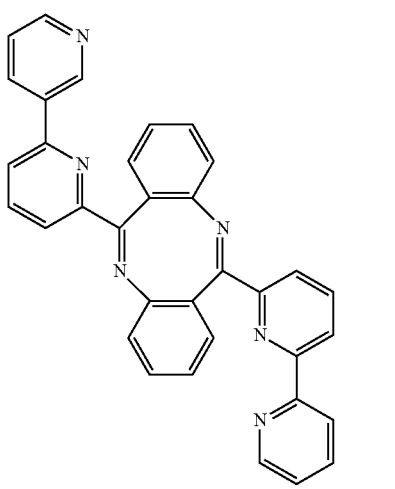 | |

-continued
141
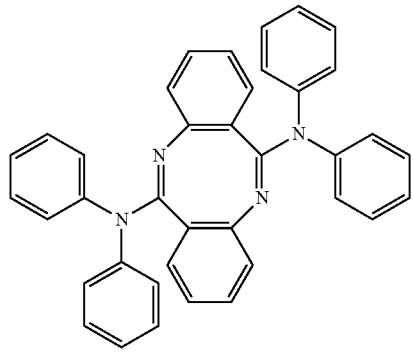
142
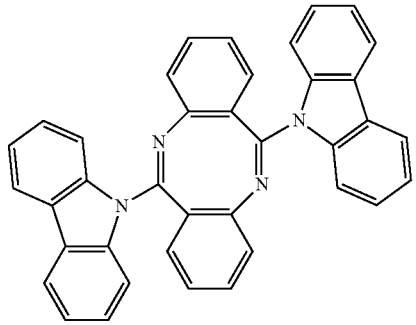
143
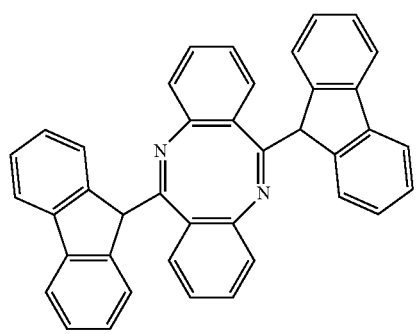
144
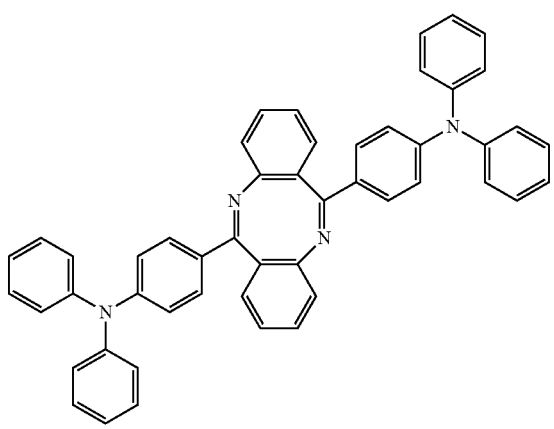
145
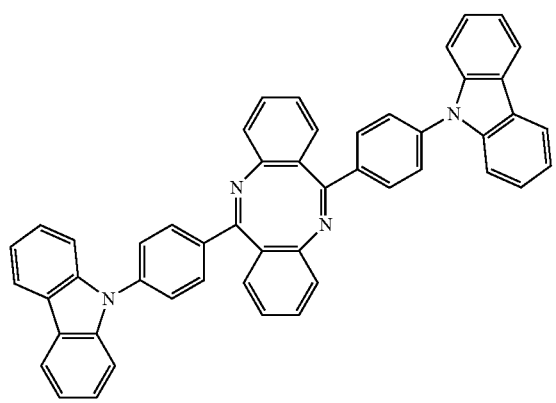
146
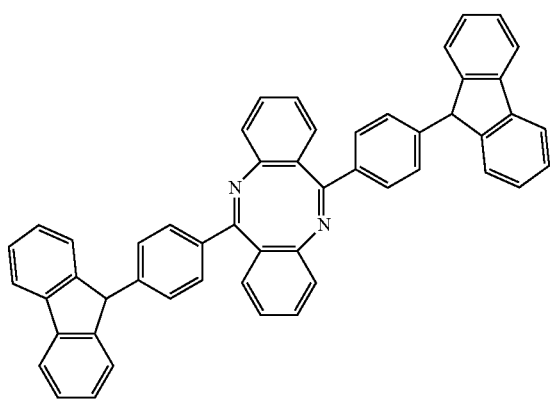
147
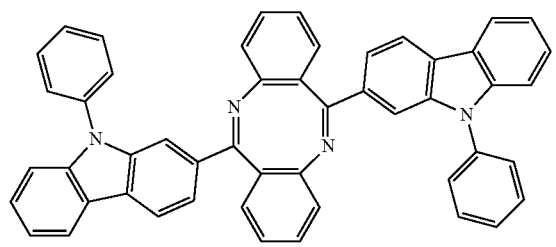
148
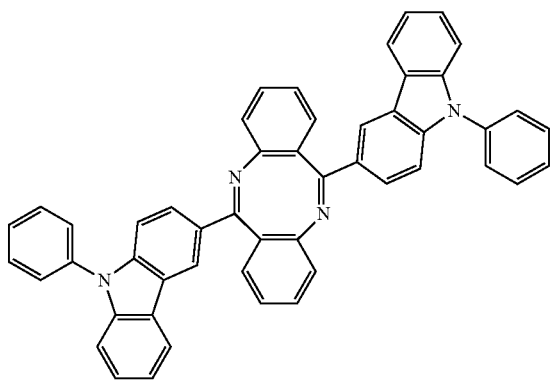

149
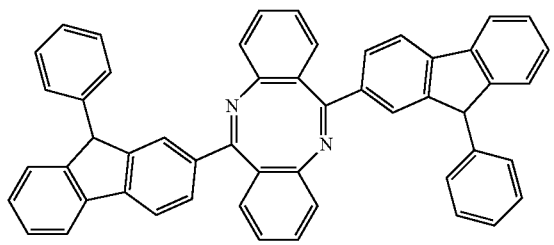
150
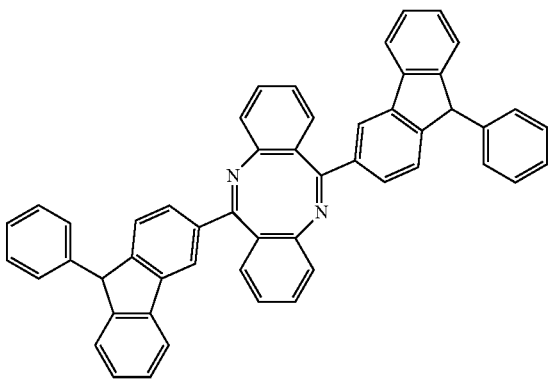
151
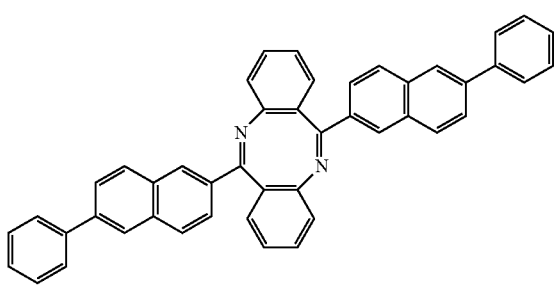
152
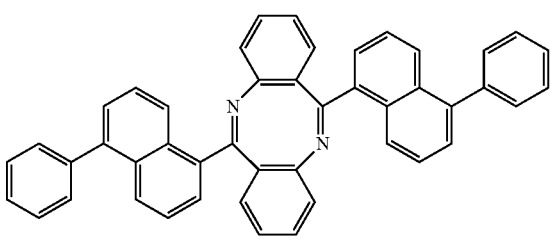
153
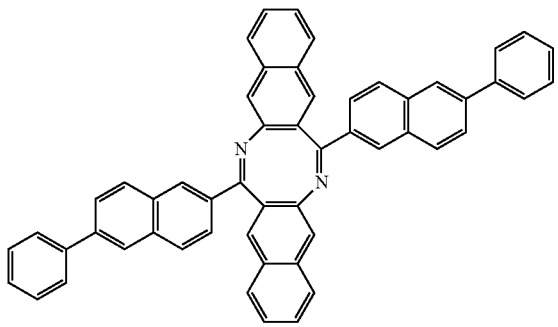
154
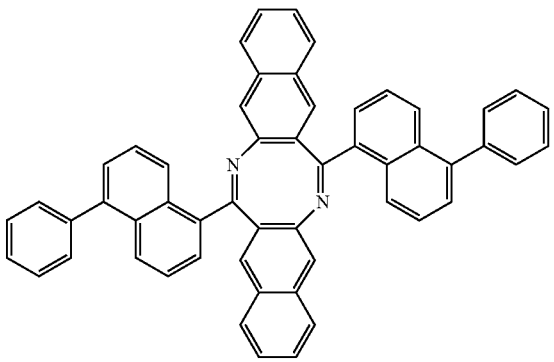
155
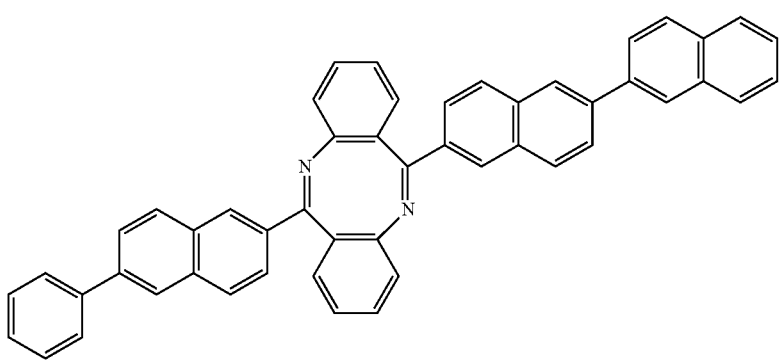

156
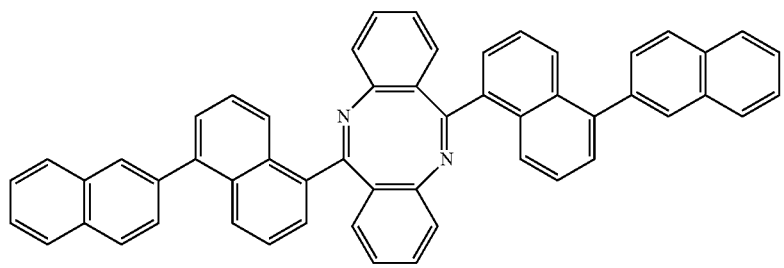
157
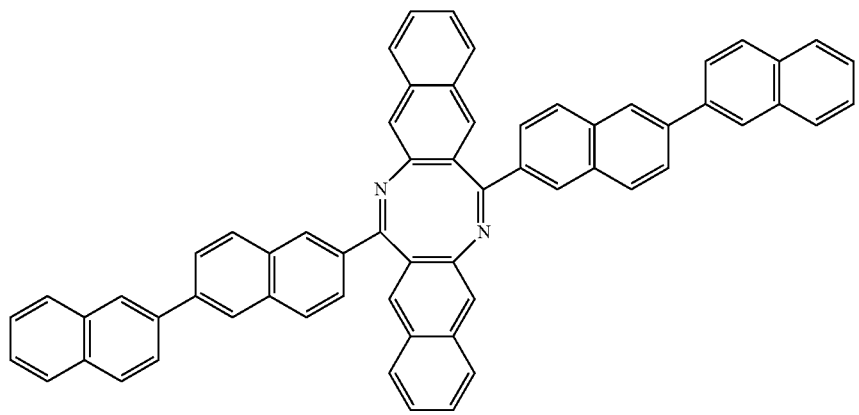
158
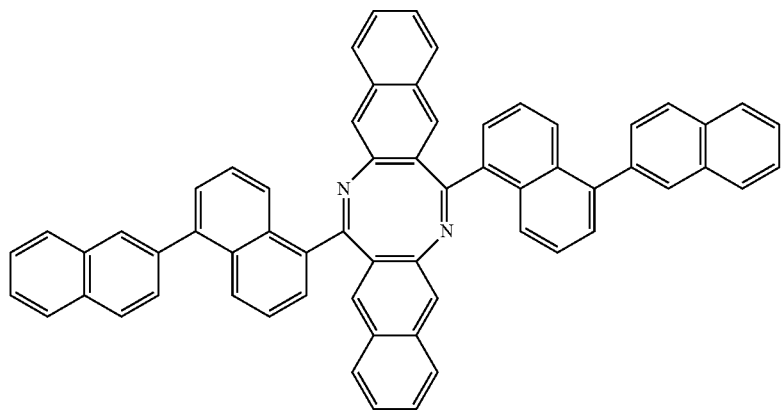
159 160
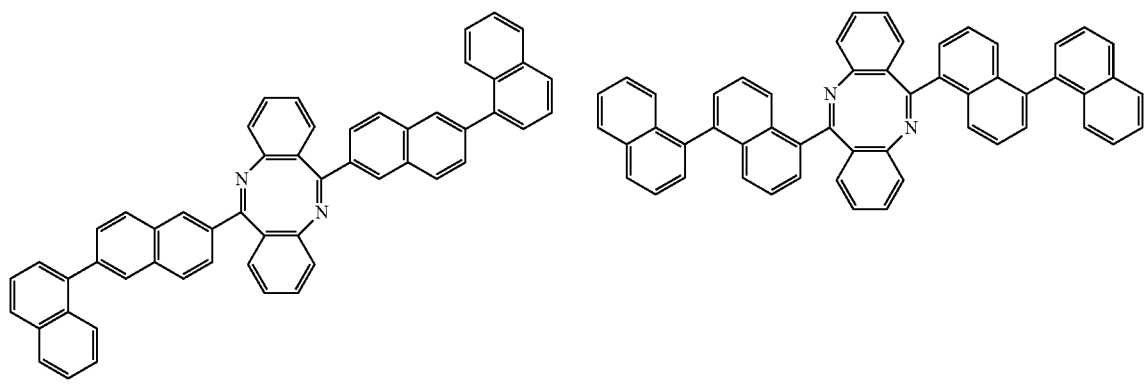

161
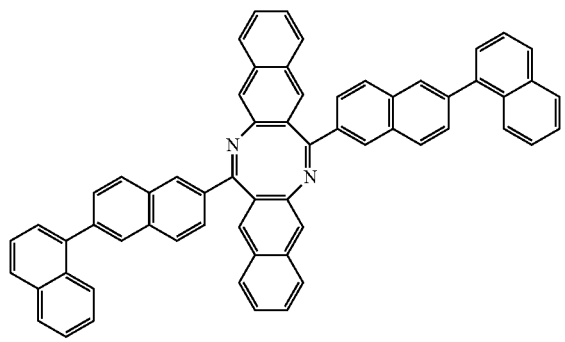
162
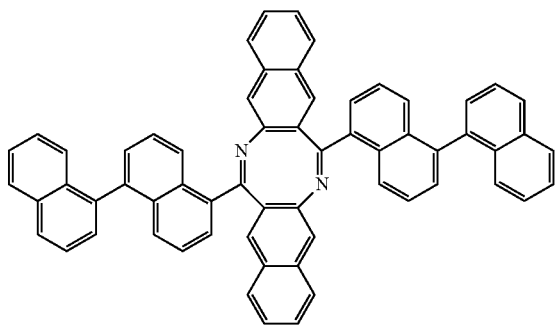
163
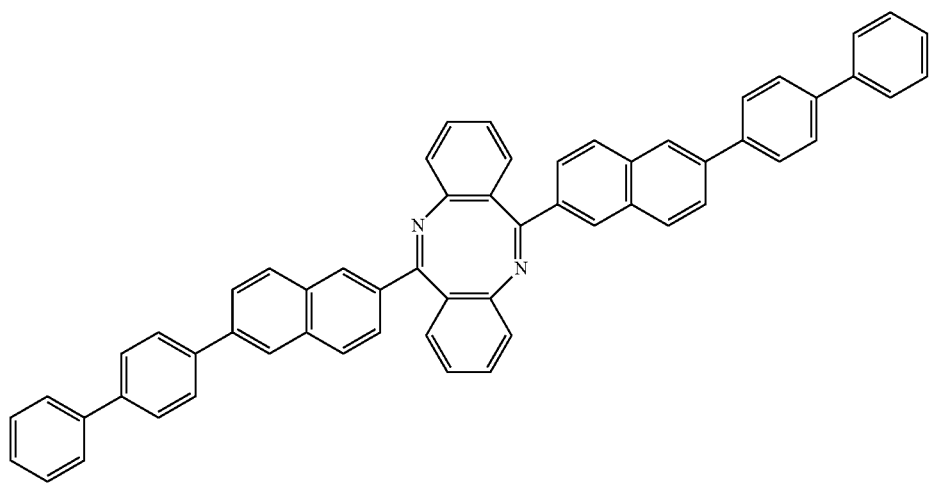
164
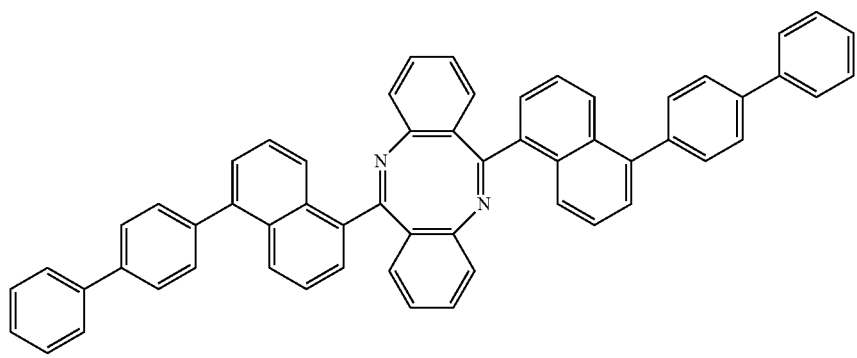

-continued
165
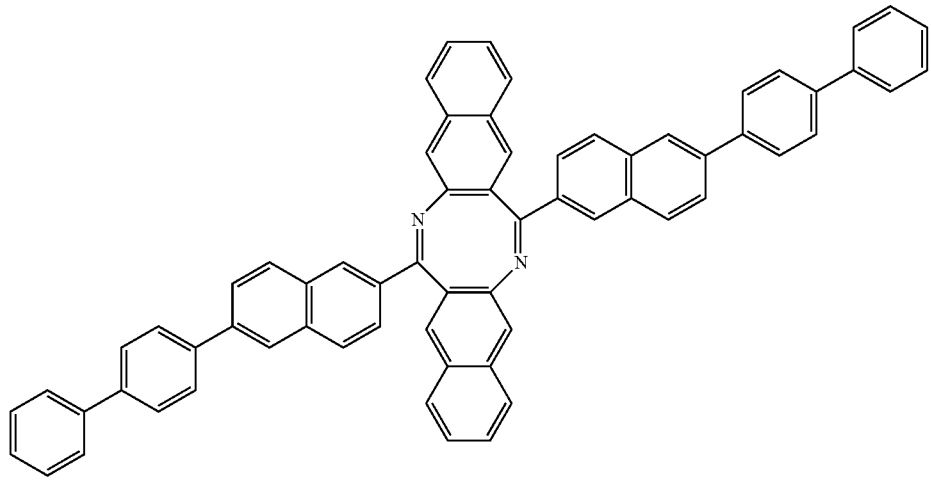
166
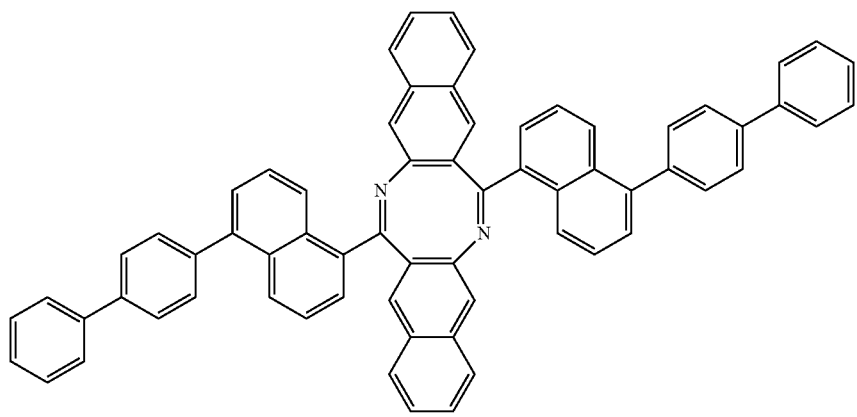
167
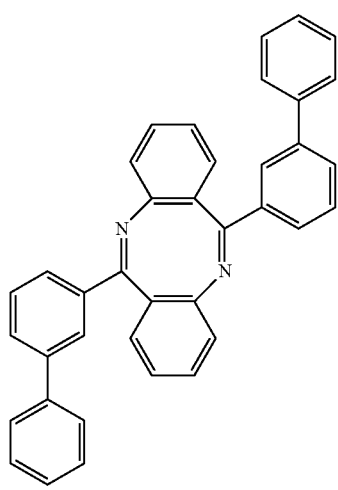
168

169
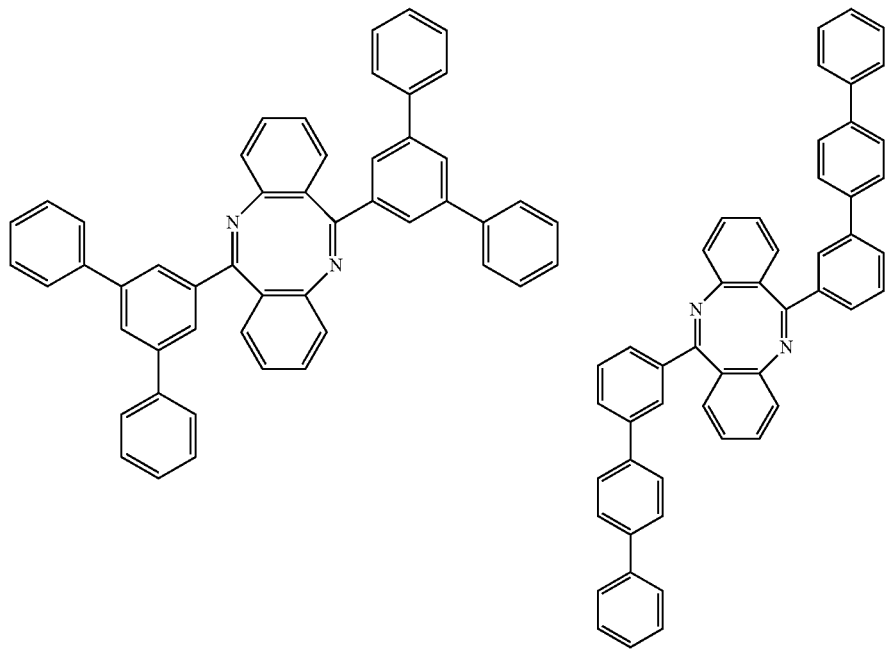
170
171
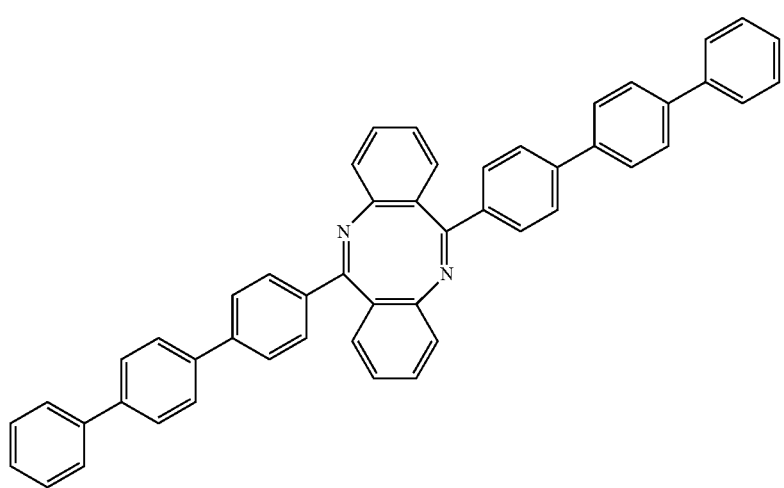

172
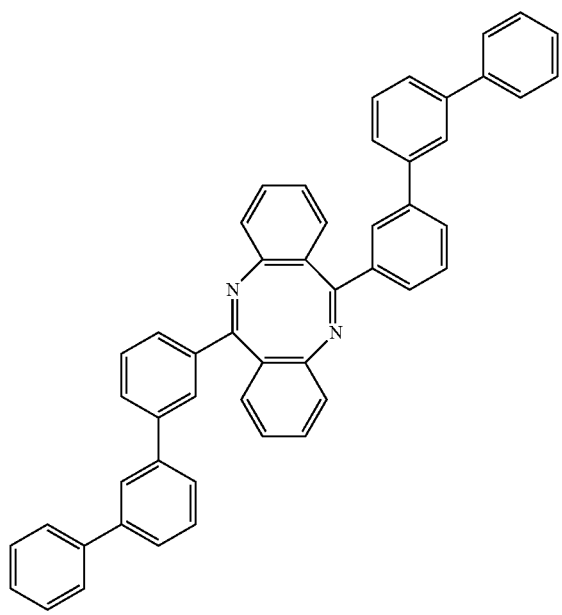
173
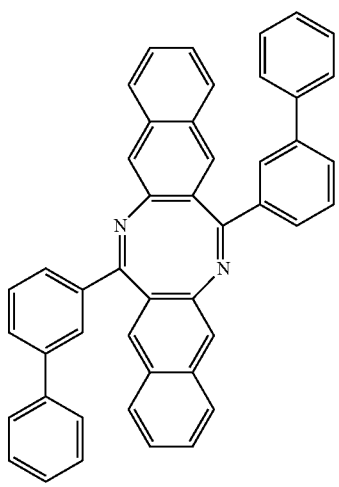
174
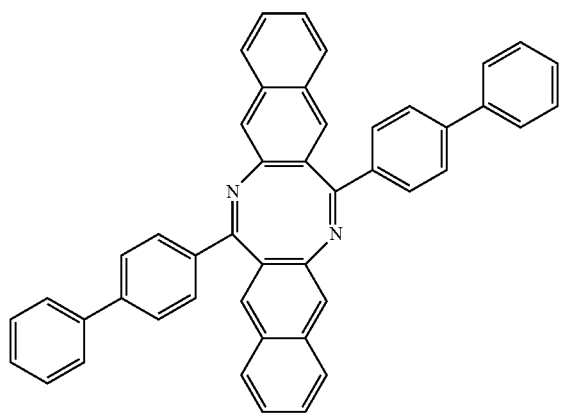
175
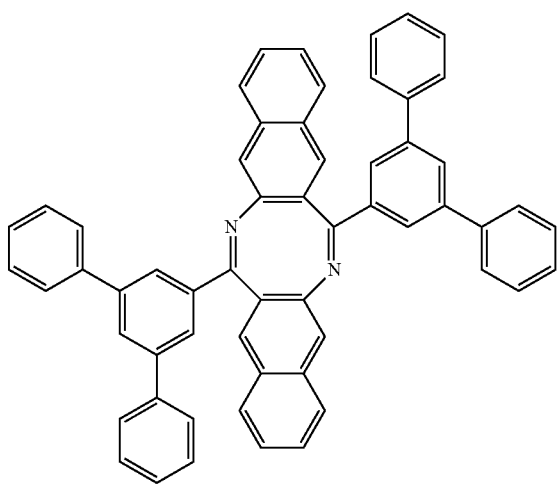

176
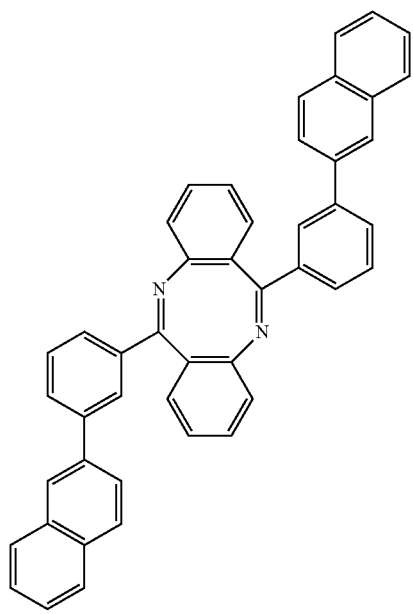
177
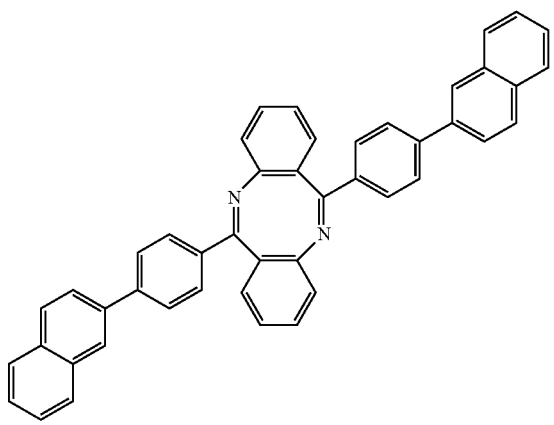
178
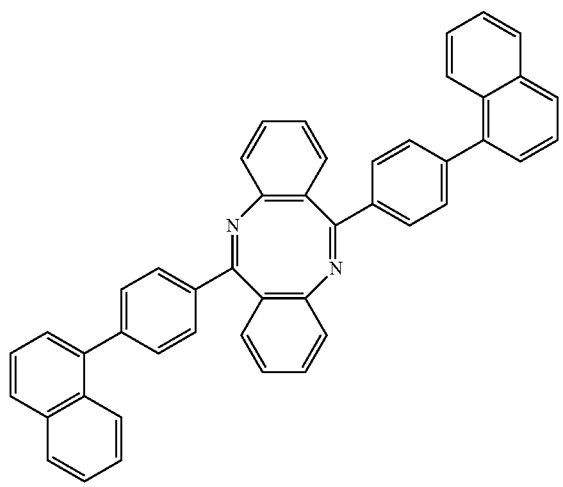
179
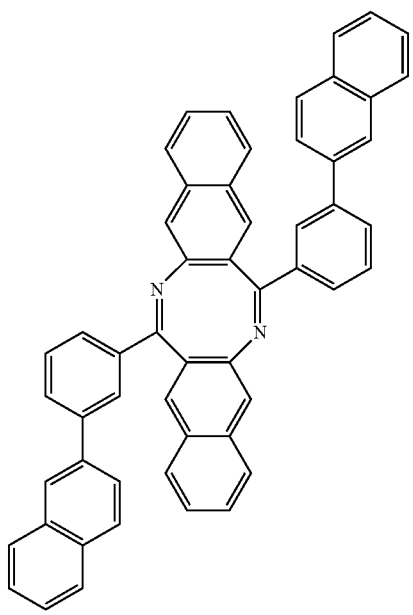

301
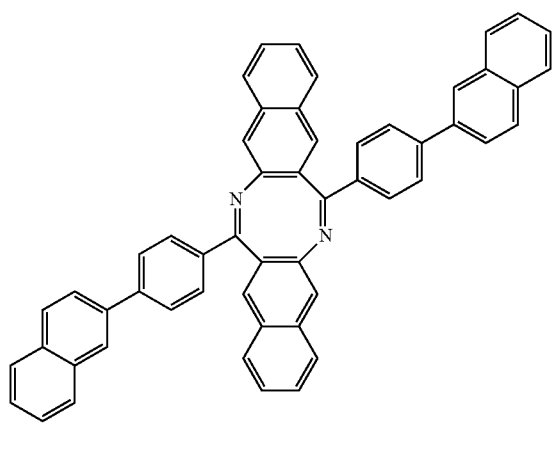
302
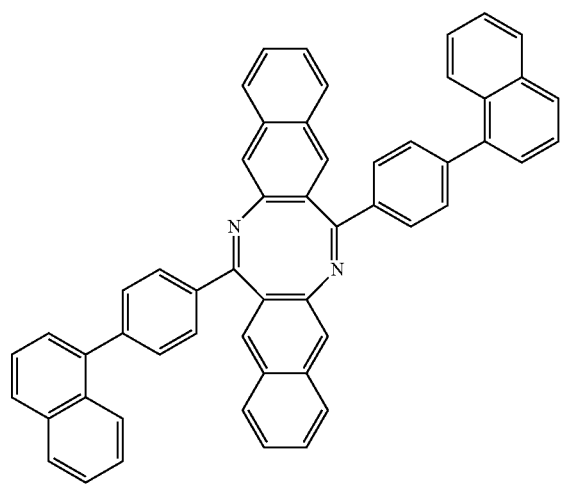
200
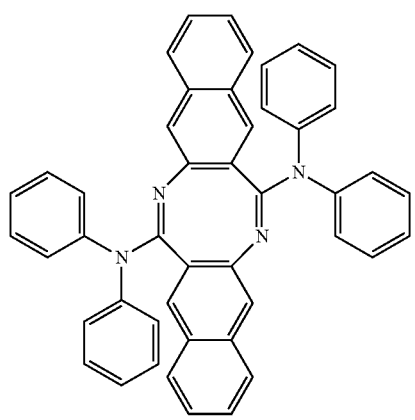
201
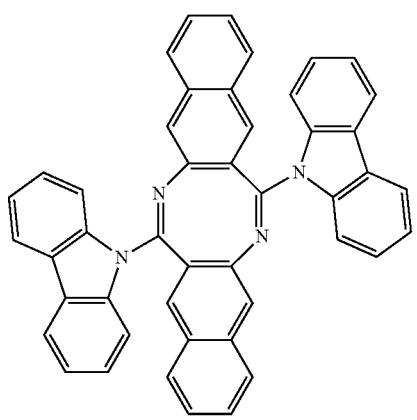
202
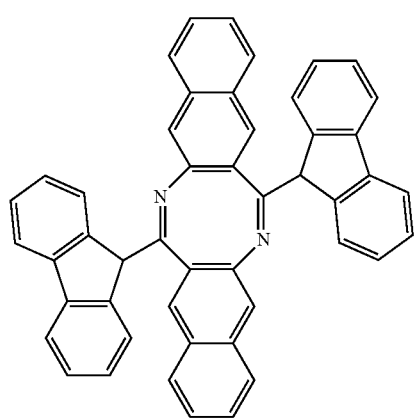
203
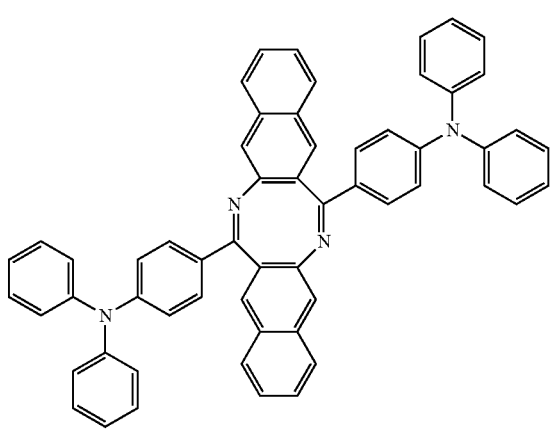

-continued
204
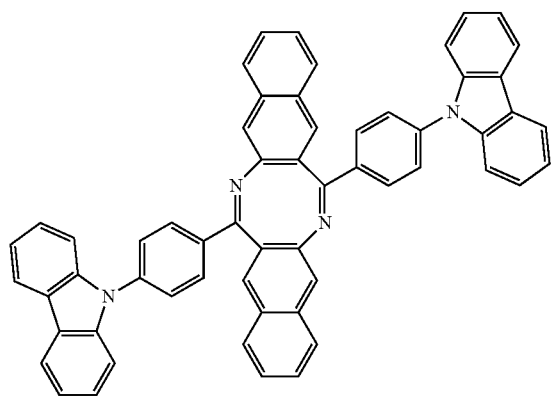
205
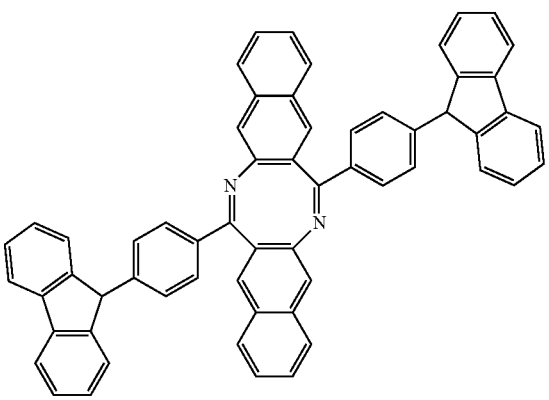
206
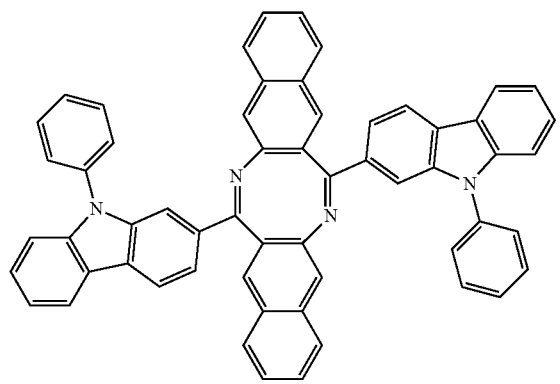
207
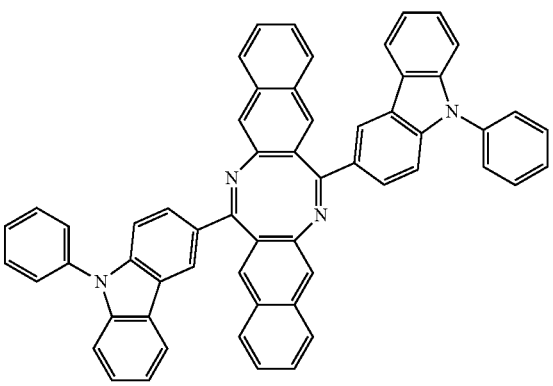
208
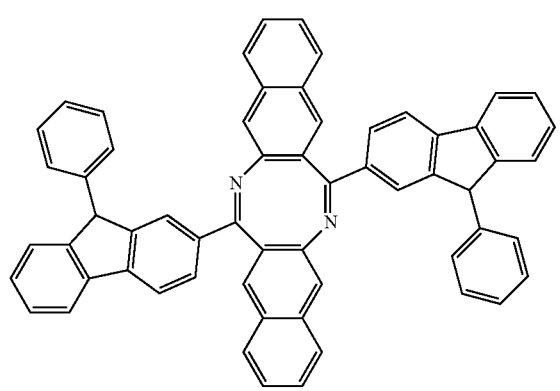
209
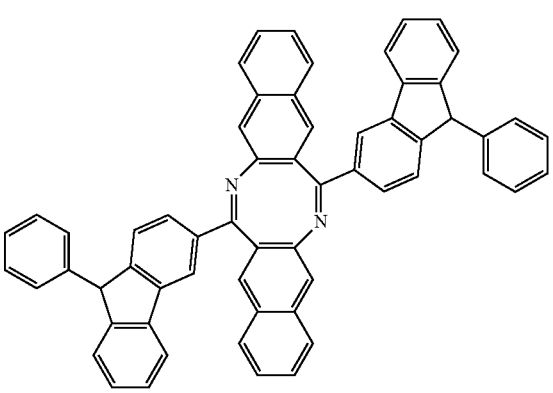
210
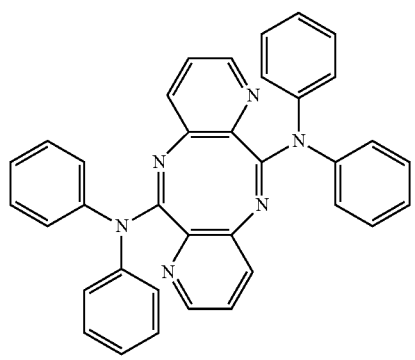

-continued
212
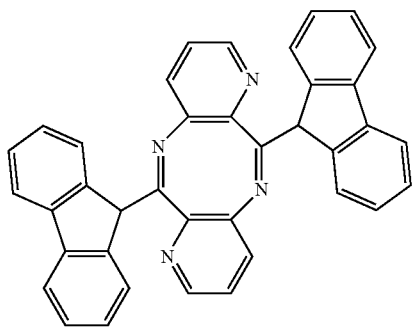
213
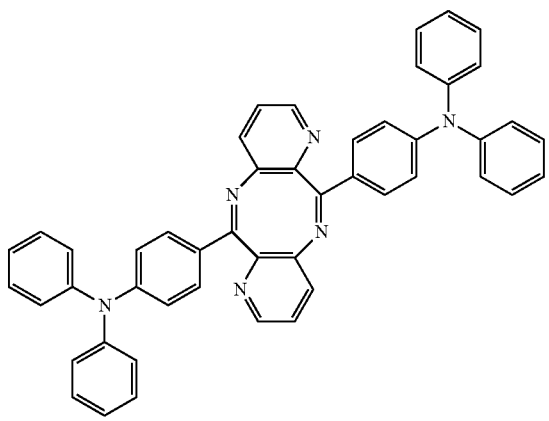
214
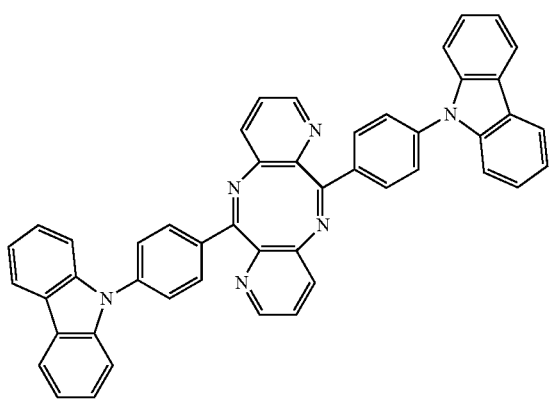
215
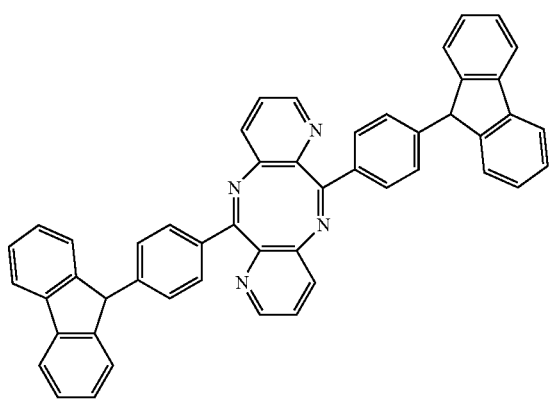
216
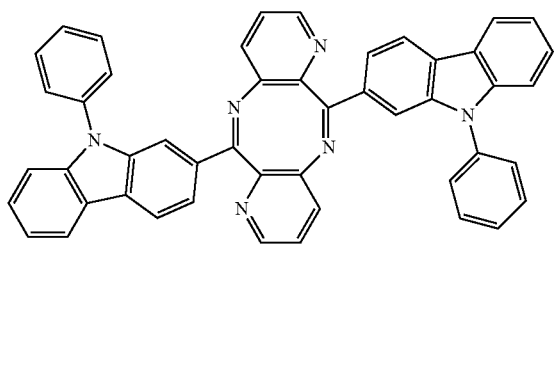
217
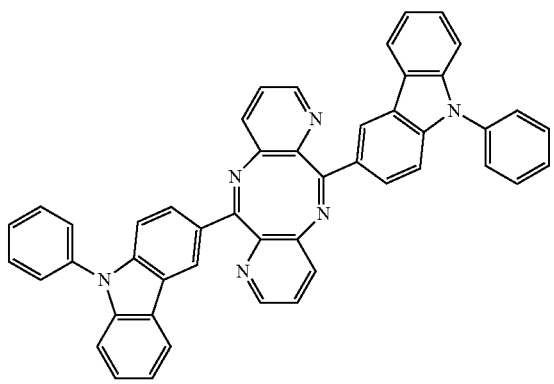
218
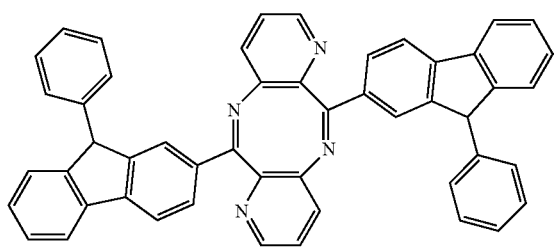
219
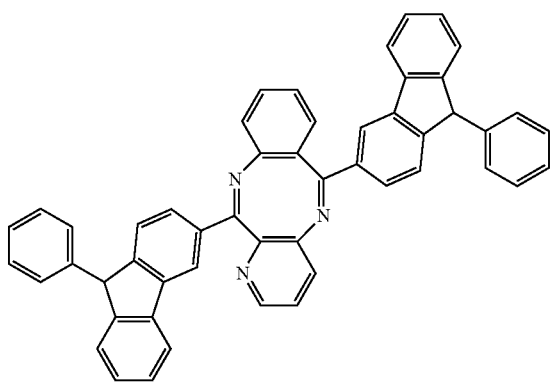

-continued
220
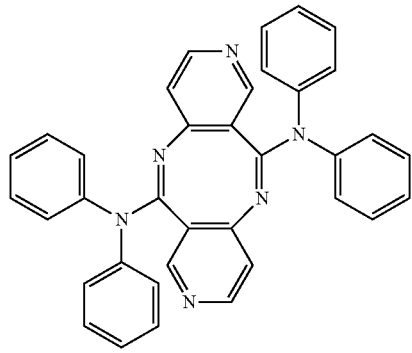
221
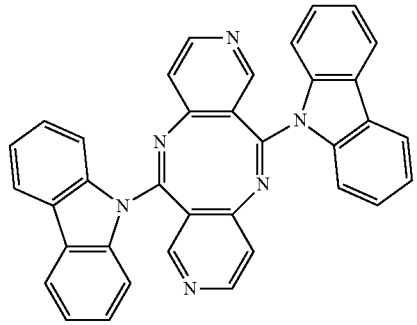
222
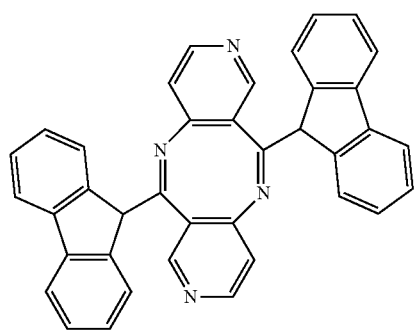
223
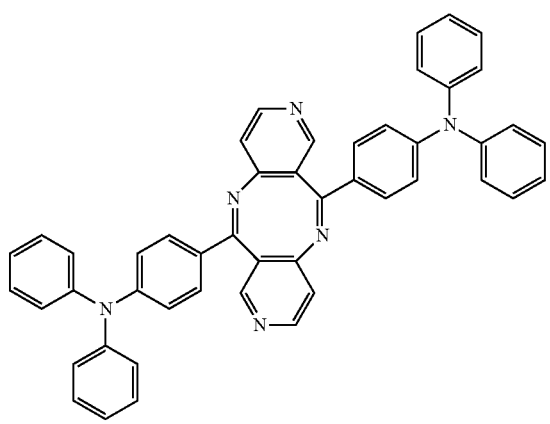
224
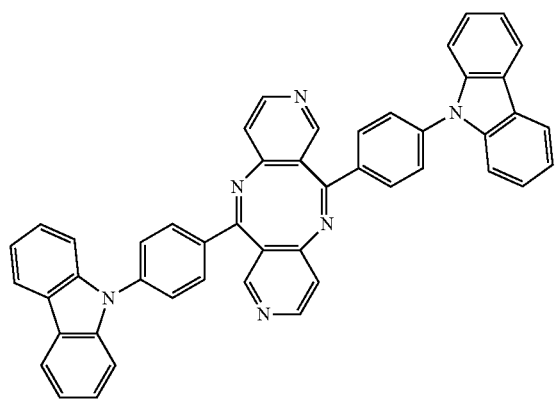
225
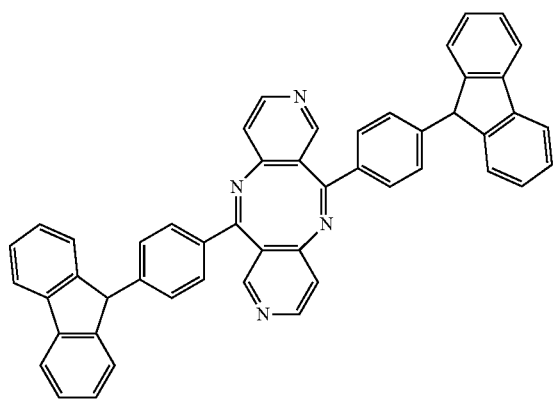
226
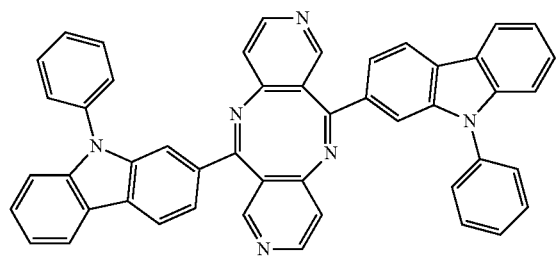
227
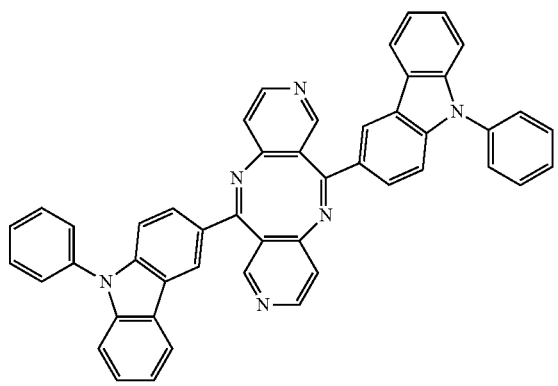

-continued
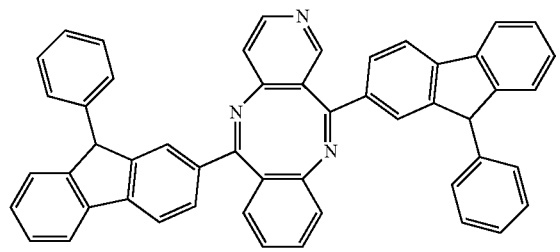
228
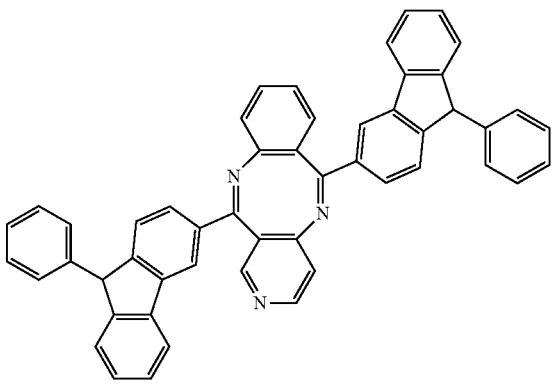
229
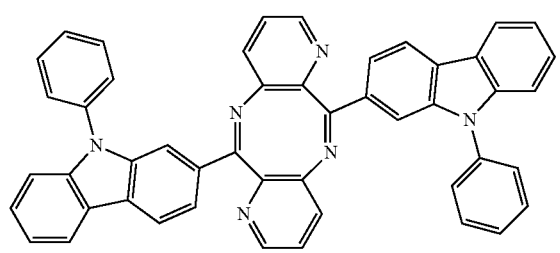
230
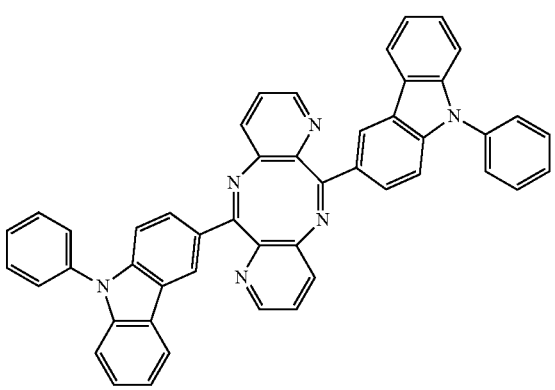
231
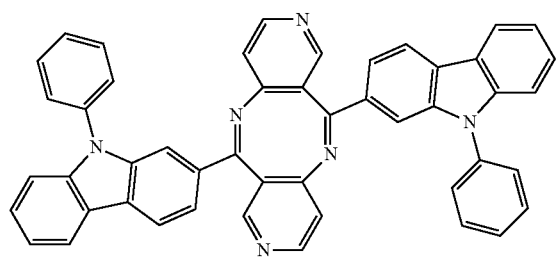
232
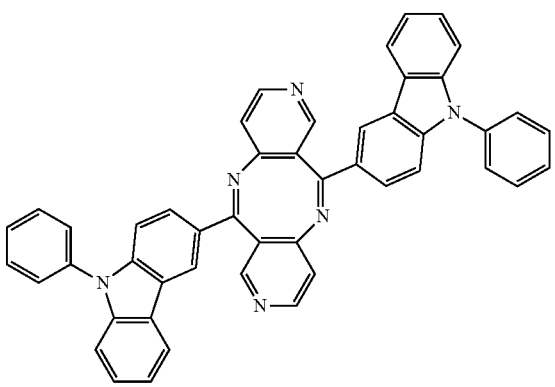
233
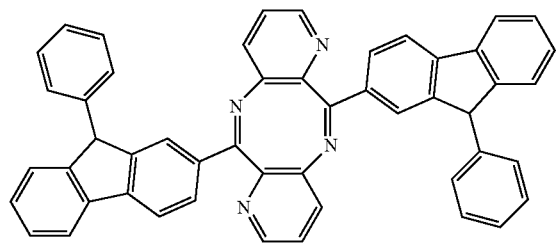
234
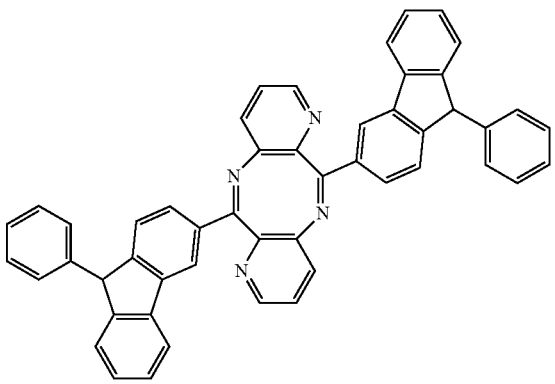
235

-continued
236
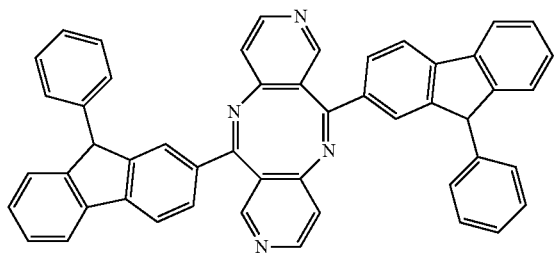
237
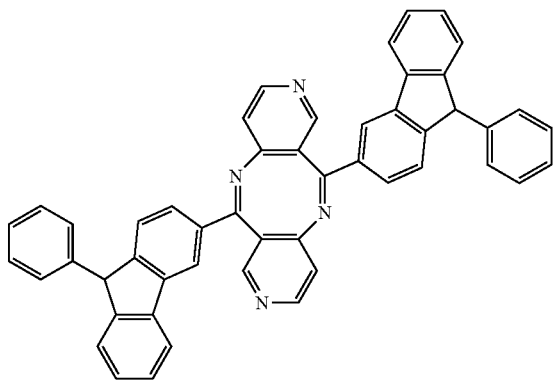
238
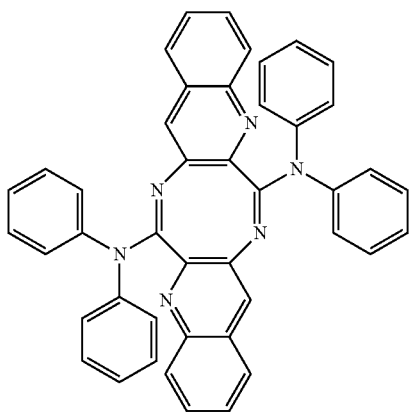
239
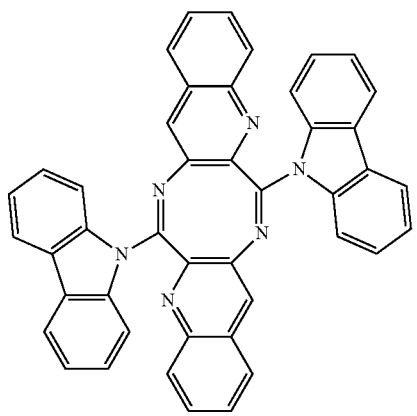
240
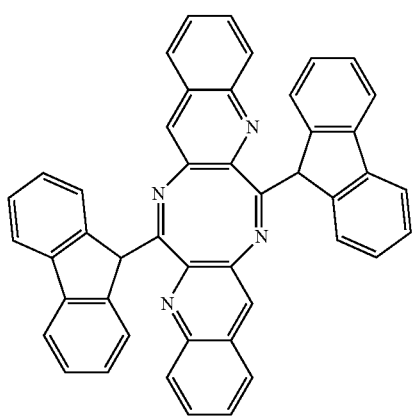
241
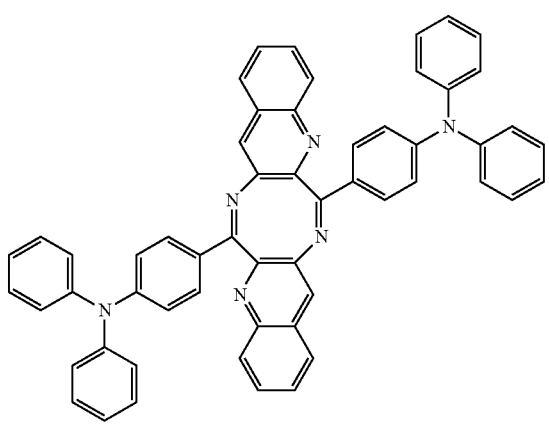

242
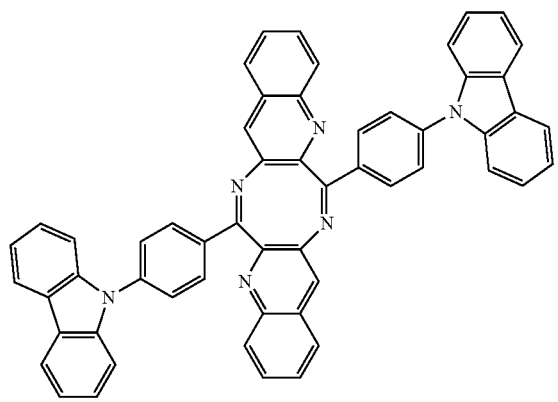
243
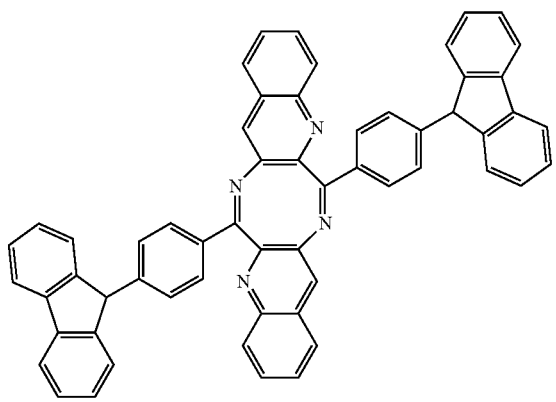
244
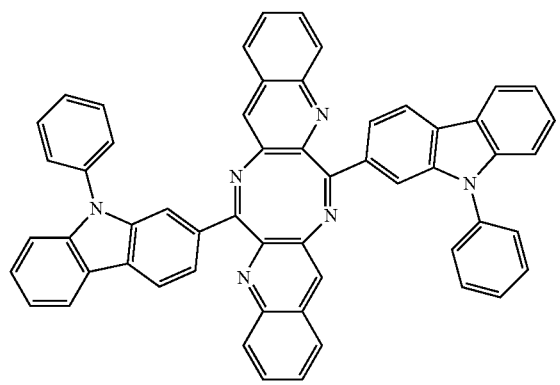
245
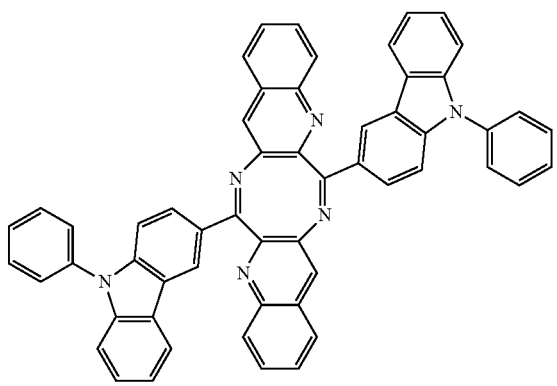
246
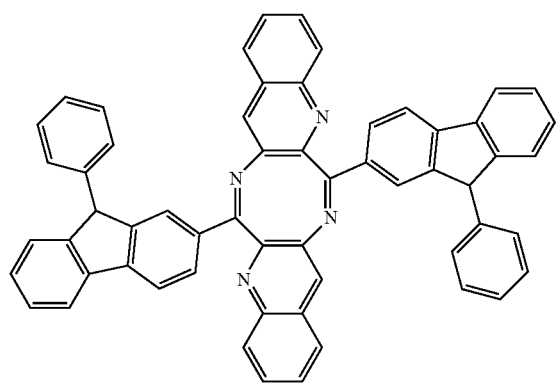
247
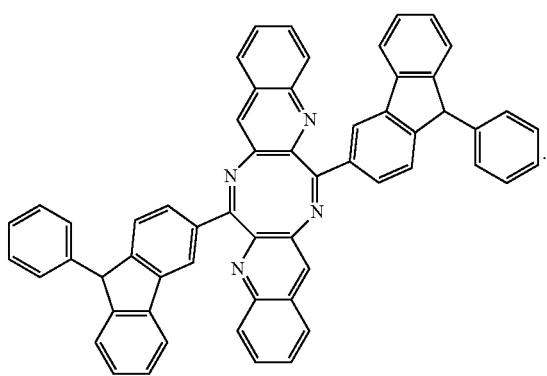

17. An organic light-emitting device comprising:
a first electrode;
a second electrode facing the first electrode; and
an organic layer between the first electrode and the second electrode, and comprising an emission layer,
wherein the organic layer comprises at least one of an antiaromatic compound represented by Formula 1:

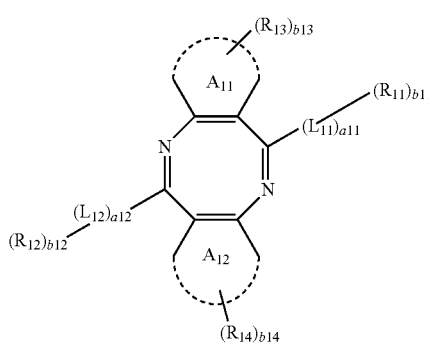

Formula 1 wherein, in Formula 1,
$A_{11}$ and $A_{12}$ are each independently selected from a $C_6$-$C_{60}$ arene and a $C_1$-$C_{60}$ heteroarene;
$L_{11}$ and L12 are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted heteroarylene group, a substituted or unsubstituted non-aromatic condensed polycyclic group, and a substituted or unsubstituted non-aromatic condensed heteropolycyclic group;
at least one substituent of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted non-aromatic condensed polycyclic group, and the substituted non-aromatic condensed heteropolycyclic group is selected from:
a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and $C_1$-$C_{60}$ alkoxy group;
a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group;
a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group; and
a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group, each substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group;
a11 and a12 are each independently selected from 0, 1, 2, 3, 4, 5 and 6;
$R_{11}$ and $R_{12}$ are each independently selected from a substituted or unsubstituted $C_6$-$C_{60}$ aryl group, a substituted or unsubstituted $C_1$-$C_{60}$ heteroaryl group, a substituted or unsubstituted non-aromatic condensed polycyclic group, a substituted or unsubstituted non-aromatic condensed heteropolycyclic group, -N($Q_{11}$)($Q_{12}$), -Si($Q_{13}$)($Q_{14}$)($Q_{15}$), and -P($Q_{16}$)($Q_{17}$);
$Q_{11}$ to $Q_{17}$ are each independently selected from a substituted or unsubstituted $C_6$-$C_{60}$ aryl group, and a substituted or unsubstituted $C_1$-$C_{60}$ heteroaryl group;
at least one substituent of the substituted $C_6$-$C_{60}$ aryl group, the substituted $C_1$-$C_{60}$ heteroaryl group, the substituted non-aromatic condensed polycyclic group, and the substituted non-aromatic condensed heteropolycyclic group is selected from:
a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;
a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group, each substituted with at least one of a deuterium atom, a halogen atom, a hydroxyl group, a cyano group, a nitro group, an amino group, and amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group;

b11 and b12 are each independently an integer selected from 1 to 3;

R13 and R14 are each independently selected from:

a hydrogen atom, a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group; and a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group, each substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic condensed heteropolycyclic group; and b13 and b14 are each independently selected from 1, 2, 3, 4, 5, 6, 7, 8, 9 and 10.

18. The organic light-emitting device of claim 17, wherein the organic layer comprises an electron transport region between the emission layer and the second electrode, and the electron transport region comprises the antiaromatic compound.

19. The organic light-emitting device of claim 18, wherein the electron transport region comprises an electron transport layer, and the electron transport layer comprises the antiaromatic compound.

* * * * *